(12) United States Patent
Rothschild et al.

(10) Patent No.: US 7,312,060 B2
(45) Date of Patent: Dec. 25, 2007

(54) METHODS FOR THE DETECTION, ANALYSIS AND ISOLATION OF NASCENT PROTEINS

(75) Inventors: Kenneth J. Rothschild, Newton, MA (US); Sadanand Gite, Cambridge, MA (US); Jerzy Olejnik, Allston, MA (US); Mark Lim, Reading, MA (US)

(73) Assignee: Ambergen, Inc., Watertown, MA (US)

( * ) Notice: Subject to any disclaimer, the term of this patent is extended or adjusted under 35 U.S.C. 154(b) by 468 days.

(21) Appl. No.: 10/339,712

(22) Filed: Jan. 10, 2003

(65) Prior Publication Data
US 2004/0014071 A1 Jan. 22, 2004

Related U.S. Application Data

(63) Continuation-in-part of application No. 10/049,332, filed as application No. PCT/US00/23233 on Aug. 23, 2000, which is a continuation-in-part of application No. 09/382,736, filed on Aug. 25, 1999, now Pat. No. 6,306,628.

(51) Int. Cl.
*C07H 21/04* (2006.01)
(52) U.S. Cl. .................................. 435/194; 536/24.33
(58) Field of Classification Search ..................... None
See application file for complete search history.

(56) References Cited

OTHER PUBLICATIONS

Hopkins, PNAS vol. 90, 1993, pp. 8759-8760.*

* cited by examiner

*Primary Examiner*—James Ketter
(74) *Attorney, Agent, or Firm*—Medlen & Carroll, LLP

(57) ABSTRACT

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents. Preferred markers are dipyrromethenboron difluoride(4,4-difluoro-4-bora-3a,4a-diaza-s-indacene)dyes.

3 Claims, 82 Drawing Sheets

R = —CH₃     ALANINE

R = —CH(CH₃)₂     VALINE

⁻OOC—ALANINE-VALINE-TYROSINE-LYSINE-TRYPTOPHAN—NH₃⁺

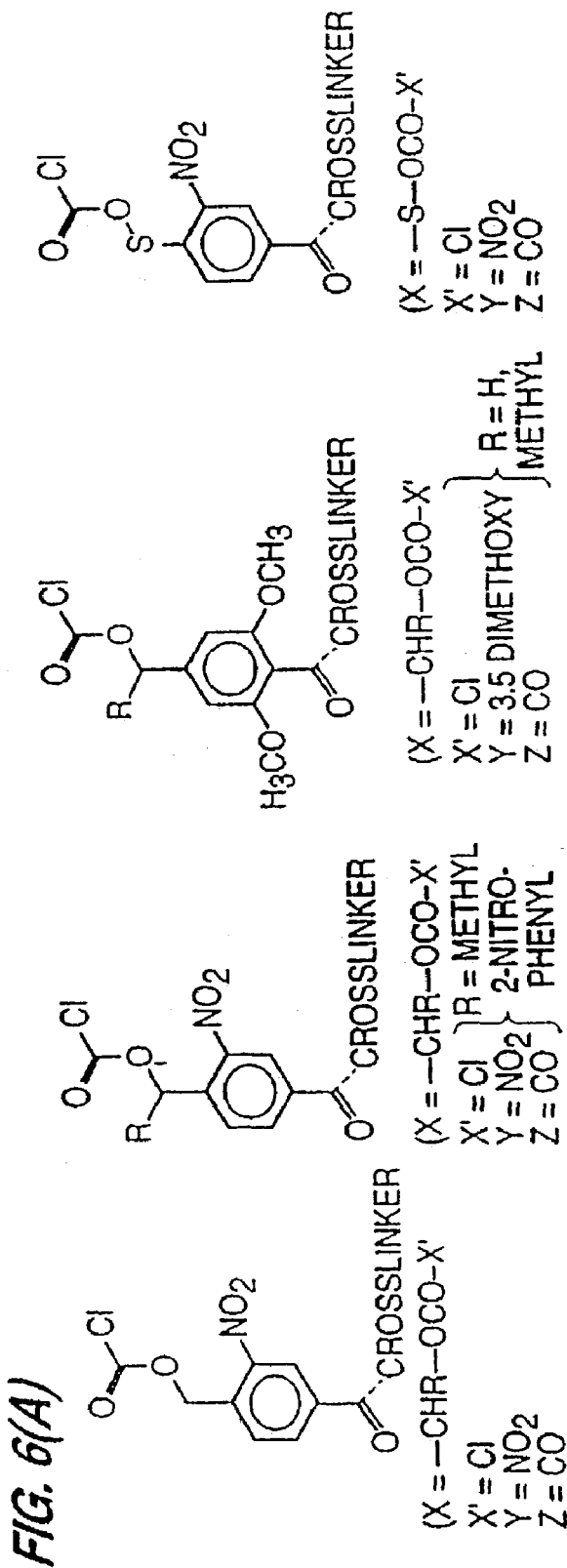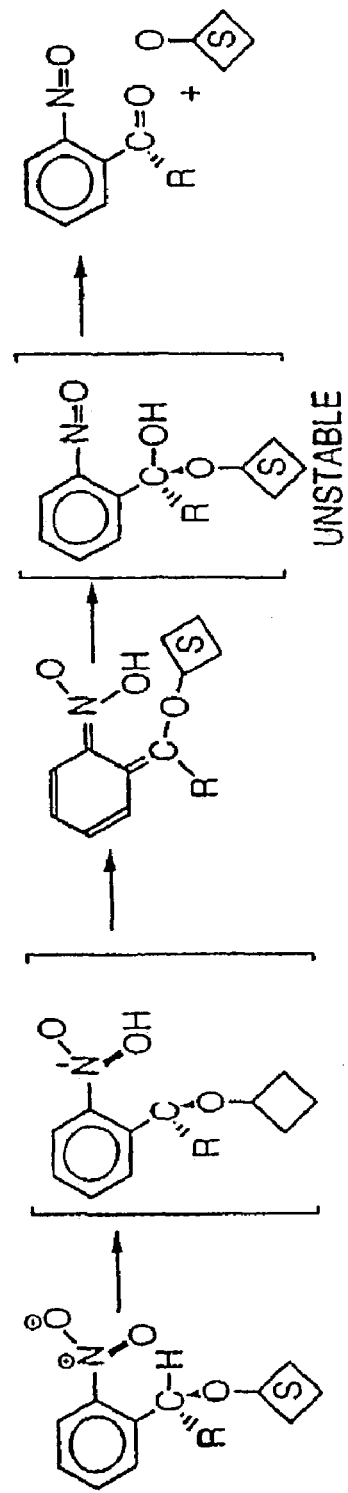
FIG. 6(A)
FIG. 6(B)

Probe dual Fluorescence of 2D array

| Donor | Acceptor | $R_o$ (Å) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | QSY 7 and QSY 9 dyes | 57 |
| Fluorescein | QSY 7 and QSY 9 dyes | 61 |

Figure 68

```
  1 meepqsdpsv epplsqetfs dlwkllpenn vlsplpsqam ddlmlspddi eqwftedpgp
 61 deaprmpeaa prvapapaap tpaapapaps wplsssvpsq ktyqgsygfr lgflhsgtak
121 svtctyspal nkmfcqlakt cpvqlwvdst pppgtrvram aiykqsqhmt evvrrcphhe
181 rcsdsdglap pqhlirvegn lrveylddrn tfrhsvvvpy eppevgsdct tihynymcns
241 scmggmnrrp iltiitleds sgnllgrnsf evrvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd
```

Figure 70

```
   1 ccacctgaag tccaaaaagg gtcagtctac ctcccgccat aaaaaactca tgttcaagac
  61 agaagggcct gactcagact gacattctcc acttcttgtt ccccactgac agcctcccac
 121 ccccatctct ccctcccctg ccattttggg ttttgggtct ttgaacccct gcttgcaata
 181 ggtgtgcgtc agaagcaccc aggacttcca tttgctttgt cccggggctc cactgaacaa
 241 gttggcctgc actggtgttt tgttgtgggg aggaggatgg ggagtaggac ataccagctt
 301 agattttaag gttttractg tgagggatgt ttgggagatg taagaaatgt tcttgcagtt
 361 aagggttagt ttacaatcag ccacattcta ggtaggggcc cacttcaccg tactaaccag
 421 ggaagctgtc cctcactgtt gaattttctc taacttcaag gcccatatct gtgaaatgct
 481 ggcatttgca cctacctcac agagtgcatt gtgagggtta atgaaataat gtacatctgg
 541 ccttgaaacc acctttttatt acatggggtc tagaacttga ccccttgag ggtgcttgtt
 601 ccctctccct gttggtcggt gggttggtag tttctacagt tgggcagctg gttaggtaga
 661 gggagttgtc aagtctctgc tggcccagcc aaaccctgtc tgacaacctc ttggtgaacc
 721 ttagtaccta aaaggaaatc tcacccatc ccacaccctg gaggatttca tctcttgtat
 781 atgatgatct ggatccacca agacttgttt tatgctcagg gtcaatttct ttttctttt
 841 tttttttttt tttcttttc tttgagactg ggtctcgctt tgttgcccag gctggagtgg
 901 agtggcgtga tcttggctta ctgcagcctt tgcctcccg gctcgagcag tcctgcctca
 961 gcctcggag tagctggac acaggttca tgccaccatg ccagccaac ttttgcatgt
1021 tttgtagaga tggggtctca cagtgttgcc caggctggtc tcaaactcct gggctcaggc
1081 gatccacctg tctcagcctc ccagagtgct gggattacaa ttgtgagcca ccacgtccag
1141 ctggaagggt caacatcttt tacattctgc aagcacatct gcattttcac cccacccttc
1201 ccctccttct ccctttttat atcccatttt tatatcgatc tcttatttta caataaaact
1261 ttgctgccac ctgtgtgtct gagggtg
```

Figure 71

```
                         SEQUENCE LISTING

<160> NUMBER OF SEQ IDS: 84

<210> SEQ ID NO 1
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: The n at this position can be a or g.

<400> SEQUENCE: 1 gccnccatgg                                                        10

<210> SEQ ID NO 2
<211> LENGTH: 9
<212> TYPE: RNA
<213> ORGANISM: Artificial Sequence
<220> FEATURE:
<223> OTHER INFORMATION: Synthetic

<400> SEQUENCE: 2 uaaggaggu                                                          9

<210> SEQ ID NO 3
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(19)
<223> OTHER INFORMATION: N at this position can be a, c, g, or u, and
      five to ten of these bases may be present or absent.

<400> SEQUENCE: 3
uaaggaggun nnnnnnnnna ug                                          22
```

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Trp Glu Ala Ala Ala Arg Glu Ala Cys Cys Arg Glu Cys Cys Ala Arg
1               5                   10                  15

Ala

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

His His His His His His
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Glu Gln Lys Leu Ile Ser Glu Glu Asp Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Asp Tyr Lys Asp Asp Asp Asp Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Trp Ser His Pro Gln Phe Glu Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Tyr Pro Tyr Asp Val Pro Asp Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Met Trp Ser Pro Gln Phe Glu Lys
1               5

<210> SEQ ID NO 11
<211> LENGTH: 111
<212> TYPE: DNA
<213> ORGANISM: Artificial Sequence
<220> FEATURE:
<223> OTHER INFORMATION: Synthetic

<400> SEQUENCE: 11
gaattctaat acgactcact atagggttaa ctttaagaag gagatataca tatggaacaa     60
aaattaatct cggaagagga tttggcagat tctgatatta atattaaaac c              111

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
agcttcatta atgatggtga tggtggtgac                                       30

<210> SEQ ID NO 13
<211> LENGTH: 94
<212> TYPE: DNA
<213> ORGANISM: Artificial Sequence
<220> FEATURE:
<223> OTHER INFORMATION: Synthetic

<400> SEQUENCE: 13
ggatcctaat acgactcact atagggagac caccatggaa caaaaattaa tatcggaaga     60
ggatttgaat gtttctccat acaggtcacg ggga                                  94

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
ttattaatga tggtgatggt ggtgttctgt aggaatggta tctcgttttt c               51

<210> SEQ ID NO 15
<211> LENGTH: 114
<212> TYPE: DNA
<213> ORGANISM: Artificial Sequence
<220> FEATURE:
<223> OTHER INFORMATION: Synthetic

<400> SEQUENCE: 15
ggatcctaat acgactcact atagggagac caccatggga caccaccatc accatcacgg     60
agattacaaa gatgacgatg acaaagagga gccgcagtca gatcctagcg tcga            114

<210> SEQ ID NO 16
<211> LENGTH: 68
<212> TYPE: DNA
<213> ORGANISM: Artificial Sequence
<220> FEATURE:
<223> OTHER INFORMATION: Synthetic

<400> SEQUENCE: 16
attattacaa atcctcttcc gagattaatt tttgttcgtc tgagtcaggc ccttctgtct    60
tgaacatg                                                             68

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
ctcattcagc tctcggaaca tctcgaagcg                                     30

<210> SEQ ID NO 18
<211> LENGTH: 58
<212> TYPE: DNA
<213> ORGANISM: Artificial Sequence
<220> FEATURE:
<223> OTHER INFORMATION: Synthetic

<400> SEQUENCE: 18
ggatcctaat acgactcact atagggagac caccatggat gcatgtggaa ctttgtgg     58

<210> SEQ ID NO 19
<211> LENGTH: 28
<212> TYPE: DNA
<213> ORGANISM: Artificial Sequence
<220> FEATURE:
<223> OTHER INFORMATION: Synthetic

<400> SEQUENCE: 19
gaggatccat tagatgaagg tgtggacg                                       28

<210> SEQ ID NO 20
<211> LENGTH: 115
<212> TYPE: DNA
<213> ORGANISM: Artificial Sequence
<220> FEATURE:
<223> OTHER INFORMATION: Synthetic

<400> SEQUENCE: 20
ggatcctaat acgactcact atagggagac caccatgcac caccatcacc atcacggagg    60
agattacaaa gatgacgatg acaaagtttc tccatacagg tcacggggag ccaat        115

<210> SEQ ID NO 21
<211> LENGTH: 67
<212> TYPE: DNA
<213> ORGANISM: Artificial Sequence
<220> FEATURE:
<223> OTHER INFORMATION: Synthetic

<400> SEQUENCE: 21
attattacaa atcctcttcc gagattaatt tttgttcact tctgccttct gtaggaatgg    60
tatctcg                                                              67

```
<210> SEQ ID NO 22
<211> LENGTH: 99
<212> TYPE: DNA
<213> ORGANISM: Artificial Sequence
<220> FEATURE:
<223> OTHER INFORMATION: Synthetic

<400> SEQUENCE: 22
ggatcctaat acgactcact atagggagac caccatgggc tacaccgaca tcgagatgaa      60
ccgcctggca aggtttctcc atacaggtca cggggagcc                             99

<210> SEQ ID NO 23
<211> LENGTH: 59
<212> TYPE: DNA
<213> ORGANISM: Artificial Sequence
<220> FEATURE:
<223> OTHER INFORMATION: Synthetic

<400> SEQUENCE: 23
ttattacagc agcttgtgca ggtcgctgaa ggtacttctg ccttctgtag gaatgtatc       59

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Thr Phe Ser Asp Leu His Lys Leu Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Thr Phe Ser Asp Leu Tyr Lys Leu Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Thr Phe Ser Asp Leu Gly Lys Leu Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Thr Phe Ser Asp Leu Asn Lys Leu Leu
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Thr Phe Ser Asp Leu Phe Lys Leu Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Thr Phe Ser Asp Leu Asp Lys Leu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Thr Phe Ser Asp Leu Thr Lys Leu Leu
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Glu Thr Phe Ser Asp Leu His Lys Leu Leu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic

<400> SEQUENCE: 32

Gln Glu Thr Phe Ser Asp Leu His Lys Leu Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Ser Gln Glu Thr Phe Ser Asp Leu His Lys Leu Leu
1               5                   10

<210> SEQ ID NO 34
```

```
<211> LENGTH: 13
<212> TYPE: PRT
<213> ORGANISM: Artificial Sequence
<220> FEATURE:
<223> OTHER INFORMATION: Synthetic

<400> SEQUENCE: 34

Leu Ser Gln Glu Thr Phe Ser Asp Leu His Lys Leu Leu
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Glu Thr Phe Ser Asp Leu His Lys Leu Leu Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Gln Glu Thr Phe Ser Asp Leu His Lys Leu Leu Pro
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Ser Gln Glu Thr Phe Ser Asp Leu His Lys Leu Leu Pro
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Leu Ser Gln Glu Thr Phe Ser Asp Leu His Lys Leu Leu Pro Glu
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Tyr Thr Asp Ile Glu Met Asn Arg Leu Gly Lys
1               5                   10

<210> SEQ ID NO 40
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 40

Tyr Ala Asp Ile Glu Met Asn Arg Leu Gly Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Tyr Thr Asp Ile Glu Met Asn Arg Ser Gly Lys
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42

Tyr Thr Asp Ile Glu Met Asn Arg Leu Ser Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Tyr Ser Asp Ile Glu Met Asn Arg Ser Gly Lys
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Tyr Ala Asp Ile Glu Met Asn Arg Leu Leu Lys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Tyr Thr Asp Ile Glu Met Asn Arg Ser Ser Lys
1               5                   10

<210> SEQ ID NO 46
<211> LENGTH: 11
<212> TYPE: PRT
```

<213> ORGANISM: Artificial Sequence
<220> FEATURE:
<223> OTHER INFORMATION: Synthetic

<400> SEQUENCE: 46

Tyr Ala Asp Ile Glu Met Asn Arg Ser Gly Lys
1               5                   10

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
tttttggttg gcactcttac ttaccggagc                                       30

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
agatgcttgc tggacctggt ccattatctt                                       30

<210> SEQ ID NO 49
<211> LENGTH: 393
<212> TYPE: PRT
<213> ORGANISM: Homo sapiens

<400> SEQUENCE: 49

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

-continued

```
Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 50
<211> LENGTH: 1288
<212> TYPE: DNA
<213> ORGANISM: Homo sapiens

<400> SEQUENCE: 50

```
ccacctgaag tccaaaaagg gtcagtctac ctcccgccat aaaaaactca tgttcaagac    60
agaagggcct gactcagact gacattctcc acttcttgtt ccccactgac agcctcccac   120
ccccatctct ccctcccctg ccatttggg ttttgggtct ttgaacccct gcttgcaata   180
ggtgtgcgtc agaagcaccc aggacttcca tttgctttgt cccggggctc cactgaacaa   240
gttggcctgc actggtgttt tgttgtgggg aggaggatgg ggagtaggac ataccagctt   300
agattttaag gttttactg tgagggatgt ttgggagatg taagaaatgt tcttgcagtt   360
aagggttagt ttacaatcag ccacattcta ggtagggcc cacttcaccg tactaaccag   420
ggaagctgtc cctcactgtt gaattttctc taacttcaag gcccatatct gtgaaatgct   480
ggcatttgca cctacctcac agagtgcatt gtgagggtta atgaaataat gtacatctgg   540
ccttgaaacc acctttttatt acatggggtc tagaacttga ccccccttgag ggtgcttgtt   600
ccctctccct gttggtcggt gggttggtag tttctacagt tgggcagctg gttaggtaga   660
gggagttgtc aagtctctgc tggcccagcc aaaccctgtc tgacaacctc ttggtgaacc   720
ttagtaccta aaaggaaatc tcaccccatc ccacaccctg gaggatttca tctcttgtat   780
atgatgatct ggatccacca agacttgttt tatgctcagg gtcaatttct ttttttcttt   840
tttttttttt tttctttttc tttgagactg ggtctcgctt tgttgcccag gctggagtgg   900
agtggcgtga tcttggctta ctgcagcctt tgcctcccg gctcgagcag tcctgcctca   960
gcctccggag tagctgggac cacaggttca tgccaccatg gccagccaac ttttgcatgt  1020
```

```
tttgtagaga tggggtctca cagtgttgcc caggctggtc tcaaactcct gggctcaggc    1080
gatccacctg tctcagcctc ccagagtgct gggattacaa ttgtgagcca ccacgtccag    1140
ctggaagggt caacatcttt tacattctgc aagcacatct gcattttcac cccacccttc    1200
ccctccttct cccttttat atcccatttt tatatcgatc tcttatttta caataaaact    1260
ttgctgccac ctgtgtgtct gagggtg                                         1288
```

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa at this position can be alanine, arginine, asparagine, aspartic acid, cysteine, glutamine, glutamic acid, glycine, histidine, isoleucine, leucine, lysine, methionine, phenylalanine, proline, serine, threonine, tyrosine, or valine.

<400> SEQUENCE: 51

Thr Phe Ser Asp Leu Xaa Lys Leu Leu
1               5

<210> SEQ ID NO 52
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Xaa at these positions can be any amino acid, and one to ten may be present or absent.
<220> FEATURE:
<221> NAME/KEY: MISC_FEATURE
<222> LOCATION: (16)..(16)
<223> OTHER INFORMATION: Xaa at this position can be alanine, arginine, asparagine, aspartic acid, cysteine, glutamine, glutamic acid, glycine, histidine, isoleucine, leucine, lysine, methionine, phenylalanine, proline, serine, threonine, tyrosine, or valine.

<400> SEQUENCE: 52

Xaa Xaa Xaa Xaa Xaa Xaa Xaa Xaa Xaa Xaa Thr Phe Ser Asp Leu Xaa
1               5                   10                  15

Lys Leu Leu

<210> SEQ ID NO 53
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Xaa at these positions can be any amino acid, and one to ten may be present or absent.
<220> FEATURE:
<221> NAME/KEY: MISC_FEATURE
<222> LOCATION: (16)..(16)
<223> OTHER INFORMATION: Xaa at this position can be alanine, arginine, asparagine, aspartic acid, cysteine, glutamine, glutamic acid, glycine, histidine, isoleucine, leucine, lysine, methionine, phenylalanine, proline, serine, threonine, tyrosine, or valine.
<220> FEATURE:
<221> NAME/KEY: MISC_FEATURE
<222> LOCATION: (20)..(29)

<223> OTHER INFORMATION: Xaa at these positions can be any amino acid,
      and one to ten may be present or absent.

<400> SEQUENCE: 53

Xaa Xaa Xaa Xaa Xaa Xaa Xaa Xaa Xaa Xaa Thr Phe Ser Asp Leu Xaa
1               5                   10                  15

Lys Leu Leu Xaa Xaa Xaa Xaa Xaa Xaa Xaa Xaa Xaa
            20                  25

<210> SEQ ID NO 54
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at this position can be Serine or Alanine.

<400> SEQUENCE: 54

Tyr Xaa Asp Ile Glu Met Asn Arg Leu Gly Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at this position can be Serine.

<400> SEQUENCE: 55

Tyr Thr Asp Ile Glu Met Asn Arg Xaa Gly Lys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at this position can be Serine or Leucine.

<400> SEQUENCE: 56

Tyr Thr Asp Ile Glu Met Asn Arg Leu Xaa Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at this position can be Serine or Alanine.
<220> FEATURE:
<221> NAME/KEY: MISC_FEATURE
<222> LOCATION: (9)..(9)
<223> OTHER INFORMATION: Xaa at this position can be Serine.

<400> SEQUENCE: 57

Tyr Xaa Asp Ile Glu Met Asn Arg Xaa Gly Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at this position can be Serine or Alanine.
<220> FEATURE:
<221> NAME/KEY: MISC_FEATURE
<222> LOCATION: (10)..(10)
<223> OTHER INFORMATION: Xaa at this position can be Glycine or Serine.

<400> SEQUENCE: 58

Tyr Xaa Asp Ile Glu Met Asn Arg Leu Xaa Lys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at this position can be Serine.
<220> FEATURE:
<221> NAME/KEY: MISC_FEATURE
<222> LOCATION: (10)..(10)
<223> OTHER INFORMATION: Xaa at this position can be Leucine or Serine.

<400> SEQUENCE: 59

Tyr Thr Asp Ile Glu Met Asn Arg Xaa Xaa Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at this position can be Serine or Alanine.
<220> FEATURE:
<221> NAME/KEY: MISC_FEATURE
<222> LOCATION: (9)..(9)
<223> OTHER INFORMATION: Xaa at this position can be Serine.
<220> FEATURE:
<221> NAME/KEY: MISC_FEATURE
<222> LOCATION: (10)..(10)
<223> OTHER INFORMATION: Xaa at this position can be Glycine, Leucine,
      or Serine.

<400> SEQUENCE: 60

Tyr Xaa Asp Ile Glu Met Asn Arg Xaa Xaa Lys
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

His His His His His His
1               5

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
catcaccatc accatcac                                                  18

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Asp Tyr Lys Asp Asp Asp Asp Lys
1               5

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gactacaagg acgacgacga caag                                            24

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Glu Gln Lys Leu Ile Ser Glu Glu Asp Leu
1               5                   10

<210> SEQ ID NO 66
<211> LENGTH: 30
<212> TYPE: DNA
<213> ORGANISM: Artificial Sequence
<220> FEATURE:
<223> OTHER INFORMATION: Synthetic

<400> SEQUENCE: 66
gagcagaagc tgatcagcga ggaggacctg                                      30

<210> SEQ ID NO 67
<211> LENGTH: 8
<212> TYPE: PRT
<213> ORGANISM: Artificial Sequence
<220> FEATURE:
<223> OTHER INFORMATION: Synthetic

<400> SEQUENCE: 67

Trp Ser His Pro Gln Phe Glu Lys

<210> SEQ ID NO 68
<211> LENGTH: 24
<212> TYPE: DNA
<213> ORGANISM: Artificial Sequence
<220> FEATURE:
<223> OTHER INFORMATION: Synthetic

<400> SEQUENCE: 68
tggagccacc cccagttcga gaag                                          24

<210> SEQ ID NO 69
<211> LENGTH: 16
<212> TYPE: PRT
<213> ORGANISM: Artificial Sequence
<220> FEATURE:
<223> OTHER INFORMATION: Synthetic

<400> SEQUENCE: 69

Cys Ser Pro Phe Glu Val Gln Val Ser Pro Glu Ala Gly Ala Gln Lys
1               5                   10                  15

<210> SEQ ID NO 70
<211> LENGTH: 48
<212> TYPE: DNA
<213> ORGANISM: Artificial Sequence
<220> FEATURE:
<223> OTHER INFORMATION: Synthetic

<400> SEQUENCE: 70
tgcagcccct cgaggtgca ggtgagcccc gaggccggcg cccagaag                 48

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Met Ala Ser Met Thr Gly Gly Gln Gln Met Gly
1               5                   10

<210> SEQ ID NO 72
<211> LENGTH: 33
<212> TYPE: DNA
<213> ORGANISM: Artificial Sequence
<220> FEATURE:
<223> OTHER INFORMATION: Synthetic

<400> SEQUENCE: 72
atggccagca tgaccggcgg ccagcagatg ggc                                33

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Tyr Thr Asp Ile Glu Met Asn Arg Leu Gly Lys
1               5                   10

<210> SEQ ID NO 74

-continued

```
<211> LENGTH: 33
<212> TYPE: DNA
<213> ORGANISM: Artificial Sequence
<220> FEATURE:
<223> OTHER INFORMATION: Synthetic

<400> SEQUENCE: 74
tacaccgaca tcgagatgaa ccgcctgggc aag                                33

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Tyr Pro Tyr Asp Val Pro Asp Tyr Ala
1               5

<210> SEQ ID NO 76
<211> LENGTH: 27
<212> TYPE: DNA
<213> ORGANISM: Artificial Sequence
<220> FEATURE:
<223> OTHER INFORMATION: Synthetic

<400> SEQUENCE: 76
tacccctacg acgtgcccga ctacgcc                                      27

<210> SEQ ID NO 77
<211> LENGTH: 12
<212> TYPE: PRT
<213> ORGANISM: Artificial Sequence
<220> FEATURE:
<223> OTHER INFORMATION: Synthetic

<400> SEQUENCE: 77

Glu Asp Gln Val Asp Pro Arg Leu Ile Asp Gly Lys
1               5                   10

<210> SEQ ID NO 78
<211> LENGTH: 36
<212> TYPE: DNA
<213> ORGANISM: Artificial Sequence
<220> FEATURE:
<223> OTHER INFORMATION: Synthetic

<400> SEQUENCE: 78
gaggaccagg tggacccccg cctgatcgac ggcaag                            36

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Gln Pro Glu Leu Ala Pro Glu Asp Pro Glu Asp
1               5                   10

<210> SEQ ID NO 80
<211> LENGTH: 33
<212> TYPE: DNA
<213> ORGANISM: Artificial Sequence
<220> FEATURE:
```

-continued

```
<223> OTHER INFORMATION: Synthetic

<400> SEQUENCE: 80
cagcccgagc tggcccccga ggacccccgag gac         33

<210> SEQ ID NO 81
<211> LENGTH: 5
<212> TYPE: PRT
<213> ORGANISM: Artificial Sequence
<220> FEATURE:
<223> OTHER INFORMATION: Synthetic

<400> SEQUENCE: 81

Ala Val Tyr Lys Trp
1               5

<210> SEQ ID NO 82
<211> LENGTH: 33
<212> TYPE: RNA
<213> ORGANISM: Artificial Sequence
<220> FEATURE:
<223> OTHER INFORMATION: Synthetic

<400> SEQUENCE: 82
auguacacua aacaugauga uauccgaaaa uga         33

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Met Tyr Thr Lys Asp His Asp Ile Arg Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Lys Arg Ile Asp Asp His Lys Thr Tyr Met
1               5                   10
```

METHODS FOR THE DETECTION, ANALYSIS AND ISOLATION OF NASCENT PROTEINS

This is a Continuation-In-Part of copending application(s) Ser. No. 10/049,332 filed on Jun. 21, 2002 which is a U.S. entry of application PCT/US00/23233 filed on 23 Aug. 2000, which is a continuation in part of U.S. Ser. No. 09/382,736, filed Aug. 25, 1999 now U.S. Pat. No. 6,306,628 issued on Oct. 23, 2001.

FIELD OF THE INVENTION

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents.

BACKGROUND OF THE INVENTION

Cells contain organelles, macromolecules and a wide variety of small molecules. Except for water, the vast majority of the molecules and macromolecules can be classified as lipids, carbohydrates, proteins or nucleic acids. Proteins are the most abundant cellular components and facilitate many of the key cellular processes. They include enzymes, antibodies, hormones, transport molecules and components for the cytoskeleton of the cell.

Proteins are composed of amino acids arranged into linear polymers or polypeptides. In living systems, proteins comprise over twenty common amino acids. These twenty or so amino acids are generally termed the native amino acids. At the center of every amino acid is the alpha carbon atom (Cα) which forms four bonds or attachments with other molecules (FIG. 1). One bond is a covalent linkage to an amino group ($NH_2$) and another to a carboxyl group (COOH) which both participate in polypeptide formation. A third bond is nearly always linked to a hydrogen atom and the fourth to a side chain which imparts variability to the amino acid structure. For example, alanine is formed when the side chain is a methyl group (—$CH_3$) and a valine is formed when the side chain is an isopropyl group (—$CH(CH_3)_2$). It is also possible to chemically synthesize amino acids containing different side-chains, however, the cellular protein synthesis system, with rare exceptions, utilizes native amino acids. Other amino acids and structurally similar chemical compounds are termed non-native and are generally not found in most organisms.

A central feature of all living systems is the ability to produce proteins from amino acids. Basically, protein is formed by the linkage of multiple amino acids via peptide bonds such as the pentapeptide depicted in FIG. 1B. Key molecules involved in this process are messenger RNA (mRNA) molecules, transfer RNA (tRNA) molecules and ribosomes (rRNA-protein complexes). Protein translation normally occurs in living cells and in some cases can also be performed outside the cell in systems referred to as cell-free translation systems. In either system, the basic process of protein synthesis is identical. The extra-cellular or cell-free translation system comprises an extract prepared from the intracellular contents of cells. These preparations contain those molecules which support protein translation and depending on the method of preparation, post-translational events such as glycosylation and cleavages as well. Typical cells from which cell-free extracts or in vitro extracts are made are *Escherichia coli* cells, wheat germ cells, rabbit reticulocytes, insect cells and frog oocytes.

Both in vivo and in vitro syntheses involve the reading of a sequence of bases on a mRNA molecule. The mRNA contains instructions for translation in the form of triplet codons. The genetic code specifies which amino acid is encoded by each triplet codon. For each codon which specifies an amino acid, there normally exists a cognate tRNA molecule which functions to transfer the correct amino acid onto the nascent polypeptide chain. The amino acid tyrosine (Tyr) is coded by the sequence of bases UAU and UAC, while cysteine (Cys) is coded by UGU and UGC. Variability associated with the third base of the codon is common and is called wobble.

Translation begins with the binding of the ribosome to mRNA (FIG. 2). A number of protein factors associate with the ribosome during different phases of translation including initiation factors, elongation factors and termination factors. Formation of the initiation complex is the first step of translation. Initiation factors contribute to the initiation complex along with the mRNA and initiator tRNA (fmet and met) which recognizes the base sequence UAG. Elongation proceeds with charged tRNAs binding to ribosomes, translocation and release of the amino acid cargo into the peptide chain. Elongation factors assist with the binding of tRNAs and in elongation of the polypeptide chain with the help of enzymes like peptidyl transferase. Termination factors recognize a stop signal, such as the base sequence UGA, in the message terminating polypeptide synthesis and releasing the polypeptide chain and the mRNA from the ribosome.

The structure of tRNA is often shown as a cloverleaf representation (FIG. 3A). Structural elements of a typical tRNA include an acceptor stem, a D-loop, an anticodon loop, a variable loop and a TΨC loop. Aminoacylation or charging of tRNA results in linking the carboxyl terminal of an amino acid to the 2'-(or 3'-) hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase. These tRNA synthetases have evolved to be extremely accurate in charging a tRNA with the correct amino acid to maintain the fidelity of the translation process. Except in special cases where the non-native amino acid is very similar structurally to the native amino acid, it is necessary to use means other than enzymatic aminoacylation to charge a tRNA.

Molecular biologists routinely study the expression of proteins that are coded for by genes. A key step in research is to express the products of these genes either in intact cells or in cell-free extracts. Conventionally, molecular biologists use radioactively labeled amino acid residues such as $^{35}$S-methionine as a means of detecting newly synthesized proteins or so-called nascent proteins. These nascent proteins can normally be distinguished from the many other proteins present in a cell or a cell-free extract by first separating the proteins by the standard technique of gel electrophoresis and determining if the proteins contained in the gel possess the specific radioactively labeled amino acids. This method is simple and relies on gel electrophoresis, a widely available and practiced method. It does not require prior knowledge of the expressed protein and in general does not require the protein to have any special properties. In addition, the protein can exist in a denatured or unfolded form for detection by gel electrophoresis. Furthermore, more specialized techniques such as blotting to membranes and coupled enzymatic assays are not needed. Radioactive assays also have the advantage that the structure of the nascent protein is not altered or can be restored, and thus, proteins can be isolated in a functional form for subsequent biochemical and biophysical studies.

Radioactive methods suffer from many drawbacks related to the utilization of radioactively labeled amino acids. Handling radioactive compounds in the laboratory always involves a health risk and requires special laboratory safety procedures, facilities and detailed record keeping as well as special training of laboratory personnel. Disposal of radioactive waste is also of increasing concern both because of the potential risk to the public and the lack of radioactive waste disposal sites. In addition, the use of radioactive labeling is time consuming, in some cases requiring as much as several days for detection of the radioactive label. The long time needed for such experiments is a key consideration and can seriously impede research productivity. While faster methods of radioactive detection are available, they are expensive and often require complex image enhancement devices.

The use of radioactive labeled amino acids also does not allow for a simple and rapid means to monitor the production of nascent proteins inside a cell-free extract without prior separation of nascent from preexisting proteins. However, a separation step does not allow for the optimization of cell-free activity. Variables including the concentration of ions and metabolites and the temperature and the time of protein synthesis cannot be adjusted.

Radioactive labeling methods also do not provide a means of isolating nascent proteins in a form which can be further utilized. The presence of radioactivity compromises this utility for further biochemical or biophysical procedures in the laboratory and in animals. This is clear in the case of in vitro expression when proteins cannot be readily produced in vivo because the protein has properties which are toxic to the cell. A simple and convenient method for the detection and isolation of nascent proteins in a functional form could be important in the biomedical field if such proteins possessed diagnostic or therapeutic properties. Recent research has met with some success, but these methods have had numerous drawbacks.

Radioactive labeling methods also do not provide a simple and rapid means of detecting changes in the sequence of a nascent protein which can indicate the presence of potential disease causing mutations in the DNA which code for these proteins or fragments of these proteins. Current methods of analysis at the protein level rely on the use of gel electrophoresis and radioactive detection which are slow and not amenable to high throughput analysis and automation. Such mutations can also be detected by performing DNA sequence analysis on the gene coding for a particular protein or protein fragment. However, this requires large regions of DNA to be sequenced, which is time-consuming and expensive. The development of a general method which allows mutations to be detected at the nascent protein level is potentially very important for the biomedical field.

Radioactive labeling methods also do not provide a simple and rapid means of studying the interaction of nascent proteins with other molecules including compounds which might be have importance as potential drugs. If such an approach were available, it could be extremely useful for screening large numbers of compounds against the nascent proteins coded for by specific genes, even in cases where the genes or protein has not yet been characterized. In current technology, which is based on affinity electrophoresis for screening of potential drug candidates, both in natural samples and synthetic libraries, proteins must first be labeled uniformly with a specific marker which often requires specialized techniques including isolation of the protein and the design of special ligand markers or protein engineering.

Special tRNAs, such as tRNAs which have suppressor properties, suppressor tRNAs, have been used in the process of site-directed non-native amino acid replacement (SNAAR) (C. Noren et al., Science 244:182-188, 1989). In SNAAR, a unique codon is required on the mRNA and the suppressor tRNA, acting to target a non-native amino acid to a unique site during the protein synthesis (PCT WO90/05785). However, the suppressor tRNA must not be recognizable by the aminoacyl tRNA synthetases present in the protein translation system (Bain et al., Biochemistry 30:5411-21, 1991). Furthermore, site-specific incorporation of non-native amino acids is not suitable in general for detection of nascent proteins in a cellular or cell-free protein synthesis system due to the necessity of incorporating nonsense codons into the coding regions of the template DNA or the mRNA.

Products of protein synthesis may also be detected by using antibody based assays. This method is of limited use because it requires that the protein be folded into a native form and also for antibodies to have been previously produced against the nascent protein or a known protein which is fused to the unknown nascent protein. Such procedures are time consuming and again require identification and characterization of the protein. In addition, the production of antibodies and amino acid sequencing both require a high level of protein purity.

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRNA$^{nscend}$™: Non-radioactive Translation Detection System, September 1993). These reactions are referred to as post-aminoacylation modifications. For example, the ε-amino group of the lysine linked to its cognate tRNA (tRNA$^{LYS}$), could be modified with an amine specific photoaffinity label (U. C. Krieg et al., Proc. Natl. Acad. Sci. USA 83:8604-08, 1986). These types of post-aminoacylation modifications, although useful, do not provide a general means of incorporating non-native amino acids into the nascent proteins. The disadvantage is that only those non-native amino acids that are derivatives of normal amino acids can be incorporated and only a few amino acid residues have side chains amenable to chemical modification. More often, post-aminoacylation modifications can result in the tRNA being altered and produce a non-specific modification of the α-amino group of the amino acid (e.g. in addition to the ε-amino group) linked to the tRNA. This factor can lower the efficiency of incorporation of the non-native amino acid linked to the tRNA. Non-specific, post-aminoacylation modifications of tRNA structure could also compromise its participation in protein synthesis. Incomplete chain formation could also occur when the α-amino group of the amino acid is modified.

In certain other cases, a nascent protein can be detected because of its special and unique properties such as specific enzymatic activity, absorption or fluorescence. This approach is of limited use since most proteins do not have special properties with which they can be easily detected. In many cases, however, the expressed protein may not have been previously characterized or even identified, and thus, its characteristic properties are unknown.

SUMMARY OF THE INVENTION

The present invention overcomes the problems and disadvantages associated with current strategies and designs and provides methods for the labeling, detection, quantitation, analysis and isolation of nascent proteins produced in a cell-free or cellular translation system without the use of radioactive amino acids or other radioactive labels. One embodiment of the invention is directed to methods for detecting nascent proteins translated in a translation system. A tRNA molecule is aminoacylated with a fluorescent marker to create a misaminoacylated tRNA. The misaminoacylated, or charged, tRNA can be formed by chemical, enzymatic or partly chemical and partly enzymatic techniques which place a fluorescent marker into a position on the tRNA molecule from which it can be transferred into a growing peptide chain. Markers may comprise native or non-native amino acids with fluorescent moieties, amino acid analogs or derivatives with fluorescent moieties, detectable labels, coupling agents or combinations of these components with fluorescent moieties. The misaminoacylated tRNA is introduced to the translation system such as a cell-free extract, the system is incubated and the fluorescent marker incorporated into nascent proteins.

It is not intended that the present invention be limited to the nature of the particular fluorescent moiety. A variety of fluorescent compounds are contemplated, including fluorescent compounds that have been derivatized (e.g. with NHS) to be soluble (e.g. NHS-derivatives of coumarin). Nonetheless, compared to many other fluorophores with high quantum yields, several BODIPY compounds and reagents have been empirically found to have the additional important and unusual property that they can be incorporated with high efficiency into nascent proteins for both UV and visible excited fluorescence detection. These methods utilizing fluorescent moieties may be used to detect, isolate and quantitate such nascent proteins as recombinant gene products, gene fusion products, truncated proteins caused by mutations in human genes, enzymes, cytokines, hormones, immunogenic proteins, human proteins, carbohydrate and lipid binding proteins, nucleic acid binding proteins, viral proteins, bacterial proteins, parasitic proteins and fragments and combinations thereof.

Another embodiment of the invention is directed to methods for labeling nascent proteins at their amino terminus. An initiator tRNA molecule, such as methionine initiator tRNA or formylmethionine-initiator tRNA is misaminoacylated with a fluorescent moiety (e.g. a BODIPY moiety) and introduced to a translation system. The system is incubated and marker is incorporate at the amino terminus of the nascent proteins. Nascent proteins containing marker can be detected, isolated and quantitated. Markers or parts of markers may be cleaved from the nascent proteins which substantially retain their native configuration and are functionally active.

Thus, the present invention contemplates compositions, methods and systems. In terms of compositions, the present invention specifically contemplates a tRNA molecule misaminoacylated with a BODIPY marker.

In one embodiment, the present invention contemplates a method, comprising: a) providing a tRNA molecule and a BODIPY marker; and b) aminoacylating said tRNA molecule with said BODIPY marker to create a misaminoacylated tRNA. In a particular embodiment, the method further comprises c) introducing said misaminoacylated tRNA into a translation system under conditions such that said marker is incorporated into a nascent protein. In yet another embodiment, the method further comprises d) detecting said nascent protein containing said marker. In still another embodiment, the method further comprises e) isolating said detected nascent protein.

The present invention contemplates aminoacylation of the tRNA molecule by chemical or enzymatic misaminoacylation. The present invention also contemplates embodiments wherein two or more different misaminoacylated tRNAs are introduced into the translation system. In a preferred embodiment, the nascent protein detected (by virtue of the incorporated marker) is functionally active.

It is not intended that the present invention be limited by the particular nature of the nascent protein. In one embodiment, the present invention contemplates a method for detecting nascent proteins which are conjugated to the mRNA message which codes for all or part of the nascent protein. In general, a variety of modifications of the nascent protein are envisioned including post-translational modifications, proteolysis, attachment of an oligonucleotide through a puromycin linker to the C-terminus of the protein, and interaction of the nascent protein with other components of the translation system including those which are added exogenously.

It is not intended that the present invention be limited by the particular nature of the tRNA molecule. In one embodiment, the tRNA molecule is an initiator tRNA molecule. In another embodiment, the tRNA molecule is a suppressor tRNA molecule.

The present invention also contemplates kits. In one embodiment, the kit comprises a) a first containing means (e.g. tubes, vials, etc) containing at least one component of a protein synthesis system; and b) a second containing means containing a misaminoacylated tRNA, wherein said tRNA is misaminoacylated with a BODIPY marker. Such kits may include initiator tRNA and/or suppressor tRNA. Importantly, the kit is not limited to the particular components of said protein synthesis system; a variety of components are contemplated (e.g. ribosomes).

Another embodiment of the invention is directed to methods for detecting nascent proteins translated in a translation system. A tRNA molecule is aminoacylated with one component of a binary marker system. The misaminoacylated, or charged, tRNA can be formed by chemical, enzymatic or partly chemical and partly enzymatic techniques which place a component of a binary marker system into a position on the tRNA molecule from which it can be transferred into a growing peptide chain. The component of the binary marker system may comprise native or non-native amino acids, amino acid analogs or derivatives, detectable labels, coupling agents or combinations of these components. The misaminoacylated tRNA is introduced to the translation system such as a cell-free extract, the system is incubated and the marker incorporated into nascent proteins. The second component of the binary marker system is then introduced making the first component incorporated into the nascent protein specifically detectable. These methods may be used to detect, isolate and quantitate such nascent proteins as recombinant gene products, gene fusion products, enzymes, cytokines, hormones, immunogenic proteins, human proteins, carbohydrate and lipid binding proteins, nucleic acid binding proteins, viral proteins, bacterial proteins, parasitic proteins and fragments and combinations thereof.

It is not intended that the present invention be limited to a particular translation system. In one embodiment, a cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof. It is also not intended that the present invention be limited to the particular reaction conditions employed. However, typically the cell-free translation system is incubated at a temperature of between about 25° C. to about 45° C. The present invention contemplates both continuous flow systems or dialysis systems.

Another embodiment of the invention is directed to methods for the detection of nascent proteins translated in a cellular or cell-free translation system using non-radioactive markers which have detectable electromagnetic spectral properties. As before, a non-radioactive marker is misaminoacylated to a tRNA molecule and the misaminoacylated tRNA is added to the translation system. The system is incubated to incorporate marker into the nascent proteins. Nascent proteins containing marker can be detected from the specific electromagnetic spectral property of the marker. Nascent proteins can also be isolated by taking advantage of unique properties of these markers or by conventional means such as electrophoresis, gel filtration, high-pressure or fast-pressure liquid chromatography, affinity chromatography, ion exchange chromatography, chemical extraction, magnetic bead separation, precipitation or combinations of these techniques.

Another embodiment of the invention is directed to the synthesis of nascent proteins containing markers which have reporter properties when the reporter is brought into contact with a second agent. Reporter markers are chemical moieties which have detectable electromagnetic spectral properties when incorporated into peptides and whose spectral properties can be distinguished from unincorporated markers and markers attached to tRNA molecules. As before, tRNA molecules are misaminoacylated, this time using reported markers. The misaminoacylated tRNAs are added to a translation system and incubated to incorporate marker into the peptide. Reporter markers can be used to follow the process of protein translation and to detect and quantitate nascent proteins without prior isolation from other components of the protein synthesizing system.

Another embodiment of the invention is directed to compositions comprised of nascent proteins translated in the presence of markers, isolated and, if necessary, purified in a cellular or cell-free translation system. Compositions may further comprise a pharmaceutically acceptable carrier and be utilized as an immunologically active composition such as a vaccine, or as a pharmaceutically active composition such as a drug, for use in humans and other mammals.

Another embodiment of the invention is directed to methods for detecting nascent proteins translated in a translation system by using mass spectrometry. A non-radioactive marker of known mass is misaminoacylated to a tRNA molecule and the misaminoacylated tRNA is added to the translation system. The system is incubated to incorporate the mass marker into the nascent proteins. The mass spectrum of the translation system is then measured. The presence of the nascent protein can be directly detected by identifying peaks in the mass spectrum of the protein synthesis system which correspond to the mass of the unmodified protein and a second band at a higher mass which corresponds to the mass of the nascent protein plus the modified amino acid containing the mass of the marker. When the mass marker is photocleavable, the assignment of the second band to a nascent protein containing the mass marker can be verified by removing the marker with light.

Another embodiment of the invention is directed to methods for detecting nascent proteins with mutations which are translated in a translation system. RNA or DNA coding for the protein which may contain a possible mutation is added to the translation system. The system is incubated to synthesize the nascent proteins. The nascent protein is then separated from the translation system using an affinity marker. In one embodiment the affinity marker is located at or close to the N-terminal end of the protein while in another embodiment the affinity marker can be distributed randomly throughout the sequence of the protein. The protein is then analyzed for the presence of a detectable marker located at or close to the N-terminal of the protein (N-terminal marker). A separate measurement is then made on a sequence dependent detectable marker located at or close to the C-terminal end of the protein (C-terminal marker). A comparison is then made of the level of incorporation of the N-terminal and C-terminal markers in the nascent protein. It is not intended that the present invention be limited by the nature of the N- and C-terminal markers, or the type of affinity marker utilized. A variety of markers are contemplated. In one embodiment, the affinity marker comprises an epitope recognized by an antibody or other binding molecule. In another embodiment, the affinity marker is biotin and is distributed randomly on lysine residues. In one embodiment, the N-terminal marker comprises a fluorescent marker (e.g. a BODIPY marker), while the C-terminal marker comprises a metal binding region (e.g. His tag).

The present invention contemplates a variety of methods wherein the three markers (e.g. the N- and C-terminal markers and the affinity markers) are introduced into a nascent protein. In one embodiment, the method comprises: a) providing i) a misaminoacylated initiator tRNA molecule which only recognizes the first AUG codon that serves to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker, said C-terminal marker and (in some embodiments) said affinity marker. In one embodiment, the method further comprises, after step b), isolating said nascent protein.

In another embodiment, the method comprises: a) providing i) a misaminoacylated initiator tRNA molecule which only recognizes the first AUG codon that serves to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker at the N-terminus of said protein, a C-terminal marker, and (in some embodiments) said affinity marker adjacent to said first marker. In one embodiment, the method further comprises, after step b), isolating said nascent protein.

In yet another embodiment, the method comprises: a) providing i) a misaminoacylated tRNA molecule which only recognizes the first codon designed to serve to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker, said C-terminal marker and (in some embodiments) said affinity marker. In one embodiment, the method further comprises, after step b), isolating said nascent protein.

In still another embodiment, the method comprises: a) providing i) a misaminoacylated tRNA molecule which only recognizes the first codon designed to serve to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker at the N-terminus of said protein, a C-terminal marker, and (in some embodiments) said affinity marker adjacent to said first marker. In one embodiment, the method further comprises, after step b), isolating said nascent protein.

The present invention also contemplates embodiments where only two markers are employed (e.g. a marker at the N-terminus and a marker at the C-terminus). In one embodiment, the nascent protein is non-specifically bound to a solid support (e.g. beads, microwells, strips, etc.), rather than by the specific interaction of an affinity marker. In this context, "non-specific" binding is meant to indicate that binding is not driven by the uniqueness of the sequence of the nascent protein. Instead, binding can be by charge interactions as well as hydrophilic or hydrophobic interactions. In one embodiment, the present invention contemplates that the solid support is modified (e.g. functionalized to change the charge of the surface) in order to capture the nascent protein on the surface of the solid support. In one embodiment, the solid support is poly-L-lysine coated. In yet another embodiment, the solid support is nitrocellulose (e.g. strips, nitrocellulose containing microwells, etc.) or alternatively polystyrene. Regardless of the particular nature of the solid support, the present invention contemplates that the nascent protein containing the two markers is captured under conditions that permit the ready detection of the markers.

In both the two marker and three marker embodiments described above, the present invention contemplates that one or more of the markers will be introduced into the nucleic acid template by primer extension or PCR. In one embodiment, the present invention contemplates a primer comprising (on or near the 5'-end) a promoter, a ribosome binding site ("RBS"), and a start codon (e.g. ATG), along with a region of complementarity to the template. In another embodiment, the present invention contemplates a primer comprising (on or near the 5'-end) a promoter, a ribosome binding site ("RBS"), a start codon (e.g. ATG), a region encoding an affinity marker, and a region of complementarity to the template. It is not intended that the present invention be limited by the length of the region of complementarity; preferably, the region is greater than 8 bases in length, more preferably greater than 15 bases in length, and still more preferably greater than 20 bases in length.

It is also not intended that the present invention be limited by the ribosome binding site. In one embodiment, the present invention contemplates primers comprising the Kozak sequence, a string of non-random nucleotides (consensus sequence 5'-GCCA/GCCATGG-3') (SEQ ID NO:1) which are present before the translation initiating first ATG in majority of the mRNAs which are transcribed and translated in eukaryotic cells. See M. Kozak, *Cell* 44:283-292 (1986). In another embodiment, the present invention contemplates a primer comprising the the prokaryotic mRNA ribosome binding site, which usually contains part or all of a polypurine domain UAAGGAGGU (SEQ ID NO:2) known as the Shine-Dalgarno (SD) sequence found just 5' to the translation initiation codon: mRNA 5'-UAAGGAGGU-$N_{5-10}$-AUG. (SEQ ID NO:3)

For PCR, two primers are used. In one embodiment, the present invention contemplates as the forward primer a primer comprising (on or near the 5'-end) a promoter, a ribosome binding site ("RBS"), and a start codon (e.g. ATG), along with a region of complementarity to the template. In another embodiment, the present invention contemplates as the forward primer a primer comprising (on or near the 5'-end) a promoter, a ribosome binding site ("RBS"), a start codon (e.g. ATG), a region encoding an affinity marker, and a region of complementarity to the template. The present invention contemplates that the reverse primer, in one embodiment, comprises (at or near the 5'-end) one or more stop codons and a region encoding a C-terminus marker (such as a HIS-tag).

The present invention also contemplates embodiments where the affinity marker is introduced through a misaminoacylated tRNA. In one embodiment the misaminoacylated tRNA only recognizes a codon which codes for a particular amino acid such as a codon for lysine. In this case, the affinity marker is incorporated randomly throughout the protein sequence. In another embodiment, more than one misaminoacylated tRNA is utilized. In this case, the affinity marker may be randomly distributed throughout the protein sequence at more than a single amino acid such as lysine or tyrosine. In another embodiment the misaminoacylated tRNA is a suppressor tRNA and incorporates the affinity marker at a specific position in the protein sequence.

Another embodiment of the invention is directed to methods for detecting by electrophoresis (e.g. capillary electrophoresis) the interaction of molecules with nascent proteins which are translated in a translation system. A tRNA misaminoacylated with a detectable marker is added to the protein synthesis system. The system is incubated to incorporate the detectable marker into the nascent proteins. One or more specific molecules are then combined with the nascent proteins (either before or after isolation) to form a mixture containing nascent proteins/molecule conjugates. Aliquots of the mixture are then subjected to capillary electrophoresis. Nascent proteins/molecule conjugates are identified by detecting changes in the electrophoretic mobility of nascent proteins with incorporated markers.

The present invention also contemplates using the above described methods and compositions in a method for drug/proteome screening. For example, the present invention contemplates a method of identifying a protein or portion of a protein which interacts with a ligand (such as a drug), which method comprises the steps of preparing a cDNA library from a cell that expresses said desired protein; inserting said cDNA library into an expression vector, thereby forming an expression cDNA library; transforming said expression library into bacterial cells and culturing said bacterial cells to produce individual bacterial colonies, wherein each colony contains a member of said expression library; collecting pools of a predetermined number of said individual bacterial colonies; isolating cDNA from said pools of bacterial colonies; expressing proteins (or portions of proteins) encoded by said cDNAs; and identifying a desired protein (or portion thereof) and the cDNA encoding said desired protein (or portion); wherein pools of approximately 50 individual bacterial colonies are collected (more preferably less than 50, still more preferably less than 40, still more preferably less than 30, and most preferably 25 or less, but more than 10), wherein each colony contains a member of an expression cDNA library, thereby forming cDNA pools; and wherein proteins (or portions thereof) encoded by the cDNA in said cDNA pools are expressed in an in vitro transcription/translation system in a common reaction mixture, and wherein a desired protein (or portion thereof) is identified from said reaction mixture.

Another aspect of the present invention contemplates an oligonucleotide, comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for an epitope marker, wherein said epitope marker consists of a portion of the p53 amino acid sequence or variant thereof, and iii) said 3' portion comprises a sequence complementary to a portion of the APC gene (or another gene whose truncated products are associated with disease, i.e. a "disease related gene"). In one embodiment, said oligonucleotide is less than one hundred bases in length. In another embodiment, said oligonucleotide has the sequence set forth in SEQ ID NO: 22. In one embodiment, said 5' portion is between ten and forty bases in length (preferably between eight and sixty bases in length, and more preferably between fifteen and thirty bases in length). In one embodiment, said middle portion is between ten and three thousand bases in length (preferably between eight and sixty bases in length, and more preferably between fifteen and thirty bases in length). In one embodiment, said 3' portion is between ten and three thousand bases in length (preferably between eight and sixty bases in length, and more preferably between fifteen and thirty bases in length). In one embodiment, said sequence complementary to the portion of the APC gene is greater than 15 bases in length. In another embodiment, said sequence complementary to the portion of the APC gene is greater than 20 bases in length. In one embodiment, said sequence coding for an epitope marker codes for the amino acid sequence selected from SEQ ID NOS:24-38. In another embodiment, said sequence coding for an epitope marker codes for the amino acid sequence selected from SEQ ID NOS: 39-46.

Another aspect of the present invention contemplates an oligonucleotide, comprising a 5' portion, a middle portion contiguous with said 5' portion, and a 3' portion contiguous with said middle portion, wherein i) said 5' portion comprises at least one stop codon, ii) said middle portion comprises a sequence encoding for an epitope marker, wherein said epitope marker consists of a portion of the VSV-G amino acid sequence or variant thereof, and iii) said 3' portion comprises a sequence complementary to a portion of the APC gene (or another gene whose truncated products are associated with disease). In one embodiment, said oligonucleotide is less than one hundred bases in length. In another embodiment, said oligonucleotide has the sequence set forth in SEQ ID NO: 23. In one embodiment, said 5' portion is between ten and forty bases in length (preferably between eight and sixty bases in length, and more preferably between fifteen and thirty bases in length). In one embodiment, said middle portion is between ten and forty bases in length (preferably between eight and sixty bases in length, and more preferably between fifteen and thirty bases in length). In one embodiment, said 3' portion is between ten and forty bases in length (preferably between eight and sixty bases in length, and more preferably between fifteen and thirty bases in length). In one embodiment, said sequence complementary to the portion of the APC gene is greater than 15 bases in length. In another embodiment, said sequence complementary to the portion of the APC gene is greater than 20 bases in length. In one embodiment, said sequence coding for an epitope marker codes for the amino acid sequence selected from SEQ ID NOS:24-38. In another embodiment, said sequence coding for an epitope marker codes for the amino acid sequence selected from SEQ ID NOS: 39-46.

Another aspect of the present invention contemplates a kit, comprising: a) a first oligonucleotide comprising a 5' portion, a middle portion contiguous with said 5' portion, and a 3' portion contiguous with said middle portion, wherein i) said 5' portion comprises a sequence corresponding to a promoter, ii) said middle portion comprises a sequence corresponding to a ribosome binding site, a start codon, and a sequence coding for a first epitope marker, and iii) said 3' portion comprises a sequence complementary to a first portion of the APC gene (or other disease related gene); b) a second oligonucleotide comprising a 5' portion, a middle portion contiguous with said 5' portion, and a 3' portion contiguous with said middle portion, wherein i) said 5' portion comprises at least one stop codon, ii) said middle portion comprises a sequence encoding for a second epitope marker, and iii) said 3' portion comprises a sequence complementary to a second portion of the APC gene (or other disease related gene), wherein either said first epitope marker or said second epitope marker consist of a portion of the p53 amino acid sequence or variant thereof. In one embodiment, said sequence coding for said first epitope marker codes for the amino acid sequence selected from SEQ ID NOS: 39-46. In one embodiment, said sequence coding for said second epitope marker codes for the amino acid sequence selected from SEQ ID NOS: 24-38. In one embodiment, said first oligonucleotide has the sequence set forth in SEQ ID NO: 22. In one embodiment, said second oligonucleotide has the sequence set forth in SEQ ID NO: 23. In one embodiment, said kit further comprises a polymerase. In another embodiment, said kit further comprises a misaminoacylated tRNA. In another embodiment, said kit further comprises antibodies directed against said epitopes.

Another aspect of the present invention contemplates a method of introducing coding sequence for one or more epitope markers into nucleic acid, comprising: a) providing: a first oligonucleotide primer comprising a 5' portion, a middle portion contiguous with said 5' portion, and a 3' portion contiguous with said middle portion, wherein 1) said 5' portion comprises a sequence corresponding to a promoter, 2) said middle portion comprises a sequence corresponding to a ribosome binding site, a start codon, and a sequence coding for a first epitope marker, and 3) said 3' portion comprises a sequence complementary to a first portion of the APC gene (or other disease related gene); ii) a second oligonucleotide primer comprising a 5' portion, a middle portion contiguous with said 5' portion, and a 3' portion contiguous with said middle portion, wherein 1) said 5' portion comprises at least one stop codon, 2) said middle portion comprises a sequence encoding for a second epitope marker, and 3) said 3' portion comprises a sequence complementary to a second portion of the APC gene (or other disease related gene), wherein either said first epitope marker or said second epitope marker consist of a portion of the p53 amino acid sequence or variant thereof; iii) a polymerase; and iv) template nucleic acid comprising a region of the APC gene (or other disease related gene), said region comprising at least said first portion of the APC gene; and b) mixing said template nucleic acid with said first primer, second primer and said polymerase under conditions such that amplified template is produced, said amplified template comprising said sequence coding for an epitope marker. In one embodiment, said first and said second oligonucleotide are each less than one hundred bases in length. In one embodiment, said sequence complementary to a portion of the APC gene of said first and said second oligonucleotide is 10 bases or greater, but preferably greater than 15 bases in length. In another embodiment, said sequence complementary to a portion of the APC gene of said first and said second oligonucleotide is greater than 20 bases in length. In one embodiment, said first oligonucleotide has the sequence set forth in SEQ ID NO: 22 and said second oligonucleotide has the sequence set forth in SEQ ID NO: 23. Not intending to limit the present invention, it is understood by one skilled in the art, that "a region of the APC gene" is larger than "a portion of the APC gene" (just as "regions" of any other gene associated with disease are larger than "portions" of the same). For example, a region of the APC gene may comprise, but is not limited to, the region coding for amino acids 1098-1696 (i.e., segment 3).

Another aspect of the present invention contemplates a method, comprising: a) providing: i) an amplified template comprising a first oligonucleotide having the sequence set forth in SEQ ID NO: 22 and a second oligonucleotide having the sequence set forth in SEQ ID NO: 23; ii) a misaminoacylated tRNA comprising an affinity marker; and iii) a translation system; and b) introducing said amplified template and said misaminoacylated tRNA into said translation system under conditions such that said affinity marker is incorporated into a nascent protein in a reaction mixture. In one embodiment, said translation system comprises a rabbit reticulocyte lysate. In one embodiment, said affinity marker comprises a biotinyl moiety. In one embodiment, said misaminoacylated tRNA comprises biotin-lysyl-tRNA. In one embodiment, said method comprises after step b), step c) adding a first antibody and a second antibody to said reaction mixture, or portion thereof, so as to create a diluted reaction mixture. In one embodiment, said first antibody comprises an antibody reactive with a VSV-derived epitope, said first antibody conjugated to a first enzyme. In one embodiment, said second antibody comprises an antibody reactive with a p53-derived epitope, said second antibody conjugated to a second enzyme. In one embodiment, said method further comprises step d) immobilizing said nascent protein by contacting said nascent protein with a ligand which binds biotin, wherein said ligand is attached to a solid support. In one embodiment, said ligand is selected from the group consisting of avidin and strepavidin, and variants, mutants and derivatives thereof. In one embodiment, said misaminoacylated tRNA is a plurality of misaminoacylated tRNAs, wherein said plurality of misaminoacylated tRNAs is capable of incorporating said affinity marker at a plurality of amino acid residues. In one embodiment, said affinity marker comprises a fluorescent label.

Other embodiments and advantages of the invention are set forth, in part, in the description which follows and, in part, will be obvious from this description, or may be learned from the practice of the invention.

Definitions

To facilitate understanding of the invention, a number of terms are defined below.

The term "portion" may refer to a relatively small segment of a protein or an oligonucleotide. Specifically, a portion of a protein refers to a range of between 5-100 contiguous amino acids while a portion of a nucleic acid refers to a range of between 15-300 contiguous nucleic acids.

The term "region" may refer to a relatively large segment of a protein or an oligonucleotide. Specifically, a region of a protein refers to a range of between 101-1700 contiguous amino acids which a region of an oligonucleotides refers to a range of between 303-5100 contiguous nucleic acids.

The term "contiguous" refers to a continuous, finite, sequence of units wherein each unit has physical contact with at least one other unit in the sequence. For example, a contiguous sequence of amino acids are physically connected by peptide bonds and a contiguous sequence of nucleic acids are physically connect by phosphodiester bonds.

The term "sequence corresponding to a promoter" refers to a non-coding nucleic acid region that is responsible for the regulation of transcription (an open reading frame) of the DNA coding for the protein of interest.

The term "sequence corresponding to a ribosome binding site" refers to a coding nucleic acid region that, when transcribed, allows the binding a mRNA in such a manner that translation occurs.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may have 5' and 3' ends.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refers to the annealing of a complementary sequence to the target nucleic acid. The ability of two polymers of nucleic acid containing complementary sequences to find each other and anneal through base pairing interaction is a well-recognized phenomenon. Marmur and Lane, Proc. Natl. Acad. Sci. USA 46:453 (1960) and Doty et al., Proc. Natl. Acad. Sci. USA 46:461 (1960). The terms "annealed" and "hybridized" are used interchangeably throughout, and are intended to encompass any specific and reproducible interaction between an oligonucleotide and a target nucleic acid, including binding of regions having only partial complementarity.

The complement of a nucleic acid sequence as used herein refers to an oligonucleotide which, when aligned with the nucleic acid sequence such that the 5' end of one sequence is paired with the 3' end of the other, is in "antiparallel association." The term "complement" or "complementary" does not imply or limit pairing to the sense strand or the antisense strand of a gene; the term is intended to be broad enough to encompass either situation. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

As used herein, the term "poly-histidine tract" or (HIS-tag) refers to the presence of two to ten histidine residues at either the amino- or carboxy-terminus of a nascent protein A poly-histidine tract of six to ten residues is preferred. The poly-histidine tract is also defined functionally as being a number of consecutive histidine residues added to the protein of interest which allows the affinity purification of the resulting protein on a nickel-chelate column, or the identification of a protein terminus through the interaction with another molecule (e.g. an antibody reactive with the HIS-tag).

As used herein, the term "marker" is used broadly to encompass a variety of types of molecules (e.g. introduced into proteins using methods and compositions of the present invention) which are detectable through spectral properties (e.g. fluorescent markers) or through functional properties (e.g. affinity markers). An epitope marker or "epitope tag" is a marker of the latter type, functioning as a binding site for antibody or other types of binding molecules (e.g. receptors, lectins and other ligands). Of course, if the epitope marker is used to immobilize the nascent protein, the epitope marker is also an affinity marker.

As used herein, the term "total tRNA" is used to describe a mixture comprising misaminoacylated marker tRNA molecules representing each amino acid. This mixture has a distinct advantage over the limited ability of misaminoacylated lys-tRNA to reliably incorporate in large variety of proteins. It is contemplated that "total tRNA" will provide a homogenous insertion of affinity markers in all nascent proteins.

As used herein, the term "VSV-derived epitope" refers to any amino acid sequence comprising the wild type sequence (i.e., SEQ ID NO:39) or mutations thereof, wherein said mutations include, but are not limited to, site-specific mutations, deletions, additions, substitutions and truncations.

As used herein, the term "p53-derived epitope" refers to any amino acid sequence comprising the wild type sequence (i.e., SEQ ID NO:24) or mutations thereof, wherein said mutations include, but are not limited to, site-specific mutations, frameshift mutations, deletions, additions, substitutions and truncations.

As used herein, the term "VSV variant" refers to any amino acid sequence that differs from the wild type sequence (i.e., SEQ ID NO: 39) in at least one, but not more than three residues.

As used herein, the term "p53 variant" refers to any amino acid sequence that differs from the wild type sequence (i.e., SEQ ID NO: 24) in at least one, but not more than three residues.

DESCRIPTIONS OF THE DRAWINGS

FIG. 1 shows the structure of (A) an amino acid and (B) a peptide (SEQ NO:81).

FIG. 2 (SEQ ID NOS:82 to 84) provides a description of the molecular steps that occur during protein synthesis in a cellular or cell-free system.

FIG. 6(A) shows chemical compounds containing the 2-nitrobenzyl moiety, and FIG. 6(B) shows cleavage of substrate from a nitrobenzyl linkage.

Figure 7:
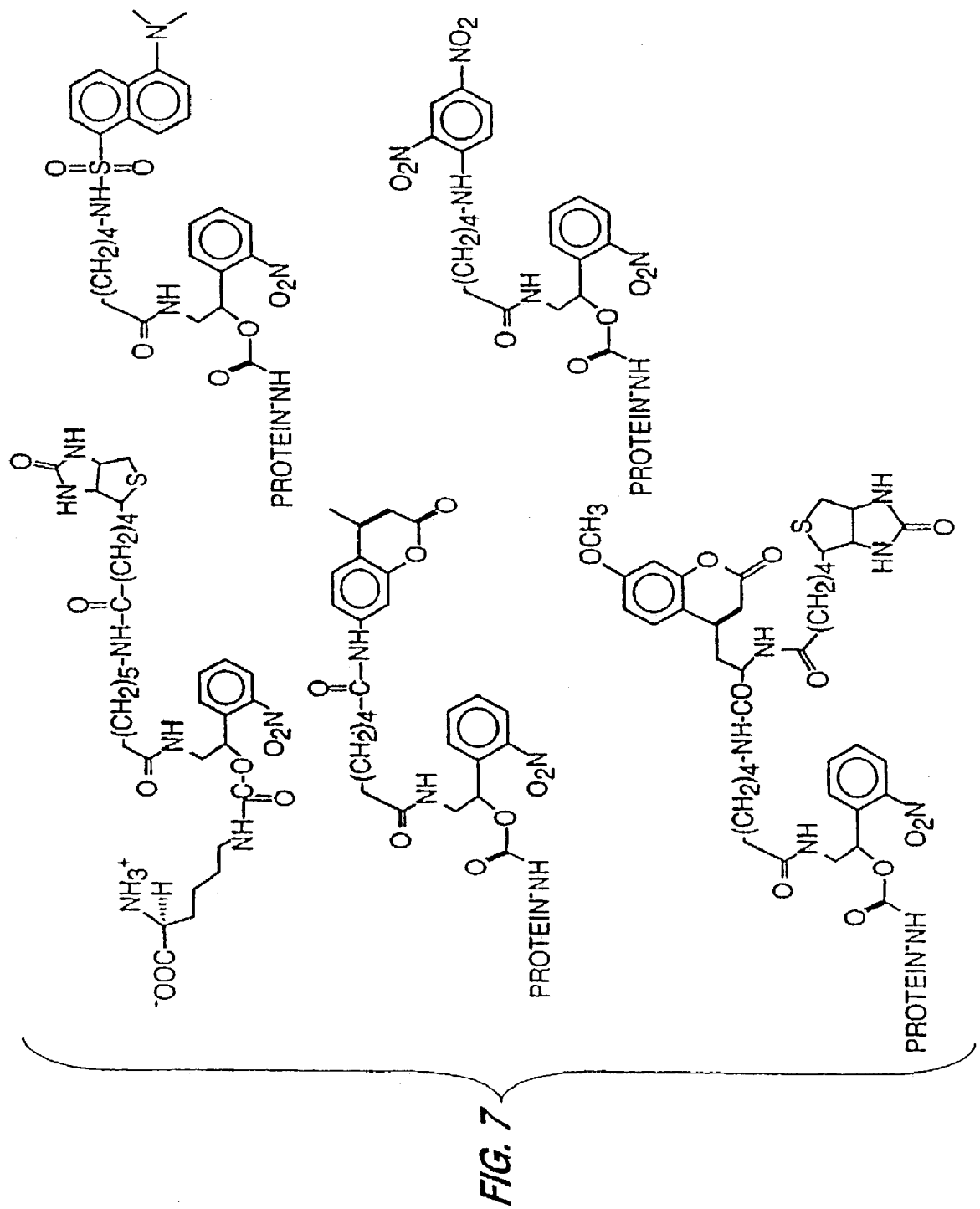

FIG. 7 provides examples of photocleavable markers.

Figure 8A:
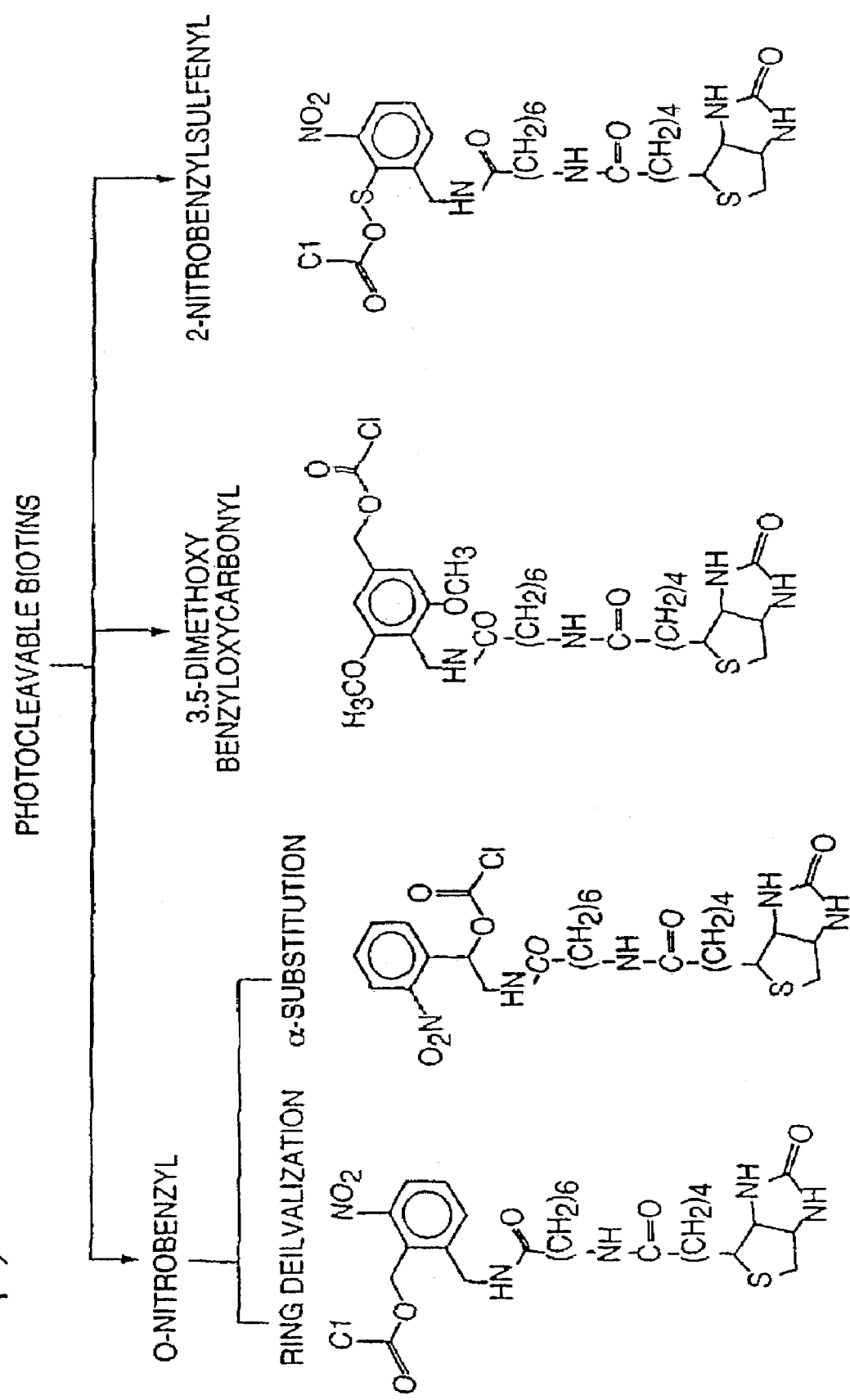
Figure 8B:
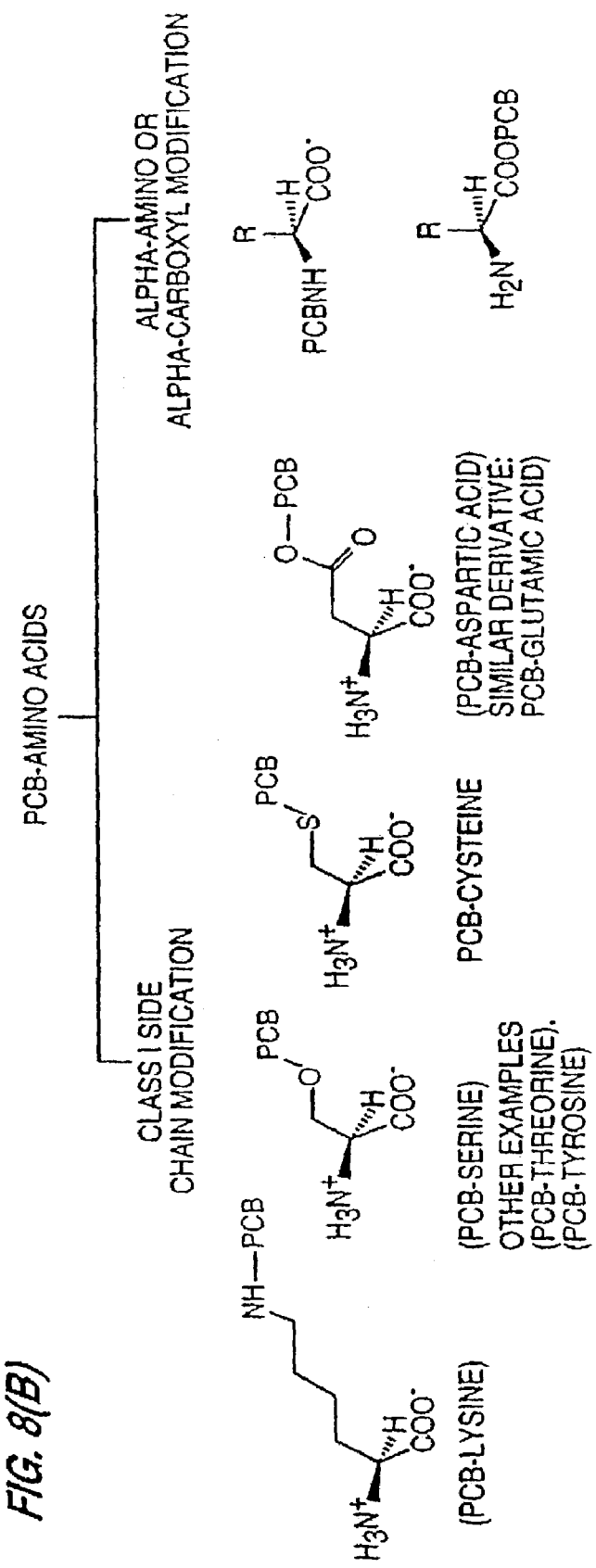

FIG. 8(A) shows chemical variations of PCB, and FIG. 8(B) depicts possible amino acid linkages.

Figure 9:
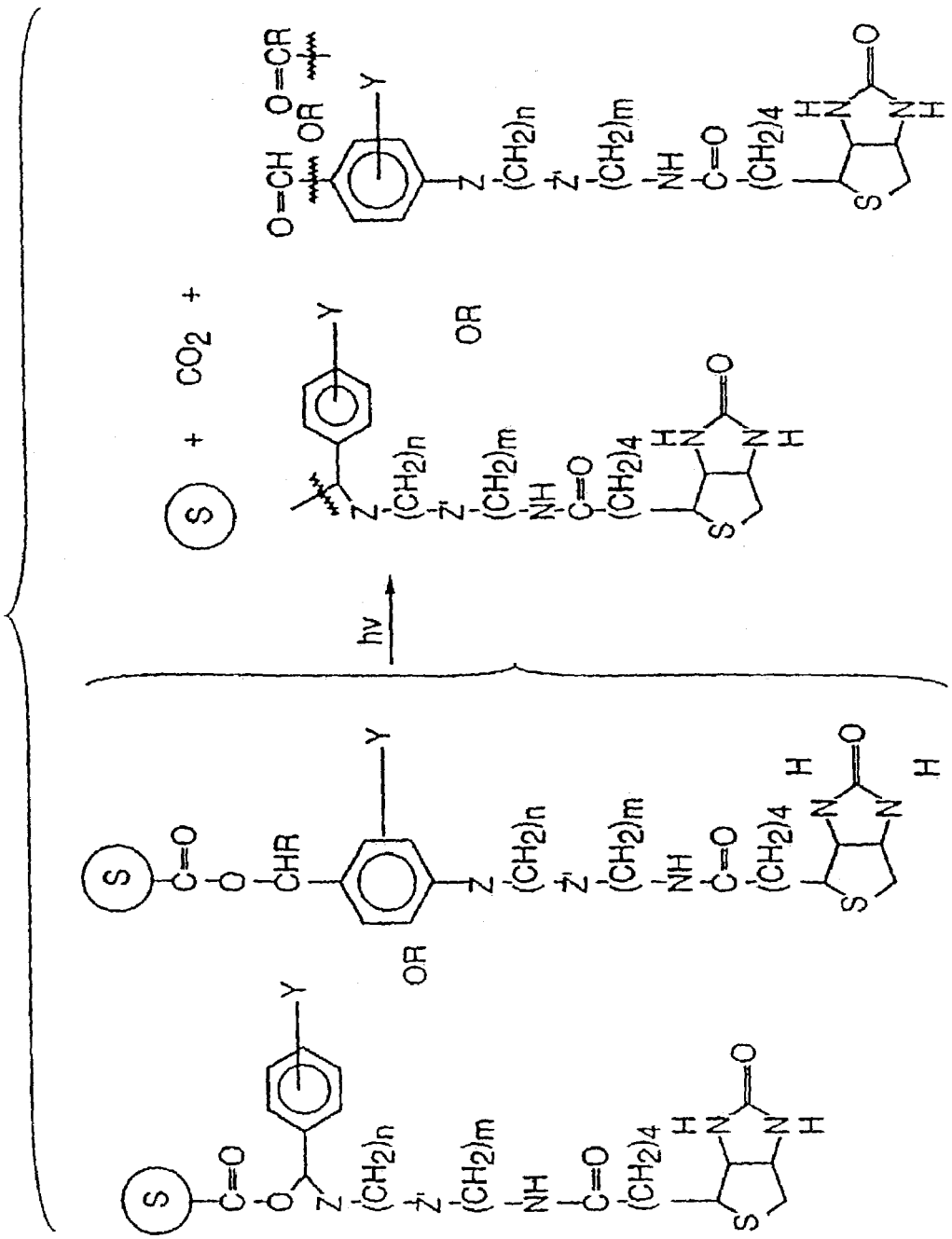

FIG. 9 shows the photolysis of PCB.

Figure 10:
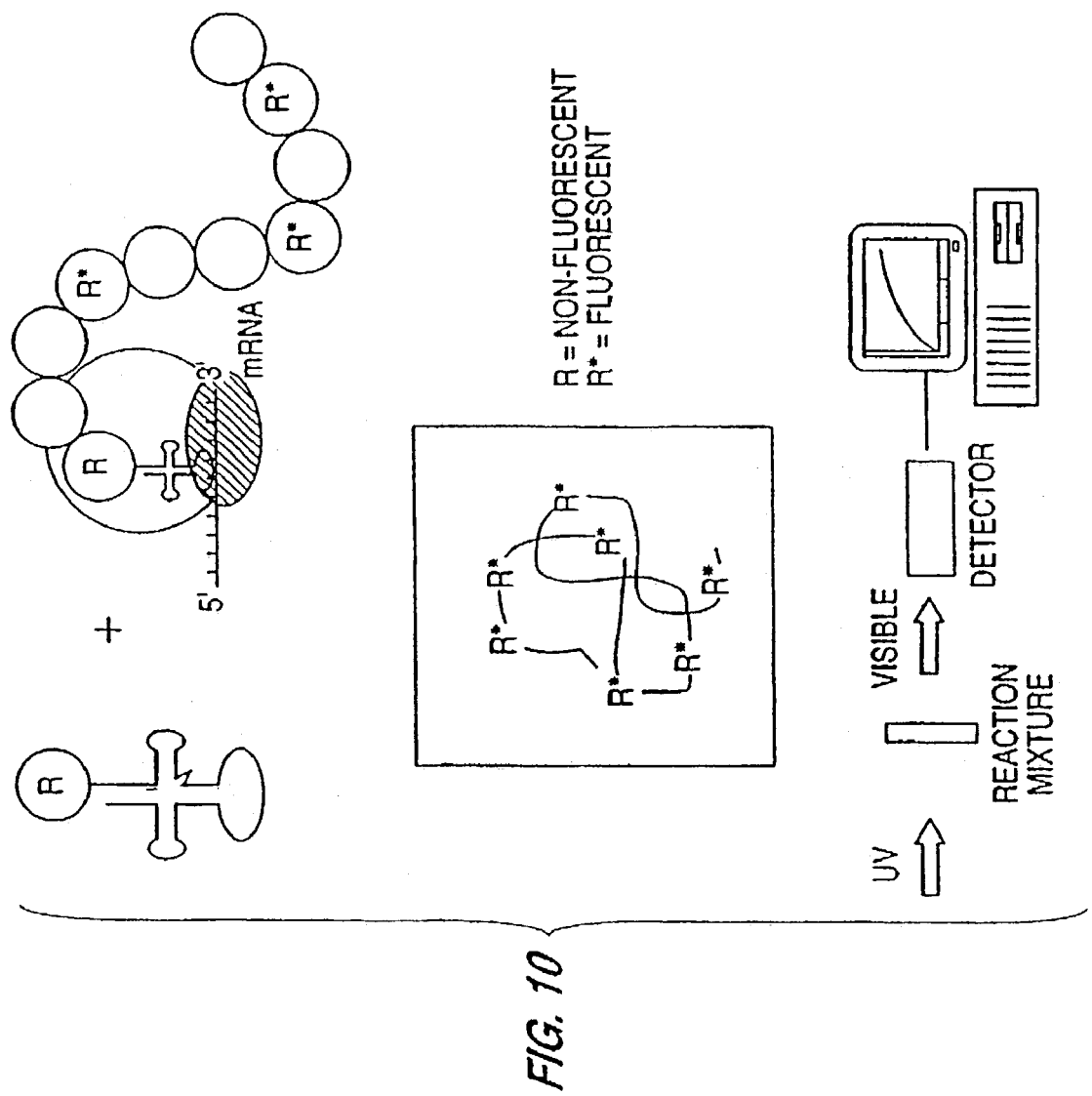

FIG. 10 is a schematic representation of the method for monitoring the production of nascent proteins in a cell-free protein expression systems without separating the proteins.

Figure 11:
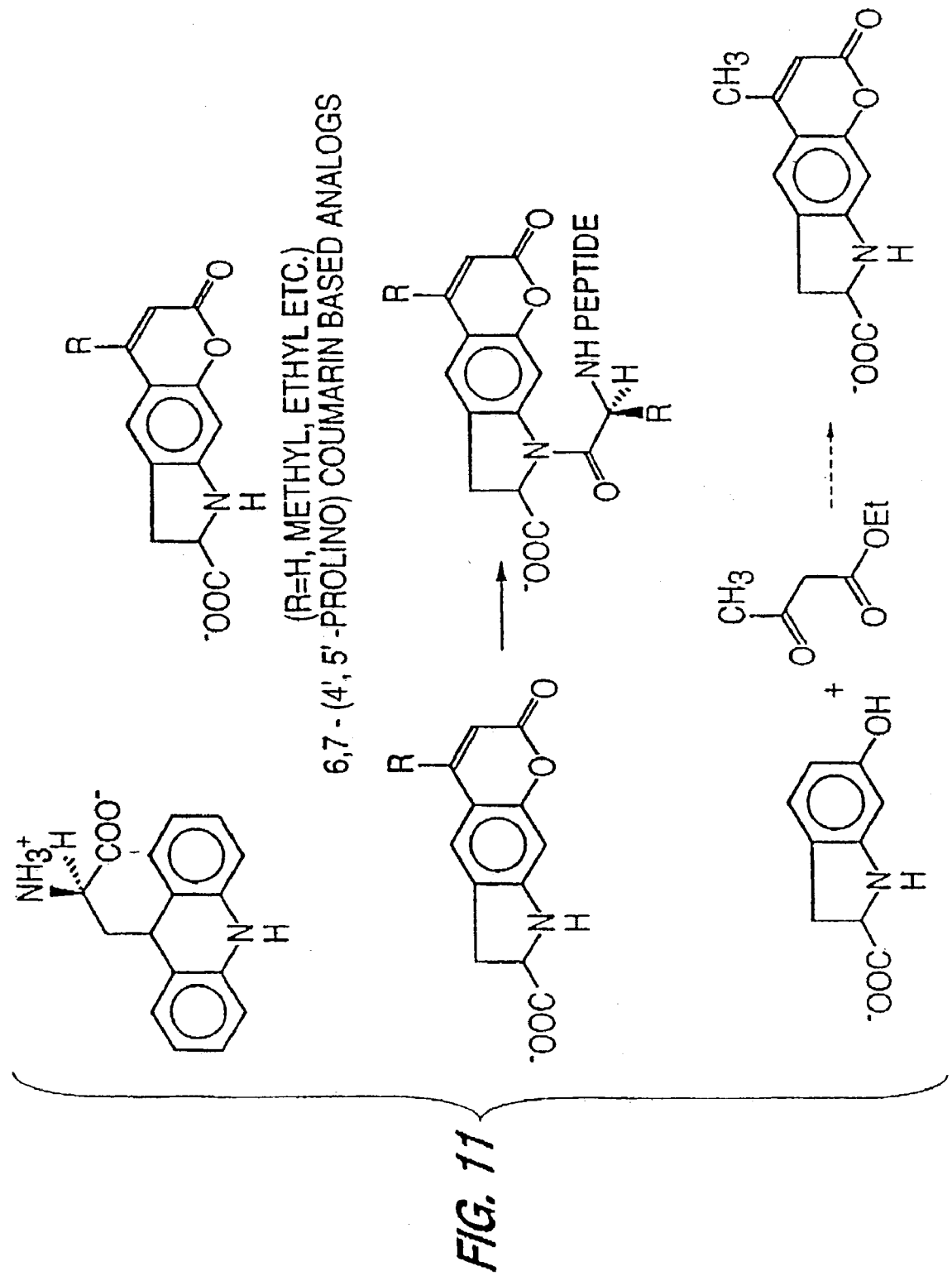

FIG. 11 provides examples of non-native amino acids with reporter properties, illustrates participation of a reporter in protein synthesis, and illustrates synthesis of a reporter.

Figure 12:
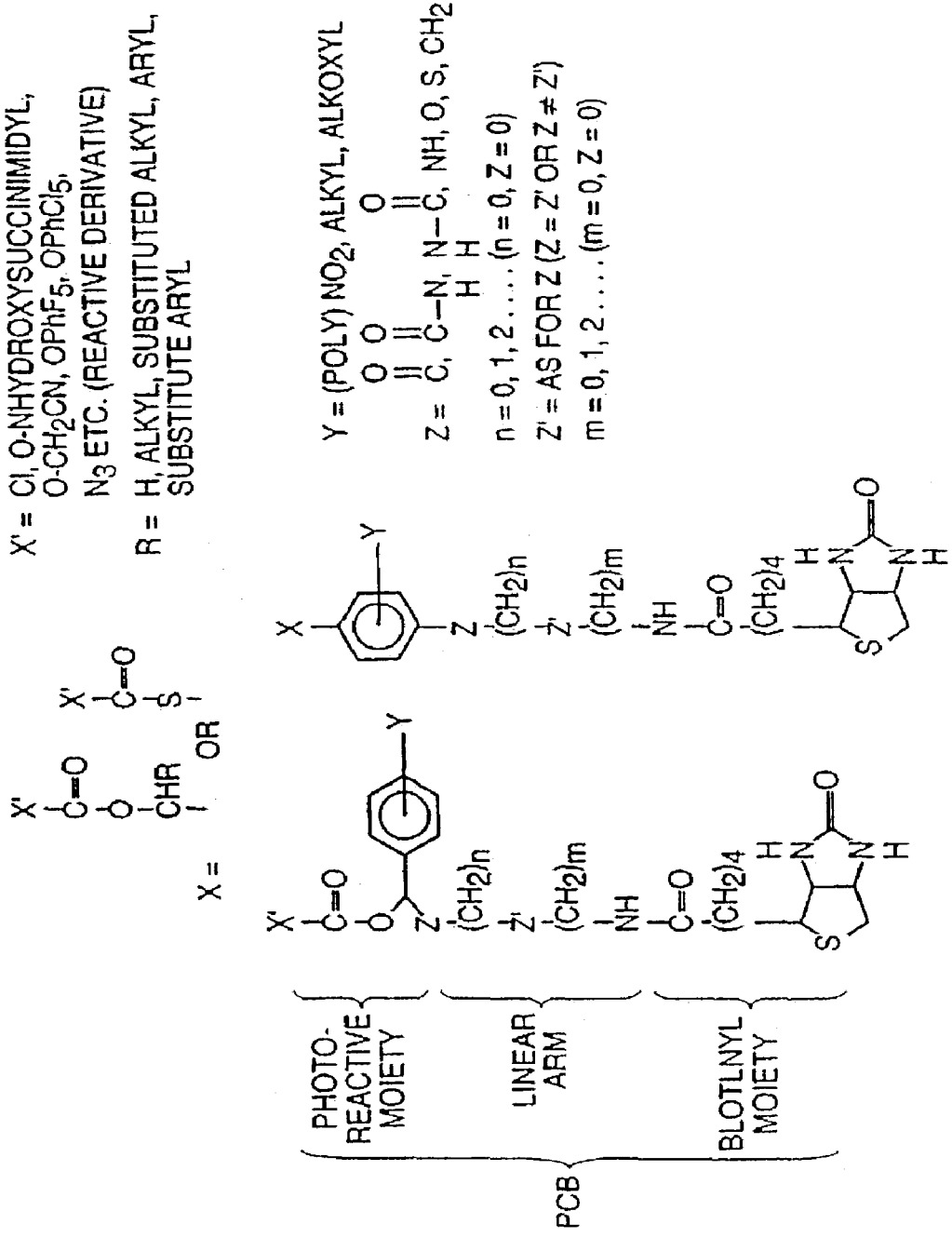

FIG. 12 shows structural components of photocleavable biotin.

Figure 13:
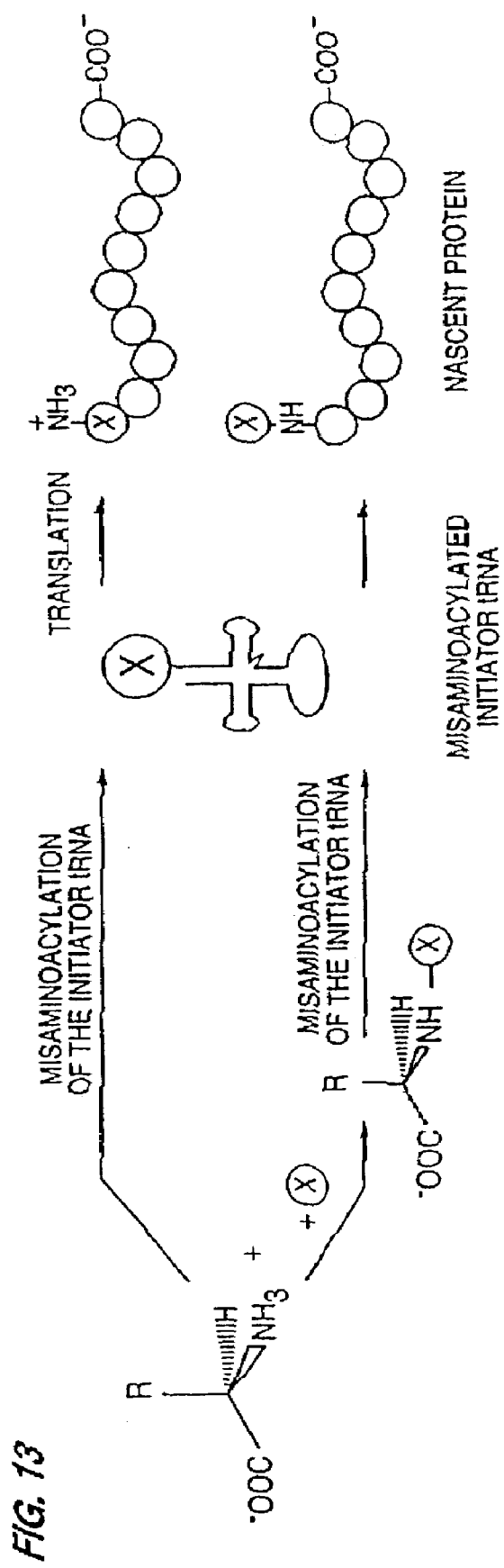

FIG. 13 is a schematic representation of the method for introduction of markers at the N-termini of nascent proteins.

Figure 14:
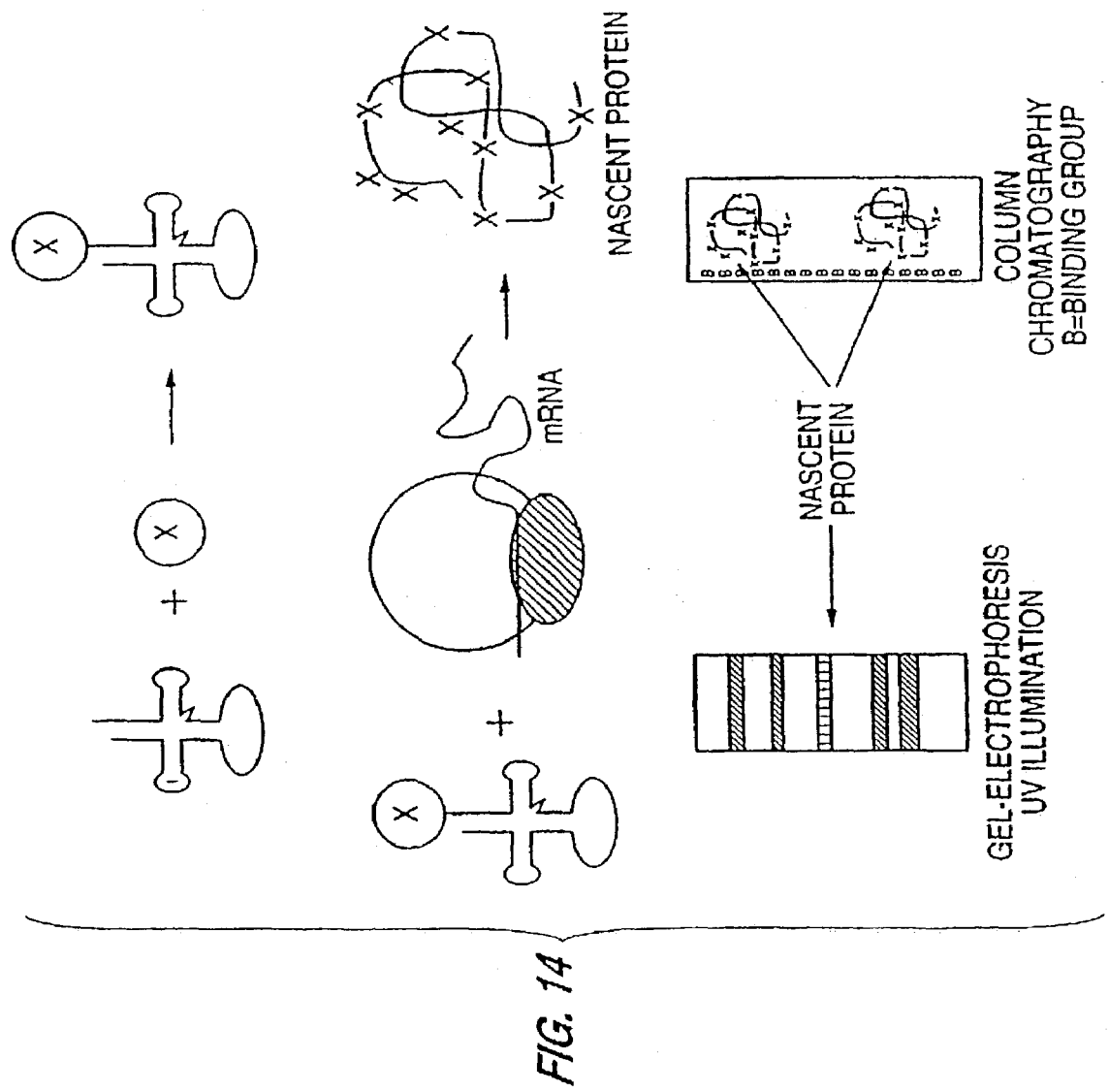

FIG. 14 provides a description of the method of detection and isolation of marker in nascent proteins.

Figure 15:
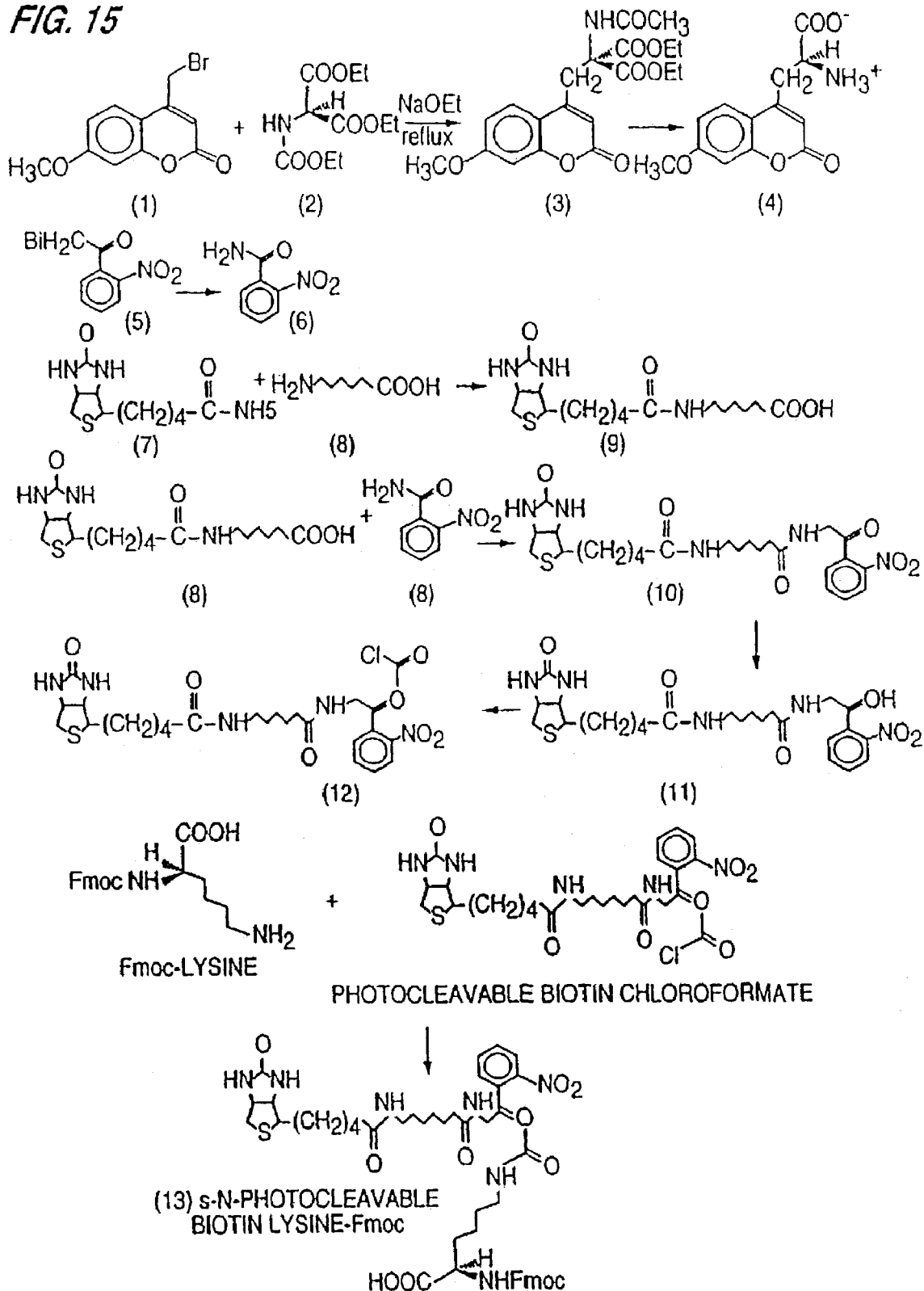

FIG. 15 shows the steps in one embodiment for the synthesis of PCB-lysine.

Figure 16:
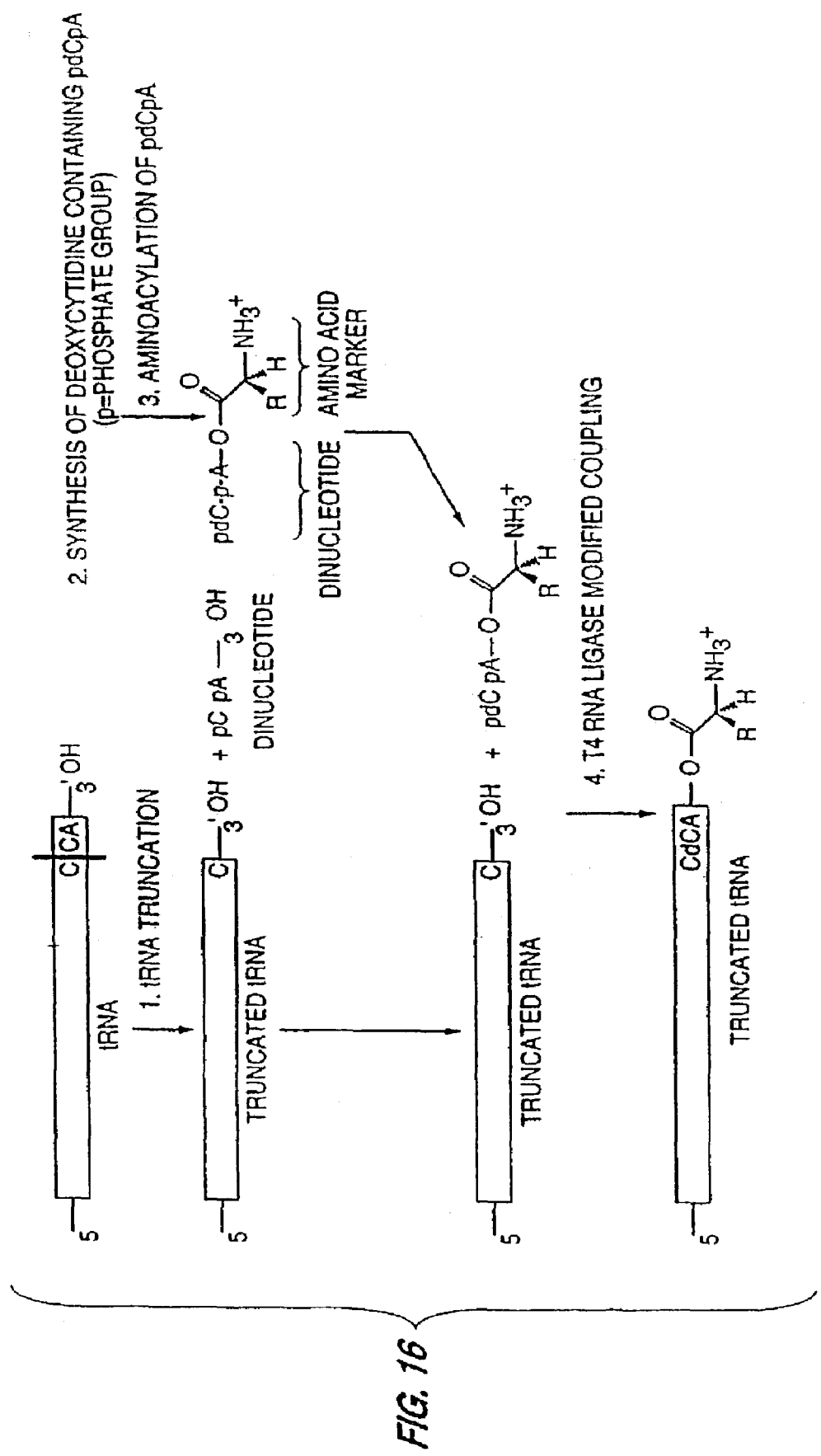

FIG. 16 provides an experimental strategy for the misaminoacylation of tRNA.

Figure 17:
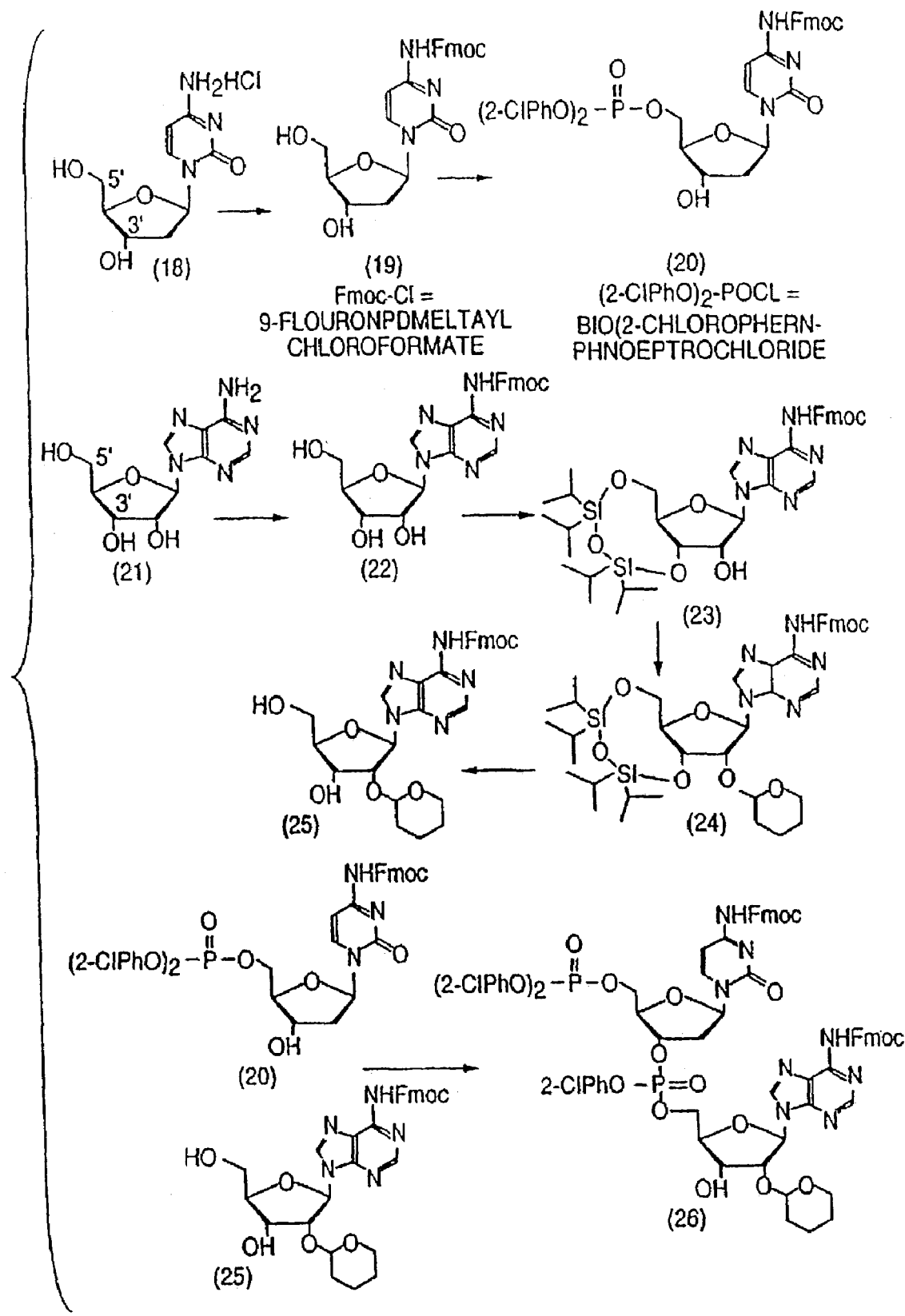

FIG. 17 illustrates dinucleotide synthesis including (i) deoxycytidine protection, (ii) adenosine protection, and (iii) dinucleotide synthesis.

Figure 18:
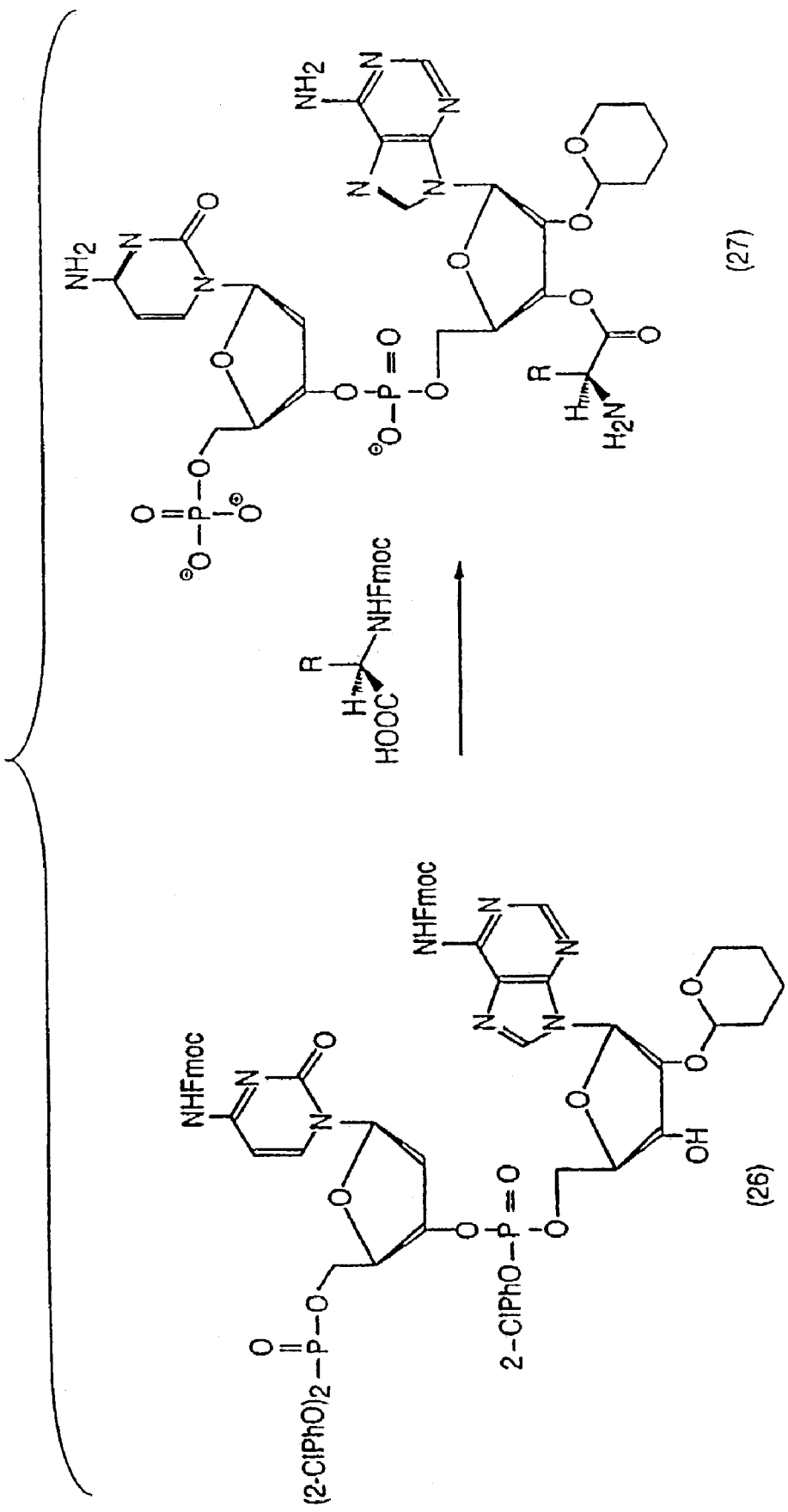

FIG. 18 depicts aminoacylation of a dinucleotide using marker amino acids.

Figure 19:
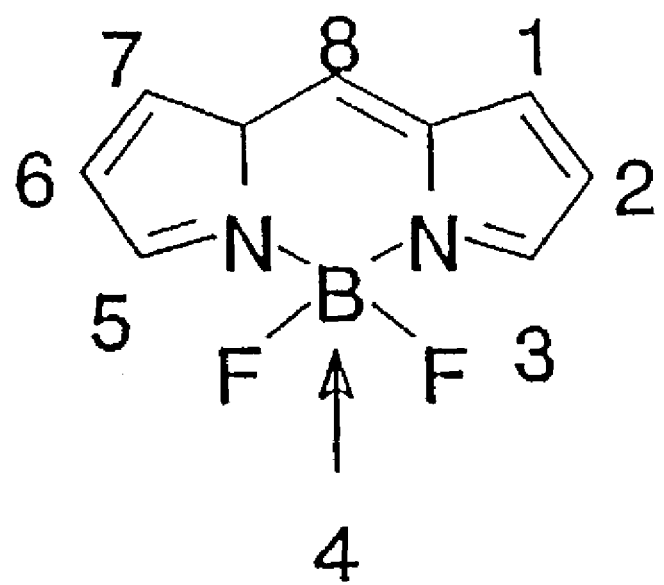

FIG. 19 shows the structure of dipyrromethenboron difluoride(4,4-difluoro-4-bora-3a,4a-diaza-s-indacene)dyes.

Figure 20:
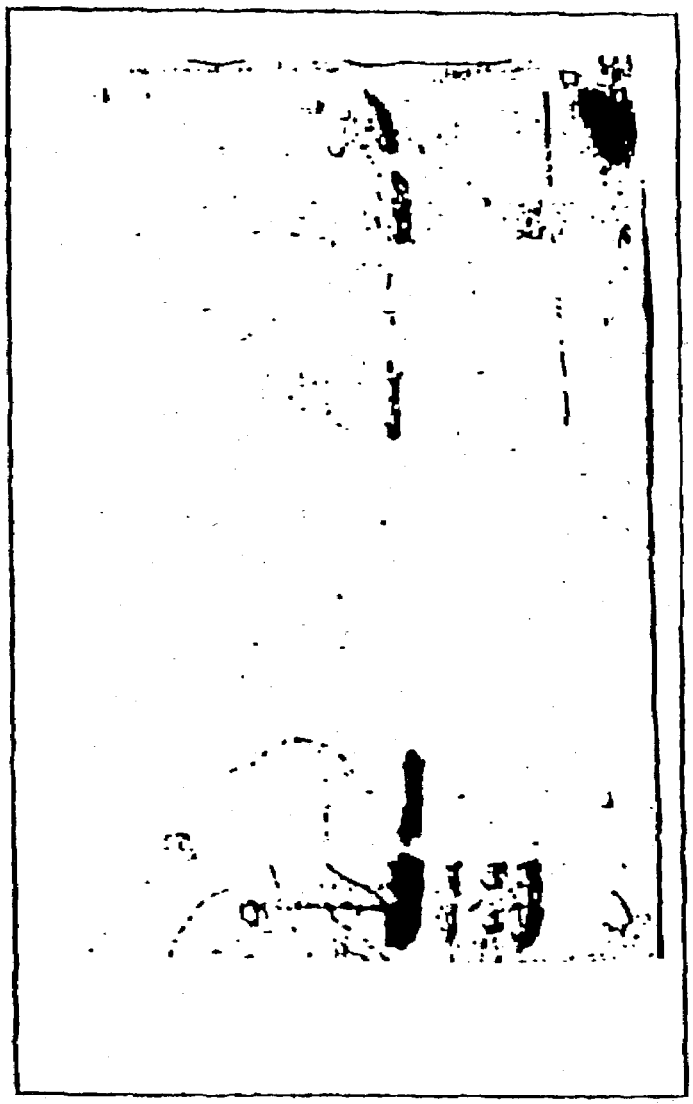

FIG. 20 is a photograph of a gel showing the incorporation of various fluorescent molecules into hemolysin during translation.

Figure 21A:
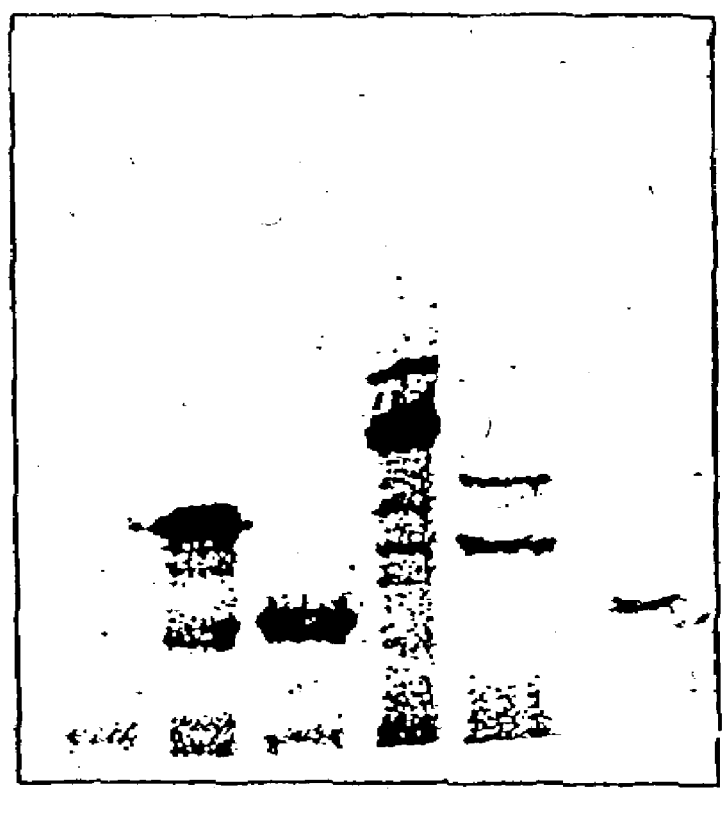
Figure 21B:
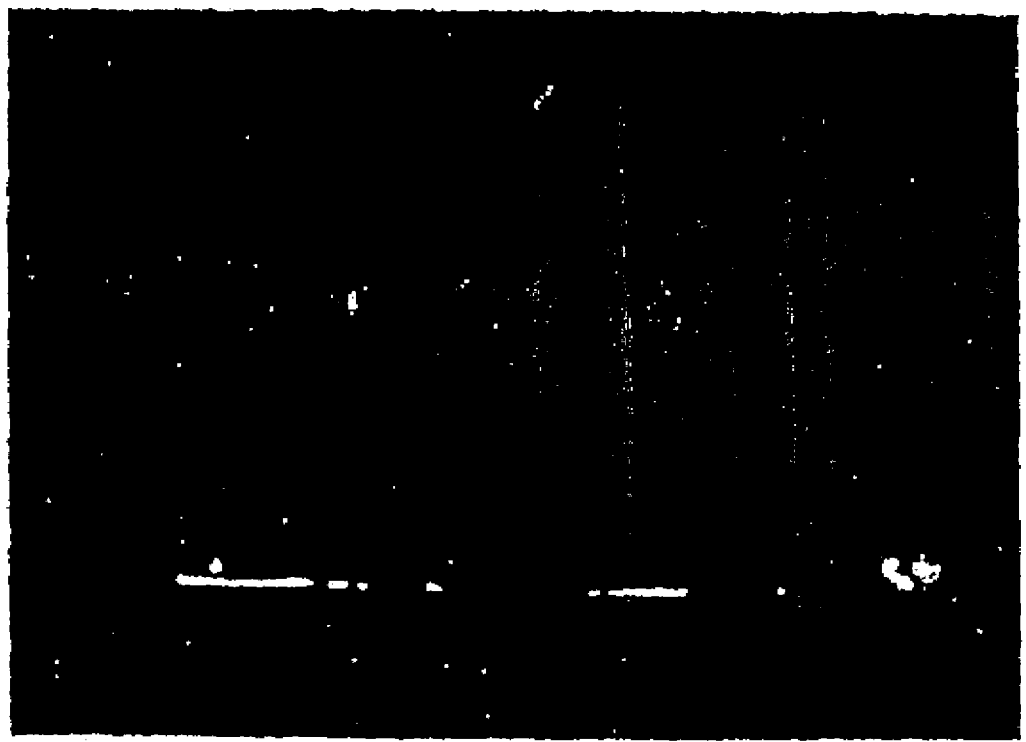

FIG. 21 shows the incorporation of BODIPY-FL into various proteins. FIG. 21A shows the results visualized using laser based Molecular Dynamics FluorImager 595, while FIG. 21B shows the results visualized using a UV-transilluminator.

Figure 22A:
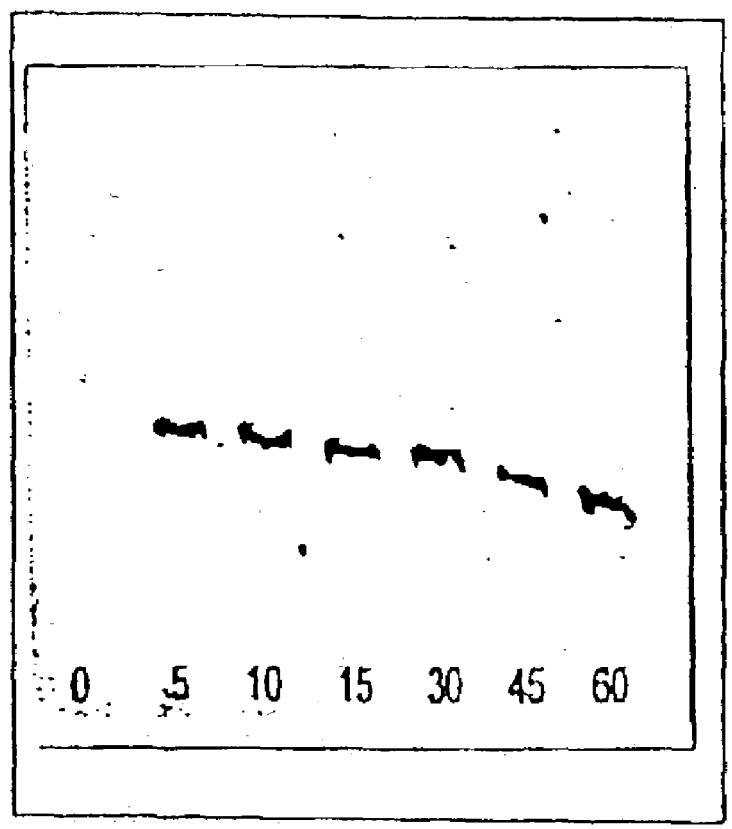
Figure 22B:
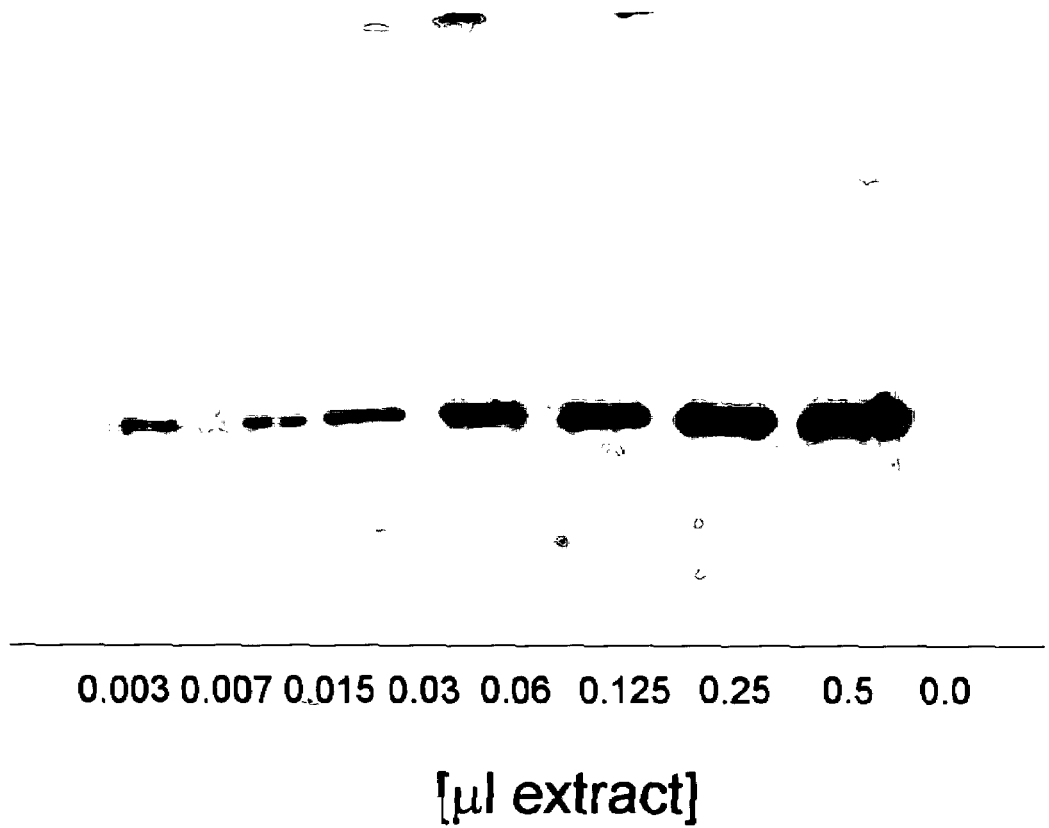

FIG. 22A shows a time course of fluorescence labeling. FIG. 22B shows the SDS-PAGE results of various aliquots of the translation mixture, demonstrating the sensitivity of the system.

Figure 23A:
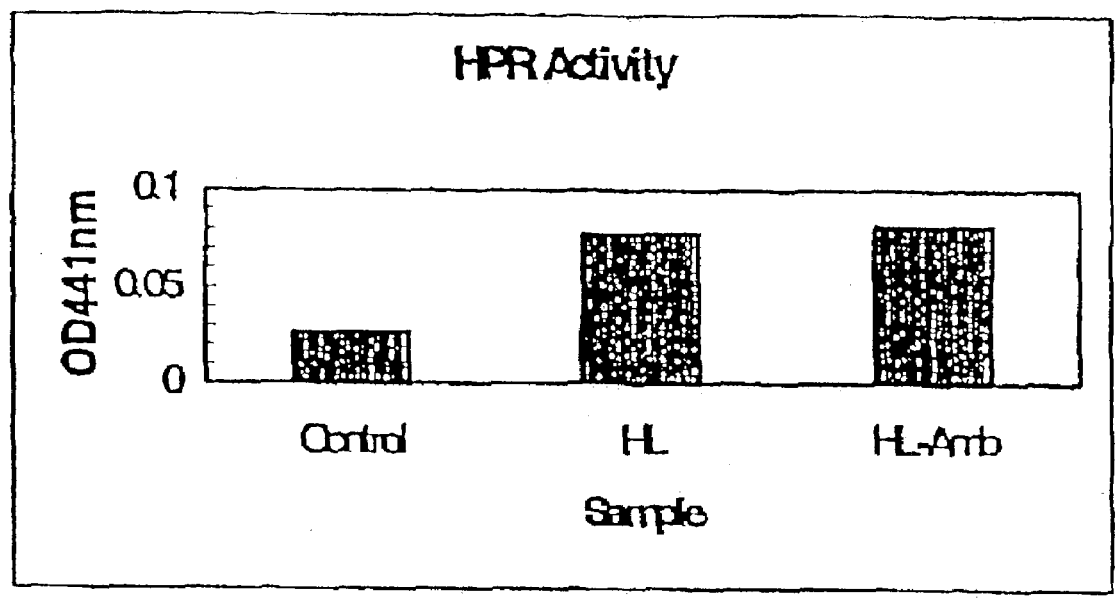
Figure 23B:
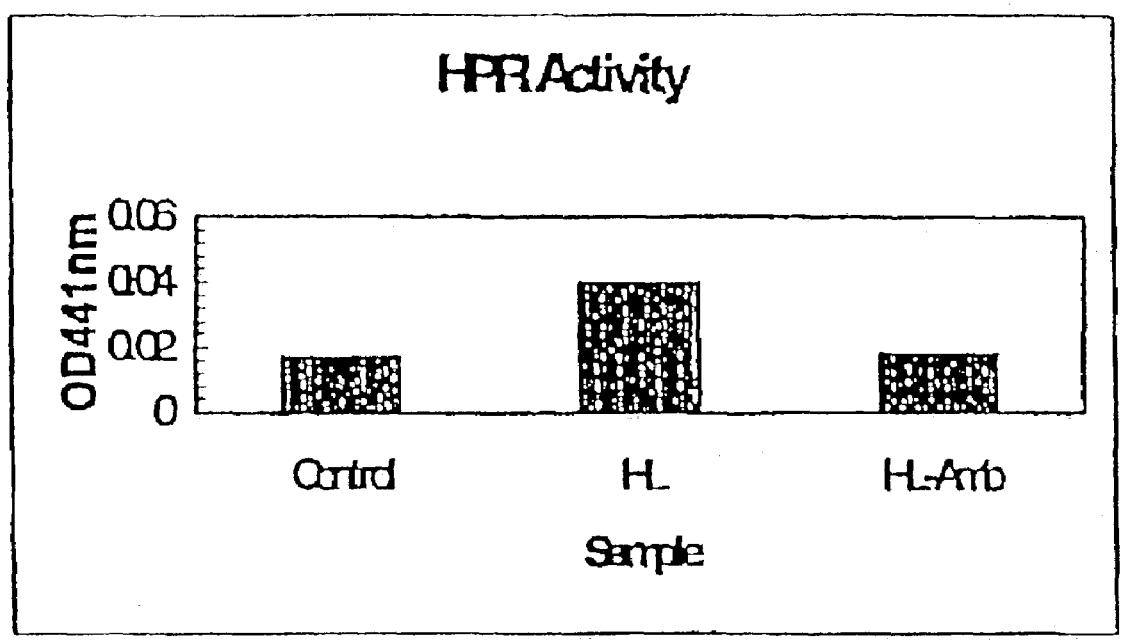

FIG. 23A is a bar graph showing gel-free quantitation of an N-terminal marker introduced into a nascent protein in accordance with the method of the present invention. FIG. 23B is a bar graph showing gel-free quantitation of an C-terminal marker of a nascent protein quantitated in accordance with the method of the present invention.

Figure 24:
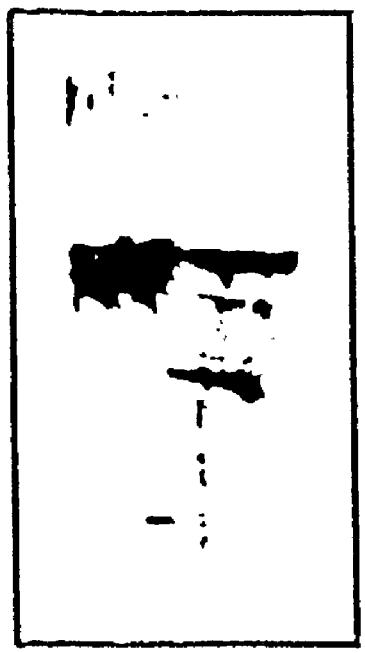

FIG. 24 shows gel results for protease treated and untreated protein.

Figure 25:

FIG. 25 shows gel results for protein treated with RBCs and untreated protein.

Figure 26A:
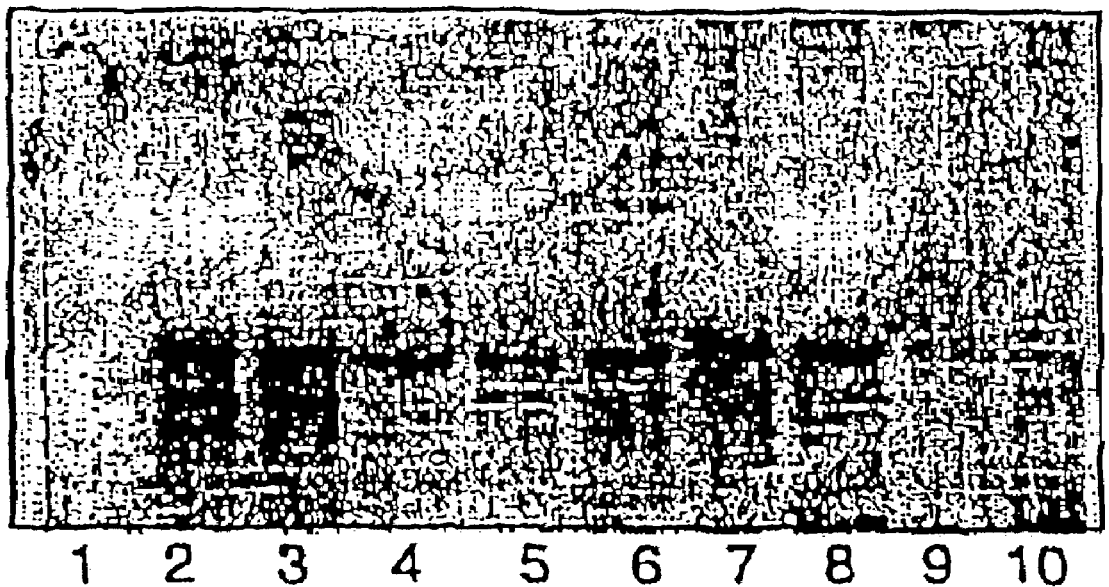

FIG. 26A is a gel showing the incorporation of various fluorescent molecules into α-hemolysin in E. coli translation system using misaminoacylated lysyl-tRNA$^{lys}$.

Figure 26B:
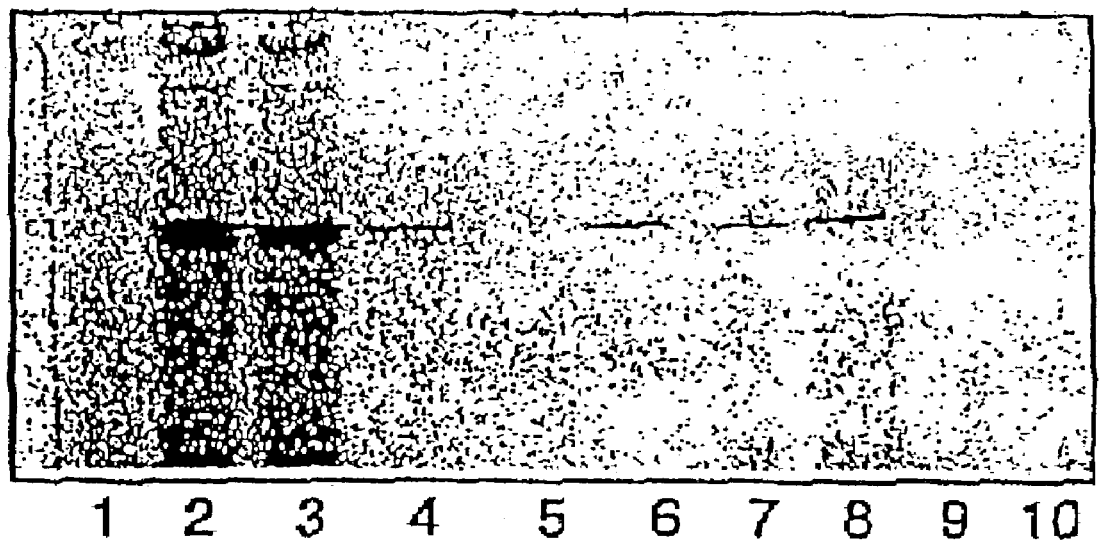

FIG. 26B shows the incorporation of various fluorescent molecules into luciferase in a TnT wheat germ system using misaminoacylated lysyl-tRNA$^{lys}$.

Figure 27:

FIG. 27 shows gel results of in vitro translation of α-HL carried out in the presence of various fluorescent-tRNAs, including a tRNA-coumarin derivative.

Figure 28A:
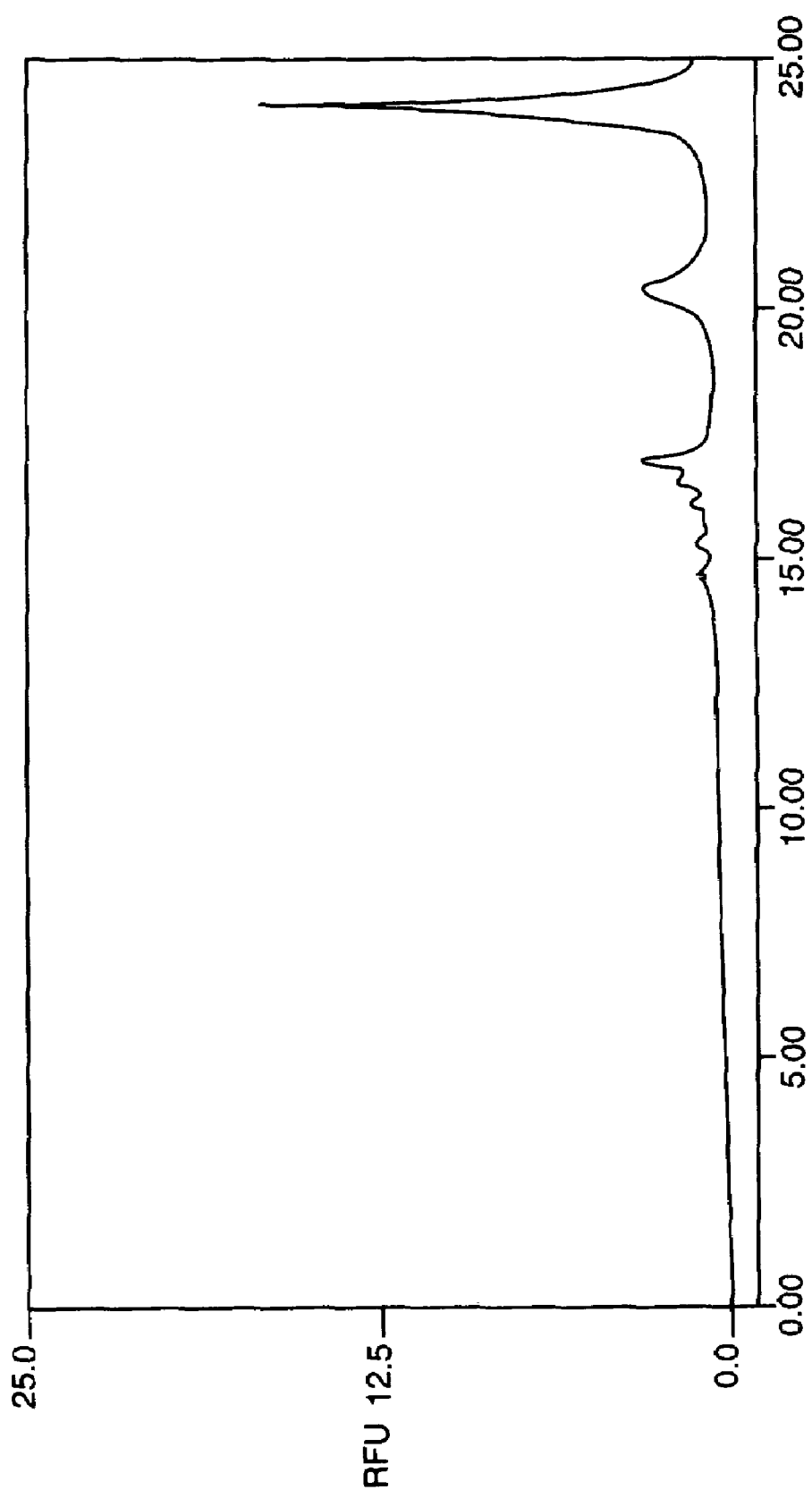
Figure 28B:
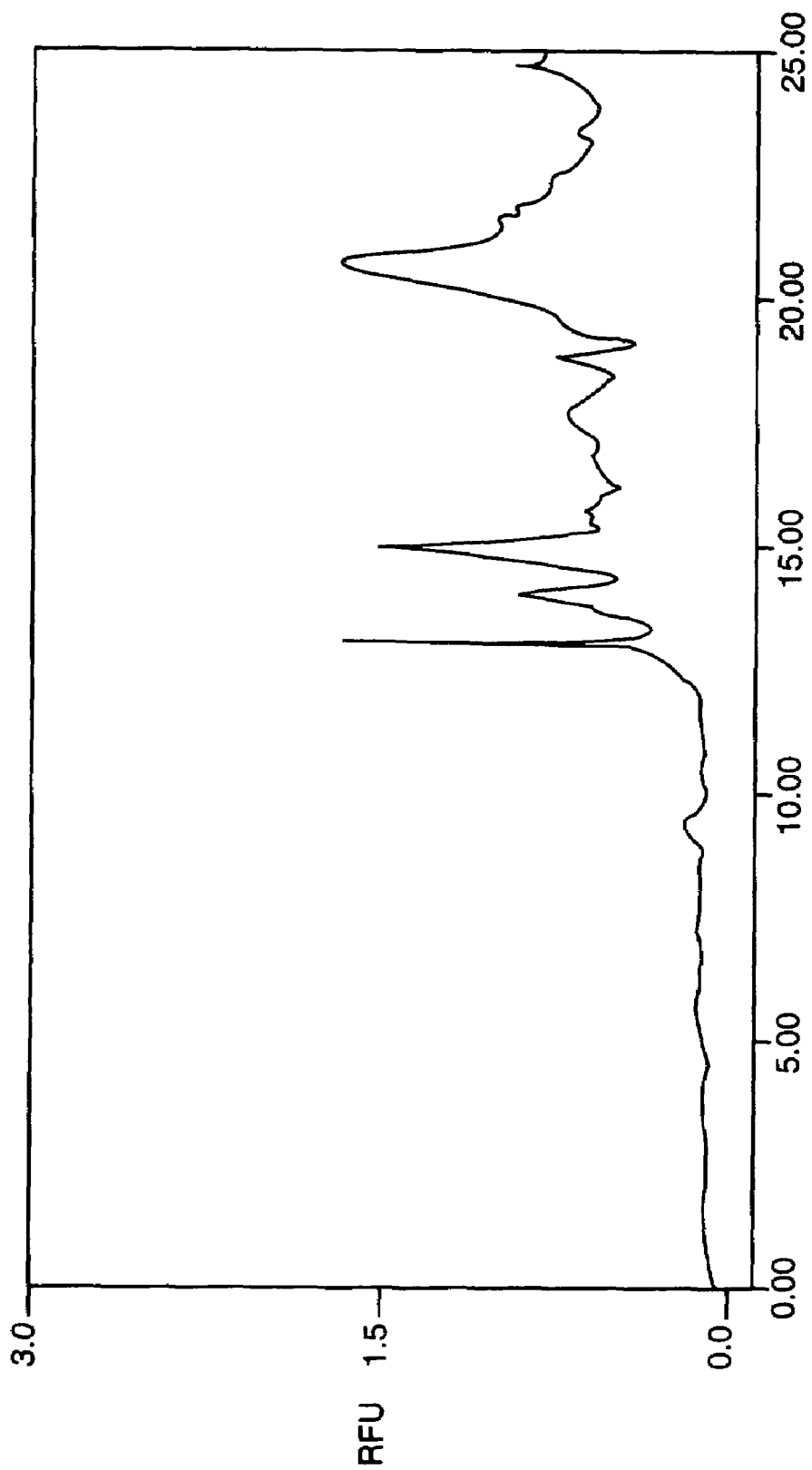

FIGS. 28A and 28B show mobility shift results by capillary electrophoresis.

Figure 29:
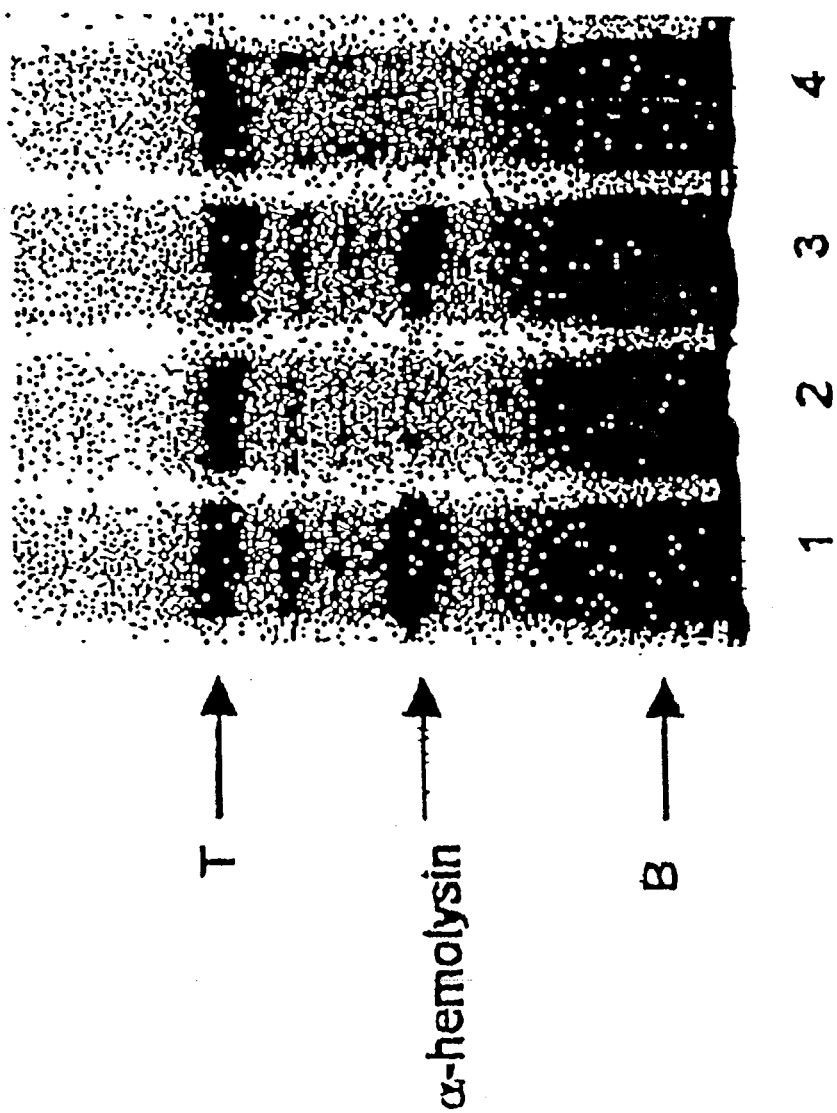

FIG. 29 are gel results of in vitro translation results wherein three markers were introduced into a nascent protein.

Figure 30A:
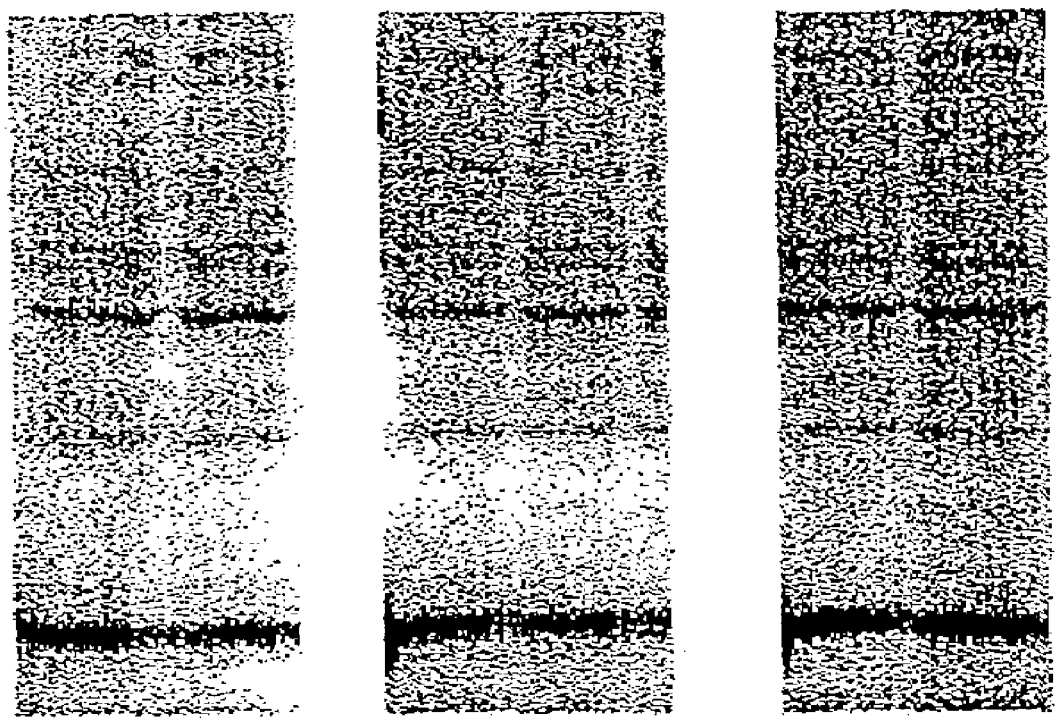
Figure 30B:
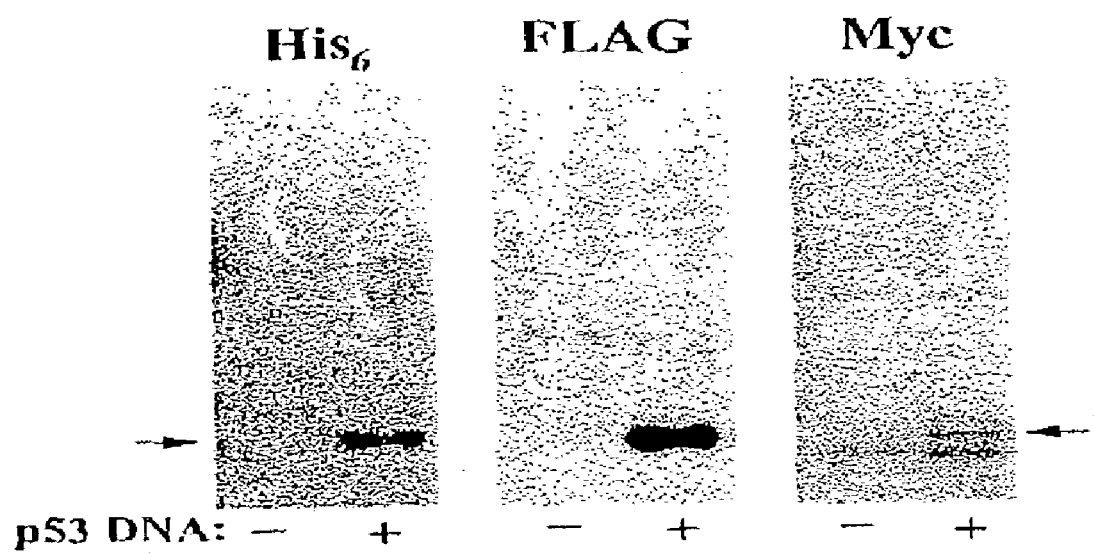

FIG. 30 shows Western blot analysis of in vitro translated triple-epitope-tagged wild-type p53 (RT-PCR derived DNA). FIG. 30A shows the total protein staining. FIG. 30B presents the Western blot analysis.

Figure 31:
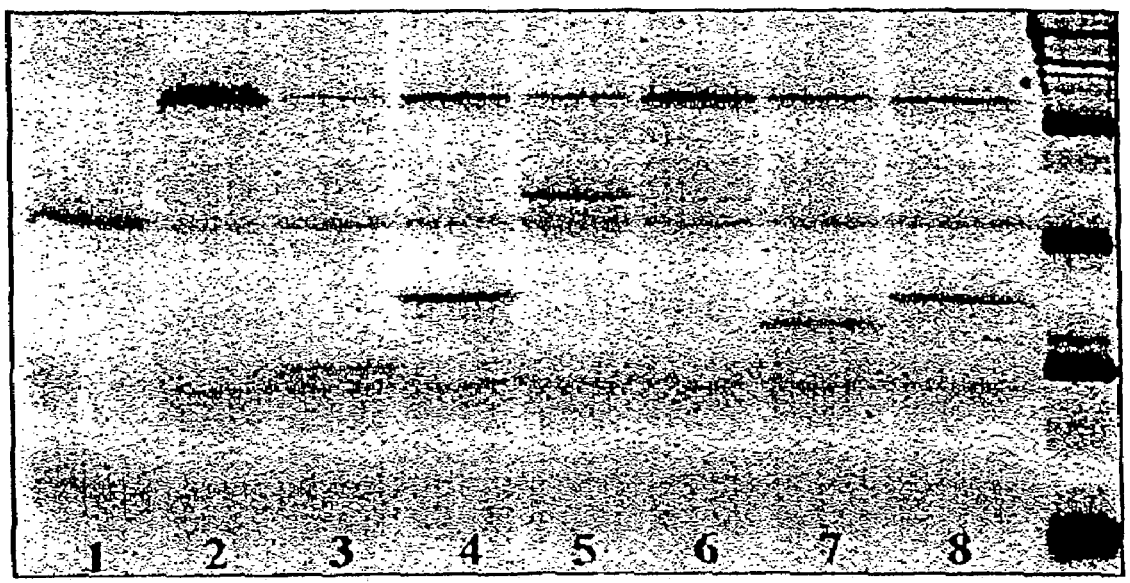

FIG. 31 shows the results for a gel-based PTT of APC Exon 15, segment 2.

Figure 32A:
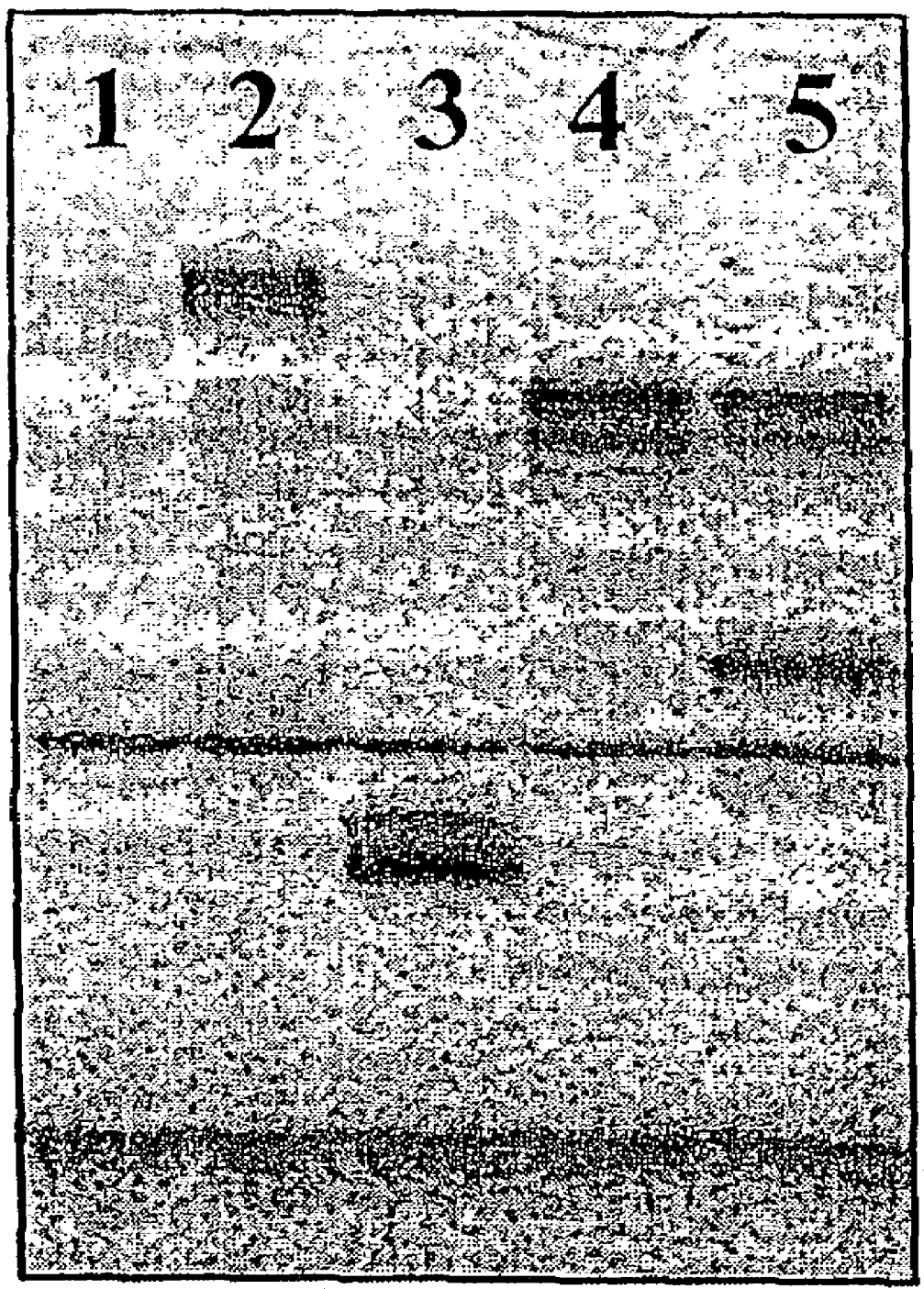
Figure 32B:
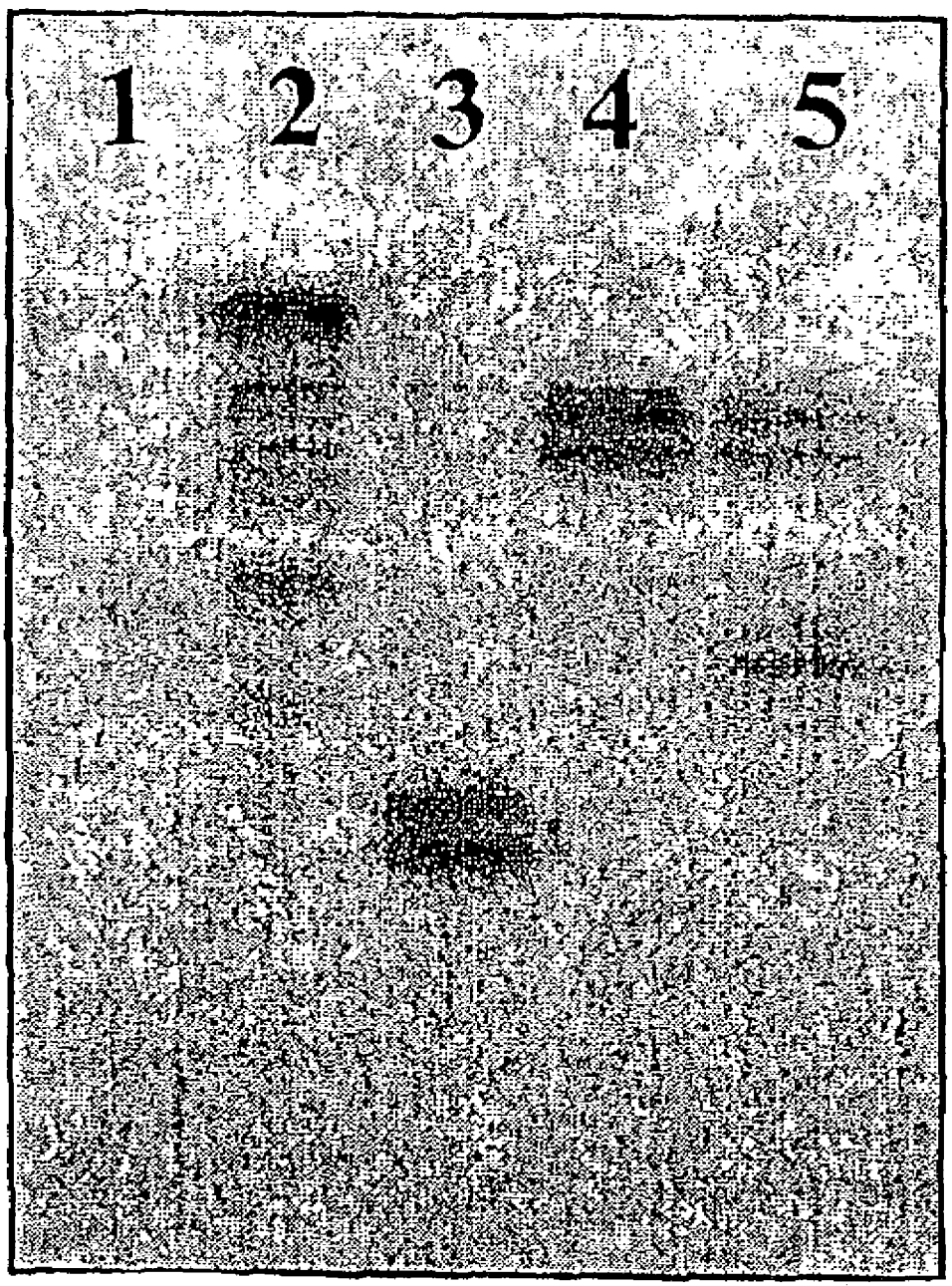

FIG. 32 shows the detection of in vitro translated BODIPY-labeled proteins by Western blotting. FIG. 32A shows the results by fluorescence imaging and FIG. 32B shows the results by Western blotting.

Figure 33A:
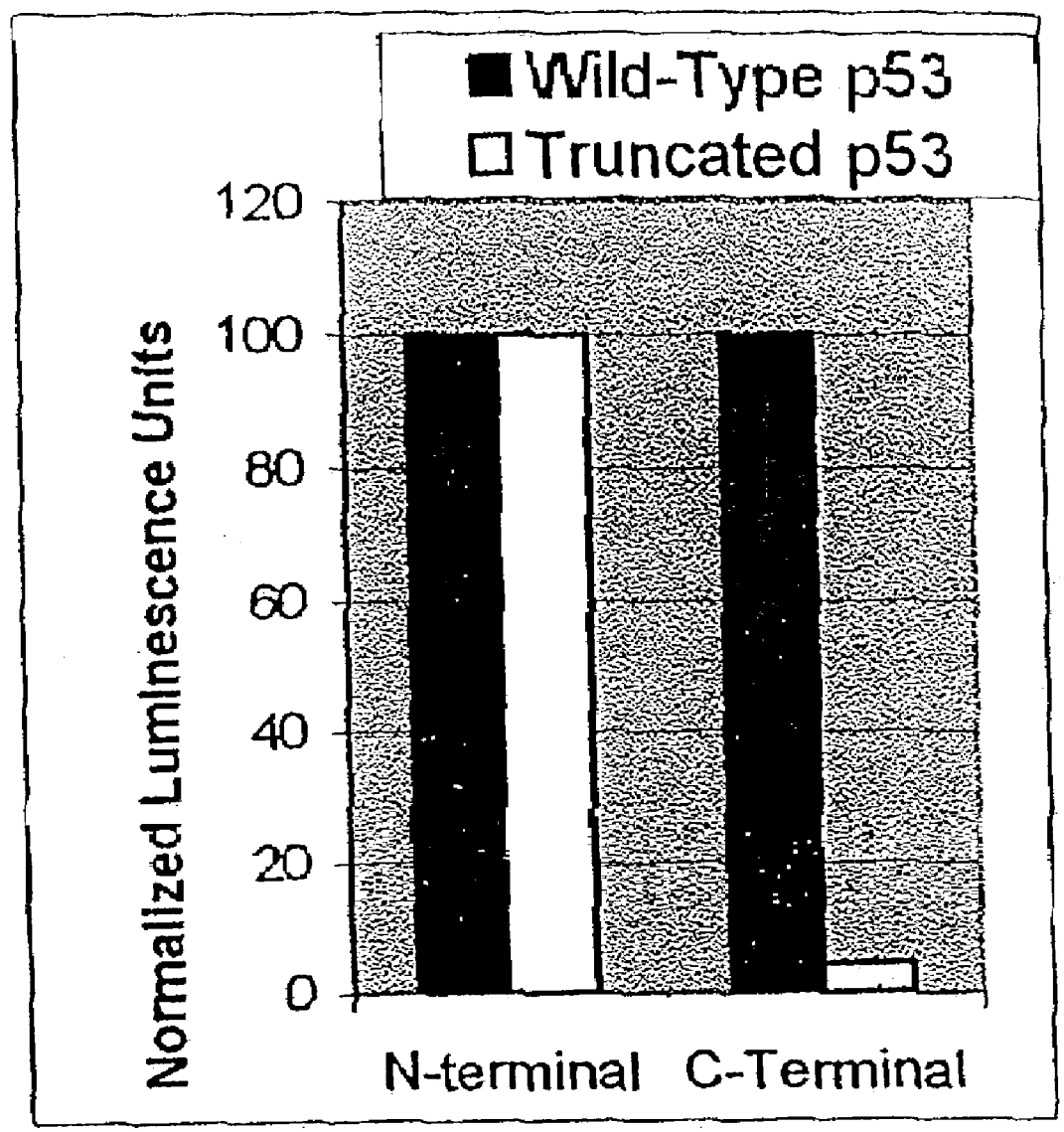
Figure 33B:
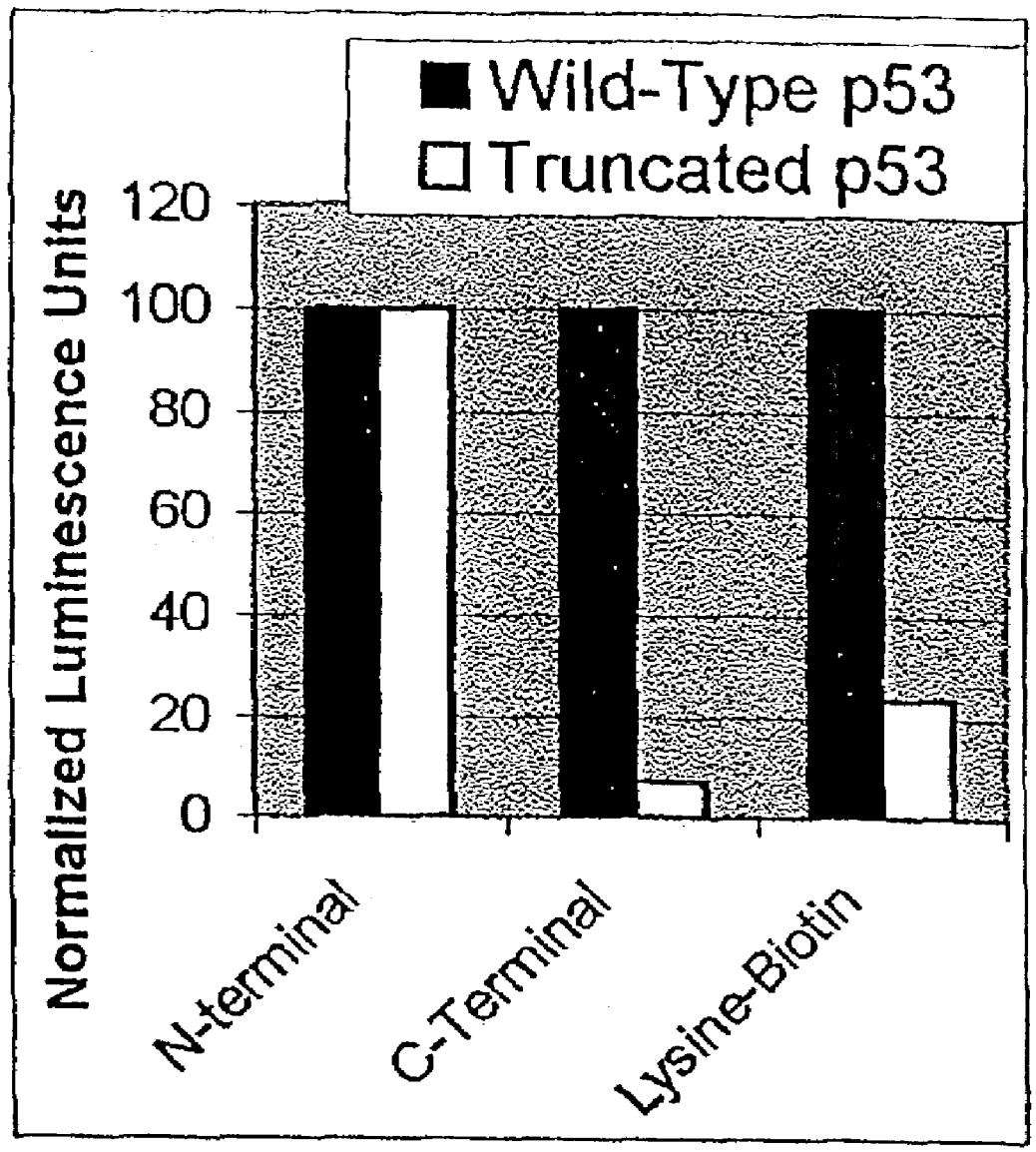
Figure 33C:
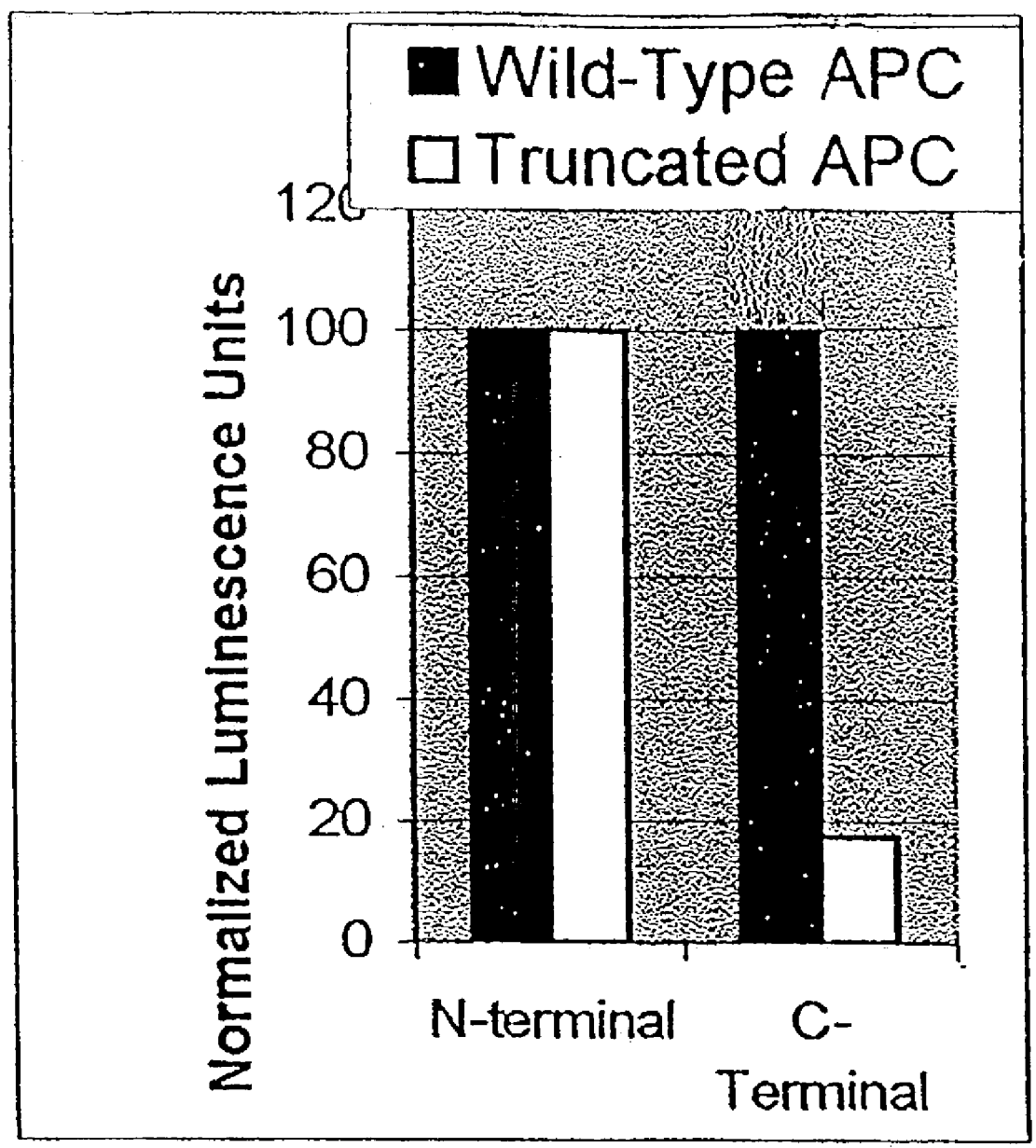

FIG. 33 shows three bar graphs representing the results of a gel-free chemiluminescent protein truncation assay of p53 and APC. FIG. 33A shows the results for p53 produced by in vitro translation, where the product is captured in a 96-well ELISA plate format using a mouse monoclonal antibody directed against the N-terminal FLAG epitope. FIG. 33B shows the results for p53 produced by in vitro translation, where the product is captured in a 96-well ELISA plate format using a nickel chelate plate. FIG. 33C shows the results for APC produced by in vitro translation, where the product is captured on nickel metal chelate 96-well ELISA plates. All WT N- and C-terminal signals as well as mutant N-terminal signals were normalized to 100%.

Figure 34:
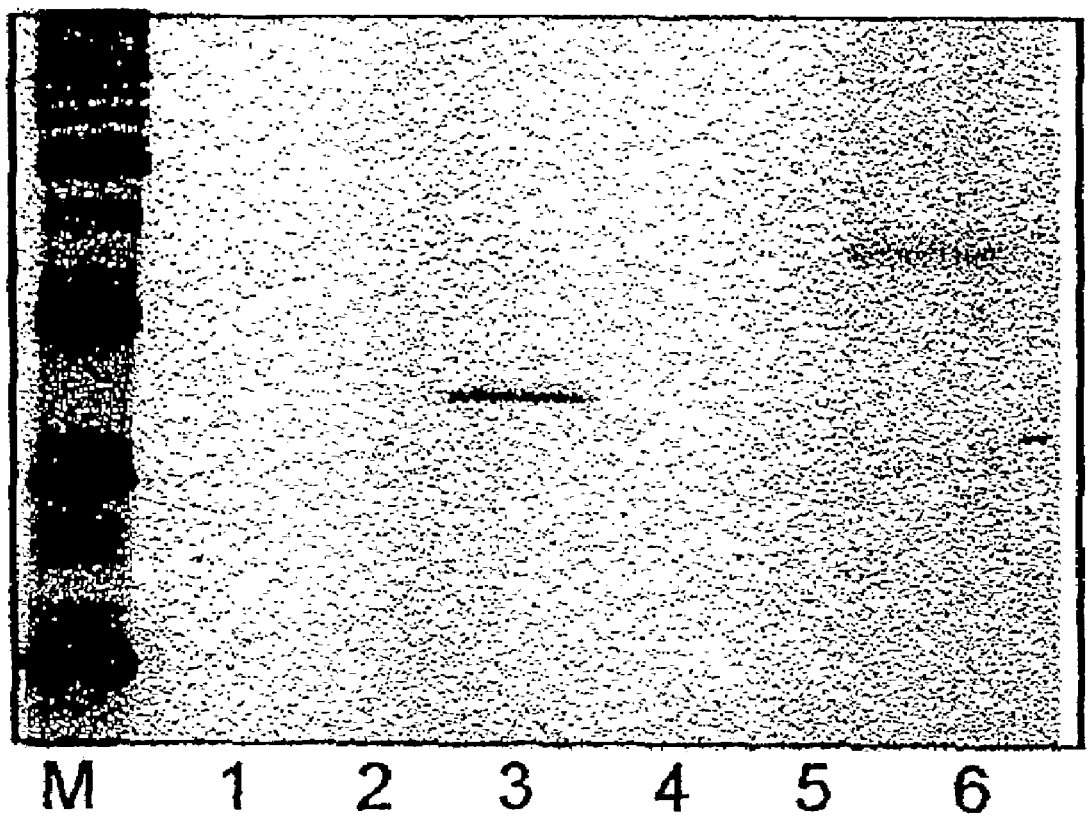

FIG. 34 is a gel showing immunoprecipitation results for p53 and Hemolysin.

Figure 35:
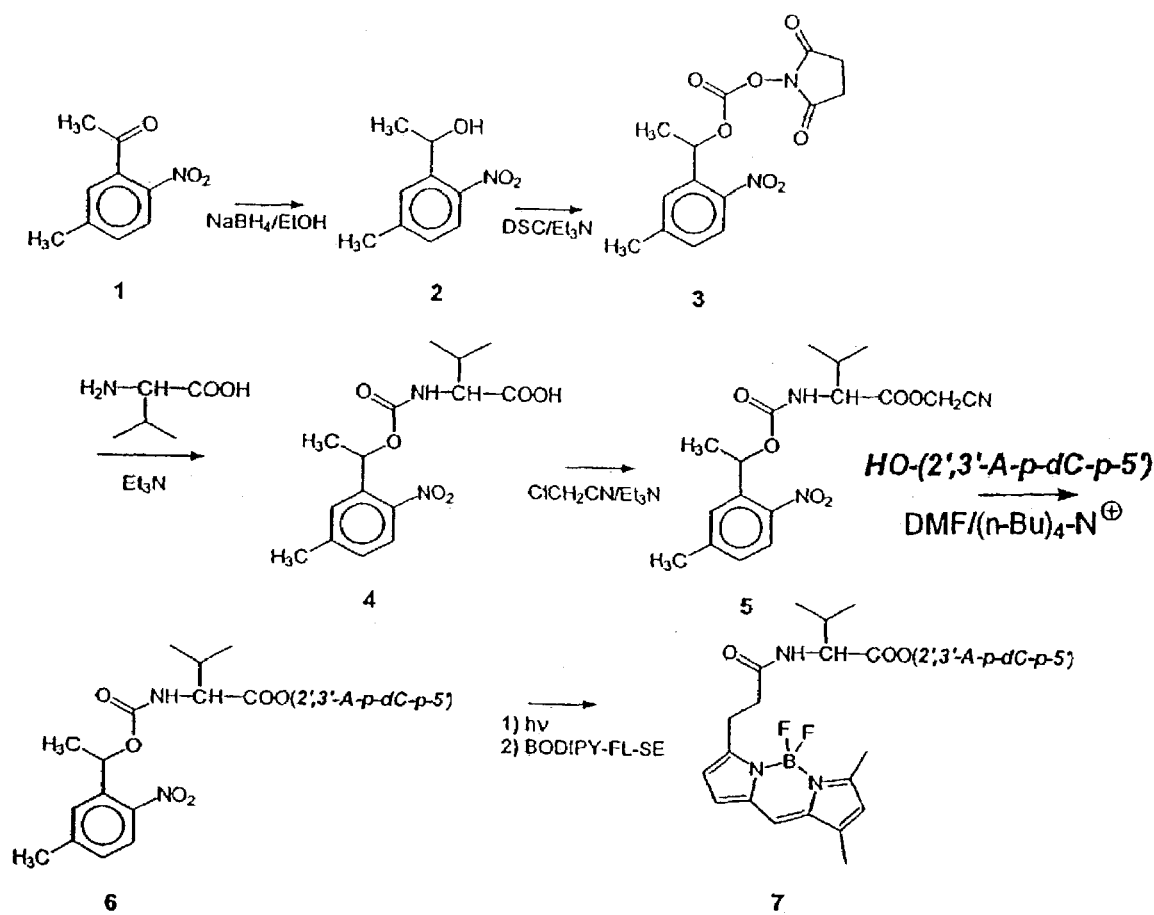

FIG. 35 schematically shows a synthesis scheme for the preparation of BODIPY-Val-pdCpA.

Figure 36:
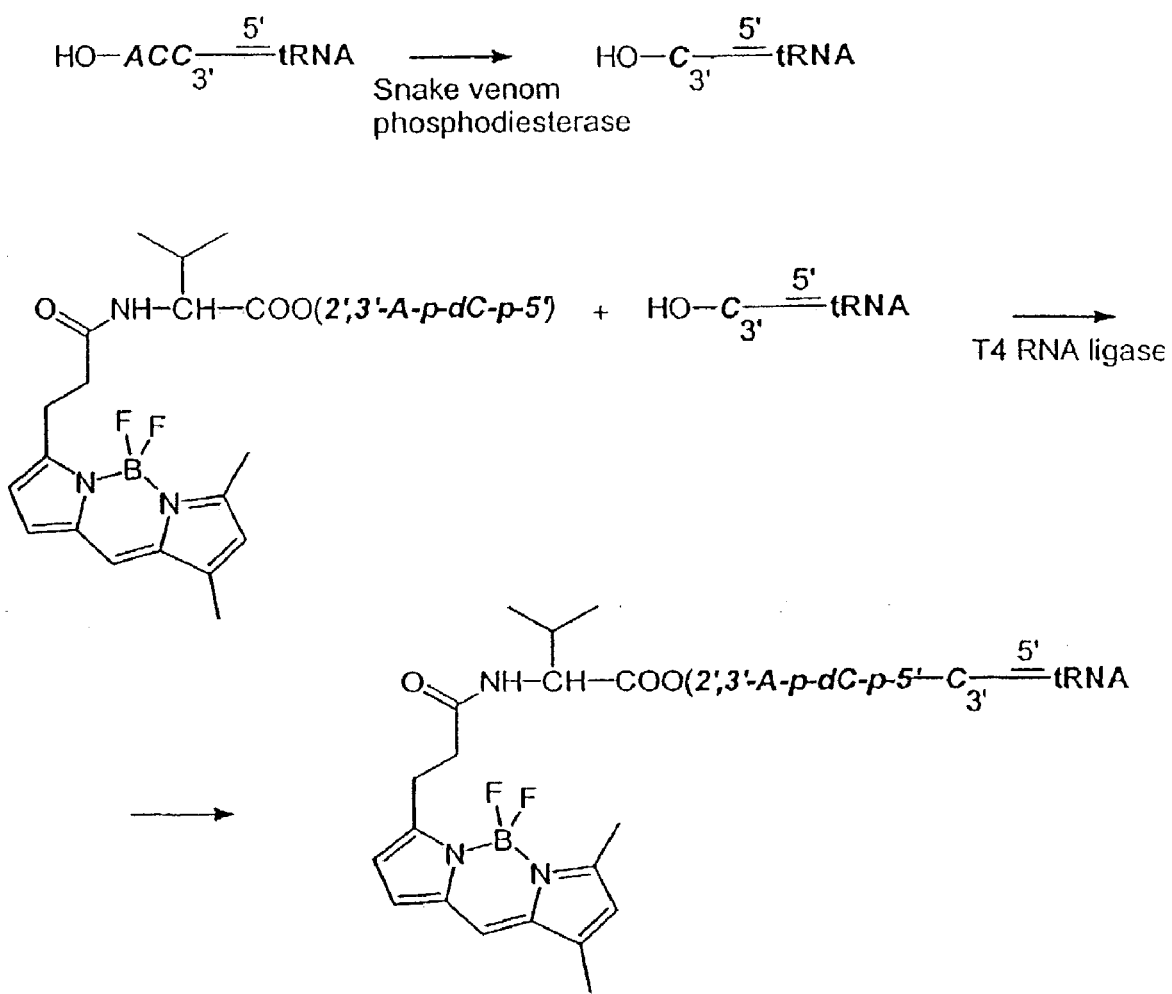

FIG. 36 schematically shows a synthesis scheme for the attachment of the BODIPY-Val-pdCpA conjugate of FIG. 35 to tRNA.

Figure 37:
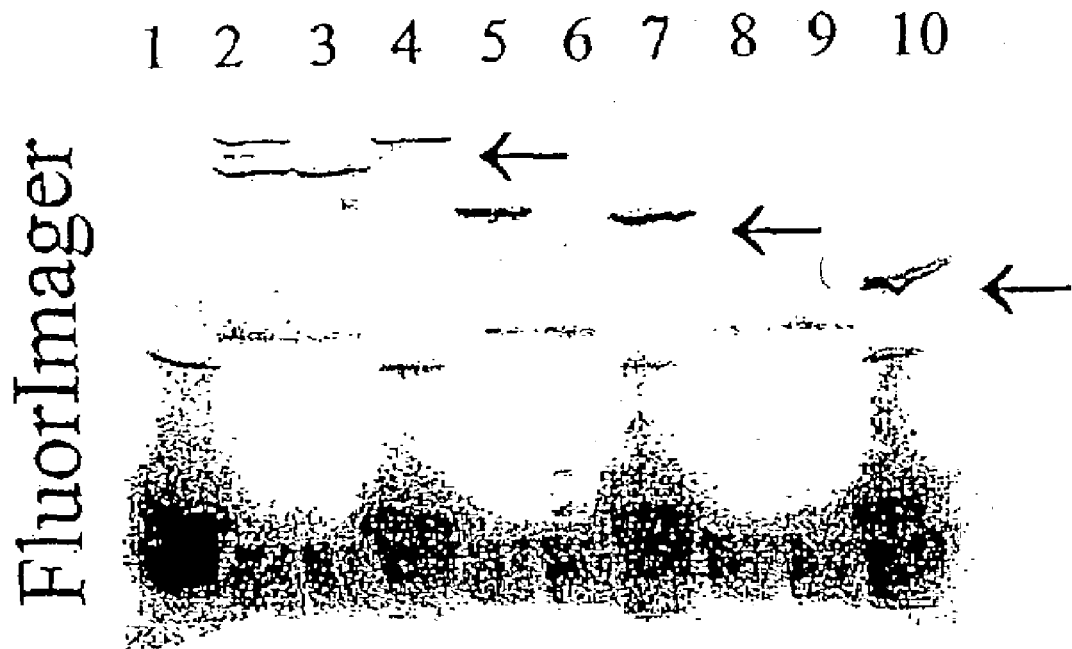

FIG. 37 shows the result of translation reactions using the charged tRNA of FIG. 36.

Figure 38:
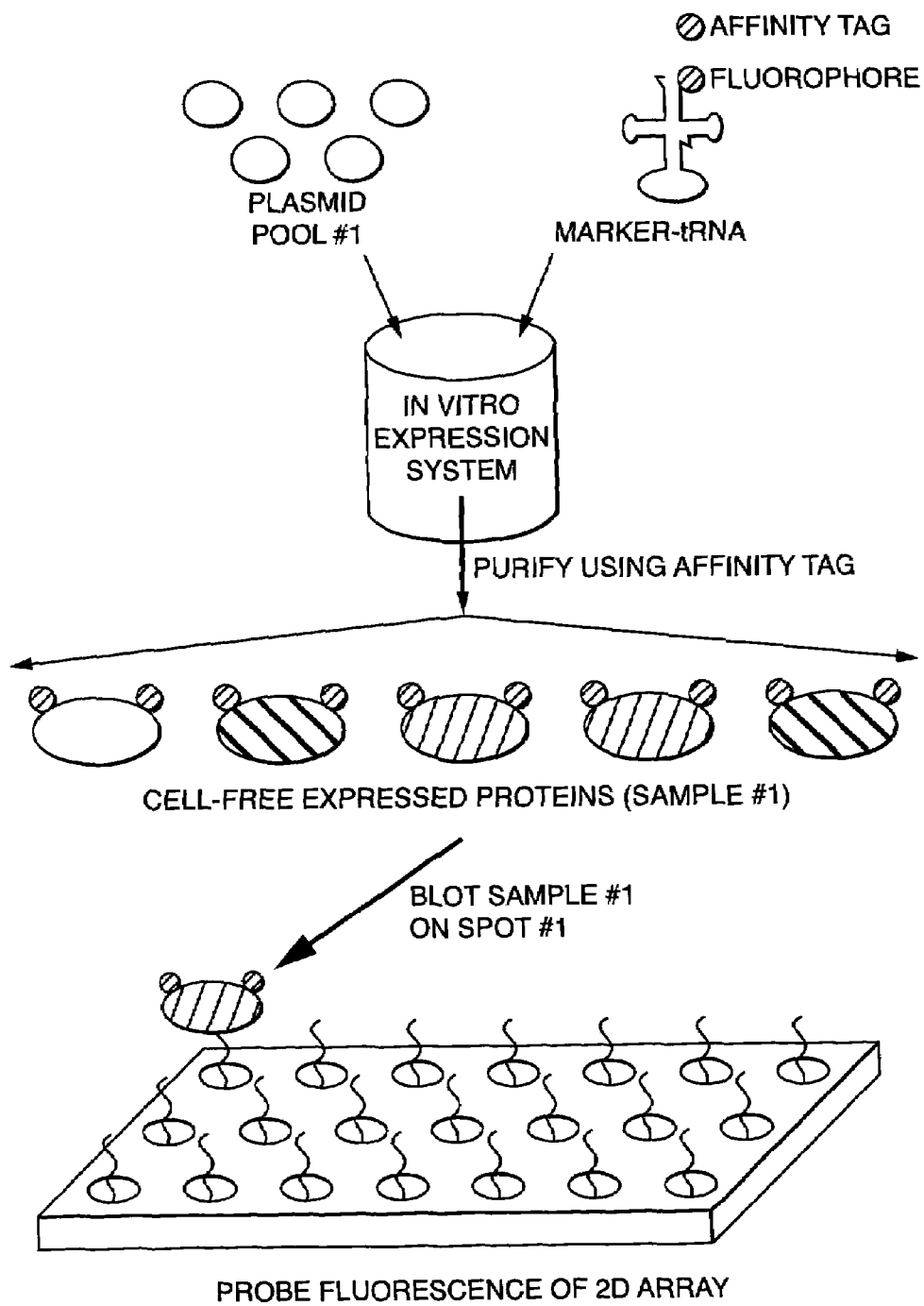

FIG. 38 schematically shows one embodiment of a drug/proteome screening assay.

Figure 39:
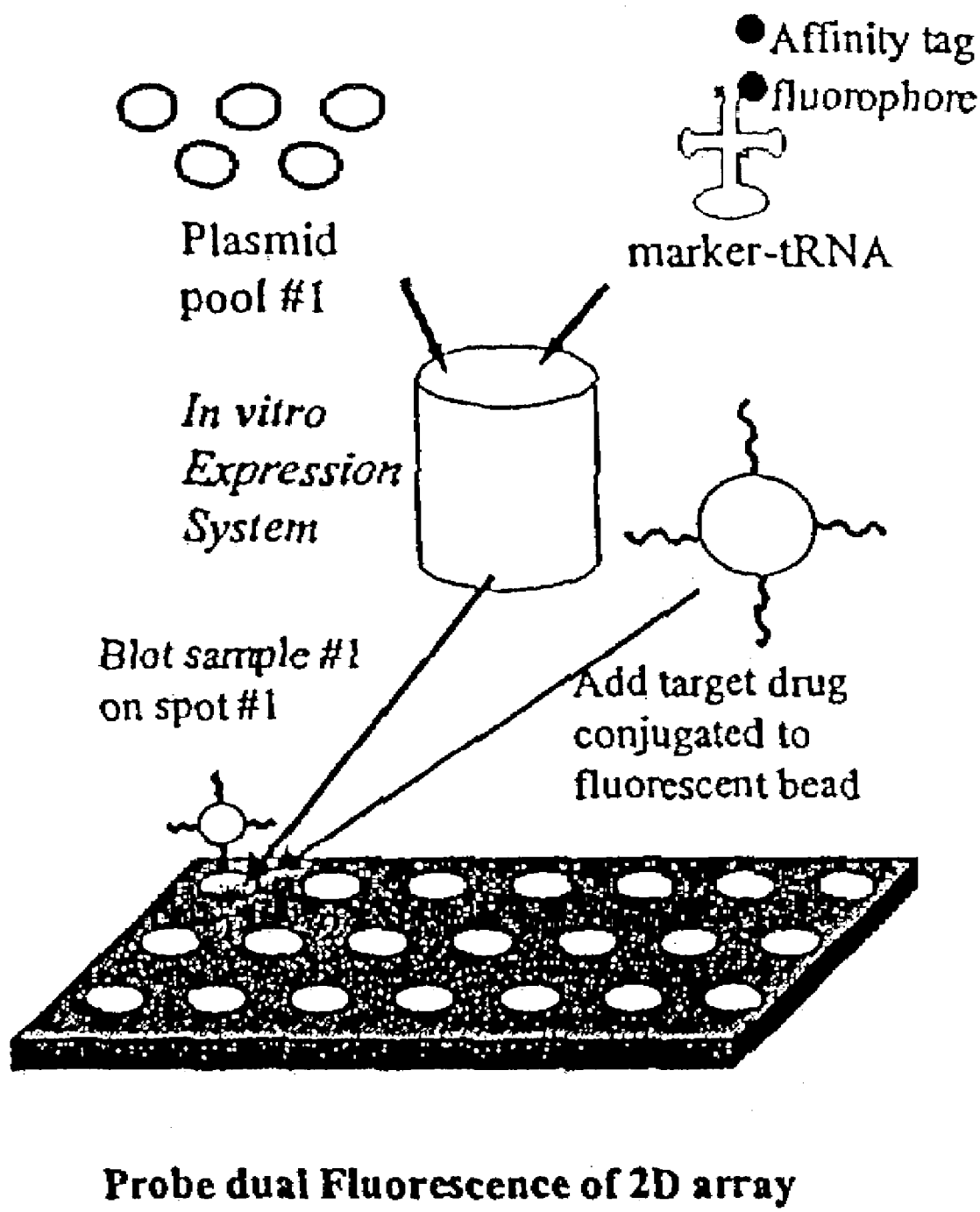

FIG. 39 schematically shows one embodiment of a drug/proteome screening assay.

Figure 40:
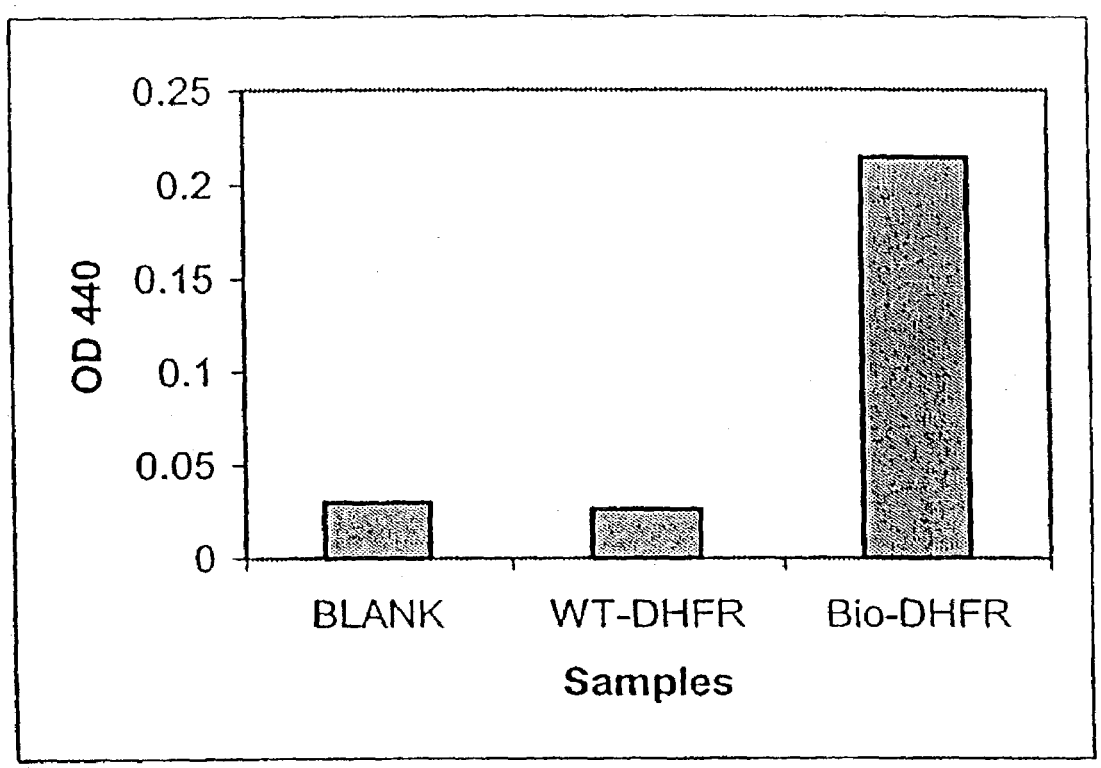

FIG. 40 is a bar graph showing the results of a drug/proteome screening assay.

Figure 41:
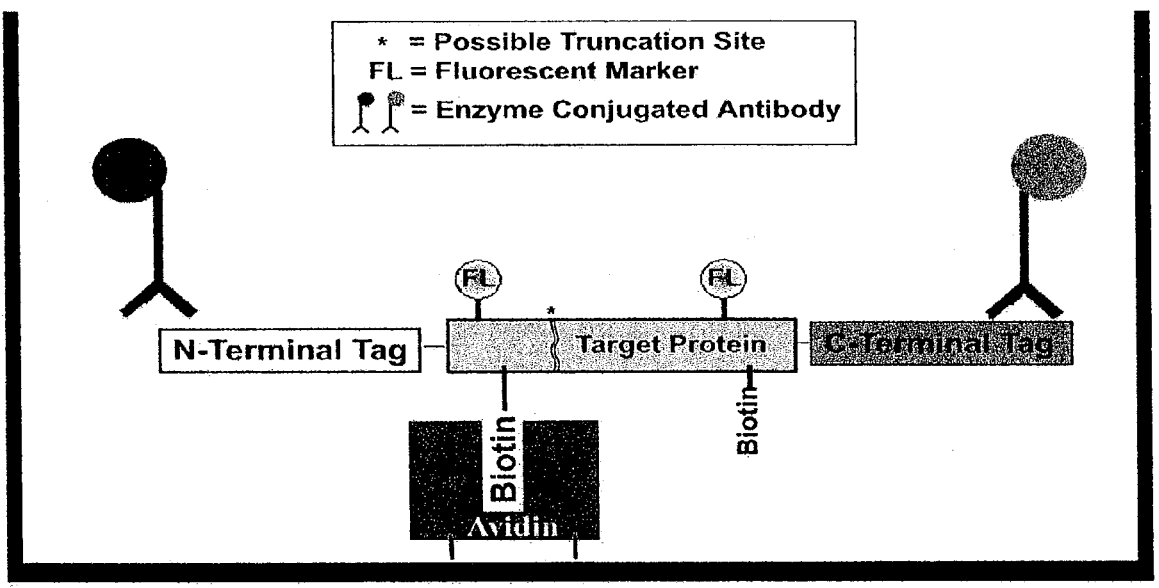

FIG. 41 depicts a schematic representation of one embodiment of a High-Throughput Solid-phase Protein Truncation Test (HTS-PTT).

Figure 42:
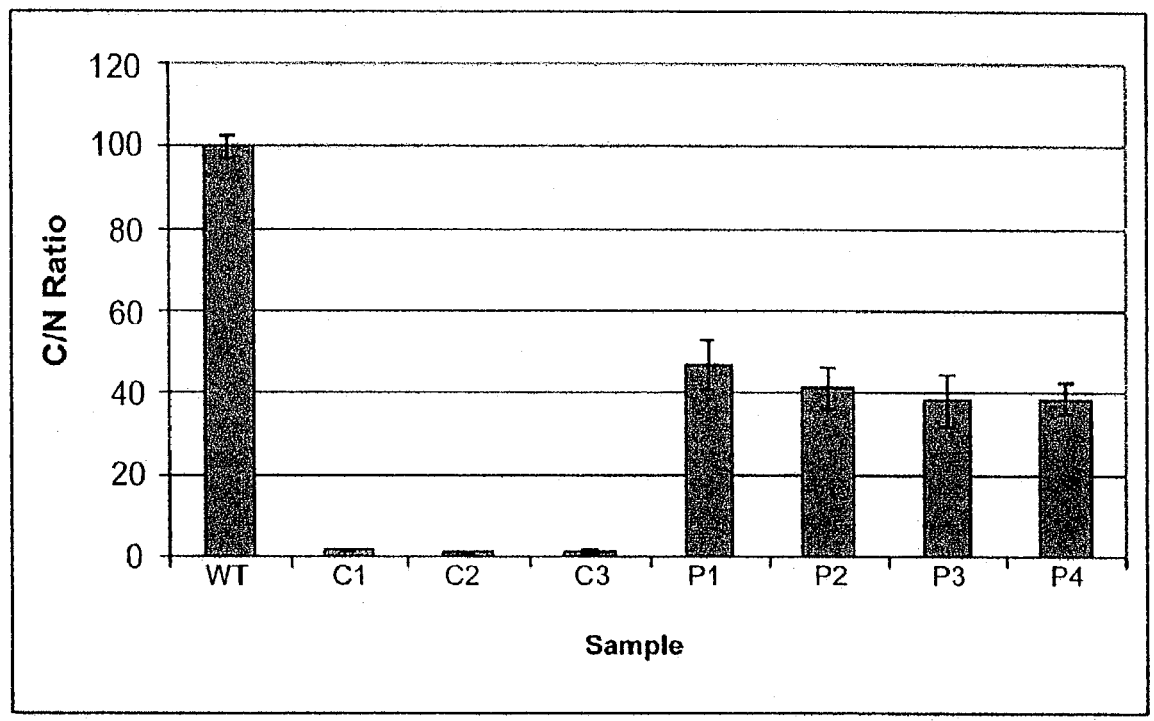

FIG. 42 displays ELISA-based HTS-PTT data for mutations in the APC segment 3 gene. Four FAP patients (P1-P4) are compared to cell-line homozygous mutations ($C_1$-$C_3$) and assay normalization of 100 based on data from wild-type (WT) DNA. Selective capture occurred on NeutrAvidin™ plates via biotin incorporated by biotin-lysyl-tRNA. Epitope tags were detected by using either antibody-conjugated horseradish peroxidase (HRP) or alkaline phosphatase (AP). All data points represent and average of ≧3 replicates and error bars indicate the standard deviation.

Figure 43:
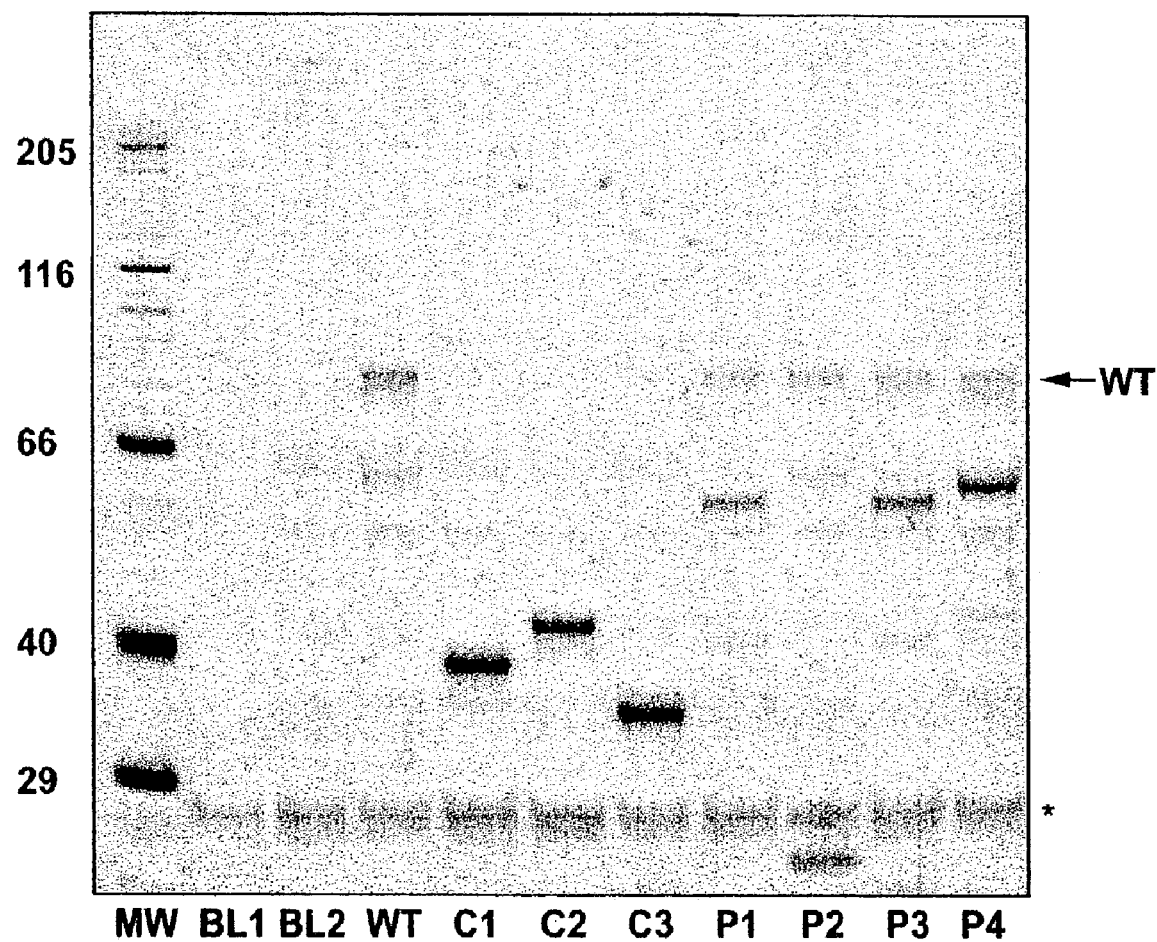

FIG. 43 shows a gel-based PTT assay with fluorescent readout performed on 4 µl aliquots of samples comprising the data of FIG. 42. BL1: controls without tRNAs and DNA. BL2: controls without DNA. Asterisk: Auto-fluorescent control protein marker band. The mutations confirmed by DNA sequencing are: C1: Q1367→Stop; C2: ΔC at codon 1416; C3: Q1338→Stop; P1: ΔAG at codon 1536; P2: ΔC at codon 1200; P3: ΔC at codon 1536 and P4: Insertion of A at codon 1555. All mutations are found in the APC mutation database.

Figure 44:
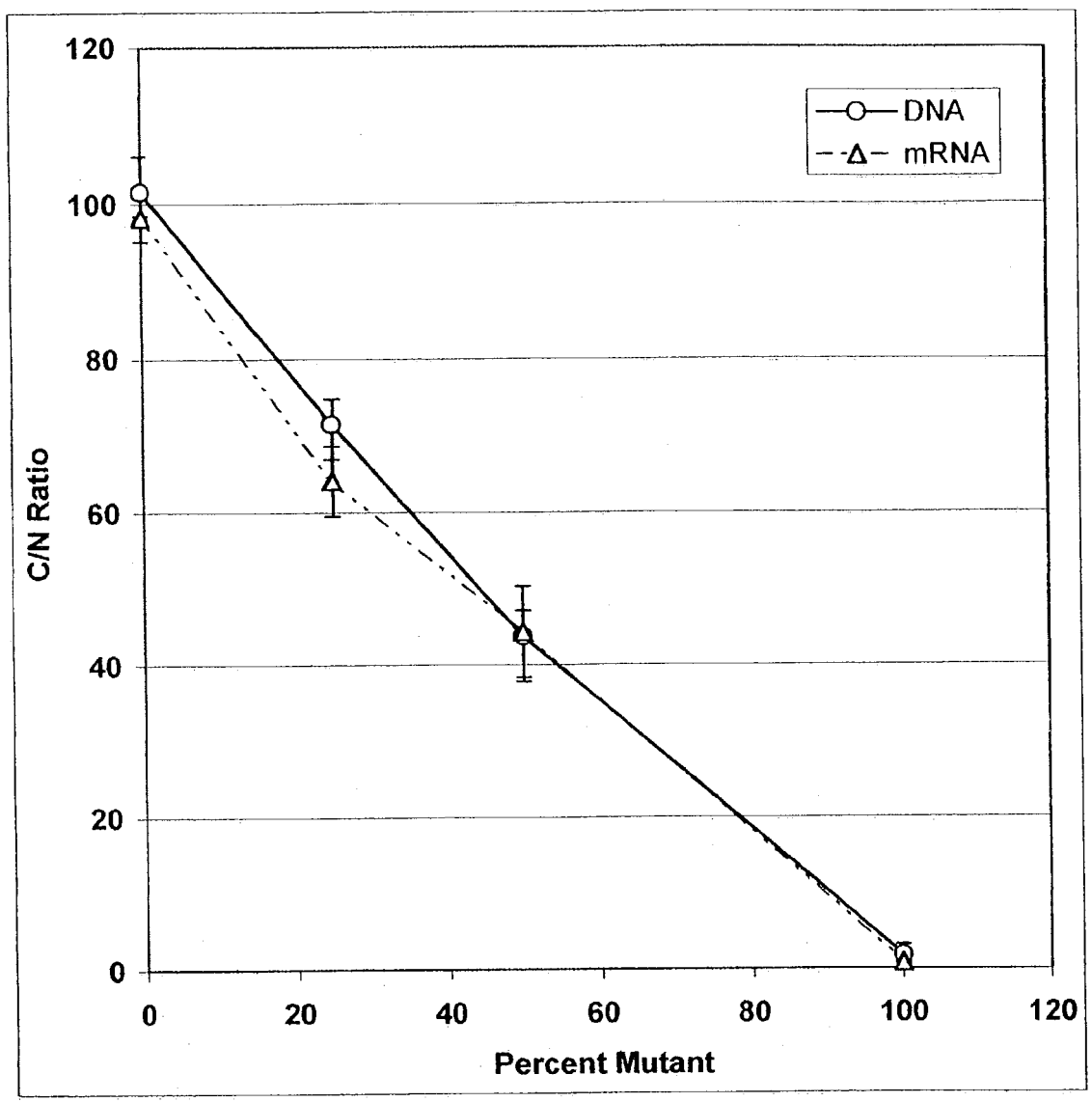

FIG. 44 displays HTS-PTT truncation mutation detection in APC gene at various dilutions of WT:C3 DNA (circles-solid line) or mRNA (triangles-broken line). The DNA were mixed prior to PCR. The mRNA were mixed prior to isolation. All data points represent an average of ≧3 replicates and error bars indicate the standard deviation.

Figure 45:
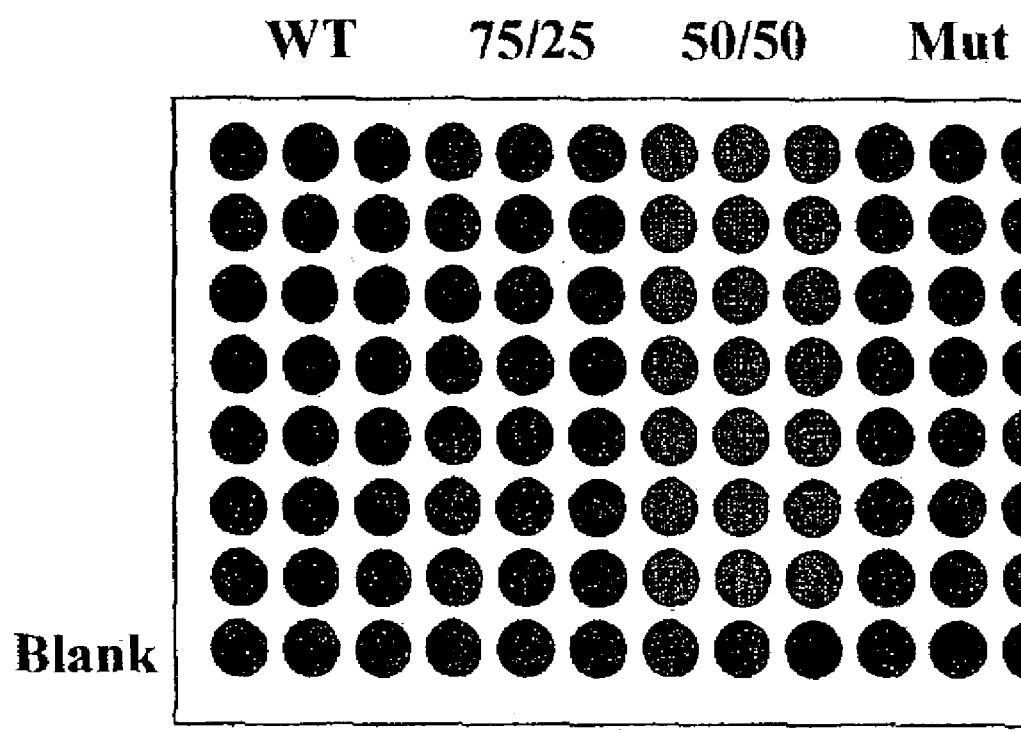

FIG. 45 displays the same data as in FIG. 44 using a color coded matrix array. C/N terminal ratios were reproduced by using MICROSOFT POWERPOINT XP software to mix Green (g) and Red (r) RGB values. Blue was set at 0 while Red and Green ranged from 0-255. Color adjustments were made based on R value and C/N terminal ratio by using the formulas; r=255 (R/100) and g=255 [1−(R/100)].

Figure 46:
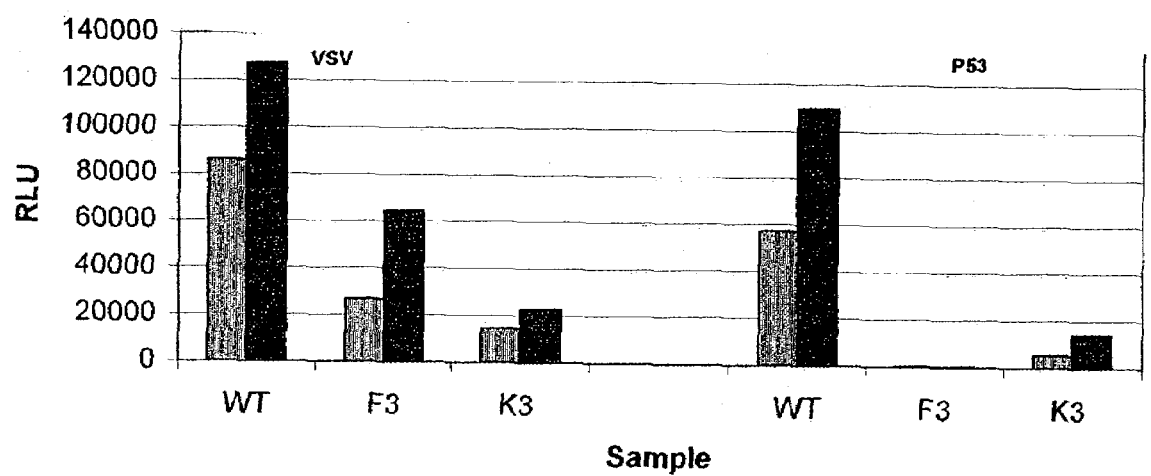

FIG. 46 displays data comparing the signals between biotin-tRNA$^{lys}$ (grey bars) and biotin-tRNA$^{TOTAL}$ (black bars) for the VSV epitope or the P53 epitope. WT: Wild-type DNA. F3: Human Truncated Mutant DNA K3: Human Truncated Mutant DNA. The differences in translation efficiency is reflected in the respective signal intensities between the VSV and P53 markers.

Figure 47:
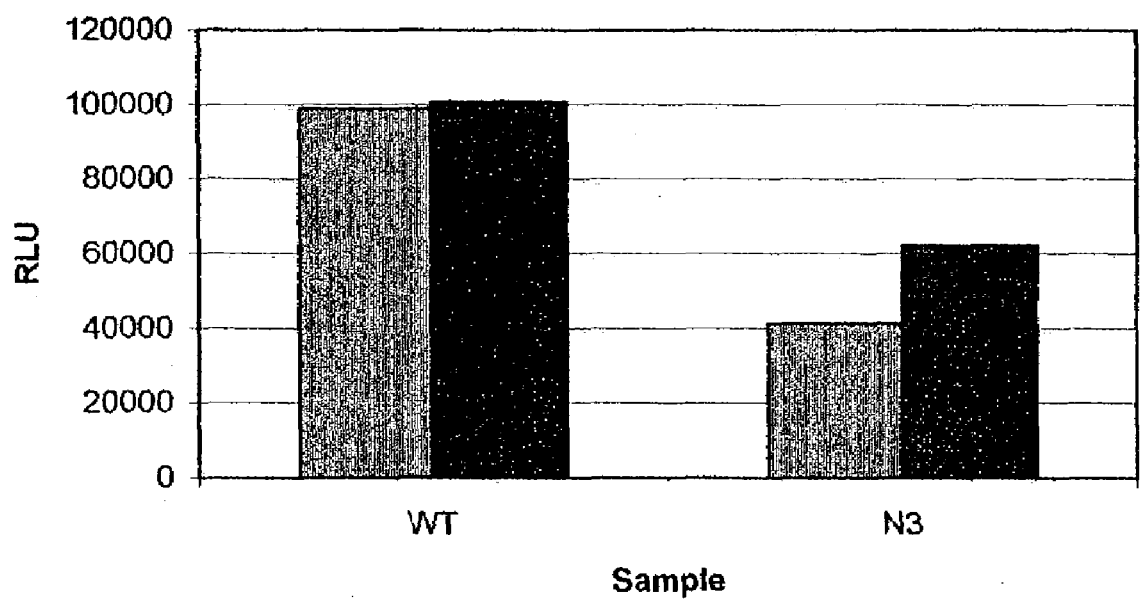

FIG. 47 displays data comparing the signals between standard incorporation of biotin-tRNA$^{lys}$ on an unmodified nascent protein (grey bars) and PCR insertion of five (5) extra terminal lysine residues on a nascent protein (black bars). WT: Wild-Type DNA. N3: Human Truncated Mutant DNA.

Figure 48:
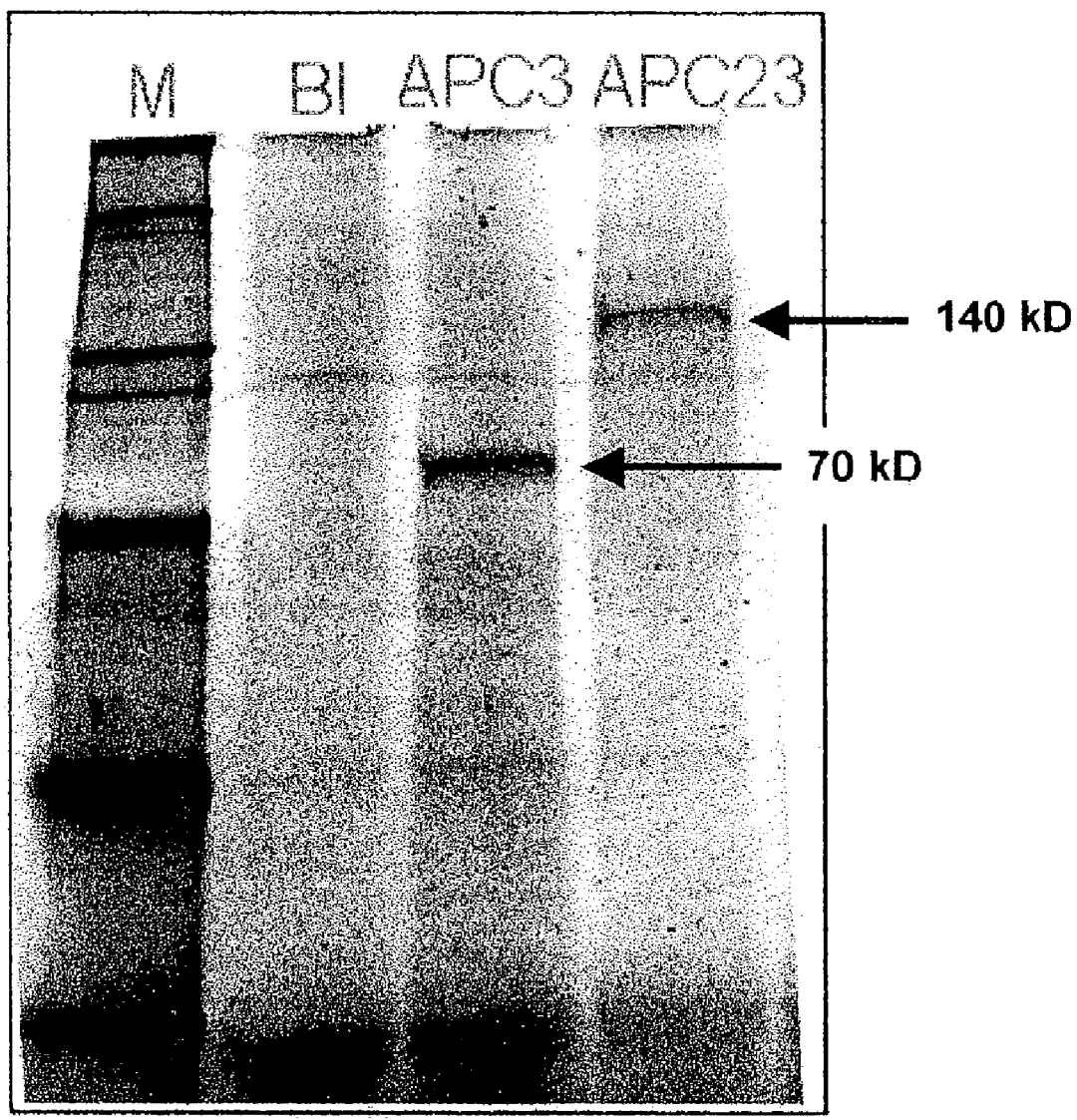

FIG. 48 depicts the separation by SDS-PAGE of APC-23 DNA (140 kD) from APC-3 DNA (70 kD).

Figure 49:
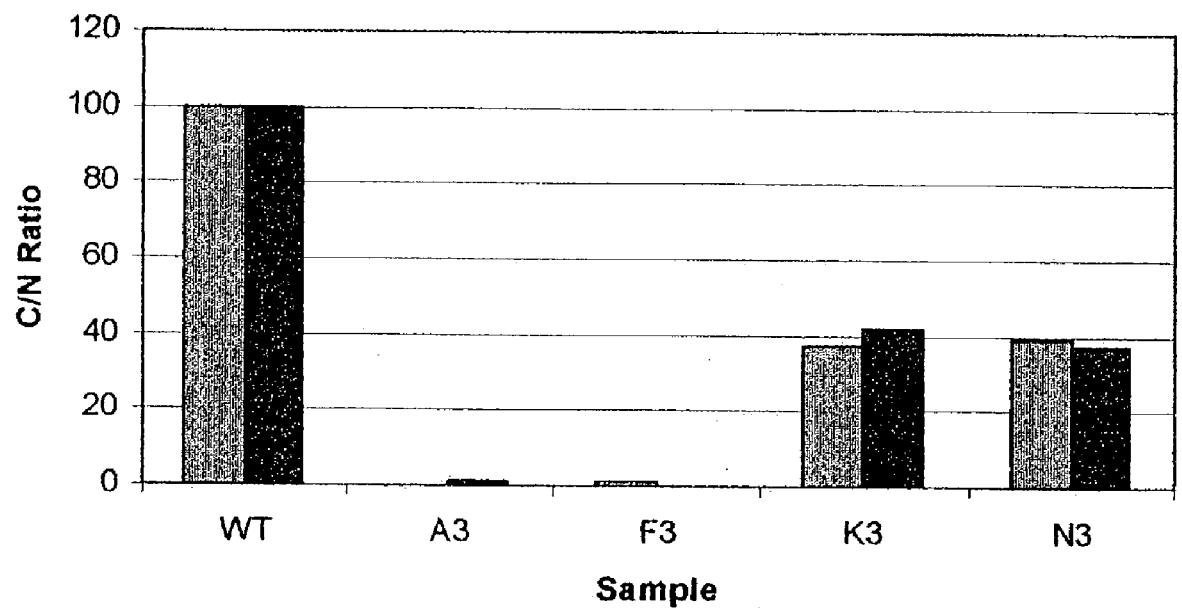

FIG. 49 compares HTS-PTT evaluation of APC-3 DNA (grey bars) and APC-23 DNA (black bars) in WT: Wild type DNA. A3: Homozygous Mutant Human DNA. F3: Homozygotic Mutant Human DNA. K3: Heterozygous Mutant DNA. N3: Heterozygotic Mutant Human DNA.

Figure 50:
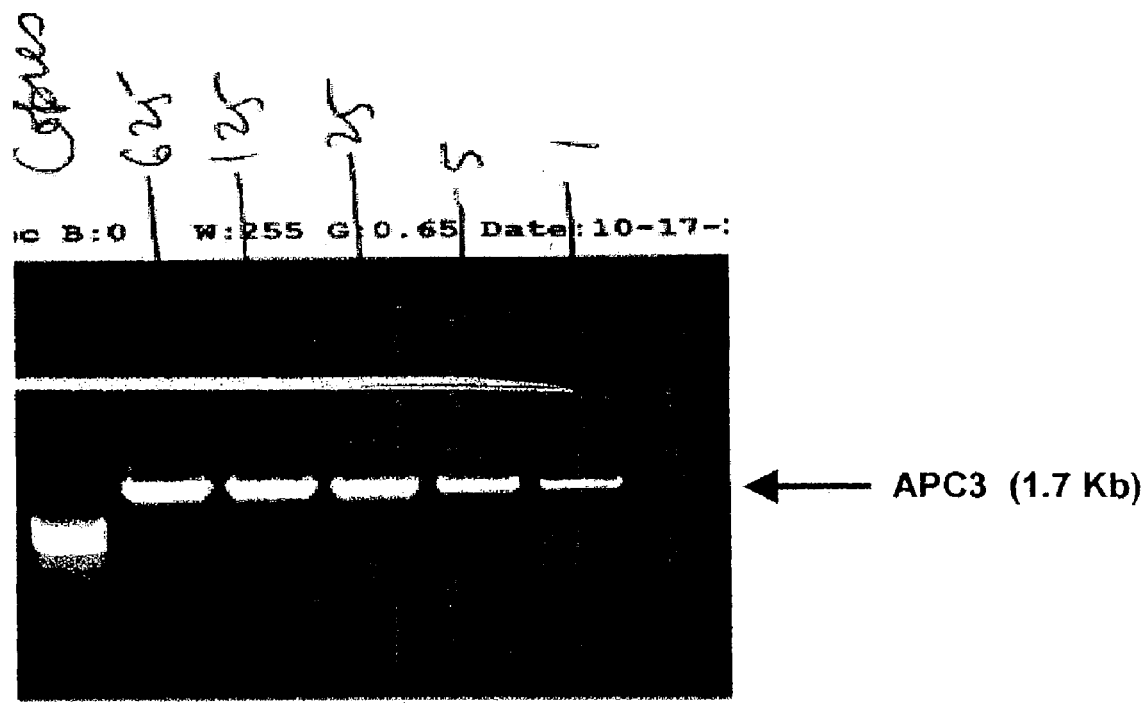

FIG. 50 shows separation of PCR APC-3 product corresponding to a single DNA copy following amplification with a very small amount of DNA.

Figure 51:
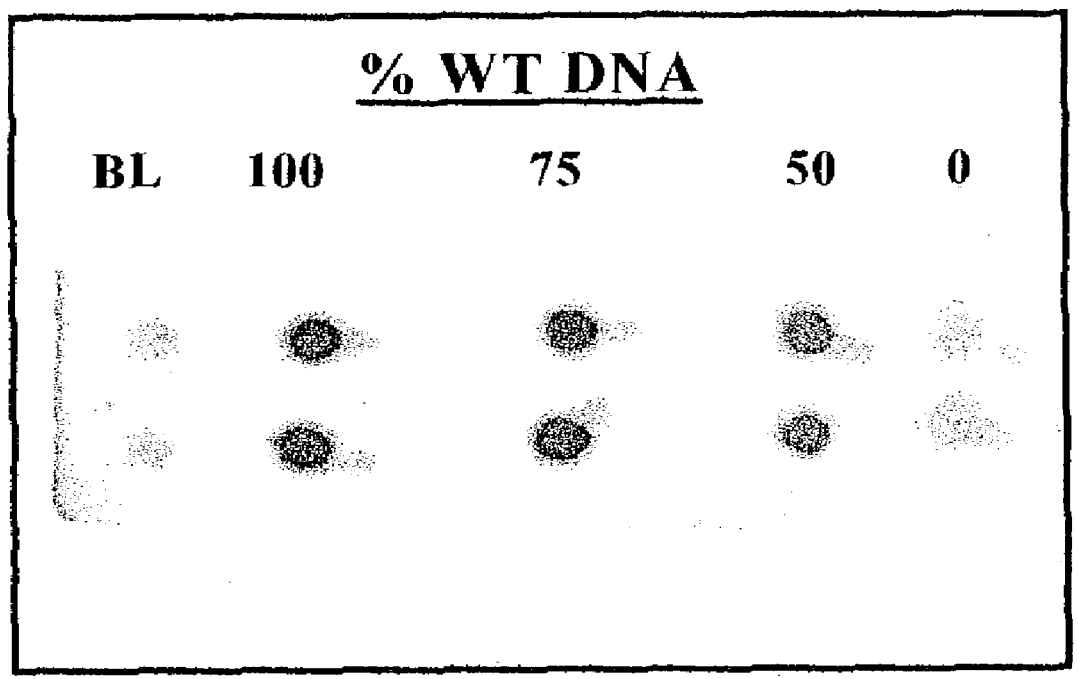

FIG. 51 displays C-Terminal fluorescence signal using MicroArray PTT. BL: Negative control. 0, 50, 75 and 100 represent percentage of WT DNA.

Figure 52:
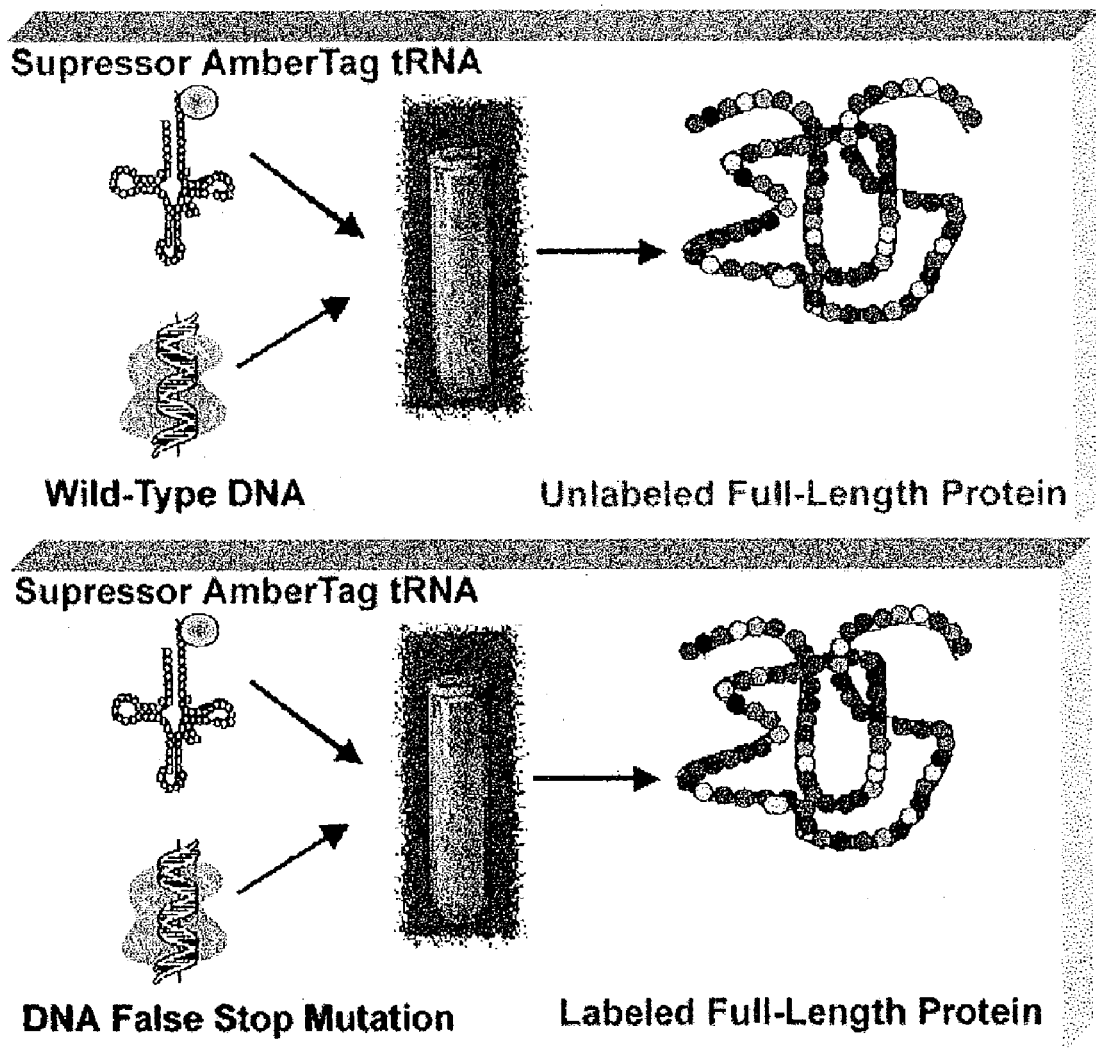

FIG. 52 illustrates High Sensitivity Chemiluminescent "Gel-Free" PTT for non-invasive colorectal cancer screening.

Figure 53:
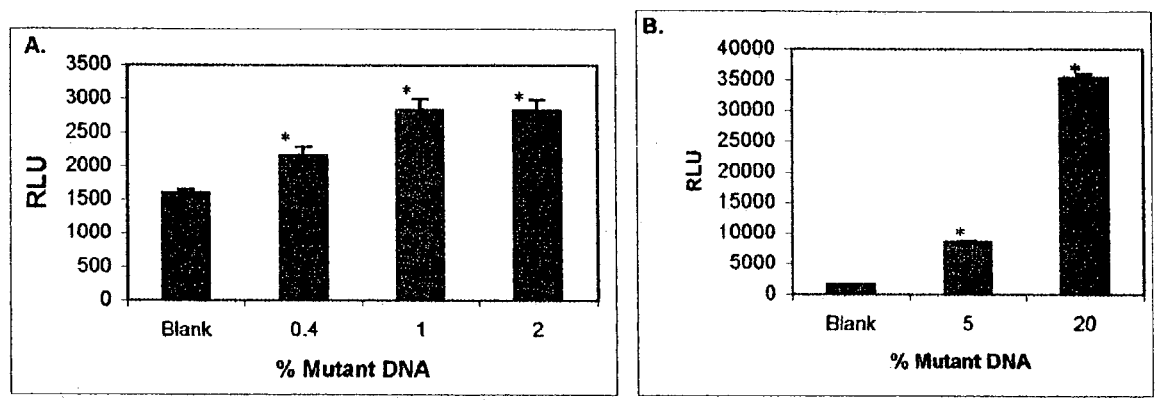

FIG. 53 demonstrates the detection of truncation mutations via selective incorporation of photocleavable (PC)-Biotin. Panel A shows signals obtained for mixtures containing 2%, 1% and 0.4% mixtures of Wild-Type:Mutant DNA of α-hemolysin. Panel B shows signals obtained for mixtures containing 5% and 20% DNA mixtures.

Figure 54:
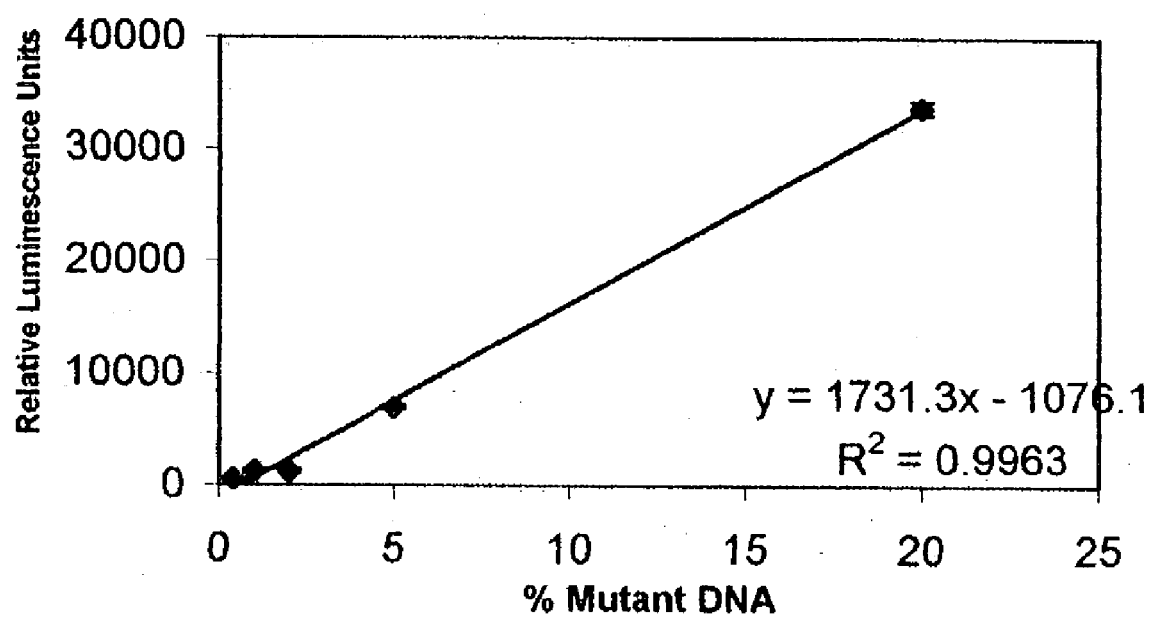

FIG. 54 shows the data of FIG. 53 replotted into a regression curve.

Figure 55:
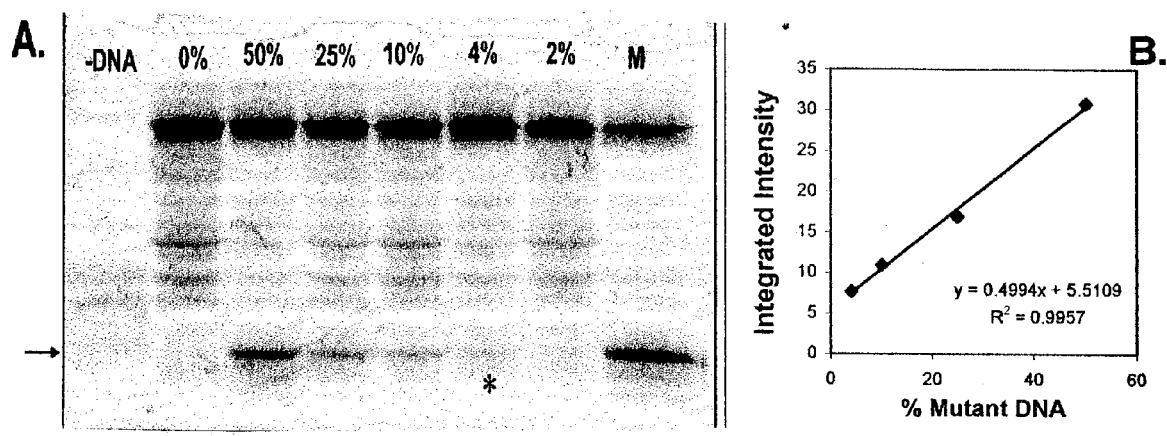
Figure 55A:
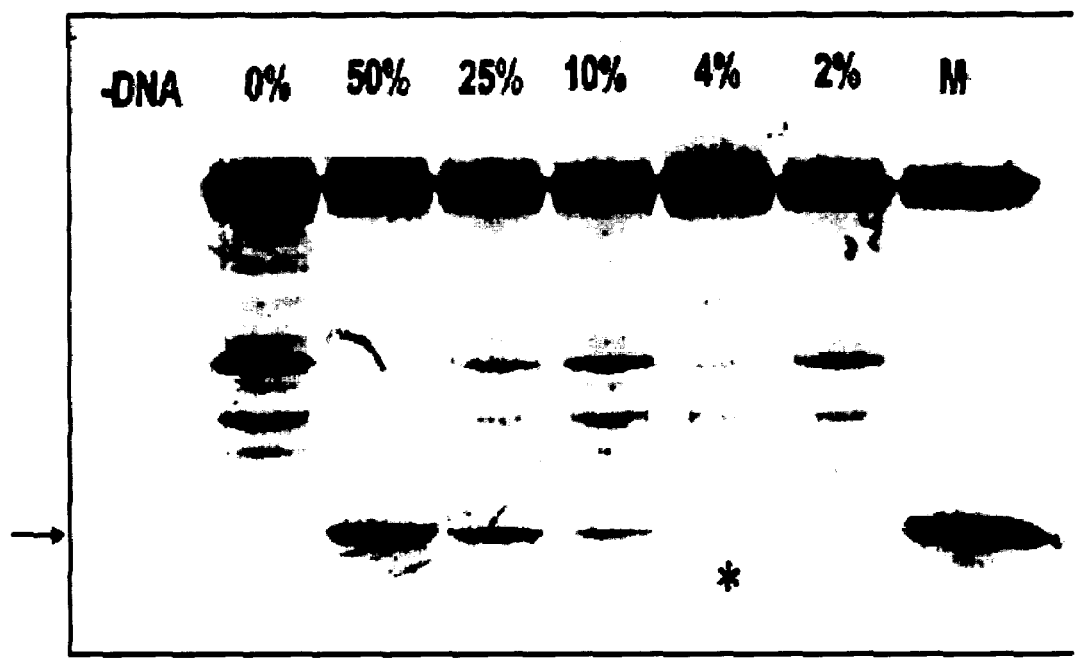

FIG. 55 demonstrates High Sensitivity Gel-Based Fluorescent PTT analysis of APC segment 2 (APC-2) for non-invasive colorectal cancer screening. Panel A: 0%, 50%, 25%, 10%, 4% and 2% represent mixtures of Wild-Type to mutant DNA. −DNA: Negative control without DNA. M: 100% mutant DNA. Panel B: Regression curve calculated from densitometry data.

Figure 56:
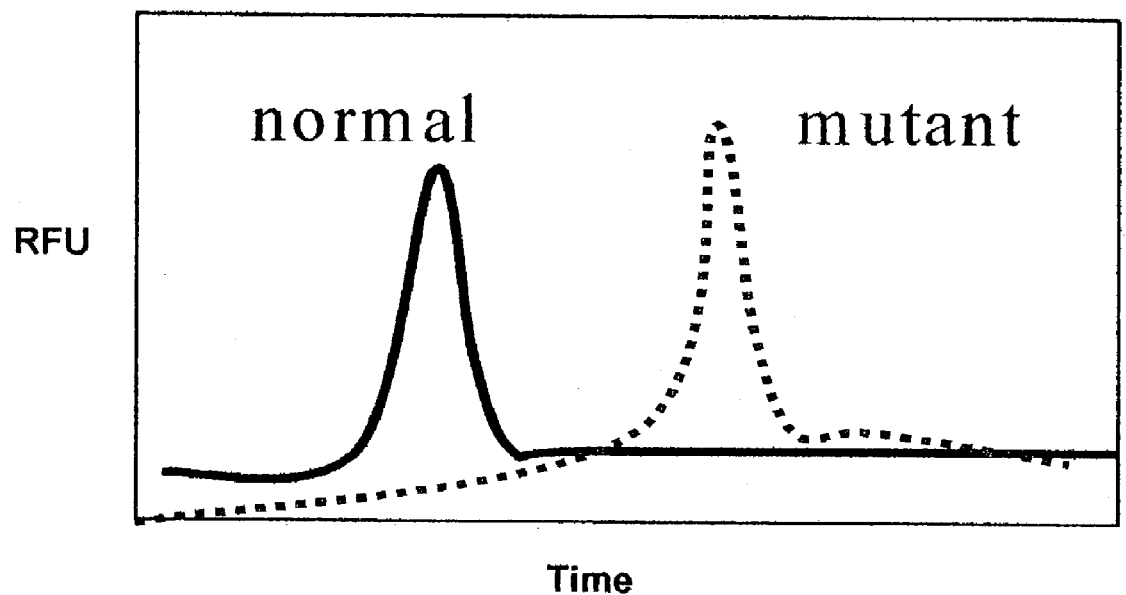

FIG. 56 shows an expected elution pattern using capillary electrophoresis.

Figure 57:
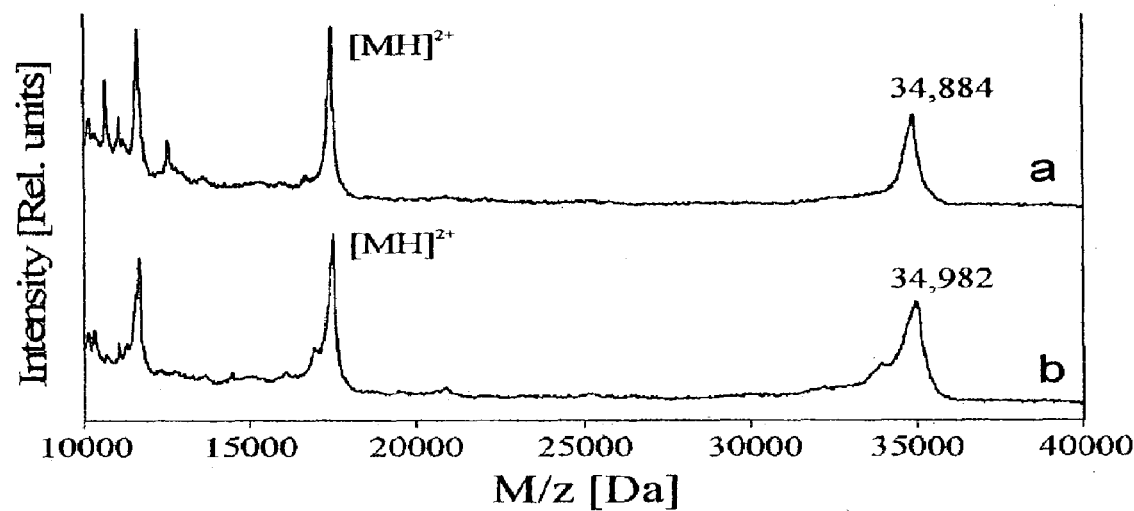

FIG. 57 displays the detection of a point mutation in in vitro expressed α-hemolysin by MALDI-TOF. Tracing a: 34,884-WT singly ionized species; [MH]$^{2+}$-WT doubly ionized species. Tracing b: 34,982-mutant singly ionized species; [MH]$^{2+}$-mutant doubly ionized species.

Figure 58:
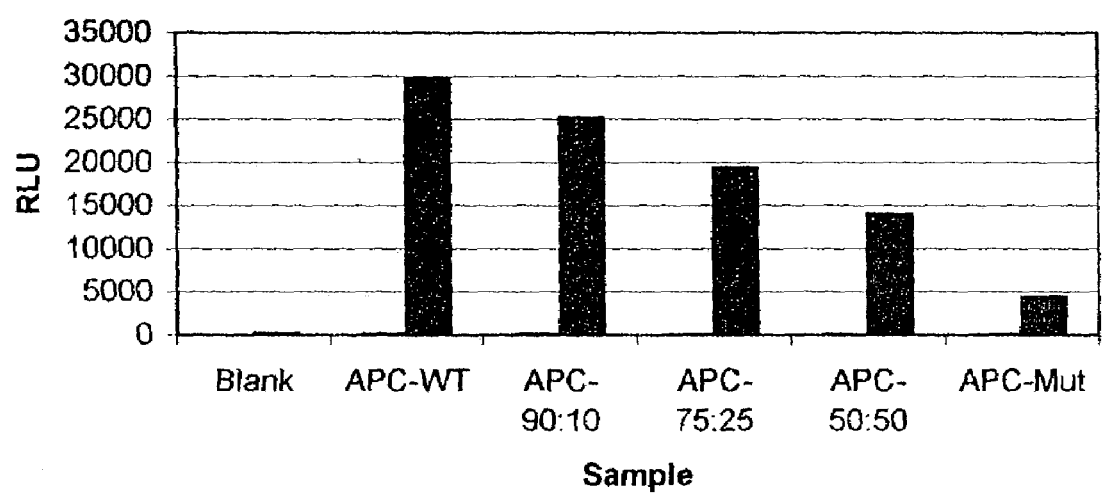

FIG. 58 compares the signal strength of equal amounts of VSV sandwich antibody detection (grey bars) with VSV-HRP directly conjugated antibody detection (black bars) in 100% WT, 90% WT:10% Mutant, 75% WT:25% Mutant, 50% WT:50% Mutant, and 100% Mutant samples.

Figure 59:
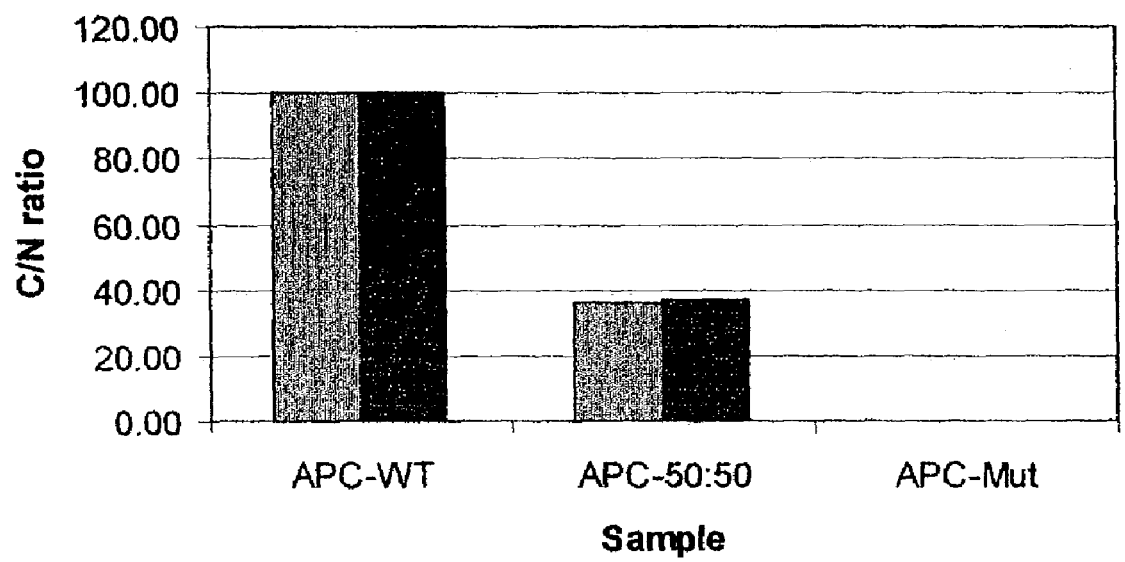

FIG. 59 compares the 2-Step ELISA (grey bars) with the 1-Step ELISA (black bars).

Figure 60:
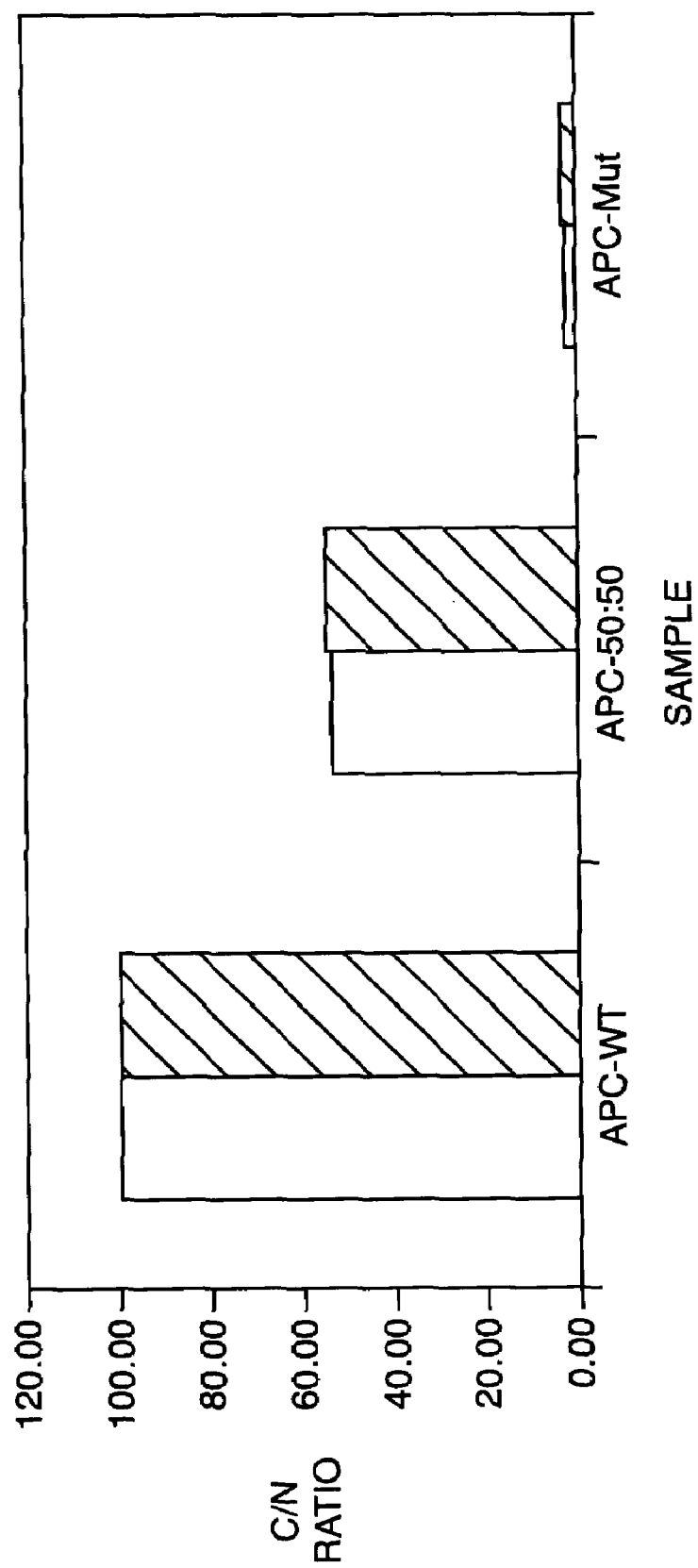

FIG. 60 depicts C/N ratios after separate antibody incubation (grey bars) or mixed antibody incubation (black bars).

Figure 61:
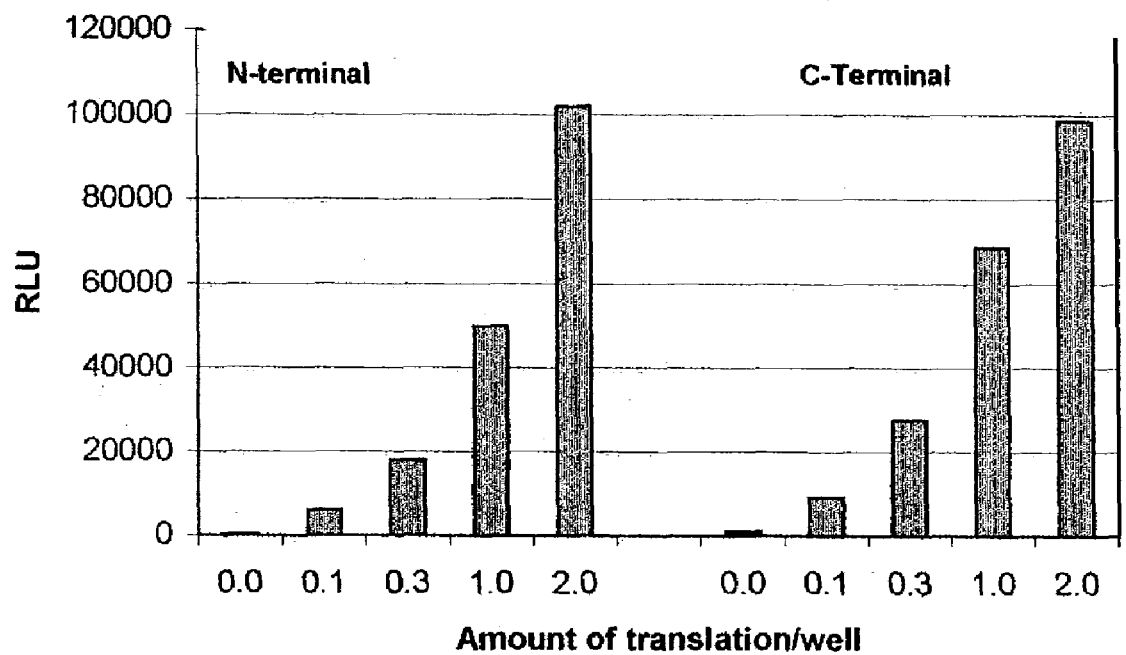

FIG. 61 demonstrates the high sensitivity of ELISA-PTT. C-terminal and N-terminal data from samples containing from between 0-2 μl of translation mix are shown.

Figure 62:
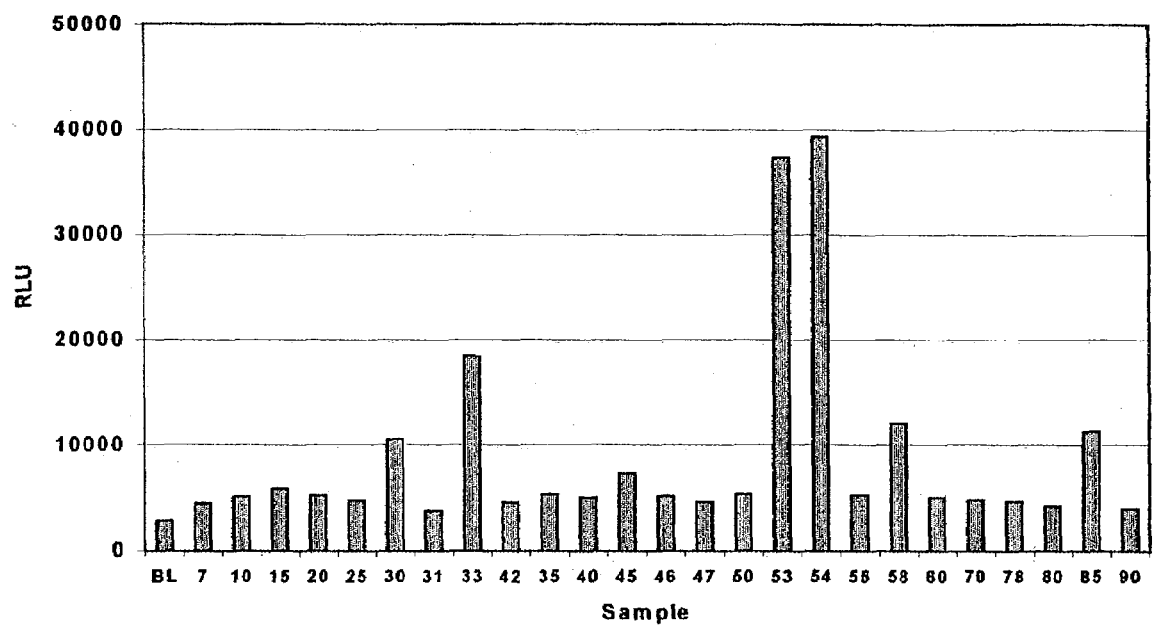

FIG. 62 illustrates the application of ELISA to rapid screening of cDNA library expression.

Figure 63:
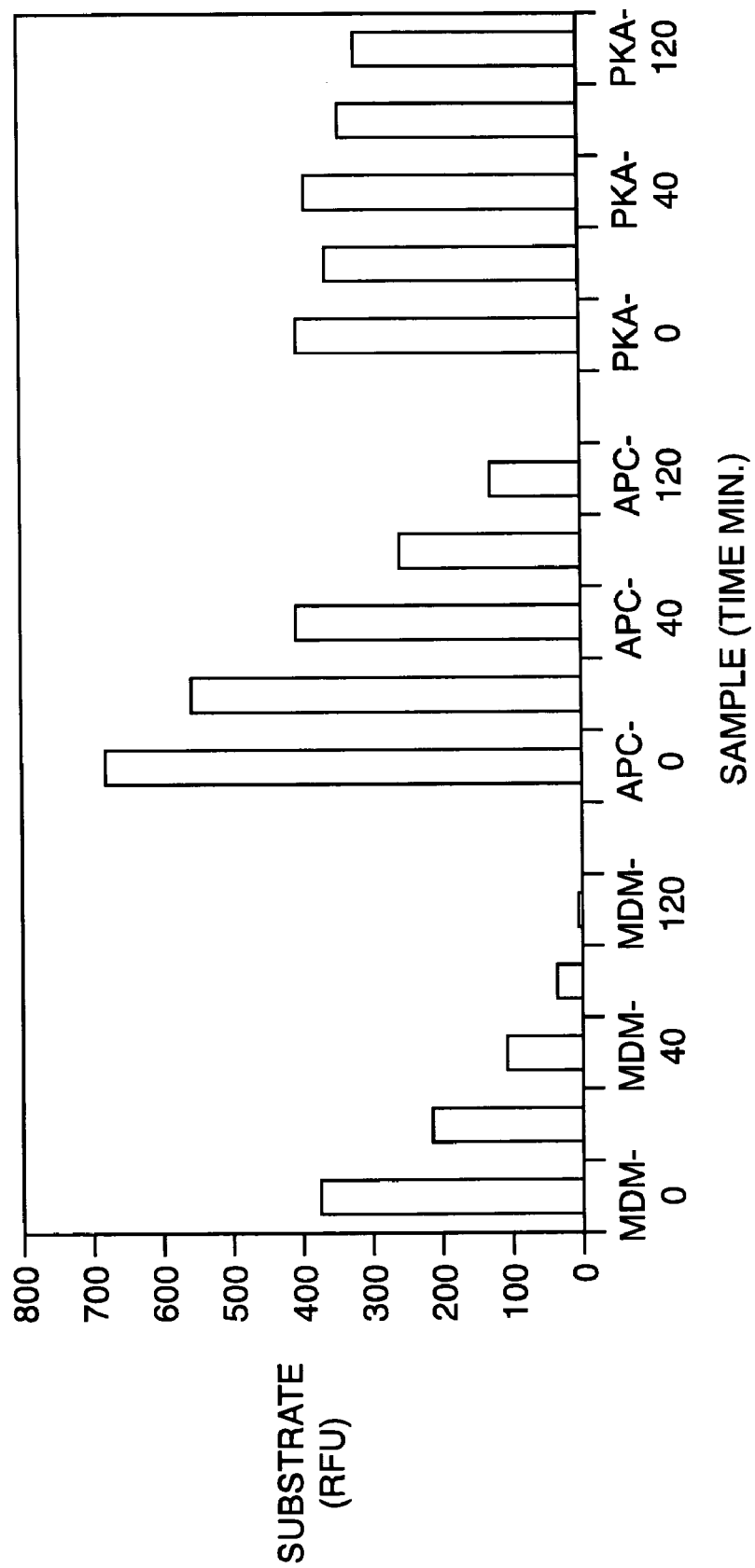

FIG. 63 provides data showing a time course of protease substrate degradation monitored by ELISA.

Figure 64:
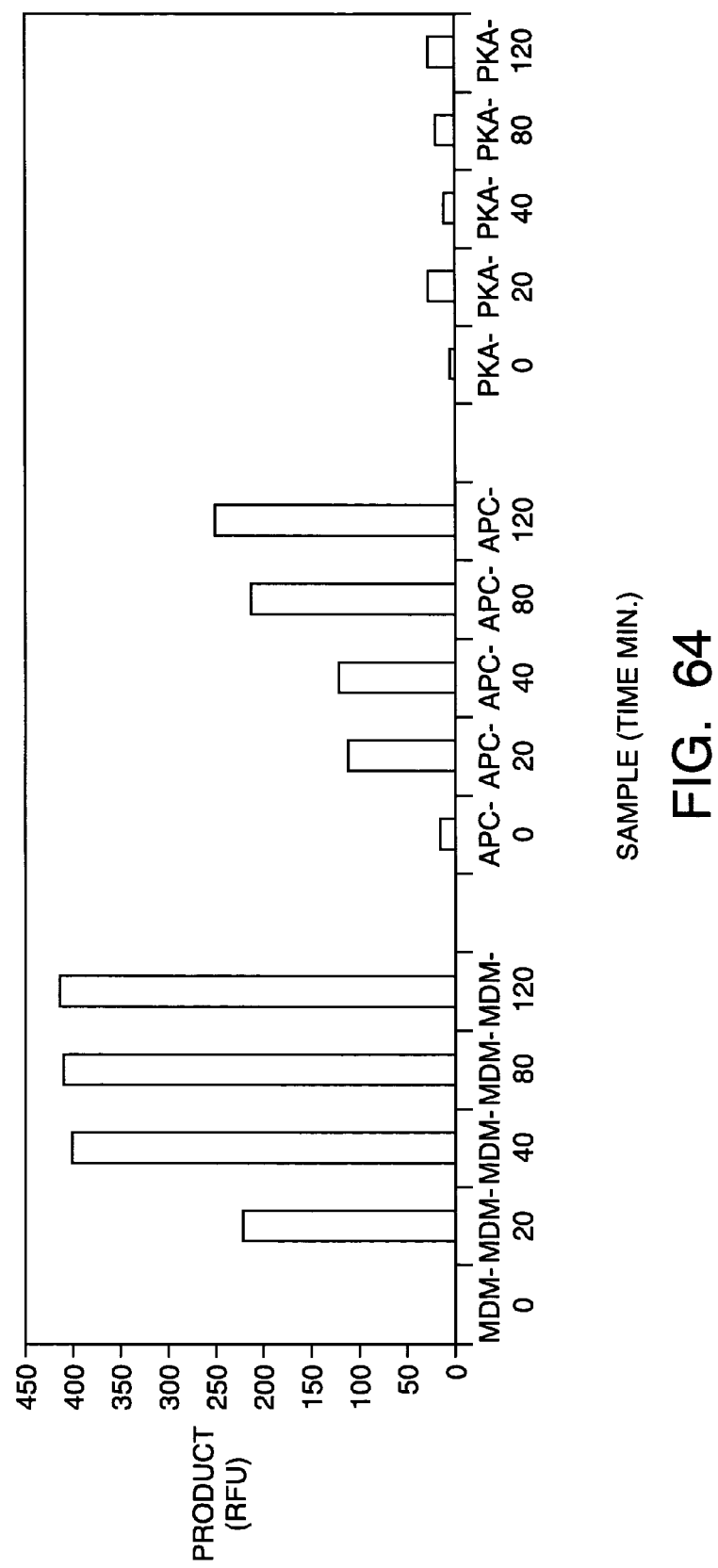

FIG. 64 provides data showing a time course of product appearance during caspase-3 digestion using C-terminal tags monitored by ELISA.

Figure 65:
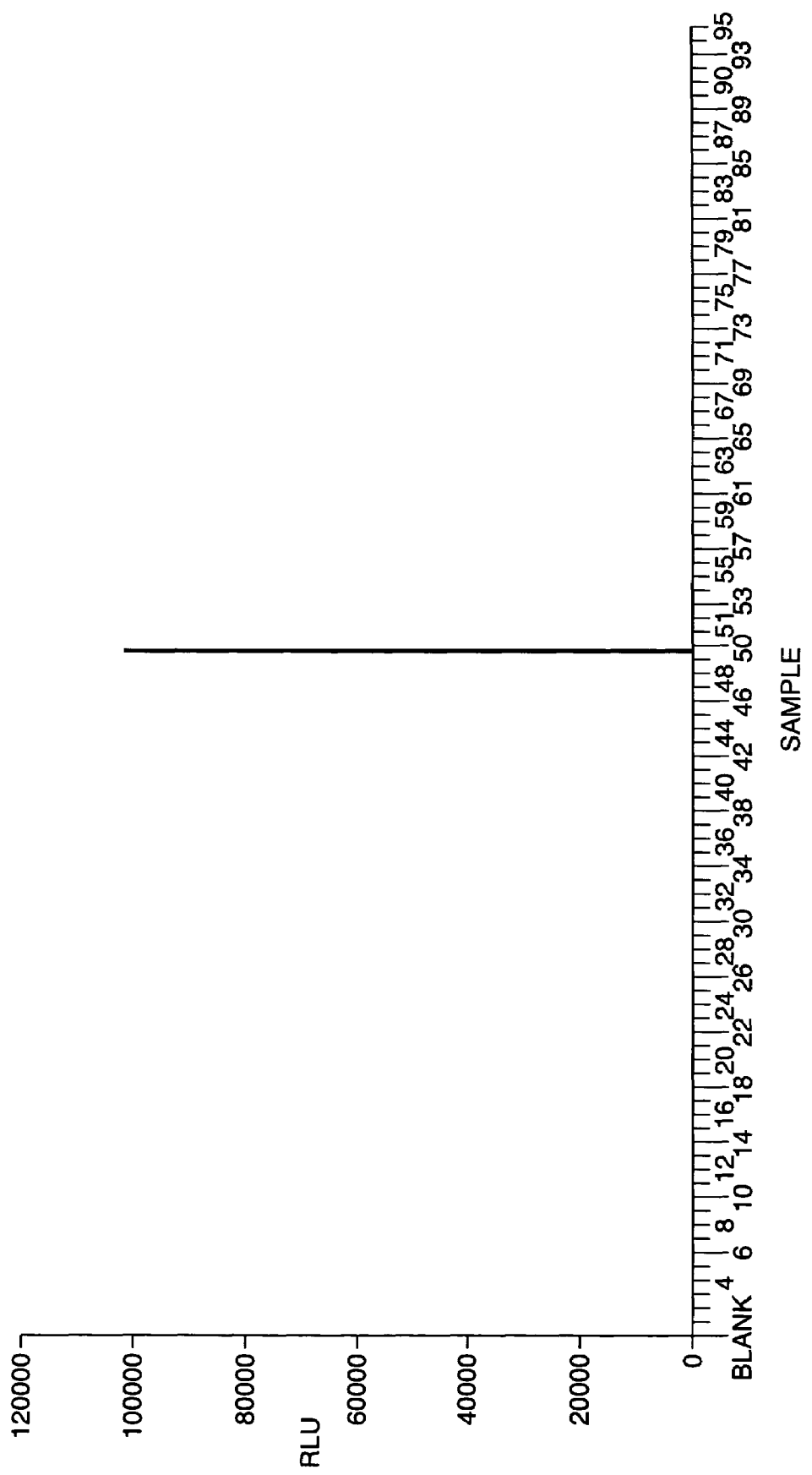

FIG. 65 exemplifies the use of ELISA in monitoring plasmid expression by enzyme markers.

Figure 66:
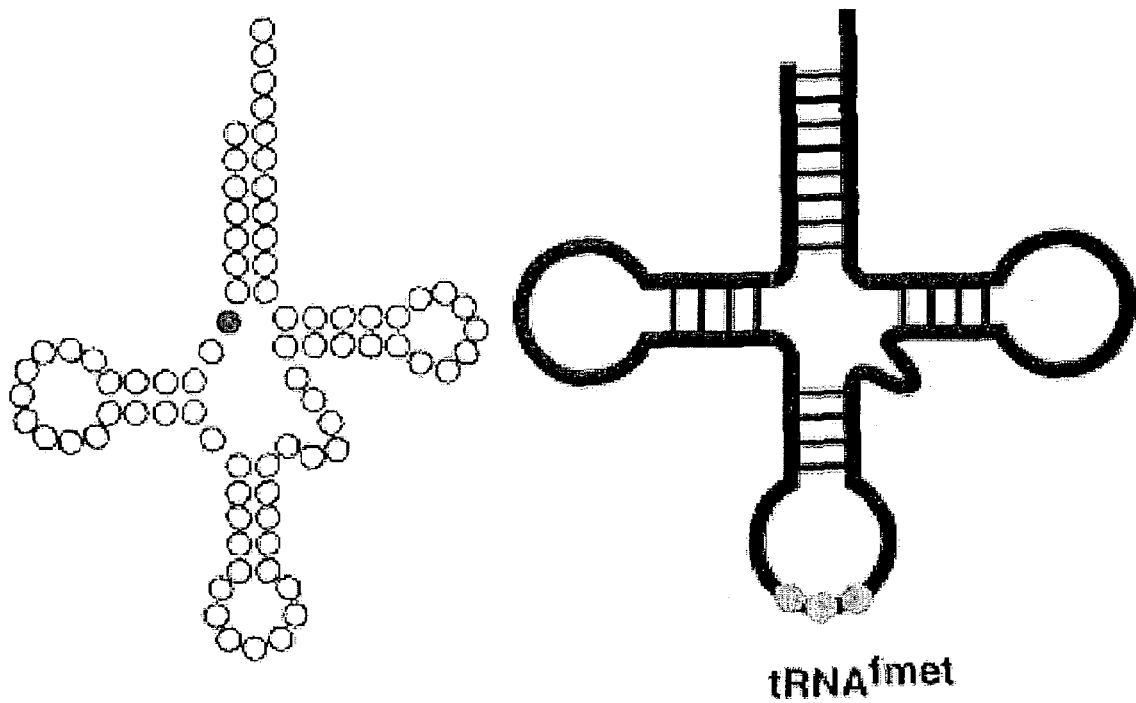

FIG. 66 shows an schematic for an E. coli initiator tRNA comprising a fluorescent reporter group such as 4-thio-uridine (black dot).

Figure 67:
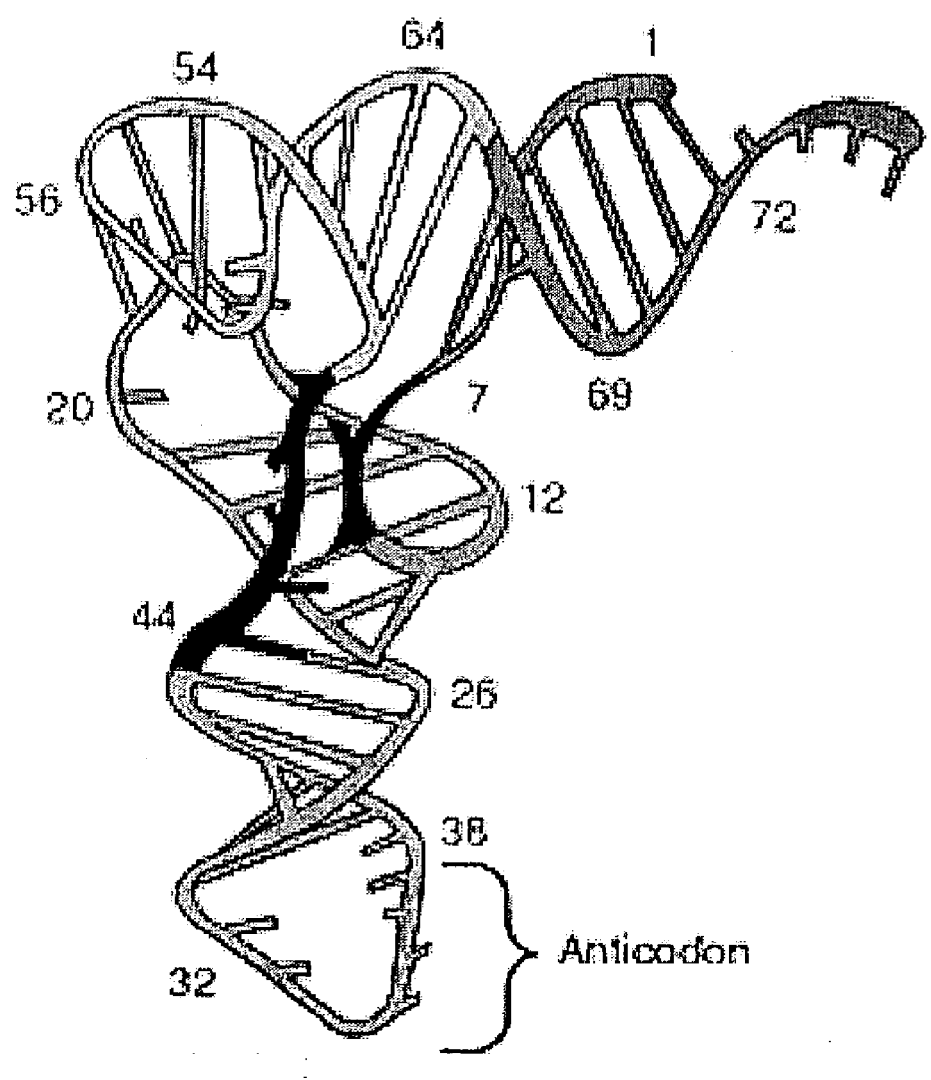

FIG. 67 shows one possible tertiary structure for an E. coli initiator tRNA.

Figure 69:
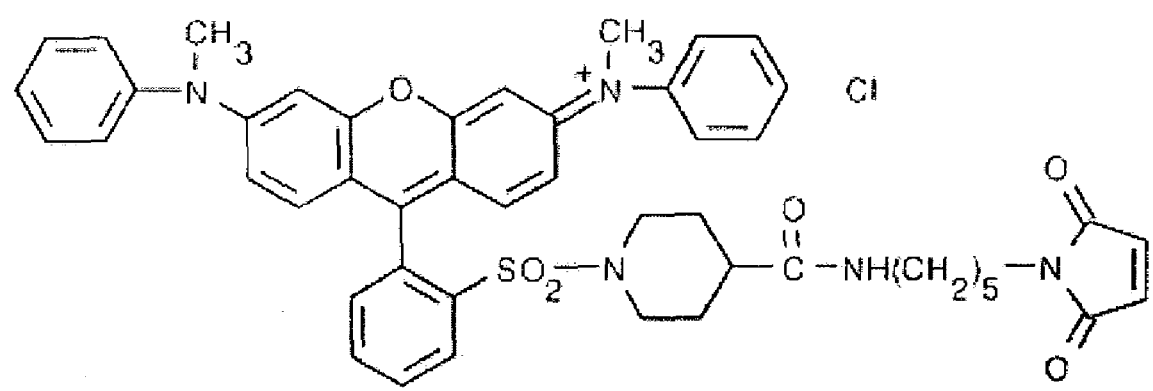

FIG. 68 provides several exemplary quencher-fluorescent pairs identifying their respective R$_0$ values FIG. 69 shows the structure of QSY® 7 maleimide (Q-10257) exemplifying one embodiment of a fluorescent reporter.

FIG. 70 displays the amino acid sequence for the full-length wild-type cellular tumor antigen p53 (Accession No.: DNHU53) (SEQ ID NO:49).

FIG. 71 displays the nucleic acid sequence of the human phosphoprotein p53 gene exon 11 encoding the full length wild-type cellular tumor antigen p53 (Accession No.: M13121 N00032) (SEQ ID NO:50).

DESCRIPTION OF THE INVENTION

As embodied and described herein, the present invention comprises methods for the non-radioactive labeling and detection of the products of new or nascent protein synthesis, and methods for the isolation of these nascent proteins from preexisting proteins in a cellular or cell-free translation system. As radioactive labels are not used, there are no special measures which must be taken to dispose of waste materials. There is also no radioactivity danger or risk which would prevent further utilization of the translation product as occurs when using radioactive labels and the resulting protein product may be used directly or further purified. In addition, no prior knowledge of the protein sequence or structure is required which would involve, for example, unique suppressor tRNAs. Further, the sequence of the gene or mRNA need not be determined. Consequently, the existence of non-sense codons or any specific codons in the coding region of the mRNA is not necessary. Any tRNA can be used, including specific tRNAs for directed labeling, but such specificity is not required. Unlike post-translational labeling, nascent proteins are labeled with specificity and without being subjected to post-translational modifications which may effect protein structure or function.

One embodiment of the invention is directed to a method for labeling nascent proteins synthesized in a translation system. These proteins are labeled while being synthesized with detectable markers which are incorporated into the peptide chain. Markers which are aminoacylated to tRNA molecules, may comprise native amino acids, non-native amino acids, amino acid analogs or derivatives, or chemical moieties. These markers are introduced into nascent proteins from the resulting misaminoacylated tRNAs during the translation process. Aminoacylation is the process whereby a tRNA molecule becomes charged. When this process occurs in vivo, it is referred to as natural aminoacylation and the resulting product is an aminoacylated tRNA charged with a native amino acid. When this process occurs through artificial means, it is called misaminoacylation and a tRNA charged with anything but a native amino acid molecule is referred to as a misaminoacylated tRNA.

According to the present method, misaminoacylated tRNAs are introduced into a cellular or cell-free protein synthesizing system, the translation system, where they function in protein synthesis to incorporate detectable marker in place of a native amino acid in the growing peptide chain. The translation system comprises macromolecules including RNA and enzymes, translation, initiation and elongation factors, and chemical reagents. RNA of the system is required in three molecular forms, ribosomal RNA (rRNA), messenger RNA (mRNA) and transfer RNA (tRNA). mRNA carries the genetic instructions for building a peptide encoded within its codon sequence. tRNAs contain specific anti-codons which decode the mRNA and individually carry amino acids into position along the growing peptide chain. Ribosomes, complexes of rRNA and protein, provide a dynamic structural framework on which the translation process, including translocation, can proceed. Within the cell, individualized aminoacyl tRNA synthetases bind specific amino acids to tRNA molecules carrying the matching anti-codon creating aminoacylated or charged tRNAs by the process of aminoacylation. The process of translation including the aminoacylation or charging of a tRNA molecule is described in *Molecular Cell Biology* (J. Darnell et al. editors, Scientific American Books, N.Y., N.Y. 1991), which is hereby specifically incorporated by reference. Aminoacylation may be natural or by artificial means utilizing native amino acids, non-native amino acid, amino acid analogs or derivatives, or other molecules such as detectable chemicals or coupling agents. The resulting misaminoacylated tRNA comprises a native amino acid coupled with a chemical moiety, non-native amino acid, amino acid derivative or analog, or other detectable chemicals. These misaminoacylated tRNAs incorporate their markers into the growing peptide chain during translation forming labeled nascent proteins which can be detected and isolated by the presence or absence of the marker.

Any proteins that can be expressed by translation in a cellular or cell-free translation system may be nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known. Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors.

Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

Site-directed incorporation of the normative analogs into the protein during translation is also not required. Incorporation of markers can occur anywhere in the polypeptide and can also occur at multiple locations. This eliminates the need for prior information about the genetic sequence of the translated mRNA or the need for modifying this genetic sequence.

In some cases, it may be desirable to preserve the functional properties of the nascent protein. A subset of tRNAs which will incorporate markers at sites which do not interfere with protein function or structure can be chosen. Amino acids at the amino or carboxyl terminus of a polypeptide do not alter significantly the function or structure. tRNA molecules which recognize the universal codon for the initiation of protein translation (AUG), when misaminoacylated with marker, will place marker at the amino terminus. Prokaryotic protein synthesizing systems utilize initiator tRNA$^{fMet}$ molecules and eukaryotic systems initiator tRNA$^{Met}$ molecules. In either system, the initiator tRNA molecules are aminoacylated with markers which may be non-native amino acids or amino acid analogs or derivatives that possess marker, reporter or affinity properties. The resulting nascent proteins will be exclusively labeled at their amino terminus, although markers placed internally do not necessarily destroy structural or functional aspects of a protein. For example, a tRNA$^{Lys}$ may be misaminoacylated with the amino acid derivative dansyllysine which does not interfere with protein function or structure. In addition, using limiting amounts of misaminoacylated tRNAs, it is possible to detect and isolate nascent proteins having only a very small fraction labeled with marker which can be very useful for isolating proteins when the effects of large quantities of marker would be detrimental or are unknown.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example tRNA$^{fMet}$, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334-338', 1987). Run-off transcription allows for the production of any specific tRNA in high purity, but its applications can be limited due to lack of post-transcriptional modifications (Bruce and Uhlenbeck, Biochemistry 21:3921, 1982).

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4° C. to −70° C. The method of preparing such reaction mixtures is described by J. M. Pratt (*Transcription and Translation*, B. D. Hames and S. J. Higgins, Editors, p. 209, IRL Press, Oxford, 1984) which is hereby incorporated by reference. Many different translation systems are commercially available from a number of manufacturers.

The misaminoacylated tRNA is added directly to the reaction mixture as a solution of predetermined volume and concentration. This can be done directly prior to storing the reaction mixture at −70° C. in which case the entire mixture is thawed prior to initiation of protein synthesis or prior to the initiation of protein synthesis. Efficient incorporation of markers into nascent proteins is sensitive to the final pH and magnesium ion concentration. Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 μg/ml to about 1.0 mg/ml, preferably at between about 10 μg/ml to about 500 μg/ml, and more preferably at about 150 μg/ml.

Initiation of protein synthesis occurs upon addition of a quantity of mRNA or DNA to the reaction mixture containing the misaminoacylated tRNAs. mRNA molecules may be prepared or obtained from recombinant sources, or purified from other cells by procedure such as poly-dT chromatography. One method of assuring that the proper ratio of the reaction mixture components is to use predetermined volumes that are stored in convenient containers such as vials or standard microcentrifuge tubes. For example, DNA and/or mRNA coding for the nascent proteins and the misaminoacylated tRNA solution are premixed in proper amounts and stored separately in tubes. Tubes are mixed when needed to initiate protein synthesis.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162-64, 1988). This process may be desirable for large scale production of nascent proteins. Incubations may also be performed using a dialysis system where consumable reagents are available for the translation system in an outer reservoir which is separated from larger components of the translation system by a dialysis membrane [Kim, D., and Choi, C. (1996) *Biotechnol Prog* 12, 645-649]. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, Hepes or another suitable buffering agent to maintain the pH of the solution between about 6 to 8, and preferably at about 7. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In cellular protein synthesis, it is necessary to introduce misaminoacylated tRNAs or markers into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner et al., Proc. Natl. Acad. Sci. USA 84:7413-17, 1987), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Useful detergents include Nonidet-P 40 (NP40), Triton X-100 (TX- 100) or deoxycholate at concentrations of about 0.01 nM to 1.0 mM, preferably between about 0.1 µM to about 0.01 mM, and more preferably about 1 µM. Permeabilized cells allow marker to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker could be introduced to cells and incorporated into translated product.

Figure 4:
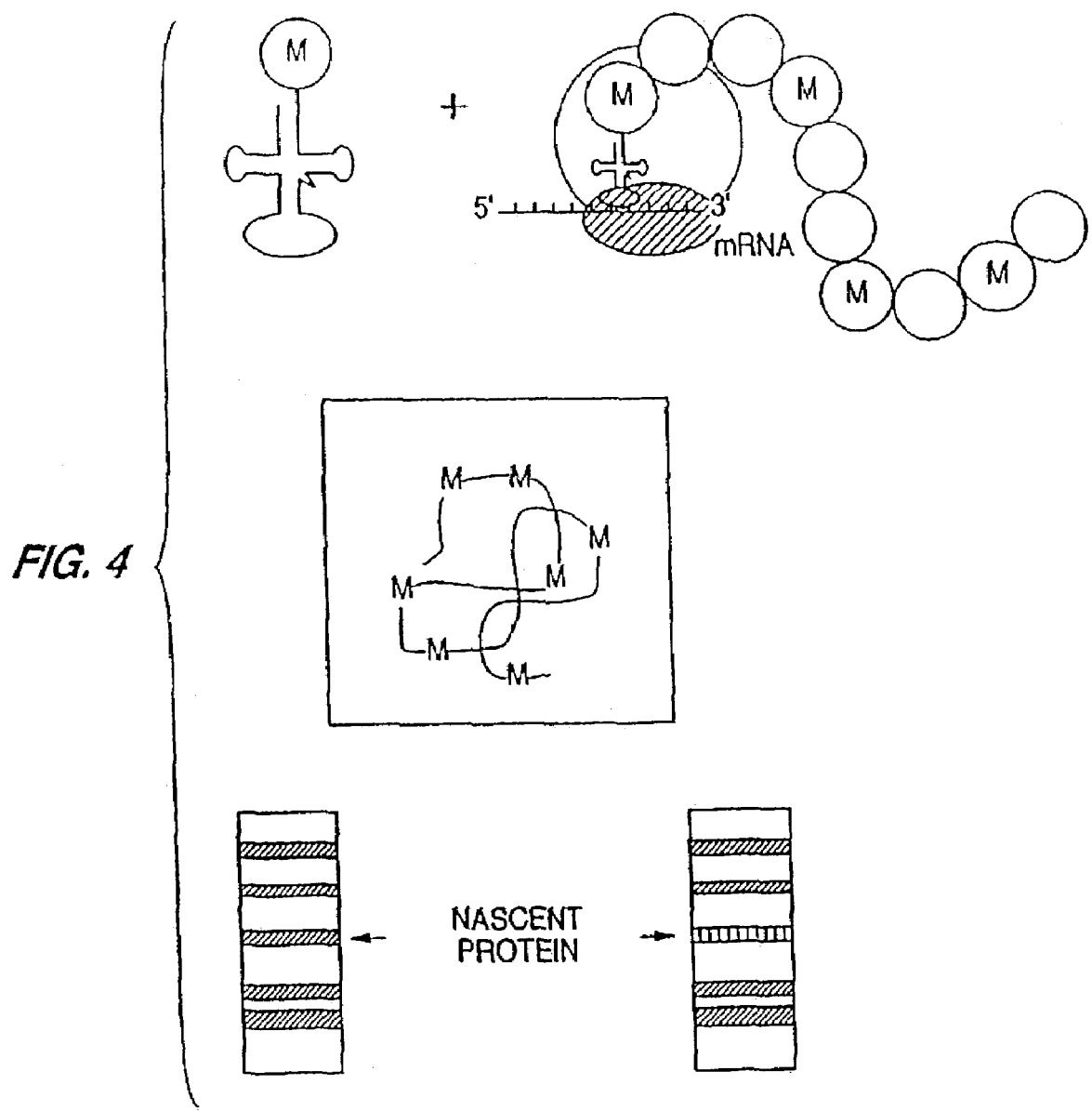
FIG. 4 is a schematic representation of the method of detecting nascent proteins using fluorescent marker amino acids.

One example of the use of misaminoacylation to detect nascent protein is schematically represented in FIG. 4. A tRNA molecule is misaminoacylated with the marker which is highly fluorescent when excited with UV (ultraviolet) radiation. The misaminoacylated tRNA is then introduced into a cell-free protein synthesis extract and the nascent proteins containing the marker analog produced. Proteins in the cell-free extract are separated by polyacrylamide gel electrophoresis (PAGE). The resulting gel contains bands which correspond to all of the proteins present in the cell-free extract. The nascent protein is identified upon UV illumination of the gel by detection of fluorescence from the band corresponding to proteins containing marker. Detection can be through visible observation or by other conventional means of fluorescence detection.

The misaminoacylated tRNA can be formed by natural aminoacylation using cellular enzymes or misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3'-terminal residues of any tRNA molecule generating tRNA-OH-3' with a mononucleotide or dinucleotide deletion from the 3'-terminus (Neu and Heppel, J. Biol. Chem. 239:2927-34, 1964). Alternatively, tRNA molecules may be genetically manipulated to delete specific portions of the tRNA gene. The resulting gene is transcribed producing truncated tRNA molecules (Sampson and Uhlenbeck, Proc. Natl. Acad. Sci. USA 85:1033-37, 1988). Next, a dinucleotide is chemically linked to a modified amino acid or other marker by, for example, acylation. Using this procedure, markers can be synthesized and acylated to dinucleotides in high yield (Hudson, J. Org. Chem. 53:617-624, 1988; Happ et al., J. Org. Chem. 52:5387-91, 1987). These modified groups are bound together and linked via the dinucleotide to the truncated tRNA molecules in a process referred to as ligase coupling (FIG. 3B).

Figure 1A:
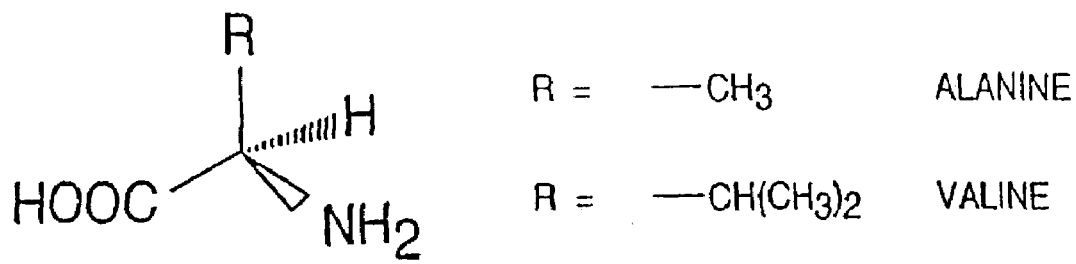
Figure 1B:
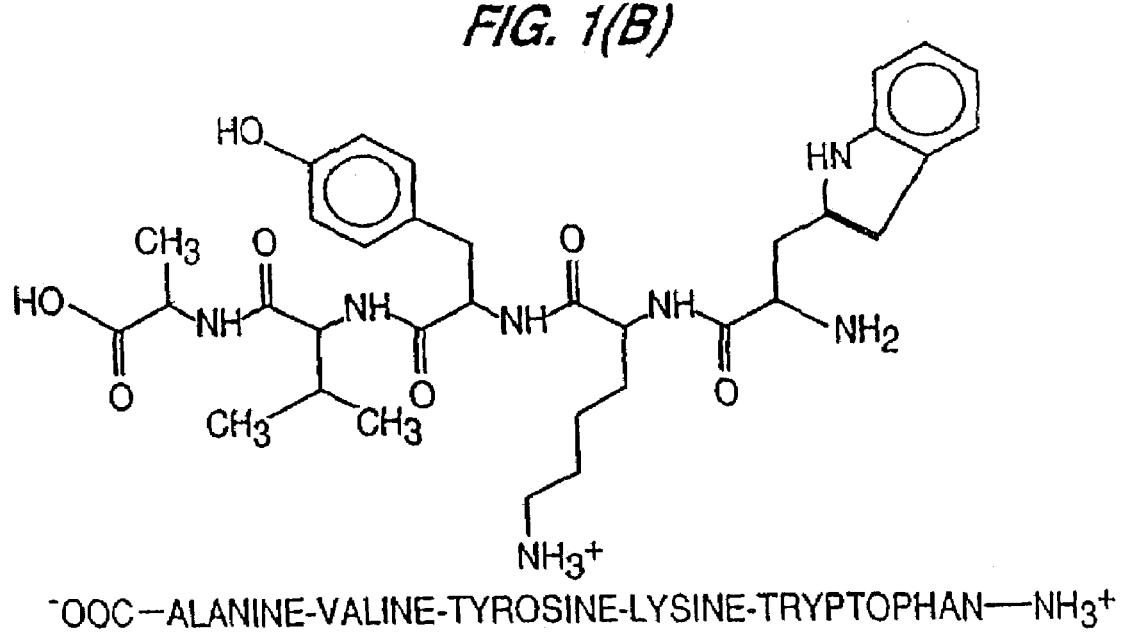
Figure 2:
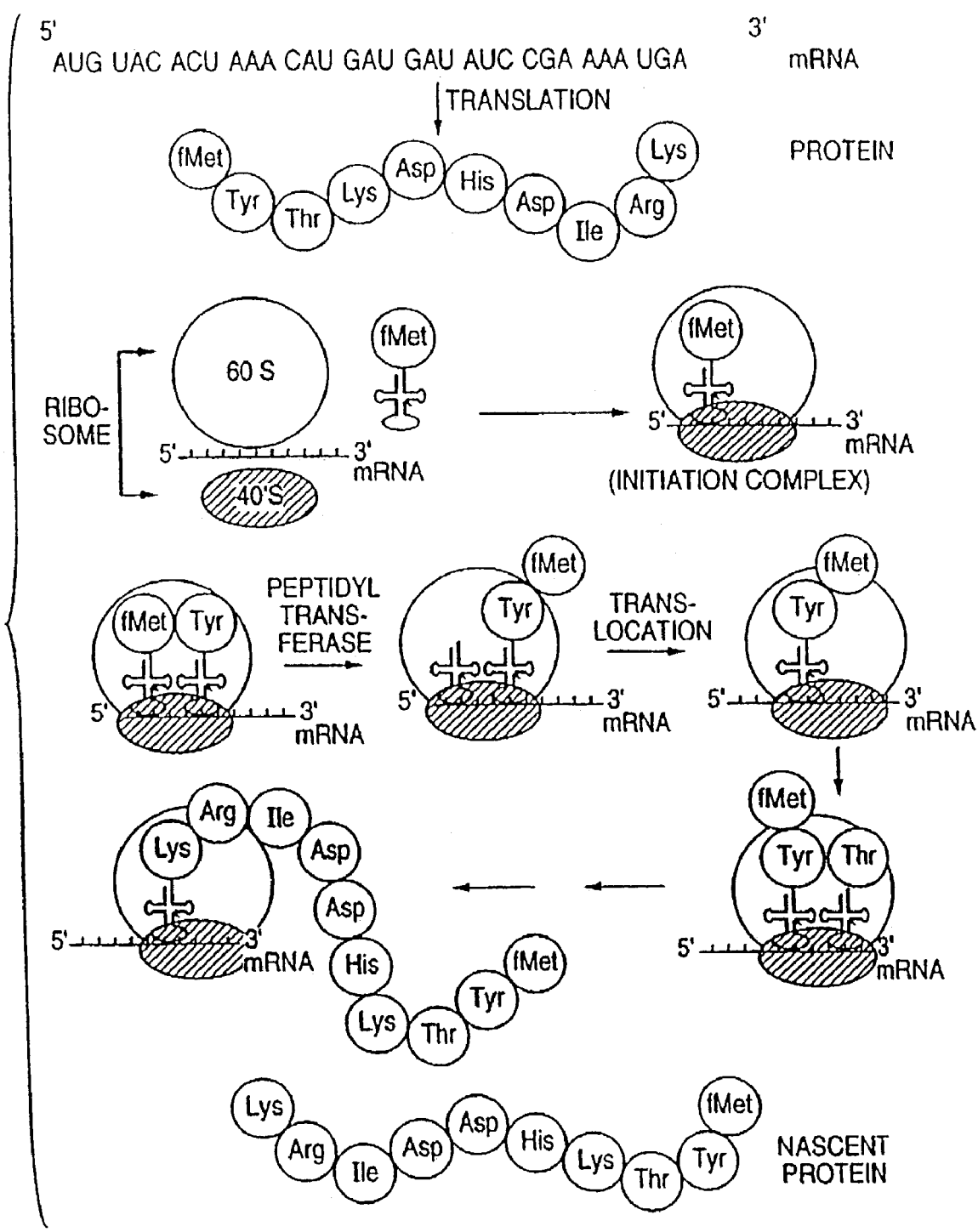
Figures 3A, 3B:
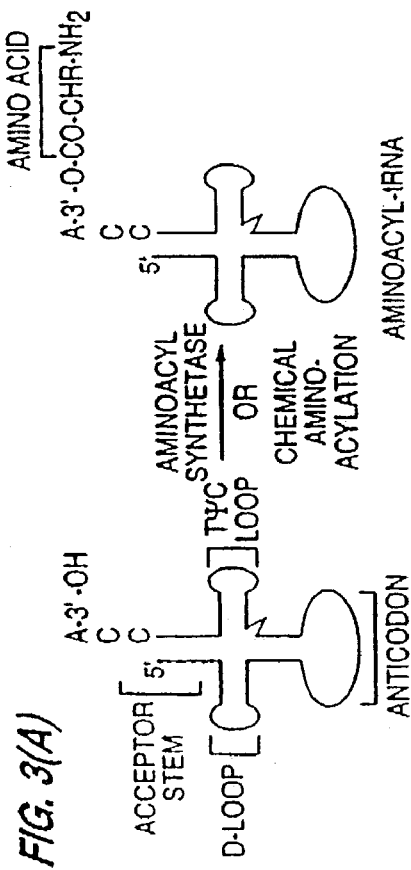
FIG. 3 shows a structure of (A) a tRNA molecule and (B) approaches involved in the aminoacylation of tRNAs.

A different bond is involved in misaminoacylation (FIG. 3B, link B) than the bond involved with activation of tRNA by aminoacyl tRNA synthetase (FIG. 3B, link A). As T4 RNA ligase does not recognize the acyl substituent, tRNA molecules can be readily misaminoacylated with few chemical complications or side reactions (link B, FIG. 3B) (T. G. Heckler et al., Biochemistry 23:1468-73, 1984; and T. G. Heckler et al., Tetrahedron 40:87-94, 1984). This process is insensitive to the nature of the attached amino acid and allows for misaminoacylation using a variety of non-native amino acids. In contrast, purely enzymatic aminoacylation (link A) is highly sensitive and specific for the structures of substrate tRNA and amino acids.

Markers are basically molecules which will be recognized by the enzymes of the translation process and transferred from a charged tRNA into a growing peptide chain. To be useful, markers must also possess certain physical and physio-chemical properties. Therefore, there are multiple criteria which can be used to identify a useful marker. First, a marker must be suitable for incorporation into a growing peptide chain. This may be determined by the presence of chemical groups which will participate in peptide bond formation. Second, markers should be attachable to a tRNA molecule. Attachment is a covalent interaction between the 3'-terminus of the tRNA molecule and the carboxy group of the marker or a linking group attached to the marker and to a truncated tRNA molecule. Linking groups may be nucleotides, short oligonucleotides or other similar molecules and are preferably dinucleotides and more preferably the dinucleotide CA. Third, markers should have one or more physical properties that facilitate detection and possibly isolation of nascent proteins. Useful physical properties include a characteristic electromagnetic spectral property such as emission or absorbance, magnetism, electron spin resonance, electrical capacitance, dielectric constant or electrical conductivity.

Useful markers are native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent, chromatic or have a distinctive mass. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids and more preferably has high quantum yield of fluorescence can be excited in both the UV and visible portion of the spectrum. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152-59, 1993). These markers are detectable at the femtomolar ranges and below.

In addition to fluorescent markers, a variety of markers possessing other specific physical properties can be used to detect nascent protein production. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity and nuclear magnetic resonances and use of a mass spectrometer to detect presence of a marker with a specific molecular mass. These electromagnetic spectroscopic properties are preferably not possessed by native amino acids or are readily distinguishable from the properties of native amino acids. For example, the amino acid tryptophan absorbs near 290 nm, and has fluorescent emission near 340 nm when excited with light near 290 nm. Thus, tryptophan analogs with absorption and/or fluorescence properties that are sufficiently different from tryptophan can be used to facilitate their detection in proteins.

Many different modified amino acids which can be used as markers are commercially available (Sigma Chemical; St.

Figure 5:
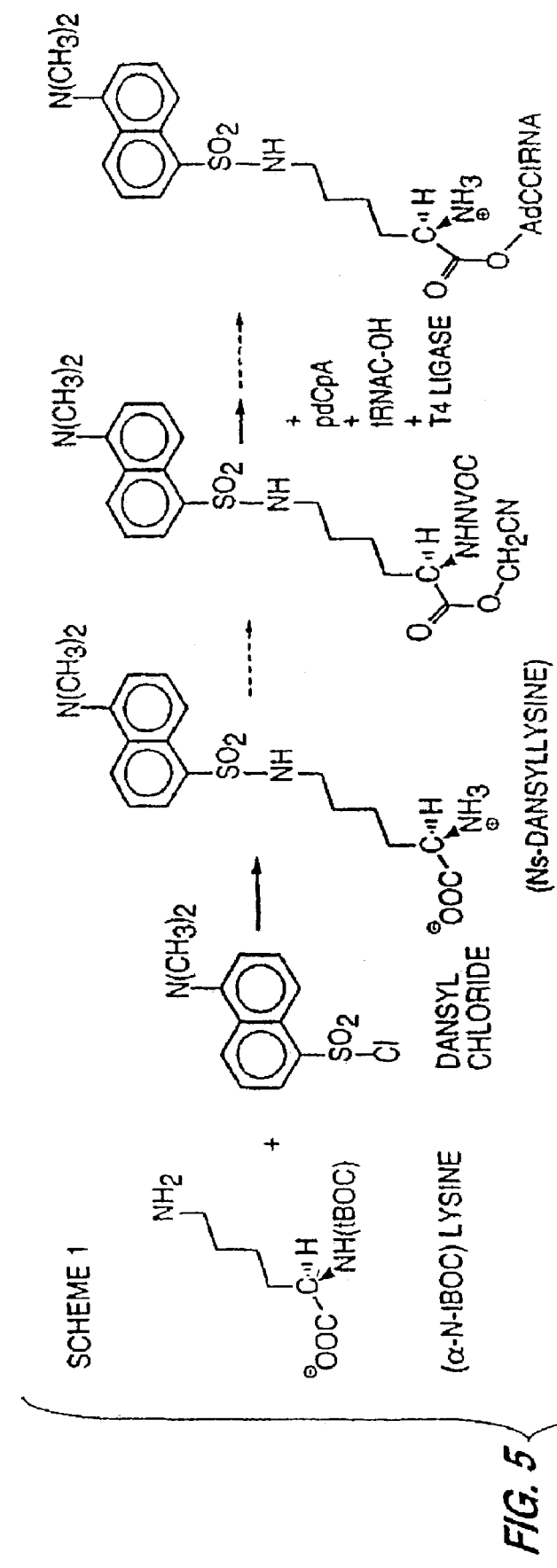
FIG. 5 shows schemes for synthesis and misaminoacylation to tRNA of two different marker amino acids, dansyll-ysine (scheme 1) and coumarin (scheme 2), with fluorescent properties suitable for the detection of nascent proteins using gel electrophoresis and UV illumination.
Figure 5:
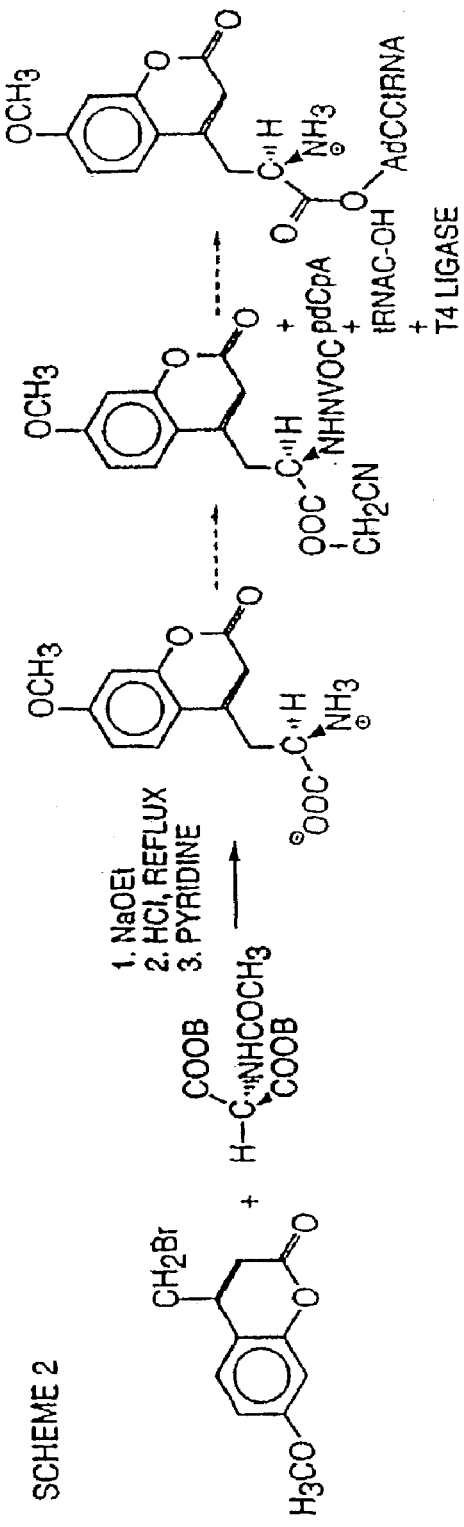

Louis, Mo.; Molecular Probes; Eugene, Oreg.). One such marker is Nε-dansyllysine created by the misaminoacylation of a dansyl fluorophore to a tRNA molecule (FIG. 5; scheme 1). The α-amino group of Nε-dansyllysine is first blocked with NVOC (ortho-nitro veratryl oxycarbonyl chloride) and the carboxyl group activated with cyanomethyl ester. Misaminoacylation is performed as described. The misaminoacylated tRNA molecules are then introduced into the protein synthesis system, whereupon the dansyllysine is incorporated directly into the newly synthesized proteins.

Another such marker is a fluorescent amino acid analog based on the highly fluorescent molecule coumarin (FIG. 5; scheme 2). This fluorophore has a much higher fluorescence quantum yield than dansyl chloride and can facilitate detection of much lower levels of nascent protein. In addition, this coumarin derivative has a structure similar to the native amino acid tryptophan. These structural similarities are useful where maintenance of the nascent proteins' native structure or function are important or desired. Coumarin is synthesized as depicted in FIG. 5 (scheme 2). Acetamidomalonate is alkylated with a slight excess of 4-bromomethyl coumarin (Aldrich Chemicals; Milwaukee; Wis.) in the presence of sodium ethoxide followed by acid hydrolysis. The corresponding amino acid as a hydrochloride salt that can be converted to the free amino acid analog.

The coumarin derivative can be used most advantageously if it misamino-acylates the tryptophan-tRNA, either enzymatically or chemically. When introduced in the form of the misaminoacylated tryptophan-tRNA, the coumarin amino acid will be incorporated only into tryptophan positions. By controlling the concentration of misaminoacylated tRNAs or free coumarin derivatives in the cell-free synthesis system, the number of coumarin amino acids incorporated into the nascent protein can also be controlled. This procedure can be utilized to control the amount of most any markers in nascent proteins.

Markers can be chemically synthesized from a native amino acid and a molecule with marker properties which cannot normally function as an amino acid. For example a highly fluorescent molecule can be chemically linked to a native amino acid group. The chemical modification can occur on the amino acid side-chain, leaving the carboxyl and amino functionalities free to participate in a polypeptide bond formation. Highly fluorescent molecules (e.g. dansyl chloride) can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

A number of factors determine the usefulness of a marker which is to be incorporated into nascent proteins through misaminoacylated tRNAs. These include the ability to incorporate the marker group into the protein through the use of a misaminoacylated tRNA in a cell-free or cellular protein synthesis system and the intrinsic detectability of the marker once it is incorporated into the nascent protein. In general, markers with superior properties will allow shorter incubation times and require smaller samples for the accurate detection of the nascent proteins. These factors directly influence the usefulness of the methods described. In the case of fluorescent markers used for the incorporation into nascent proteins, favorable properties can be but are not limited to, small size, high quantum yield of fluorescence, and stability to prolonged light exposure (bleach resistance).

Even with knowledge of the above factors, the optimum conditions to incorporate a specific marker into a protein using a specific cell-free or cellular translation system is difficult to predict a priori since it depends on the detailed interaction of the marker group with components of the protein translational synthesis system including the tRNA, initiation or elongation factors and components of the ribosome. While it is generally expected that markers with smaller sizes can be accommodated more readily into the ribosome, the exact shape of the molecule and its specific interactions in the ribosomal binding site will be the most important determinant. For this reason, it is possible that some markers which are larger in size can be more readily incorporated into nascent proteins compared to smaller markers. For example, such factors are very difficult to predict using known methods of molecular modeling.

One group of fluorophores with members possessing several favorable properties (including favorable interactions with components of the protein translational synthesis system) is the group derived from dipyrrometheneboron difluoride derivatives (BODIPY) (FIG. 19). Compared to a variety of other commonly used fluorophores with advantageous properties such as high quantum yields, some BODIPY compounds have the additional unusual property that they are highly compatible with the protein synthesis system. The core structure of all BODIPY fluorophores is 4,4-difluoro-4-bora-3a,4a-diaza-s-indacene. See U.S. Pat. Nos. 4,774,339; 5,187,288; 5,248,782; 5,274,113; 5,433,896; 5,451,663, all hereby incorporated by reference. A central feature is a difluoroboron as shown in FIG. 19. All BODIPY fluorophores have several desirable properties for a marker (Molecular Probes Catalog, pages 13-18) including a high extinction coefficient, high fluorescence quantum yield, spectra that are insensitive to solvent polarity and pH, narrow emission bandwidth resulting in a higher peak intensity compared to other dyes such as fluorescein, absence of ionic charge and enhanced photostability compared to fluorescein. The addition of substituents to the basic BODIPY structure which cause additional conjugation can be used to shift the wavelength of excitation or emission to convenient wavelengths compatible with the means of detection.

These dyes were described for the first time by Vos de Waal et al. (1977) and its fluorescence properties subsequently described by Wories [See Wories et al., "A novel water-soluble fluorescent probe: Synthesis, luminescence and biological properties of the sodium salt of the 4-sulfonato-3,3', 5,5'-tetramethyl-2,2'-pyrromethen-1,1'-BF.sub.2 complex," Recl. Trav. Chim. PAYSBAS 104, 288 (1985). Dyes derived from dipyrrometheneboron difluoride have additional characteristics that make them suitable for incorporation into nascent proteins. Simple alkyl derivatives of the fluorophore 4,4-difluoro-4-bora-3a,4a-diaza-s-indacene have been described by Treibs & Kreuzer, [Difluorboryl-komplexe von di-und tripyrrylmethenen, LIEBIGS ANNALEN CHEM. 718, 208 (1968)] and by Worries, Kopek, Lodder, & Lugtenburg, [A novel water-soluble fluorescent probe: Synthesis, luminescence and biological properties of the sodium salt of the 4-sulfonato-3,3',5,5'-tetramethyl-2,2'-pyrromethen-1,1'-BF.sub.2 complex, RECL. TRAV. CHIM. PAYS-BAS 104, 288 (1985)] as being highly fluorescent with spectral properties that are similar to fluorescein, with maximum absorbance at about 490 to 510 nm and maximum emission at about 500 to 530 nm. U.S. Pat. No. 4,774,339 to Haugland et al. (1988) ('339 patent) (hereby incorporated by reference) describes 4,4-difluoro-4-bora-3a,4a-diaza-s-indacene (dipyrrometheneboron difluoride)dyes including hydrogen, halogen, alkyl, cycloalkyl, aryl, arylalkyl, acyl, and sulfo-substituted derivatives that contain reactive groups suitable for conjugation to biomolecules, that have good photostability, and which have fluorescein-like spectra. As described in the '339 patent, and by Pavlopoulos, et al., [Laser action from a tetramethylpyrromethene-BF.sub.2 complex, APP. OPTICS 27, 4998 (1988)], the emission of the alkyl derivatives of 4,4-difluoro-4-bora-3a,4a-diaza-s-indacene fluorescent dyes clearly overlaps that of fluorescein. The overlap allows the alkyl derivatives of dipyrrometheneboron difluoride to be used with the same optical equipment as used with fluorescein-based dyes without modification of the excitation sources or optical filters. Similarly, aryl/heteroaryl substituents in the dipyrrometheneboron difluoride cause the maximum of absorbance/emission to shift into longer wavelengths (See U.S. Pat. No. 5,451,663 hereby incorporated by reference).

A variety of BODIPY molecules are commercially available in an amine reactive form which can be used to derivatize aminoacylated tRNAs to yield a misaminoacylated tRNA with a BODIPY marker moiety. One example of a compound from this family which exhibits superior properties for incorporation of a detectable marker into nascent proteins is 4,4-difluoro-5,7-dimethyl-4-bora-3a,4a-diaza-s-indacene (BODIPY-FL). When the sulfonated N-hydroxysuccinimide (NHS) derivative of BODIPY-FL is used to misaminoacylate an E. coli initiator $tRNA^{fmet}$, the nascent protein produced can be easily detected on polyacyrlamide gels after electrophoresis using a standard UV-transilluminator and photographic or CCD imaging system. This can be accomplished by using purified $tRNA^{fmet}$ which is first aminoacylated with methionine and then the α-amino group of methionine is specifically modified using N-hydroxysuccinimide BODIPY. Before the modification reaction, the $tRNA^{fmet}$ is charged maximally (>90%) and confirmed by using $^{35}$S-methionine and acid-urea gels [Varshney, U., Lee, C. P., and RajBhandary, U. L. 1991. Direct analysis of aminoacylation levels of tRNA in vitro. J. Biol. Chem. 266:24712-24718].

Less than 10 nanoliters of a commercially available E. coli extract (E. coli T7 translation system, Promega, Madison, Wis.) are needed for analysis corresponding to less than 1 ng of synthesized protein. Incubation times required to produce detectable protein is approximately 1 hour but can be as little as 5 minutes (or less). BODIPY-FL can also be detected with higher sensitivity using commercially available fluorescent scanners with 488 nm excitation and emission measurement above 520 nm. Similar tests using other commercially available dyes including NBD (7-Nitrobenz-2-Oxa-1,3-Diazole), and Pyrine-PyMPO show approximately an order of magnitude reduction in fluorescence making them more difficult to detect using standard laboratory equipment such as a UV-transilluminator or fluorescent scanner. It has previously been shown that fluorescent markers such as 3-N-(7-nitrobenz-2-oxa-1,3-diazol-4-yl)-2,3,-di-aminoproprionic acid (NBD-DAP) and coumarin could be incorporated into proteins using misaminoacylated tRNAs. However, detection of nascent proteins containing these markers was only demonstrated using highly sensitive instrumentation such a fluorescent spectrometer or a microspectrofluorometer and often require indirect methods such as the use of fluorescence resonance energy transfer (FRET) (Turcatti, G., Nemeth, K., Edgerton, M. D., Meseth, U., Talabot, F., Peitsch, M., Knowles, J., Vogel, H., and Chollet, A. (1996) J Biol Chem 271(33), 19991-8; Kudlicki, W., Odom, O. W., Kramer, G., and Hardesty, B. (1994) J Mol Biol 244(3), 319-31). Such instruments are generally not available for routine use in a molecular biology laboratory and only with special adaptation can be equipped for measurement of fluorescent bands on a gel.

An additional advantage of BODIPY-FL as a marker is the availability of monoclonal antibodies directed against it which can be used to affinity purify nascent proteins containing said marker. One example of such a monoclonal antibody is anti-BODIPY-FL antibody (Cat# A-5770, Molecular Probes, Eugene, Oreg.). This combined with the ability incorporate BODIPY-FL into nascent proteins with high efficiency relative to other commercially available markers using misaminoacylated tRNAs facilitates more efficient isolation of the nascent protein. These antibodies against BODIPY-FL can be used for quantitation of incorporation of the BODIPY into the nascent protein.

A marker can also be modified after the tRNA molecule is aminoacylated or misaminoacylated using chemical reactions which specifically modify the marker without significantly altering the functional activity of the aminoacylated tRNA. These types of post-aminoacylation modifications may facilitate detection, isolation or purification, and can sometimes be used where the modification allow the nascent protein to attain a native or more functional configuration.

Fluorescent and other markers have detectable electromagnetic spectral properties that can be detected by spectrometers and distinguished from the electromagnetic spectral properties of native amino acids. Spectrometers which are most useful include fluorescence, Raman, absorption, electron spin resonance, visible, infrared and ultraviolet spectrometers. Other markers, such as markers with distinct electrical properties can be detected by an apparatus such as an ammeter, voltmeter or other spectrometer. Physical properties of markers which relate to the distinctive interaction of the marker with an electromagnetic field is readily detectable using instruments such as fluorescence, Raman, absorption, electron spin resonance spectrometers. Markers may also undergo a chemical, biochemical, electrochemical or photochemical reaction such as a color change in response to external forces or agents such as an electromagnetic field or reactant molecules which allows its detection.

One class of fluorescent markers contemplated by the present invention is the class of small peptides that can specifically bind to molecules which, upon binding, are detectable. One example of this approach is the peptide having the sequence of WEAAAREACCRECCARA (SEQ ID NO: 4). This sequence (which contains four cysteine residues) allows the peptide to specifically bind the non-fluorescent dye molecule 4',5'-bis(1,3,2-dithioarsolan-2-yl) fluorescein (FLASH, which stands for fluorescein arsenic helix binder). This dye has the interesting property that, upon binding, it becomes fluorescent. In other words, fluorescence is observed only when this specific peptide sequence is present in the nascent protein. So by putting the peptide sequence at the N- or C-terminal, one can easily monitor the amount of protein synthesized. This peptide sequence can be introduced by designing the nucleic acid primers such that they carry a region encoding the peptide sequence.

Regardless of which class of fluorescent compounds is used, detection normally first involves physical separation of the nascent proteins from other biomolecules present in the cellular or cell-free protein synthesis system. Protein separation can be performed using, for example, gel electrophoresis or column chromatography and can be further facilitated with affinity markers which uniquely bind acceptor groups. Detection of a marker containing a fluorophore by gel electrophoresis can be accomplished using conventional fluorescence detection methods.

After protein synthesis in a cell-free system, the reaction mixture, which contains all of the biomolecules necessary for protein synthesis as well as nascent proteins, is loaded onto a gel which may be composed of polyacrylamide or agarose (R. C. Allen et al., *Gel Electrophoresis and Isoelectric Focusing of Proteins,* Walter de Gruyter, New York 1984). This mixture also contains the misaminoacylated tRNAs bearing the marker as well as uncharged tRNAs. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomassie blue staining. The migration of the protein band on the gel is a function of the molecular weight of the protein with increasing distance from the loading position being a function of decreasing molecular weight. Bands on the gel which contain nascent proteins will exhibit fluorescence when excited at a suitable wavelength. These bands can be detected visually, photographically or spectroscopically and, if desired, the nascent proteins purified from gel sections.

For example, if BODIPY-FL is used as a marker, nascent proteins will fluoresce at 510 nm when excited by UV illumination. This fluorescence can be detected visually by simply using a standard hand-held UV illuminator or a transilluminator. Approximately 10 nanograms (ng) of the protein alpha-hemolysin is detectable using this method. Also useful are electronic imaging devices which can rapidly screen and identify very low concentrations of markers such as a fluorescent scanner based on a low-temperature CCD imager. In this case as low as 0.3 ng of protein can be detected.

The molecular weight and quantity of the nascent protein can be determined by comparison of its band-position on the gel with a set of bands of proteins of predetermined molecular weight which are fluorescently labeled. For example, a nascent protein of molecular weight 25,000 could be determined because of its relative position on the gel relative to a calibration gel containing the commercially available standard marker proteins of known quantities and with known molecular weights (bovine serum albumin, 66 kD; porcine heart fumarase, 48.5 kD; carbonic anhydrase, 29 kD; β-lactoglobulin, 18.4 kD; α-lactoglobulin, 14.2 kD; Sigma Chemical; St. Louis, Mo.).

Calibration proteins may also contain a similar markers for convenient detection using the same method as the gel bearing the nascent protein. This can be accomplished in many cases by directly reacting the calibration proteins with a molecule similar to the marker. For example, the calibration proteins can be modified with dansyl chloride so as to obtain their fluorescent derivatives (R. E. Stephens, Anal. Biochem. 65, 369-79, 1975). Alternatively, the proteins could be labeled with an NHS derivitive of BODIPY-FL. These fluorescent proteins can be analyzed using PAGE. Combined detection of these fluorescent calibration proteins along with that of nascent protein which contains fluorescent marker analog will accurately determine both the molecular weight and quantity of the nascent protein synthesized. If necessary, the amounts of marker within each calibration and nascent protein can be determined to provide an accurate quantitation. Proteins with predetermined levels of fluorescent markers can be used advantageously to provide for quantitation of the gel bearing the nascent protein. This could be accomplished by genetically engineering a calibration protein so that it contains a specific reactive residue such as cysteine so that only one fluorescent dye Will be attached per protein.

Other methods of protein separation are also useful for detection and subsequent isolation and purification of nascent proteins containing markers. For example, proteins can be separated using capillary electrophoresis, isoelectric focusing, low pressure chromatography and high-performance or fast-pressure liquid chromatography (HPLC or FPLC). In these cases, the individual proteins are separated into fractions which can be individually analyzed by fluorescent detectors at the emission wavelengths of the markers. Alternatively, on-line fluorescence detection can be used to detect nascent proteins as they emerge from the column fractionation system. A graph of fluorescence as a function of retention time provides information on both the quantity and purity of nascent proteins produced.

Another embodiment of the invention is directed to a method for labeling, detecting and, if desired, isolating and purifying nascent proteins, as described above, containing cleavable markers. Cleavable markers comprise a chemical structure which is sensitive to external effects such as physical or enzymatic treatments, chemical or thermal treatments, electromagnetic radiation such as gamma rays, x-rays, ultraviolet light, visible light, infrared light, microwaves, radio waves or electric fields. The marker is aminoacylated to tRNA molecules as before using conventional technology or misaminoacylated and added to a translation system. After incubation and production of nascent proteins, marker can be cleaved by the application of specified treatments and nascent proteins detected. Alternatively, nascent proteins may also be detected and isolated by the presence or absence of the cleaved marker or the chemical moiety removed from the marker.

One example of a cleavable marker is a photocleavable marker such as chemical compounds which contain the 2-nitrobenzyl moiety (FIG. 6A). Upon illumination, these aromatic nitro compounds undergo an internal oxidation-reduction reaction (Pillai, Synthesis 1-26, 1980; Patchornik et al., *J. Am. Chem. Soc.* 92:6333-35, 1970). As a result, the nitro group is reduced to a nitroso group and an oxygen is inserted into the benzylic carbon-hydrogen bond at the ortho position. The primary photochemical process is the intramolecular hydrogen abstraction by the excited nitro group. This is followed by an electron-redistribution process to the aci-nitro form which rearranges to the nitroso product. Subsequent thermal reaction leads to the cleavage of substrate from the nitrobenzyl linkage (FIG. 6B). Examples of other cleavable markers are shown in FIG. 7.

It may sometimes be desirable to create a distance between the substrate and the cleavable moiety. To accomplish this, cleavable moieties may be separated from substrates by cross-linker arms. Cross-linkers increase substrate access and stabilize the chemical structure, and can be constructed using, for example, long alkyl chains or multiple repeat units of caproyl moieties linked via amide linkages.

There are as many methods to synthesize cleavable markers as there are different markers. One example for the synthesis of photocleavable biotins based on nitrobenzyl alcohols involves four major steps. 2-bromo-2'-nitroacetphenone, a precursor of the photoreactive moiety, is first converted into an α- or ω-amino acid like ε-aminocaprylic acid. The resulting acid and amino functionality of the photoreactive group is coupled using dicyclohexyl carbodiimide (DCC). The benzoyl carbonyl group of the resulting amide is reduced using sodium borohydride. The resulting derivative of nitrobenzyl alcohol is derivatized to obtain the final component which is able to react with biomolecular substrates, for example by the reaction with phosgene gas, to introduce the chloroformate functionality. The resulting compound is depicted in FIG. 8A along with alternative derivatives of PCB. Possible linkages to amino acids are depicted in FIG. 8B.

Cleavable markers can facilitate the isolation of nascent proteins. For example, one type of a cleavable marker is photocleavable biotin coupled to an amino acid. This marker can be incorporated into nascent proteins and the proteins purified by the specific interaction of biotin with avidin or streptavidin. Upon isolation and subsequent purification, the biotin is removed by application of electromagnetic radiation and nascent proteins utilized in useful applications without the complications of an attached biotin molecule. Other examples of cleavable markers include photocleavable coumarin, photocleavable dansyl, photocleavable dinitrophenyl and photocleavable coumarin-biotin. Photocleavable markers are cleaved by electromagnetic radiation such as UV light, peptidyl markers are cleaved by enzymatic treatments, and pyrenyl fluorophores linked by disulfide bonds are cleaved by exposure to certain chemical treatments such as thiol reagents.

Cleavage of photocleavable markers is dependent on the structure of the photoreactive moiety and the wavelength of electromagnetic radiation used for illumination. Other wavelengths of electromagnetic radiation should not damage the proteins or other chemical moieties. In the case of unsubstituted 2-nitrobenzyl derivatives, the yield of photolysis and recovery of the substrate are significantly decreased by the formation of side products which act as internal light filters and are capable to react with amino groups of the substrate. Typical illumination times vary from 1 to about 24 hours and yields are 1-95%. Radiation sources are placed within about 10 cm of the substrate proteins and set on low power so as to minimize side reactions, if any, which may occur in the nascent proteins. In the case of alpha-substituted 2-nitrobenzyl derivatives (methyl, phenyl, etc.), a considerable increase in rate of photo-removal as well as yield of the released substrate are observed. The introduction of other electron donor groups into phenyl rings of photoreactive moieties increases the yield of substrate. The general reaction for the photolysis of PCB is depicted in FIG. 9.

For enzymatic cleavage, markers introduced contain specific bonds which are sensitive to unique enzymes of chemical substances. Introduction of the enzyme or chemical into the protein mixture cleaves the marker from the nascent protein. When the marker is a modified amino acid, this can result in the production of native protein forms. Thermal treatments of, for example, heat sensitive chemical moieties operate in the same fashion. Mild application of thermal energy, such as with microwaves or radiant heat, cleaves the sensitive marker from the protein without producing any significant damage to the nascent proteins.

DESCRIPTION OF PREFERRED EMBODIMENTS

Nonsense or frameshift mutations, which result in a truncated gene product, are prevalent in a variety of disease-related genes. Den Dunnen et al., *The Protein Truncation Test: A Review.* Hum Mutat 14:95-102 (1999). Specifically, these diseases include: i) APC (colorectal cancer), Powell et al., *Molecular Diagnosis Of Familial Adenomatous Polyposis.* N Engl J Med 329:1982-1987 (1993); van der Luijt et al., *Rapid Detection Of Translation-Terminating Mutations At The Adenomatous Polyposis Coli (APC) Gene By Direct Protein Truncation Test.* Genomics 20:1-4 (1994); Traverso et al., *Detection Of APC Mutations In Fecal DNA From Patients With Colorectal Tumors.* N Engl J Med 346:311-320 (2002); Kinzler et al., *Identification Of A Gene Located At Chromosome 5q21 That Is Mutated In Colorectal Cancers.* Science 251:1366-1370 (1991); and Groden et al., *Identification And Characterization Of The Familial Adenomatous Polyposis Coli Gene.* Cell 66:589-600 (1991); ii) BRCA1 and BRCA2 (breast and ovarian cancer), Hogervosrt et al., *Rapid Detection Of BRCA1 Mutations By The Protein Truncation Test.* Nat Genet 10:208-212 (1995); Garvin et al., *A Complete Protein Truncation Test For BRAC1 and BRAC2.* Eur J Hum Genet 6:226-234 (1998); Futreal et al., *BRAC1 Mutations In Primary Breast And Ovarian Carcinomas.* Science 266:120-122 (1994); iii) polycystic kidney disease, Peral et al., *Identification Of Mutations In the Duplicated Region Of The Polycystic Kidney Disease 1 Gene (PKD1) By A Novel Approach.* Am J. Hum Genet 60:1399-1410 (1997); iv) neurofibromatosis (NF1 and NF2), Hein et al., *Distribution Of 13 Truncating Mutations In The Neurofibromatosis 1 Gene.* Hum Mol Genet 4:975-981 (1995); Parry et al, *Germ-line Mutations In The Neurofibromatosis 2 Gene: Correlations With Disease Severity And Retinal Abnormalities.* Am J Hum Genet 59:529-539 (1996).; and v) Duchenne muscular dystrophy (DMD), Roest et al., *Protein Truncation Test (PTT) To Rapidly Screen The DMD gene For Translation Terminating Mutations.* Neuromuscul Disord 3:391-394 (1993). Such chain truncating mutations can be detected using the protein truncation test (PTT). This test is based on cell-free coupled transcription-translation of PCR (RT-PCR) amplified portions of the target gene (target mRNA) followed by analysis of the translated product(s) for shortened polypeptide fragments. However, conventional PTT is not easily adaptable to high throughput applications since it involves SDS-PAGE followed by autoradiography or Western blot. It is also subject to human error since it relies on visual inspection to detect mobility shifted bands. To overcome these limitations, we have developed the first high throughput solid-phase protein truncation test (HTS-PTT). HTS-PTT uses a combination of misaminoacylated tRNAs (Rothschild et al., *tRNA-Mediated Protein Engineering.* Curr Opin Biotechnol 10:64-70 (1999); and Gite et al, *Ultrasensitive Fluorescence-Based Detection Of Nascent Proteins In Gels.* Anal Biochem 279:218-225 (2000)), which incorporate affinity tags for surface capture of the cell-free expressed protein fragments, and specially designed PCR primers, which introduce N- and C-terminal markers for measuring the relative level of shortened polypeptide produced by the chain truncation mutation. After cell-free translation of the protein fragments, capture and detection is accomplished in a single-well using a standard 96-well microtiter plate ELISA format and chemiluminescence readout. The technique is demonstrated for the detection of chain truncation mutations in the APC gene using DNA or RNA from cancer cell lines as well as DNA of individuals pre-diagnosed with familial adenomatous polyposis (FAP). HTP-PTT can also provide a high throughput method for non-invasive colorectal cancer screening when used in conjunction with methods of enriching/amplifying low-abundance mutant DNA. Traverso et al. (2002).

A. Detection of Mutations

Detection of mutations is an increasingly important area in clinical diagnosis, including but not limited to the diagnosis of cancer and/or individuals disposed to cancer. The protein truncation test (PTT) is a technique for the detection of nonsense and frameshift mutations which lead to the generation of truncated protein products. Genes associated with Duchenne muscular dystrophy, adenomatous polyposis coli, human mutL homologue and human nutS homologue (both involved in colon cancer), and BRAC1 (involved in familial breast cancer) can now be screened for mutations in this manner, along with others (see Table 1).

Typically, the PTT technique involves the incorporation of a T7 promoter site, ribosome binding site, and an artificial methionine start site into a PCR product covering the region of the gene to be investigated. The PCR product is then transcribed and translated using either an in vitro rabbit reticulocyte lysate or wheat germ lysate system, to generate a protein corresponding to the region of the gene amplified. The presence of a stop codon in the sequence, generated by a nonsense mutation or a frameshift, will result in the premature termination of protein translation, producing a truncated protein that can be detected by standard gel electrophoresis (e.g. SDS-PAGE) analysis combined with radioactive detection.

There are drawbacks to the technique as currently practiced. One of the most important problems involves the identification of the product of interest. This is made difficult because of nonspecific radiolabeled products. Attempts to address these problems have been made. One approach is to introduce an affinity tag after the start site and before the region encoding the gene of interest. See Rowan and Bodmer, "Introduction of a myc Reporter Taq to Improve the Quality of Mutation Detection Using the Protein Truncation Test," *Human Mutation* 9:172 (1997). However, such approaches still have the disadvantage that they rely on electrophoresis.

The present invention contemplates a gel-free truncation test (GFTT), wherein two or three markers are introduced into the nascent protein. The present invention contemplates both pre-natal and post-natal testing to determine predisposition to disease. In a preferred embodiment of the invention, the novel compositions and methods are directed to the detection of frameshift or chain terminating mutations. In order to detect such mutations, a nascent protein is first synthesized in a cell-free or cellular translation system from message RNA or DNA coding for the protein which may contain a possible mutation. The nascent protein is then separated from the cell-free or cellular translation system using an affinity marker located at or close to the

TABLE 1

Applications of PTT in Human Molecular Genetics

| Disease References | % Truncating Mutations | Gene |
| --- | --- | --- |
| Familial Adenomatous Polyposis | 95% | APC |
| Hereditary desmold disease | 100% | APC |
| Ataxia telangiectasia | 90% | ATM |
| Hereditary Breast and Ovarian Cancer | 90% | BRCA1 |
|  | 90% | BRCA2 |
| Cystic Fibrosis | 15% | CFTR |
| Duchenne Muscular Dystrophy | 95% | DMD |
| Emery-Dreifuss Muscular Dystrophy | 80% | EMD |
| Fanconi anaemia | 80% | FAA |
| Hunter Syndrome | ~50% | IDS |
| Hereditary non-polyposis colorectal cancer | ~80% | hMSH2 |
|  | ~70% | hMLH1 |
| Neurofibromatosis type 1 | 50% | NF1 |
| Neurofibromatosis type 2 | 65% | NF2 |
| Polycystic Kidney Disease | 95% | PKD1 |
| Rubinstein-Taybi Syndrome | 10% | RTS |

The percentage of truncating mutations reported which should be detectable using PTT.

N-terminal end of the protein. The protein is then analyzed for the presence of a detectable marker located at or close to the N-terminal of the protein (N-terminal marker). A separate measurement is then made on a sequence dependent detectable marker located at or close to the C-terminal end of the protein (C-terminal marker).

A comparison of the measurements from the C-terminal marker and N-terminal marker provides information about the fraction of nascent proteins containing frameshift or chain terminating mutations in the gene sequence coding for the nascent protein. The level of sequence dependent marker located near the C-terminal end reflects the fraction of protein which did not contain chain terminating or out-of-frame mutations. The measurement of the N-terminal marker provides an internal control to which measurement of the C-terminal marker is normalized. Normalizing the level of the C-terminal marker to the N-terminal marker eliminates the inherent variabilities such as changes in the level of protein expression during translation that can undermine experimental accuracy. Separating the protein from the translation mixture using an using an affinity marker located at or close to the N-terminal end of the protein eliminates the occurrence of false starts which can occur when the protein is initiated during translation from an internal AUG in the coding region of the message. A false start can lead to erroneous results since it can occurs after the chain terminating or out-of-frame mutation. This is especially true if the internal AUG is in-frame with the message. In this case, the peptide C-terminal marker will still be present even if message contains a mutation.

In one example, a detectable marker comprising a non-native amino acid or amino acid derivative is incorporated into the nascent protein during its translation at the amino terminal (N-terminal end) using a misaminoacylate initiator tRNA which only recognizes the AUG start codon signaling the initiation of protein synthesis. One example of a detectable marker is the highly fluorescent compound BODIPY FL. The marker might also be photocleavable such as photocleavable coumarin or photocleavable biotin. The nascent protein is then separated from the cell-free or cellular translation system by using a coupling agent which binds to an affinity marker located adjacent to the N-terminal of the protein. One such affinity marker is a specific protein sequence known as an epitope. An epitope has the property that it selectively interacts with molecules and/or materials containing acceptor groups. There are many epitope sequences reported in the literature including H is ×6 (HHH-HHH) (SEQ ID NO: 5) described by ClonTech and C-myc (−EQKLISEEDL) (SEQ ID NO:6) described by Roche-BM, Flag (DYKDDDDK) (SEQ ID NO:7) described by Stratagene), SteptTag (WSHPQFEK) (SEQ ID NO:8) described by Sigma-Genosys and HA Tag (YPYDVPDYA) (SEQ ID NO:9) described by Roche-BM.

Once the nascent protein is isolated from the translation system, it is analyzed for presence of the detectable marker incorporated at the N-terminal of the protein. In the case of BODIPY FL, it can be detected by measuring the level of fluorescence using a variety of commercially available instrument such as a Molecular Dynamics Model 595 fluorescence scanner that is equipped with excitation at 488 nm and an emission filter that allows light above 520 nm to be transmitted to the detector.

The protein is then analyzed for the presence of a sequence specific marker located near the C-terminal end of the protein. In normal practice, such a sequence specific marker will consist of a specific sequence of amino acids located near the C-terminal end of the protein which is recognized by a coupling agent. For example, an antibody can be utilized which, is directed against an amino acid sequence located at or near C-terminal end of the nascent protein can be utilized. Such antibodies can be labeled with a variety of markers including fluorescent dyes that can be easily detected and enzymes which catalyze detectable reactions that lead to easily detectable substrates. The marker chosen should have a different detectable property than that used for the N-terminal marker. An amino acid sequence can also comprise an epitope which is recognized by coupling agents other than antibodies. One such sequence is 6 histidines sometimes referred to as a his-tag which binds to cobalt complex coupling agent.

A variety of N-terminal markers, affinity markers and C-terminal markers are available which can be used for this embodiment. The N-terminal marker could be BODIPY, affinity marker could be StrepTag and C-terminal marker could be a His×6 tag. In this case, after translation, the reaction mixture is incubated in streptavidin coated microtiter plate or with streptavidin coated beads. After washing unbound material, the N-terminal marker is directly measured using a fluorescence scanner while the C-terminal marker can be quantitated using anti-his×6 antibodies conjugated with a fluorescent dye (like rhodamine or Texas Red) which has optical properties different than BODIPY, thus facilitating simultaneous dual detection.

In a different example, the N-terminal marker could be a biotin or photocleavable biotin incorporated by a misaminoacylated tRNA, the affinity marker could be a His ×6 tag and the C-terminal had C-myc marker. In this case, after the translation, the reaction mixture is incubated with metal chelating beads or microtiter plates (for example Talon, ClonTech). After washing the unbound proteins, the plates or beads can be subjected to detection reaction using streptavidin conjugated fluorescence dye and C-myc antibody conjugated with other fluorescent dye. In addition, one can also use chemiluminescent detection method using antibodies which are conjugated with peroxidases.

It will be understood by those skilled in the area of molecular biology and biochemistry that the N-terminal marker, affinity marker and C-terminal marker can all consist of epitopes that can be incorporated into the nascent protein by designing the message or DNA coding for the nascent protein to have a nucleic acid sequence corresponding to the particular epitope. This can be accomplished using known methods such as the design of primers that incorporate the desired nucleic acid sequence into the DNA coding for the nascent protein using the polymerase chain reaction (PCR). It will be understood by those skilled in protein biochemistry that a wide variety of detection methods are available that can be used to detect both the N-terminal marker and the C-terminal markers. Additional examples include the use of chemiluminescence assays where an enzyme which converts a non-chemiluminescent substrate to a chemiluminescent product is conjugated to an antibody that is directed against a particular epitope.

One example of this approach is based on using a luminometer to measure luminescent markers. A biotin detectable marker is incorporated at the N-terminal using a misaminoacylated tRNA. The biotin is detected by using a streptavidin which is conjugated to *Renilla* luciferase from sea pansy. The C-terminal sequence comprises an epitope which interacts with a binding agent that has attached firefly luciferase. After separation of the nascent protein using a distinct epitope located near the N-terminal end of the protein, the protein is subjected to a dual luminescent luciferase assay based on a procedure described by Promega Corp and known as the Dual-Luciferase® Reporter Assay. This assay consists of first adding Luciferase Assay Reagent II available from Promega Corp. to the isolated nascent protein and then measuring the level of chemiluminescence. Stop & Glo® Reagent is then added which simultaneously quenches the firefly luminescence and activates the *Renilla* luminescence. The luciferase assay can be performed and quantified in seconds. A comparison of the level of luminescence measured from the firefly and *Renilla* luciferase provides an indication of whether a mutation is present or not in the coding message of the nascent protein.

In an additional example, the N-terminal marker comprises an affinity marker which is incorporated at the N-terminal end of the protein during its translation using a misaminoacylated tRNA. The affinity marker interacts with a coupling agent which acts to separate the nascent protein from the translation mixture. The nascent protein also contains a detectable marker which is located adjacent or close to the N-terminal of the protein containing the affinity marker. In addition, it contains a sequence specific marker at or near the C-terminal end of the protein. The detectable markers near the N-terminal and C-terminal ends of the nascent protein are then measured and compared to detect the presence of chain terminating or out-of-frame mutations.

There are a variety of additional affinity markers, N-terminal markers and C-terminal markers available for this embodiment. The affinity marker could be biotin or photocleavable biotin, N-terminal marker could be StepTag and C-terminal the C-myc epitope. In this case, after the translation, the reaction mixture is incubated with streptavidin coated beads or microtiter plates coated with streptavidin. After washing the unbound proteins, the plates or beads can be subjected to detection reaction using anti-his 6 antibodies conjugated with a fluorescent dye (like rhodamine or Texas Red) and C-myc antibody conjugated with other another fluorescent dye such as BODIPY. In addition, one can also use chemiluminescent detection method using antibodies which are conjugated with peroxidases. Even in case of peroxidases conjugated antibodies, one can use fluorescent substrates and use FluorImager like device to quantitate N-terminal and C-terminal labels.

For optimal effectiveness, the N-terminal marker and affinity marker should be placed as close as possible to the N-terminal end of the protein. For example, if an N-terminal marker is incorporated using a misaminoacylated initiator, it will be located at the N-terminal amino acid. In this case, the affinity marker should be located immediately adjacent to the N-terminal marker. Thus, if a BODIPY marker which consists of a BODIPY conjugated to methionine is incorporated by a misaminoacylated initiator tRNA, it should be followed by an epitope sequence such as SteptTag (WSH-PQFEK) (SEQ ID NO:8) so that the entire N-terminal sequence will be BODIPY-MWSPQFEK (SEQ ID NO: 10). However, for specific cases it may be advantageous to add intervening amino acids between the BODIPY-M and the epitope sequence in order to avoid interaction between the N-terminal marker and the affinity marker or the coupling agent which binds the affinity marker. Such interactions will vary depending on the nature of the N-terminal marker, affinity marker and coupling agent.

For optimal effectiveness, the C-terminal marker should be placed as close as possible to the C-terminal end of protein. For example, if a His-X6 tag is utilized, the protein sequence would terminate with 6 His. In some cases, an epitope may be located several residues before the C-terminal end of the protein in order to optimize the properties of the nascent protein. This might occur for example, if a specific amino acid sequence is necessary in order to modify specific properties of the nascent protein that are desirable such as its solubility or hydrophobicity.

In the normal application of this method, the ratio of the measured level of N-terminal and C-terminal markers for a nascent protein translated from a normal message can be used to calculate a standard normalized ratio. In the case of a message which may contain a mutation, deviations from this standard ratio can then be used to predict the extent of mutations. For example, where all messages are defective, the ratio of the C-terminal marker to the N-terminal marker is expected to be zero. On the other hand, in the case where all messages are normal, the ratio is expected to be 1. In the case where only half of the message is defective, for example for a patient which is heterozygote for a particular genetic defect which is chain terminating or causes an out-of-frame reading error, the ratio would be ½.

There are several unique advantages of this method compared to existing techniques for detecting chain terminating or out-of-frame mutations. Normally, such mutations are detected by analyzing the entire sequence of the suspect gene using conventional DNA sequencing methods. However, such methods are time consuming, expensive and not suitable for rapid throughput assays of large number of samples. An alternative method is to utilize gel electrophoresis, which is able to detect changes from the expected size of a nascent protein. This approach, sometimes referred to as the protein truncation test, can be facilitated by using non-radioactive labeling methods such as the incorporation of detectable markers with misaminoacylated tRNAs. However, in many situations, such as high throughput screening, it would be desirable to avoid the use of gel electrophoresis which is time-consuming (typically 60-90 minutes). In the present method, the need for performing gel electrophoresis is eliminated. Furthermore, since the approach depends on comparison of two detectable signals from the isolated nascent protein which can be fluorescent, luminescent or some combination thereof, it is highly amenable to automation.

Measuring a sequence dependent marker located near the C-terminal end of the protein provides information about the presence of either a frameshift or chain terminating mutation since the presence of either would result in an incorrect sequence. The measurement of the N-terminal marker provides an internal control to which measurement of the C-terminal marker is normalized. Normalizing the level of the C-terminal marker to the N-terminal marker eliminates the inherent variabilities such as changes in the level of protein expression during translation that can undermine experimental accuracy. Separating the protein from the translation mixture using an using an affinity marker located at or close to the N-terminal end of the protein eliminates the occurrence of false starts which can occur when the protein is initiated during translation from an internal AUG in the coding region of the message. A false start can lead to erroneous results since it can occurs after the chain terminating or out-of-frame mutation. This is especially true if the internal AUG is in-frame with the message. In this case, the peptide C-terminal marker will still be present even if message contains a mutation.

B. Reporter Groups

Another embodiment of the invention is directed to a method for monitoring the synthesis of nascent proteins in a cellular or a cell-free protein synthesis system without separating the components of the system. These markers have the property that once incorporated into the nascent protein they are distinguishable from markers free in solution or linked to a tRNA. This type of marker, also called a reporter, provides a means to detect and quantitate the synthesis of nascent proteins directly in the cellular or cell-free translation system.

One type of reporters previously described in U.S. Pat. No. 5,643,722 (hereby incorporated by reference) has the characteristic that once incorporated into the nascent protein by the protein synthesizing system, they undergo a change in at least one of their physical or physio-chemical properties. The resulting nascent protein can be uniquely detected inside the synthesis system in real time without the need to separate or partially purify the protein synthesis system into its component parts. This type of marker provides a convenient non-radioactive method to monitor the production of nascent proteins without the necessity of first separating them from pre-existing proteins in the protein synthesis system. A reporter marker would also provide a means to detect and distinguish between different nascent proteins produced at different times during protein synthesis by addition of markers whose properties are distinguishable from each other, at different times during protein expression. This would provide a means of studying differential gene expression.

One example of the utilization of reporters is schematically represented in FIG. 10. A tRNA molecule is misaminoacylated with a reporter (R) which has lower or no fluorescence at a particular wavelength for monitoring and excitation. The misaminoacylated tRNA is then introduced into a cellular or cell-free protein synthesis system and the nascent proteins containing the reporter analog are gradually produced. Upon incorporation of the reporter into the nascent protein (R*), it exhibits an increased fluorescence at known wavelengths. The gradual production of the nascent protein is monitored by detecting the increase of fluorescence at that specific wavelength.

The chemical synthesis of a reporter can be based on the linkage of a chemical moiety or a molecular component having reporter properties with a native amino acid residue. There are many fluorescent molecules which are sensitive to their environment and undergo a change in the wavelength of emitted light and yield of fluorescence. When these chemical moieties, coupled to amino acids, are incorporated into the synthesized protein, their environments are altered because of a difference between the bulk aqueous medium and the interior of a protein which can causes reduced accessibility to water, exposure to charged ionic groups, reduced mobility, and altered dielectric constant of the surrounding medium. Two such examples are shown in FIG. 11.

One example of a reporter molecule is based on a fluorescent acridinium moiety and has the unique property of altering its emission properties, depending upon polarity or viscosity of the microenvironment. It has a higher quantum yield of fluorescence when subjected to hydrophobic environment and/or viscosity. Due to the hydrophobicity of the reporter itself, it is more likely to be associated with the hydrophobic core of the nascent protein after incorporation into the growing nascent polypeptide. An increase in the fluorescence intensity is a direct measure of protein synthesis activity of the translation system. Although, the environment of each reporter residue in the protein will be different, and in some cases, the reporter may be present on the surface of the protein and exposed to an aqueous medium, a net change occurs in the overall spectroscopic properties of the reporters incorporated into the protein relative to bulk aqueous medium. A change in the spectroscopic properties of only a subset of reporters in the protein will be sufficient to detect the synthesis of proteins that incorporate such reporters.

An alternative approach is to utilize a reporter which alters its fluorescent properties upon formation of a peptide bond and not necessarily in response to changes in its environment. Changes in the reporter's fluorescence as it partitions between different environments in the cell-free extract does not produce a large signal change compared to changes in fluorescence upon incorporation of the reporter into the nascent protein.

A second example of a reporter is a marker based on coumarmn such as 6,7-(4',5'-prolino)coumarin. This compound can be chemically synthesized by coupling a fluorophore like coumarin with an amino-acid structural element in such a way that the fluorophore would alter its emission or absorption properties after forming a peptide linkage (FIG. 11). For example, a proline ring containing secondary amino functions will participate in peptide bond formation similar to a normal primary amino group. Changes in fluorescence occur due to the co-planarity of the newly formed peptide group in relation to the existing fluorophore. This increases conjugation/delocalization due to the π-electrons of nitrogen-lone pair and carbonyl-group in the peptide bond. Synthesis of such compounds is based on coumarin synthesis using ethylacetoacetate (FIG. 11).

Reporters are not limited to those non-native amino acids which change their fluorescence properties when incorporated into a protein. These can also be synthesized from molecules that undergo a change in other electromagnetic or spectroscopic properties including changes in specific absorption bands in the UV, visible and infrared regions of the electromagnetic spectrum, chromophores which are Raman active and can be enhanced by resonance Raman spectroscopy, electron spin resonance activity and nuclear magnetic resonances. In general, a reporter can be formed from molecular components which undergo a change in their interaction and response to electromagnetic fields and radiation after incorporation into the nascent protein.

In the present invention, reporters may also undergo a change in at least one of their physical or physio-chemical properties due to their interaction with other markers or agents which are incorporated into the same nascent protein or are present in the reaction chamber in which the protein is expressed. The interaction of two different markers with each other causes them to become specifically detectable. One type of interaction would be a resonant energy transfer which occurs when two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. A second type of interaction would be based on electron transfer between the two different markers which can only occur when the markers are less than about 5 A. A third interaction would be a photochemical reaction between two markers which produces a new species that has detectable properties such as fluorescence. Although these markers may also be present on the misaminoacylated tRNAs used for their incorporation into nascent proteins, the interaction of the markers occurs primarily when they are incorporated into protein due to their close proximity. In certain cases, the proximity of two markers in the protein can also be enhanced by choosing tRNA species that will insert markers into positions that are close to each other in either the primary, secondary or tertiary structure of the protein. For example, a tyrosine-tRNA and a tryptophan-tRNA could be used to enhance the probability for two different markers to be near each other in a protein sequence which contains the unique neighboring pair tyrosine-tryptophan.

In one embodiment of this method, a reporter group is incorporated into a nascent protein using a misaminoacylated tRNA so that when it binds to a coupling agent, the reporter group interacts with a second markers or agents which causes them to become specifically detectable. Such an interaction can be optimized by incorporating a specific affinity element into the nascent protein so that once it interacts with a coupling agent the interaction between the reporter group and the second marker is optimized. Such an affinity element might comprise a specific amino acid sequence which forms an epitope or a normative amino acid. In one example, the reporter group is incorporated at the N-terminal of the nascent protein by using a misaminoacylated tRNA. The epitope is incorporated into the nascent protein so that when it interacts with the coupling agent the reporter comes into close proximity with a second marker which is conjugated to the coupling agent.

One type of interaction between the markers that is advantageously used causes a fluorescence resonant energy transfer which occurs when the two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. This could be accomplished, for example, by incorporating a fluorescent marker at the N-terminal end of the protein using the $E.\ coli$ initiator tRNA$^{fmet}$. An epitope is then incorporated near the N-terminal end such as the SteptTag (WSHPQFEK) (SEQ ID NO:8) described by Sigma-Genosys. Streptavidin is then conjugated using known methods with a second fluorescent marker which is chosen to efficiently undergo fluorescent energy transfer with marker 1. The efficiency of this process can be determined by calculating the a Forster energy transfer radius which depends on the spectral properties of the two markers. The marker-streptavidin complex is then introduced into the translation mixture. Only when nascent protein is produced does fluorescent energy transfer between the first and second marker occur due to the specific interaction of the nascent protein StreptTag epitope with the streptavidin.

In one preferred embodiment of the invention a fluorescent reporter group is incorporated into a nascent protein which is partially or fully quenched when misaminoacylating a tRNA. This is achieved by engineering the tRNA so that it contains a second group which effectively quenches the fluorescent reporter group (i.e. the quencher group). In one example, this method contemplates an initiator tRNA because of the presence of a modified base (4-thio-uridine; 4s-U) at position 8. (see FIG. 66) This modified base acts as a reactive group to which the quencher molecule can be attached. The quencher modified tRNA is then misaminoacylated with a methionine followed by coupling of the fluorescent reporter group to the $NH_2$ group of methionine. Similar to phenylalanine-tRNA (Phe-tRNA), modification with a fluorophore of a 4s-U nucleotide at base position 8 should not interfere significantly with the aminoacylation of the initiator tRNA (Johnson et al., 156:113-140 (1982)). With the proper selection of quencher and reporter molecules, the misaminoacylated tRNA can be designed to have minimum fluorescence of the reporter since the quencher and reporter are separated by a distance (e.g. 20-30 Å) in the range where quenching is effective. In contrast, once the reporter group is transferred from the tRNA to the growing nascent protein, it will exhibit fluorescence due to the separation of the quencher and reporter group (e.g. the donor and acceptor group). Furthermore, the fluorescence will be directly proportional to the amount of nascent protein produced by the in vitro expression system.

Preparation of FO-tRNA: The initiator tRNA$^{fmet}$ is first modified with quencher molecule, QSY7-malemide. The typical reactions contained 1.5 nanomoles (~1.0 OD$_{260}$) of tRNA in 50 mM potassium phosphate buffer, pH 8.4 and will be incubated with 150 nanomoles QSY7-malemide for 4-5 hours at room temperature in dark. After the modification reaction, the unincorporated dye is removed by G-25 desalting column and the modified tRNA (Q-tRNA) is ethanol precipitated. The Q-tRNA is aminoacylated with methionine using an excess of aminoacyl tRNA-synthetases under standard aminoacylation conditions. After aminoacylation, this tRNA is modified with BODIPY-FL as follows: To the aminoacylated tRNA, 2.5 µl of 1N NaHCO$_3$ is added (final conc. 50 mM, pH 8.5) followed by 10 µl of 10 mM solution of BODIPY-FL-SSE. The mixture is incubated for 10 min at 0° C. and the reaction is quenched by the addition of lysine (final concentration, 100 mM). To the resulting solution, 0.1 volume of 3 M NaOAc, pH 5.0 is added, and the modified tRNA is precipitated with 3 volumes of ethanol. The precipitate is dissolved in 50 µl of water and purified on a Sephadex G-25 gel filtration column (0.5×5 cm) to remove any free fluorescent reagent. The modified tRNA (FQ-tRNA) is stored frozen (−70° C.) in small aliquots in order to avoid repeated freeze-thaws. The extent of modification of the aminoacylated-tRNA is determined by analytical HPLC.

Cell-free synthesis of proteins and their detection: For prokaryotic translation mix, the typical translation reaction mixture (10 ul) contains 3 µl of extract, 4 µl of premix, 1 µl of complete amino acid mix, 30 picomoles of FQ-tRNA and 0.5 µg of the appropriate plasmid DNA. The translation reaction is incubated for 30 min at 37° C. For eukaryotic translation mix, the typical translation reaction mixture (10 µl) contains either 8 µl of rabbit reticulocyte or wheat germ translation extract, 0.5 µl of complete amino acid mix, 30 picomoles of FQ-tRNA and 0.5 µg of the appropriate plasmid DNA. The translation reaction is incubated for 30 min at 30° C. For SDS-PAGE, 4-10 µl aliquot of the reaction mix is precipitated with 5 volumes of acetone and the precipitated proteins are collected by centrifugation. The pellet is dissolved in 1×SDS-gel loading buffer (62 mM Tris-HCl, 2% SDS, 10% v/v glycerol, 100 mM DTT, 0.01% bromophenol blue, pH 6.8) and subjected to SDS-PAGE after boiling for 5 min. When less than 2 µl of the extract is analyzed, acetone precipitation step is not necessary. After electrophoresis, polyacrylamide gels are scanned using a FluorImager 595 (Molecular Dynamics, Sunnyvale, Calif.) equipped with an argon laser (488 nm line) as an excitation source and a 530±30 nm emission filter. Alternatively, the nascent proteins in polyacrylamide gels are detected using an UV-transilluminator combined with a Polaroid camera fitted with a green filter (Tiffen #58, Polaroid, Cambridge, Mass.). The reaction carried out in absence of any added DNA is taken as negative control.

Real-Time Monitoring of Protein Synthesis: The translation is carried out in the 96-well clear bottom black low-binding microtiter plate (Dynex Technologies, Chantilly, Va.) as explain above. The protein synthesis is initiated by the addition of the DNA and the plate will be continuously read using a FluorImager SI (Molecular Dynamics, Sunnyvale, Calif.) equipped with an argon laser (488 nm line) as an excitation source and a 530±30 nm emission filter at every 2 minutes for the period of 30 min. The reaction carried out in absence of any added DNA is taken as negative control.

Potential results: In general the crystal structures of some of the tRNAs are known which allows one to choose the position for incorporating of a quencher molecules in order to obtain a high efficiency quenching (FIG. 67). There are a variety of quencher reporter pairs known that can be utilized and listed in FIG. 68 along with their R$_0$.

The criteria for the selection of a reporter group (acceptor) include small size, high fluorescence quantum yield, photostability and insensitivity to environment. The criteria for choosing a quencher molecules are minimal background when both molecules (F and Q) are present on the tRNA molecules and its availability in suitable reactive form. In one embodiment, the quencher is QSY7 as shown in FIG. 69.

There are a variety of dyes which can be used as marker pairs in this method that will produce easily detectable signals when brought into close proximity. Previously, such dye pairs have been used for example to detect PCR products by hybridizing to probes labeled with a dye on one probe at the 5'-end and another at the 3'-end. The production of the PCR product brings a dye pair in close proximity causing a detectable FRET signal. In one application the dyes, fluorescein and LC 640 were utilized on two different primers (Roche Molecular Biochemicals-http://www.biochem.boehringer-mannheim.com/lightcycler/monitoO3.htm). When the fluorescein is excited by green light (around 500 nm) that is produced by a diode laser, the LC 640 emits red fluorescent, light (around 640 nm) which can be easily detected with an appropriate filter and detector. In the case of nascent proteins, the pair of dyes BODIPY FL and LC 640 would function in a similar manner. For example, incorporation of the BODIPY FL on the N-terminal end of the protein and the labeling of a binding agent with LC 640 which is directed against an N terminal epitope would allow detection of the production of nascent proteins.

The use of the marker pair BODIPY-FL and coumarin is a second pair which can be utilized advantageously. In one study, [Keller, R. C., Silvius, J. R., and De Kruijff, B. (1995) *Biochem Biophys Res Commun* 207(2), 508-14] it was found using the spectral overlap a Forster energy transfer radius (RO) of 50+/−2 A and 40+/−2 A for the coumarin-(beta-BODIPY FL) and the coumarin-(beta-BODIPY 530/550) couple respectively. Experimentally this was estimated to be 49.0-51.5 A and 38.5-42.5 A respectively. It is also possible to use two markers with similar or identical spectral properties for the marker pair due to the process of quenching. For example, in one study this process was used in the case of BODIPY FL in order to study the processing of exogenous proteins in intact cells [Reis, R. C., Sorgine, M. H., and Coelho-Sampaio, T. (1998) *Eur J Cell Biol* 75(2), 192-7] and in a second case to study the kinetics of intracellular viral assembly [Da Poian, A. T., Gomes, A. M., and Coelho-Sampaio, T. (1998) *J Virol Methods* 70(1), 45-58].

As stated above, a principal advantage of using reporters is the ability to monitor the synthesis of proteins in cellular or a cell-free translation systems directly without further purification or isolation steps. Reporter markers may also be utilized in conjunction with cleavable markers that can remove the reporter property at will. Such techniques are not available using radioactive amino acids which require an isolation step to distinguish the incorporated marker from the unincorporated marker. With in vitro translation systems, this provides a means to determine the rate of synthesis of proteins and to optimize synthesis by altering the conditions of the reaction. For example, an in vitro translation system could be optimized for protein production by monitoring the rate of production of a specific calibration protein. It also provides a dependable and accurate method for studying gene regulation in a cellular or cell-free systems.

C. Affinity Markers

Another embodiment of the invention is directed to the use of markers that facilitate the detection or separation of nascent proteins produced in a cellular or cell-free protein synthesis system. Such markers are termed affinity markers and have the property that they selectively interact with molecules and/or materials containing acceptor groups. The affinity markers are linked by aminoacylation to tRNA molecules in an identical manner as other markers of non-native amino acid analogs and derivatives and reporter-type markers as described. These affinity markers are incorporated into nascent proteins once the misaminoacylated tRNAs are introduced into a translation system.

An affinity marker facilities the separation of nascent proteins because of its selective interaction with other molecules which may be biological or non-biological in origin through a coupling agent. For example, the specific molecule to which the affinity marker interacts, referred to as the acceptor molecule, could be a small organic molecule or chemical group such as a sulfhydryl group (—SH) or a large biomolecule such as an antibody. The binding is normally chemical in nature and may involve the formation of covalent or non-covalent bonds or interactions such as ionic or hydrogen bonding. The binding molecule or moiety might be free in solution or itself bound to a surface, a polymer matrix, or a reside on the surface of a substrate. The interaction may also be triggered by an external agent such as light, temperature, pressure or the addition of a chemical or biological molecule which acts as a catalyst.

The detection and/or separation of the nascent protein and other preexisting proteins in the reaction mixture occurs because of the interaction, normally a type of binding, between the affinity marker and the acceptor molecule. Although, in some cases some incorporated affinity marker will be buried inside the interior of the nascent protein, the interaction between the affinity marker and the acceptor molecule will still occur as long as some affinity markers are exposed on the surface of the nascent protein. This is not normally a problem because the affinity marker is distributed over several locations in the protein sequence.

Affinity markers include native amino acids, non-native amino acids, amino acid derivatives or amino acid analogs in which a coupling agent is attached or incorporated. Attachment of the coupling agent to, for example, a non-native amino acid may occur through covalent interactions, although non-covalent interactions such as hydrophilic or hydrophobic interactions, hydrogen bonds, electrostatic interactions or a combination of these forces are also possible. Examples of useful coupling agents include molecules such as haptens, immunogenic molecules, biotin and biotin derivatives, and fragments and combinations of these molecules. Coupling agents enable the selective binding or attachment of newly formed nascent proteins to facilitate their detection or isolation. Coupling agents may contain antigenic sites for a specific antibody, or comprise molecules such as biotin which is known to have strong binding to acceptor groups such as streptavidin. For example, biotin may be covalently linked to an amino acid which is incorporated into a protein chain. The presence of the biotin will selectively bind only nascent proteins which incorporated such markers to avidin molecules coated onto a surface. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

One example of an affinity marker is dansyllysine (FIG. 5). Antibodies which interact with the dansyl ring are commercially available (Sigma Chemical; St. Louis, Mo.) or can be prepared using known protocols such as described in *Antibodies: A Laboratory Manual* (E. Harlow and D. Lane, editors, Cold Spring Harbor Laboratory Press, 1988) which is hereby specifically incorporated by reference. Many conventional techniques exist which would enable proteins containing the dansyl moiety to be separated from other proteins on the basis of a specific antibody-dansyl interaction. For example, the antibody could be immobilized onto the packing material of a chromatographic column. This method, known as affinity column chromatography, accomplishes protein separation by causing the target protein to be retained on the column due to its interaction with the immobilized antibody, while other proteins pass through the column. The target protein is then released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.).

Separation can also be performed through an antibody-dansyl interaction using other biochemical separation methods such as immunoprecipitation and immobilization of the antibodies on filters or other surfaces such as beads, plates or resins. For example, protein could be isolated by coating magnetic beads with a protein-specific antibody. Beads are separated from the extract using magnetic fields. A specific advantage of using dansyllysine as an affinity marker is that once a protein is separated it can also be conveniently detected because of its fluorescent properties.

In addition to antibodies, other biological molecules exist which exhibit equally strong interaction with target molecules or chemical moieties. An example is the interaction of biotin and avidin. In this case, an affinity analog which contains the biotin moiety would be incorporated into the protein using the methods which are part of the present invention. Biotin-lysine amino acid analogs are commercially available (Molecular Probes; Eugene, Oreg.).

Affinity markers also comprise one component of a multicomponent complex which must be formed prior to detection of the marker. One particular embodiment of this detection means involves the use of luminescent metal chelates, in particular luminescent rare earth metal chelates. It is well known that certain molecules form very stable complexes with rare earth metals. It is also well known that introduction of chromophore into these chelates sensitizes luminescence of these complexes. A variety of detection schemes based on the use of luminescent rare earth metal chelates have been described: Hemmila, I. A., "Applications of Fluorescence in Immunoassays", (Wiley&Sons 1991).

In a preferred embodiment, tRNA is misaminoacylated with a chromophore that also acts as a rare earth shelter. This modified aminoacyl tRNA is then introduced into cellular or cell-free protein translation system and the modified amino acid incorporated into nascent protein. The mixture is then separated using gel electrophoresis and the gel is incubated with a solution containing rare earth cation. Under these conditions rare earth cations form luminescent complexes with amino acids modified with a chelator present only in nascent proteins. The nascent proteins are then detected using a mid-range UV transilluminator (350 nm), which excites the formed lanthamide complex. The image is then recorded using polaroid camera or CCD array and a filter. In one embodiment, the derivatives of salicylic acid as one component and terbium ions as a second component of the binary detection system are used.

Affinity markers can also comprise cleavable markers incorporating a coupling agent. This property is important in cases where removal of the coupled agent is required to preserve the native structure and function of the protein and to release nascent protein from acceptor groups. In some cases, cleavage and removal of the coupling agent results in production of a native amino acid. One such example is photocleavable biotin coupled to an amino acid.

Photocleavable biotin contains a photoreactive moiety which comprises a phenyl ring derivatized with functionalities represented in FIG. 12 by X, Y and Z. X allows linkage of PCB to the bimolecular substrate through the reactive group X'. Examples of X' include Cl, O—N-hydroxysuccinimidyl, $OCH_2CN$, $OPhF_5$, $OPhCl_5$, $N_3$. Y represents a substitution pattern of a phenyl ring containing one or more substitutions such as nitro or alkoxyl. The functionality Z represents a group that allows linkage of the cross-linker moiety to the photoreactive moiety. The photoreactive moiety has the property that upon illumination, it undergoes a photoreaction that results in cleavage of the PCB molecule from the substrate.

A lysine-tRNA is misaminoacylated with photocleavable biotin-lysine, or chemically modified to attach a photocleavable biotin amino acid. The misaminoacylated tRNA is introduced into a cell-free protein synthesizing system and nascent proteins produced. The nascent proteins can be separated from other components of the system by streptavidin-coated magnetic beads using conventional methods which rely on the interaction of beads with a magnetic field. Alternatively, agarose beads coated with streptavidin, avidin and there derivatives be utilized. Nascent proteins are released then from beads by irradiation with UV light of approximately 280 nm wavelength. Once a nascent protein is released from by light it can be analyzed in solution (homogenous phase) or transferred to another surface such as nitrocellulose, polystyrene or glass for anlaysis (solid phase analysis) (non-specific binding surface or chemically activated). In one embodiment which involves solid phase analysis, neutravidin-coated agarose beads are used to capture nascent proteins produced in a cell-free rabbit reticulocyte protein synthesis system and the beads then separated from the synthesis system by centrifugation and washing. The nascent protein is then transferred to the surface of a microplate well by inserting the beads directly into the well and illuminating thereby facilitating transfer to the well surface.

In one experimental demonstration, nascent proteins (p53 and alpha-tubulin) were produced in a rabbit reticulocyte protein synthesis system supplemented with elongator tRNA misaminoacylated with a photocleavable biotin derivatized lysine. Without further processing, the nascent proteins were then specifically captured on NeutrAvidin biotin-binding agarose beads. After washing, the bead suspension containing the immobilized nascent protein was added directly to the wells of a high-protein-binding polystyrene micro-well plate. The UV release was performed directly in the wells of the plate thereby allowing subsequent and immediate non-specific adsorption of the released target protein onto the surface of the well. This approach, which is facilitated by photocleavable biotin, eliminates the need for stabilizers/additives (e.g proteins like albumin or non-ionic detergents) normally required when handling small quantities of pure soluble target protein separately in tubes or vials. Elimination of such stabilizers/additives facilitates non-specific immobilization of the isolated target proteins and direct transfer of the target protein from the beads to the well of the plate minimizes handling and non-specific losses. Furthermore, this approach eliminates the need for plates coated with proteinaceous capture elements and therefore should provide certain advantages (e.g. lower background/interference from capture elements in the plate-based immunoassay). Following removal of the beads from the wells by brief washes (e.g. 1-4 washes or more), the plate is ready for immunoassay. In this case, the nascent proteins contained a C-terminal HSV epitope tag and detection was achieved using an anti-HSV antibody conjugated to an alkaline phosphatase reporter. Signal was generated by the addition of a chemiluminescence-based alkaline phosphatase substrate and analyzed in a plate reader. Using a 10 μL equivalent of translated protein, this initial experiment produced signal to noise ratios of approximately 140:1 and 610:1 for alpha-tubulin and p53, respectively, relative to a blank cell-free translation lacking only the added DNA construct.

Many devices designed to detect proteins are based on the interaction of a target protein with specific immobilized acceptor molecule. Such devices can also be used to detect nascent proteins once they contain affinity markers such as biodetectors based on sensing changes in surface plasmons, light scattering and electronic properties of materials that are altered due to the interaction of the target molecule with the immobilized acceptor group.

Nascent proteins, including those which do not contain affinity-type markers, may be isolated by more conventional isolation techniques. Some of the more useful isolation techniques which can be applied or combined to isolate and purify nascent proteins include chemical extraction, such as phenol or chloroform extract, dialysis, precipitation such as ammonium sulfate cuts, electrophoresis, and chromatographic techniques. Chemical isolation techniques generally do not provide specific isolation of individual proteins, but are useful for removal of bulk quantities of non-proteinaceous material. Electrophoretic separation involves placing the translation mixture containing nascent proteins into wells of a gel which may be a denaturing or non-denaturing polyacrylamide or agarose gel. Direct or pulsed current is applied to the gel and the various components of the system separate according to molecular size, configuration, charge or a combination of their physical properties. Once distinguished on the gel, the portion containing the isolated proteins removed and the nascent proteins purified from the gel. Methods for the purification of protein from acrylamide and agarose gels are known and commercially available.

Chromatographic techniques which are useful for the isolation and purification of proteins include gel filtration, fast-pressure or high-pressure liquid chromatography, reverse-phase chromatography, affinity chromatography and ion exchange chromatography. These techniques are very useful for isolation and purification of proteins species containing selected markers.

Another embodiment of the invention is directed to the incorporation of non-native amino acids or amino acid derivatives with marker or affinity properties at the amino-terminal residue of a nascent protein (FIG. 13). This can be accomplished by using the side chain of an amino acid or by derivatizing the terminal amino group of an amino acid. In either case the resulting molecule is termed an amino acid derivative. The amino-terminal residue of a protein is free and its derivatization would not interfere with formation of the nascent polypeptide. The non-native amino acid or amino acid derivative is then used to misaminoacylate an initiator tRNA which only recognizes the first AUG codon signaling the initiation of protein synthesis. After introduction of this misaminoacylated initiator tRNA into a protein synthesis system, marker is incorporated only at the amino terminal of the nascent protein. The ability to incorporate at the N-terminal residue can be important as these nascent molecules are most likely to fold into native conformation. This can be useful in studies where detection or isolation of functional nascent proteins is desired.

Not all markers incorporated with misaminoacylated initiator tRNAs at the amino-terminal residue of the nascent protein show the same acceptance by the protein translational machinery. Furthermore, the range of incorporation of different markers can be more restrictive compared to the use of non-initiator tRNAs such as lysyl-tRNA. Although the factors influencing this discrimination between markers for incorporation by a misaminoacylated initiator tRNA are not fully elucidated, one possibility is that the initiation factor (IF2) which is used for carrying formylmethionine-tRNA$^{fmet}$ to ribosomes plays a role. A second possibility is that the interaction between the marker structure and the ribosomes plays a role. For example, the marker, BODIPY-FL is accepted by the protein translational machinery to a greater extent than smaller fluorescent markers such as NBD. For this reason, BODIPY-FL is a superior marker for use in the detection of nascent protein when incorporated through initiator tRNAs.

A marker group can also be incorporated at the N terminal by using a mutant tRNA which does not recognize the normal AUG start codon. In some cases this can lead to a higher extent of specific incorporation of the marker. For example, the mutant of initiator tRNA, where the anticodon has been changed from CAU—>CUA (resulting in the change of initiator methionine codon to amber stop codon) has shown to act as initiator suppressor tRNA (Varshney U, RajBhandary U L, Proc Natl Acad Sci USA 1990 February; 87(4):1586-90; Initiation of protein synthesis from a termination codon). This tRNA initiates the protein synthesis of a particular gene when the normal initiation codon, AUG is replaced by the amber codon UAG. Furthermore, initiation of protein synthesis with UAG and tRNA (fMet$^{CUA}$) was found to occur with glutamine and not methionine. In order to use this tRNA to introduce a marker at the N terminal of a nascent protein, this mutant tRNA can be enzymatically aminoacylated with glutamine and then modified with suitable marker. Alternatively, this tRNA could be chemically aminoacylated using modified amino acid (for example methionine-BODIPY). Since protein translation can only be initiated by this protein on messages containing UAG, all proteins will contain the marker at the N-terminal end of the protein.

D. Mass Spectrometry

Mass spectrometry measures the mass of a molecule. The use of mass spectrometry in biology is continuing to advance rapidly, finding applications in diverse areas including the analysis of carbohydrates, proteins, nucleic acids and biomolecular complexes. For example, the development of matrix assisted laser desorption ionization (MALDI) mass spectrometry (MS) has provided an important tool for the analysis of biomolecules, including proteins, oligonucleotides, and oligosacharrides [Karas, 1987 #6180; Hillenkamp, 1993 #6175]. This technique's success derives from its ability to determine the molecular weight of large biomolecules and non-covalent complexes (>500,000 Da) with high accuracy (0.01%) and sensitivity (subfemtomole quantities). Thus far, it has been found applicable in diverse areas of biology and medicine including the rapid sequencing of DNA, screening for bioactive peptides and analysis of membrane proteins.

Markers incorporated by misaminoacylated tRNAs into nascent proteins, especially at a specific position such at the N-terminal can be used for the detection of nascent proteins by mass spectrometry. Without such a marker, it can be very difficult to detect a band due to a nascent protein synthesized in the presence of a cellular or cell-free extract due the presence of many other molecules of similar mass in the extract. For example, in some cases less than 0.01% of the total protein mass of the extract may comprise the nascent protein(s). Furthermore, molecules with similar molecular weight as the nascent protein may be present in the mixture. Such molecules will overlap with peaks due to the nascent protein. This problem is particularly severe if the nascent protein is a transcription or translation factor already present in the cell-free or cellular protein synthesis. The synthesis of additional amounts of this protein in the protein synthesis system would be difficult to detect using known methods in mass spectrometry since peak intensities are not correlated in a linear manner with protein concentration.

Detection by mass spectrometry of a nascent protein produced in a translation system is also very difficult if the mass of the nascent protein produced is not known. This might situation might occur for example if the nascent protein is translated from DNA where the exact sequence is not known. One such example is the translation of DNA from individuals which may have specific mutations in particular genes or gene fragments. In this case, the mutation can cause a change in the protein sequence and even result in chain truncation if the mutation results in a stop codon. The mass of nascent proteins produced in a translation system might also not be known if DNA is derived from unknown sources such as as colonies of bacteria which can contain different members of a gene library or fragments thereof.

In one embodiment of the invention, the incorporation of markers of a specific mass (mass markers) into nascent proteins can be used to eliminate all of the above mentioned problems associated with the conventional mass spectrometric approach. First, a tRNA misaminoacylated with a marker of a known mass is added to the protein synthesis system. The synthesis system is then incubated to produce the nascent proteins. The mass spectrum of the protein synthesis system is then measured. The presence of the nascent protein can be directly detected by identifying peaks in the mass spectrum of the protein synthesis system which correspond to the mass of the unmodified protein and a second band at a higher mass which corresponds to the mass of the nascent protein plus the modified amino acid containing the mass of the marker.

There are several steps that can be taken to optimize the efficient detection of nascent proteins using this method. The mass of the marker should exceed the resolution of the mass spectrometer, so that the increased in mass of the nascent protein can be resolved from the unmodified mass. For example, a marker with a mass exceeding 100 daltons can be readily detected in proteins with total mass up to 100,000 using both matrix assisted laser desorption ionization (MALDI) or electrospray ionization (ESI) techniques. The amount of misaminoacylated tRNA should be adjusted so that the incorporation of the mass marker occurs in approximately 50% of the total nascent protein produced. An initiator tRNA is preferable for incorporation of the mass marker since it will only be incorporated at the N-terminal of the nascent protein, thus avoiding the possibility that the nascent protein will contain multiple copies of the mass marker.

One example of this method is the incorporation of the marker BODIPY-FL, which has a mass of 282, into a nascent protein using a misaminoacylated initiator tRNA. Incorporation of this marker into a nascent protein using a misaminoacylated initiator tRNA causes a band to appear at approximately 282 daltons above the normal band which appears for the nascent protein. Since the incorporation of the marker is less than one per protein due to competition of non-misaminoacylated $E.\ coli$ tRNA$^{fmet}$, a peak corresponding to the unmodified protein also appears. Identification of these two bands separated by the mass of the marker allows initial identification of the band due to the nascent protein. Further verification of the band due to the nascent protein can be made by adjusting the level of the misaminoacylated initiator tRNA in the translation mixture. For example, if the misaminoacylated initiator tRNA is left out, than only a peak corresponding to the unmodified protein appears in the mass spectrum of the protein synthesis system. By comparing the mass spectrum from the protein synthesis system containing and not containing the misaminocylated tRNA with the BODIPY-FL, the presence of the nascent protein can be uniquely identified, even when a protein with similar or identical mass is already present in the protein synthesis system.

For the purpose of mass spectrometric identification of nascent proteins, it is sometimes advantageous to utilize a photocleavable marker. In this case, peaks due to nascent proteins in the mass spectrum can be easily identified by measuring and comparing spectra from samples of the protein synthesis system that have been exposed and not exposed to irradiation which photocleaves the marker. Those samples which are not exposed to irradiation will exhibit bands corresponding the mass of the nascent protein which has the incorporated mass marker, whereas those samples which are exposed to irradiation will exhibit bands corresponding to the mass of the nascent proteins after removal of the mass marker. This shift of specific bands in the mass spectrum due to irradiation provides a unique identifier of bands which are due to the nascent proteins in the protein synthesis system.

One example of this method involves the use of the photocleavable marker, photocleavable biotin. When photocleavable biotin is incorporated into the test protein α-hemolysin, a toxin produced by $Staphyloccus$, by using the misaminoacylated $E.\ coli$ initiator tRNA$^{met}$, the mass spectrum exhibits two peaks corresponding to the mass of the nascent protein 35,904 Da, and a second peak at 36,465 Da corresponding to the mass of the nascent protein plus the mass of photocleavable biotin. After photocleavage of the marker by exposing the cell-free or cellular extract to UV light with a wavelength of approximately 365 nm for approximately 10 minutes, the two bands undergo changes in intensity due to cleavage of the marker from the nascent protein. For example, in the case of a form of photocleavable biotin containing a single spacer the change in the mass will be 561.57. These characteristic changes are then used to uniquely identify the peaks corresponding the nascent protein. In the case of MALDI mass spectrometry, the probe laser pulses when adjusted to sufficient intensity can be used to accomplish photocleavage of photocleavable biotin. In this case, changes can be conveniently measured during the course of the measurements, thereby facilitating detection of peaks associated with the nascent protein. A similar approach can also be used to identify more than one nascent protein of unknown mass in a cell or cell-free translation system.

Markers with affinity properties which are incorporated by misaminoacylated tRNAs into nascent proteins can also be very useful for the detection of such proteins by mass spectrometry. Such markers can be used to isolate nascent proteins from the rest of the cell-free or cellular translation system. In this case, the isolation of the nascent proteins from the rest of the cell-free mixture removes interference from bands due to other molecules in the protein translation system. An example of this approach is the incorporation of photocleavable biotin into the N-terminal end of a nascent proteins using misaminoacylated tRNA. When this marker is incorporated onto the N-terminal end of a nascent protein using an $E.\ coli$ tRNA$^{met}$, it provides a convenient affinity label which can be bound using streptavidin affinity media such as streptavidin agarose. Once the nascent protein is separated by this method from the rest of the protein synthesis system, it can be released by UV-light and analyzed by mass spectrometry. In the case of MALDI mass spectrometry, release of the nascent protein can most conveniently be accomplished by using the UV-laser excitation pulses of the MALDI system. Alternatively, the sample can be irradiated prior to mass spectrometric analysis in the case of MALDI or ESI mass spectrometry.

E. Electrophoresis

Another embodiment of the invention is directed to methods for detecting by electrophoresis the interaction of molecules or agents with nascent proteins which are translated in a translation system. This method allows a large number of compounds or agents to be rapidly screened for possible interaction with the expressed protein of specific genes, even when the protein has not been isolated or its function identified. It also allows a library of proteins expressed by a pool of genes to be rapidly screened for interaction with compounds or agents without the necessity of isolating these proteins or agents. The agents might be part of a combinatorial library of compounds or present in a complex biological mixture such as a natural sample. The agents might interact with the nascent proteins by binding to them or to cause a change in the structure of the nascent protein by chemical or enzymatic modification.

In addition to gel electrophoresis, which measures the electrophoretic mobility of proteins in gels such as polyacrylamide gel, this method can be performed using capillary electrophoresis. CE measures the electrophoretic migration time of a protein which is proportional to the charge-to-mass ratio of the molecule. One form of CE, sometimes termed affinity capillary electrophoresis, has been found to be highly sensitive to interaction of proteins with other molecules including small ligands as long as the binding produces a change in the charge-to-mass ratio of the protein after the binding event. The highest sensitivity can be obtained if the protein is conjugated to a marker with a specifically detectable electromagnetic spectral property such as a fluorescent dye. Detection of a peak in the electrophoresis chromatogram is accomplished by laser induced emission of mainly visible wavelengths. Examples of fluorescent dyes include fluorescein, rhodamine, Texas Red and BODIPY.

It is very difficult to detect a nascent protein synthesized in a cellular or cell-free extract by CE without subsequent isolation and labeling steps due the need for high sensitivity detection and the presence of many other molecules of similar mass/charge ratio in the extract. For example, in typical cases less than 0.01% of the total protein mass of the extract may comprise the nascent protein(s). Other molecules with similar electrophoretic migration times as the nascent protein may be present in the mixture. Such molecules will overlap with peaks due to the nascent protein.

It is also very difficult using conventional methods of CE to detect the interaction of molecules with nascent proteins produced in a cell free or cellular synthesis system. Affinity capillary electrophoresis has been found to be sensitive to interaction of proteins with other molecules including small ligands as long as the binding produces a change in the charge-to-mass ratio of the protein after the binding event. However, the selective addition of a marker such as a fluorescent dye to a nascent protein is not possible using conventional means because most markers reagents will nonspecifically label other molecules in the protein synthesis system besides the nascent proteins. In some cases, it may be possible utilize a specific substrate or ligand which binds only to the nascent protein. However this approach requires a detailed knowledge of the binding properties of the nascent protein and special design of a ligand with marker properties. The nascent protein may also be isolated from the protein synthesis system and then selectively labeled with a detectable marker. However, this also requires the development of a procedure for isolation of the nascent protein which can be time consuming and requires extensive knowledge of properties of the protein or protein engineering to incorporate an affinity epitope. Even after a nascent protein has been isolated, it is often difficult to uniformly label the protein with a marker so that the charge/mass ratio of each labeled protein remains the same. In the most advantageous form of labeling, a highly fluorescent marker is incorporated at only one specific position in the protein thus avoiding a set of proteins with different electrophoretic mobilities.

The method of the invention also overcomes major problems associated with the rapid screening of samples for new therapeutic compounds using capillary electrophoresis (CE) such as described in U.S. Pat. No. 5,783,397 (hereby incorporated by reference) when the target protein is a nascent protein expressed in a translation system. This includes the need to uniformly label expressed target proteins in a translation system with markers for high sensitivity analysis by CE which normally requires lengthy isolation steps and special techniques for uniform labeling.

The method can also be used in conjunction with expression cloning method for isolating novel cDNA clones such as described in U.S. Pat. No. 565,451, which is specifically incorporated by reference. This patent describes novel methods to identify cDNA clones by a) collecting pools of about 100 individual bacterial colonies; and b) expressing proteins encoded by the cDNAs in the pools in vitro. Proteins which can be identified in this manner include but are not limited to nucleic acid binding protein, cytoskeletal protein, growth factor, differentiation factor, post-translationally modified protein, phosphorylated protein, proteolytically cleaved protein, glycosylated protein, subunit or a multiple component of a protein complex, enzyme, isoform of a known protein, mutant form of known protein. Importantly, the method includes as a crucial step identifying a desired protein from protein translation system. Two such methods described for identifying the protein involve radioactive labeling and chemical labeling. However, these steps can be extremely time-consuming and are not conducive to rapidly screening an extract for the desired protein.

The present invention avoids all of the problems discussed above. In one embodiment of the invention a tRNA misaminoacylated with a detectable marker is added to the protein synthesis system. The system is incubated to incorporate the detectable marker into the nascent proteins. One or more molecules (agents) are then combined with the nascent proteins (either before or after isolation) to allow agents to interact with nascent proteins. Aliquots of the mixture are then subjected to electrophoresis. Nascent proteins which have interacted with the agents are identified by detecting changes in the electrophoretic mobility of nascent proteins with incorporated markers. In the case where the agents have interacted with the nascent proteins, the proteins can be isolated and subsequently subjected to further analysis. In cases where the agents have bound to the nascent proteins, the bound agents can be identified by isolating the nascent proteins.

In one example of this method, the fluorescent marker BODIPY-FL is used to misaminoacylate an $E.\ coli$ initiator $tRNA^{fmet}$ as previously described. The misaminoacylated tRNA is then added to a protein synthesis system and the system incubated to produce nascent protein containing the BODIPY-FL at the N-terminal. A specific compound which may bind to the nascent protein is then added to the protein synthesis system at a specific concentration. An aliquot from the mixture is then injected into an apparatus for capillary electrophoresis. Nascent proteins in the mixture are identified by detection of the fluorescence from the BODIPY-FL using exciting light from an Argon laser tuned to 488 nm. Interaction of the specific compound is determined by comparing the electrophoretic mobility measured of the nascent protein exposed to the specific compound with a similar measurement of the nascent protein that has not been exposed. The binding strength of the compound can then be ascertained by altering the concentration of the specific compounds added to the protein synthesis system and measuring the change in the relative intensity of bands assigned to the uncomplexed and complexed nascent protein.

The method is not limited to studying the interaction of one agent with one nascent protein translated in a protein translation system. For example, a library of compounds can be screened to identify those which serve are ligands for specific target protein. In addition to interactions which involve the binding of one or more agents to the nascent proteins interactions which result in a modification of the nascent protein including but not limited to phosphorylation, proteolysis, glycosylation, formation of a complex with other biological molecules can be detected using the marker incorporated in the nascent proteins when combined with electrophoresis. For example, the interaction of an antibody with the nascent proteins can be detected due to a change in the effective electrophoretic mobility of the complex formed. A similar approach could be used to identify the presence of one or more compounds in a complex mixture which bind to the nascent protein. Such a mixture might constitute a library of compounds produced by combinatorial chemistry or compounds which might be, present in a complex biological mixture such as natural samples which may contain therapeutic compounds.

F. Microscale Methods

While the present invention contemplates capillary electrophoresis (see above), other methods are also contemplated. In particular, microscale methods can be employed in conjunction with the novel markers (e.g. BODIPY) and methods of the present invention. The methods are "microscale" in that the dimensions of the channels on the device (and the corresponding fluid volumes) are very small (typically in the picometer range). For example, channels are typically between approximately 0.10 and 0.50 μm in depth and between approximately 5 and 500 μm in width.

Although there are many formats, materials, and size scales for constructing integrated fluidic systems, the present invention contemplates microfabricated devices as a solution to the many inefficiencies of larger scale screening. Devices can be microfabricated from a number of materials. Silicon is the material used for the construction of computing microprocessors and its fabrication technologies have developed at an unprecedented pace over the past 30 years. The principal modem method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference. While this technology was initially applied to making microelectronic devices, the same techniques are currently being used for micromechanical systems.

Continuous flow liquid transport has been described using a microfluidic device developed with silicon. See J. Pfahler et al., Sensors and Actuators, A21-A23 (1990), pp. 431-434. Pumps have also been described, using external forces to create flow, based on micromachining of silicon. See H. T. G. Van Lintel et al., Sensors and Actuators 15:153-167 (1988). SDS capillary gel electrophoresis of proteins in microfabricated channels has also been described. See Yao S, et al., "SDS capillary gel electrophoresis of proteins in microfabricated channels," *PNAS* 96:5372 (1999). Compared to more conventional two-dimensional denaturing gel electrophoresis (which is generally time consuming and requires considerable amounts of sample), this microchannel-based separation technique was shown to be quick and offer high resolution.

As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. While the present invention contemplates other substrates, such as glass or quartz, for use in photolithographic methods to construct microfabricated analysis devices, silicon is preferred because of the added advantage of allowing a large variety of electronic components to be fabricated within the same structure.

In one embodiment, the present invention contemplates silicon micromachined components in an integrated analysis system. Sample (e.g. a test compound) and one or more reagents (e.g. a BODIPY labelled nascent protein) are injected either continuously or in pulses into the device through entry ports and they are transported through channels to a reaction chamber, such as a thermally controlled reactor where mixing and reactions take place. The biochemical products can be then moved down a new channel (or by an electrophoresis module, if desired) where migration data is collected by a detector and transmitted to a recording instrument. If desired, a polymer can be used in the channels to provide resolution by molecular sieving. The biochemical products can be isolated by diverting the flow to an external port for subsequent additional analysis. Importantly, the fluidic and electronic components are designed to be fully compatible in function and construction with the biological reactions and reagents. In this embodiment, potential test compounds can be rapidly screened for interaction with a labeled nascent protein or multiple nascent proteins that are co-expressed in a translation reaction system. In this manner the system can be used to screen for interaction so as to identify useful drugs.

In another embodiment, one or more components of the protein synthesis system are introduced into the device through entry ports and they are transported through channels to a reaction chamber, such as a thermally controlled reactor, where the expression of the nascent protein which contains the marker such as BODIPY occurs. The labeled nascent protein can than be mixed with one or more reagents (e.g. a test compound) that are introduced into the device through entry ports. After the reaction takes placed, the biochemical products can be then moved down a new channel (or by an electrophoresis module, if desired) where migration data is collected by a detector and transmitted to a recording instrument. It is to be understood that components of the protein synthesis system which can be introduced into the device can include misaminoacylated tRNAs, DNA, mRNA, amino acids and nucleotides. The components can be introduced either continuously or in discrete pulses. The DNA may also be produced within the micromachined device by enzymatic reactions such as the polymerase chain reaction as has been described. See Kopp et al., "Chemical Amplification: Continuous Flow PCR on a Chip," *Science* 280:1046 (1998).

In silicon micromachining, a simple technique to form closed channels involves etching an open trough on the surface of a substrate and then bonding a second, unetched substrate over the open channel. There are a wide variety of isotropic and anisotropic etch reagents, either liquid or gaseous, that can produce channels with well-defined side walls and uniform etch depths. Since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures.

G. Multiple Misaminoacylated tRNAs

It may often be advantageous to incorporate more than one marker into a single species of protein. This can be accomplished by using a single tRNA species such as a lysine tRNA misaminoacylated with both a marker such as dansyllysine and a coupling agent such as biotin-lysine. Alternatively, different tRNAs which are each misaminoacylated with different markers can also be utilized. For example, the coumarin derivative could be used to misaminoacylate a tryptophan tRNA and a dansyl-lysine used to misaminoacylate a lysine tRNA.

One use of multiple misaminoacylated tRNAs is to study the expression of proteins under the control of different genetic elements such as repressors or activators, or promoters or operators. For example, the synthesis of proteins at two different times in response to an internal or external agent could be distinguished by introducing misaminoacylated tRNAs at different times into the cellular or cell-free protein synthesis system. A tRNA$^{tyr}$ might be charged with marker A and a tRNA$^{lys}$ charged with marker B, yielding A-tRNA$^{tyr}$ and B-tRNA$^{lys}$, respectively. In this case, protein one under the control of one promoter can be labeled by adding the A-tRNA$^{tyr}$ to the reaction system. If a second misaminoacylated tRNA, B-tRNA$^{lys}$ is then added and a second promoter for protein two activated, the nascent protein produced will contain both label A and B. Additional markers could also be added using additional tRNA molecules to further study the expression of additional proteins. The detection and analysis of multiply labeled nascent proteins can be facilitated by using the multi-colored electrophoresis pattern reading system, described in U.S. Pat. No. 5,190,632, which is specifically incorporated by reference, or other multi-label reading systems such as those described in U.S. Pat. Nos. 5,069,769 and 5,137,609, which are both hereby specifically incorporated by reference.

A second use of multiple misaminoacylated tRNAs is in the combined isolation and detection of nascent proteins. For example, biotin-lysine marker could be used to misaminoacylate one tRNA and a coumarin marker used to misaminoacylate a different tRNA. Magnetic particles coated with streptavidin which binds the incorporated lysine-biotin would be used to isolate nascent proteins from the reaction mixture and the coumarin marker used for detection and quantitation.

A schematic diagram of the basics of the above methods is shown in FIG. 14. In a first step, the marker selected (M), which may have reporter (R) or affinity (A) properties, is chemically or enzymatically misaminoacylated to a single tRNA species or a mixture of different tRNAs. Prior to protein synthesis, a predetermined amount of the misaminoacylated tRNA, charged with the fluorescent marker is mixed with the cell-free protein synthesis reaction system at concentrations sufficient to allow the misaminoacylated tRNA to compete effectively with the corresponding tRNA. After an incubation of about 1-3 hours, the reaction mixture is analyzed using conventional polyacrylamide or agarose gel electrophoresis. After electrophoresis, the gel is illuminated by UV radiation. Bands due to the nascent protein exhibit distinct fluorescence and can be easily and rapidly distinguished, either visually or photographically, from non-fluorescent bands of preexisting proteins. Nascent proteins can be isolated by excising the fluorescent band and electroeluting the protein from the extracted gel pieces. The quantities and molecular weights of the nascent proteins can be determined by comparison of its fluorescence with the fluorescence produced by a set of proteins with known molecular weights and known quantities. The results of the assay can be recorded and stored for further analysis using standard electronic imaging and photographic or spectroscopic methods.

H. Resulting Compositions

Another embodiment of the invention is directed to a composition comprising nascent proteins isolated or purified by conventional methods after translation in the presence of markers. Compositions can be utilized in manufacturing for the preparation of reagents such as coatings for tissue culture products and in the pharmaceutical industry.

Incorporation of markers into nascent proteins utilized in manufacturing facilitates analysis of the final manufactured product or process by detection of marker. For example, nascent proteins produced may be used as coatings for tissue culture products. The reproducibility of a particular coating process could be accurately determined by detecting variations of marker emissions over the surface of the coated product. In addition, non-toxic markers incorporated into proteins encompassed within a pharmaceutical preparation such as a hormone, steroid, immune product or cytokine can be utilized to facilitate safe and economical isolation of that protein preparation. Such products could be used directly without the need for removal of marker. When very low concentrations of marker are preferred, limiting amounts of marked proteins could be used to follow a protein through a purification procedure. Such proteins can be efficiently purified and the purity of the resulting composition accurately determined. In addition, the presence of markers may facilitate study and analysis of pharmaceutical compositions in testing. For example, markers can be utilized to determine serum half-life, optimum serum levels and the presence or absence of break-down products of the composition in a patient.

Alternatively, nascent proteins may contain specific markers which serve as therapeutically useful compounds such as toxic substances. These proteins are administered to a patient and the therapeutic moiety released after proteins have identified and possibly bound to their respective targets. Release may be electrical stimulation, photochemical cleavage or other means whereby the moiety is specifically deposited in the area targeted by the nascent proteins. In addition, moieties such as modified toxins may be utilized which become toxic only after release from nascent proteins. Nascent protein may also serve as a pharmaceutical carrier which bestows the incorporated marker with active therapeutic function or prevents marker from breaking down in the body prior to its therapeutic or imaging action.

The incorporation of cleavable markers in nascent proteins further provides a means for removal of the non-native portion of the marker to facilitate isolation of the protein in a completely native form. For example, a cleavable affinity marker such as photocleavable biotin introduced into a nascent protein facilitates economical isolation of the protein and allows for the removal of the marker for further use as a pharmaceutical composition.

Pharmaceutical compositions of proteins prepared by translation in the presence of markers may further comprise a pharmaceutically acceptable carrier such as, for example, water, oils, lipids, polysaccharides, glycerols, collagens or combinations of these carriers. Useful immunological compositions include immunologically active compositions, such as a vaccine, and pharmaceutically active compositions, such as a therapeutic or prophylactic drug which can be used for the treatment of a disease or disorder in a human.

I. Kits

Another embodiment of the invention is directed to diagnostic kits or aids containing, preferably, a cell-free translation containing specific misaminoacylated tRNAs which incorporate markers into nascent proteins coded for by mRNA or genes, requiring coupled transcription-translation systems, and are only detectably present in diseased biological samples. Such kits may be useful as a rapid means to screen humans or other animals for the presence of certain diseases or disorders. Diseases which may be detected include infections, neoplasias and genetic disorders. Biological samples most easily tested include samples of blood, serum, tissue, urine or stool, prenatal samples, fetal cells, nasal cells or spinal fluid. In one example, misaminoacylate fmet-tRNAs could be used as a means to detect the presence of bacteria in biological samples containing prokaryotic cells. Kits would contain translation reagents necessary to synthesize protein plus tRNA molecules charged with detectable non-radioactive markers. The addition of a biological sample containing the bacteria-specific genes would supply the nucleic acid needed for translation. Bacteria from these samples would be selectively lysed using a bacteria directed toxin such as Colicin E1 or some other bacteria-specific permeabilizing agent. Specific genes from bacterial DNA could also be amplified using specific oligonucleotide primers in conjunction with polymerase chain reaction (PCR), as described in U.S. Pat. No. 4,683,195, which is hereby specifically incorporated by reference. Nascent proteins containing marker would necessarily have been produced from bacteria. Utilizing additional markers or additional types of detection kits, the specific bacterial infection may be identified.

The present invention also contemplates kits which permit the GFTT described above. For example, the present invention contemplates kits to detect specific diseases such as familial adenomatous polyposis. In about 30 to 60% of cases of familial adenomatous polyposis, the diseased tissues also contain chain terminated or truncated transcripts of the APC gene (S. M. Powell et al., N. Engl. J. Med. 329:1982-87, 1993). Chain termination occurs when frameshift cause a stop codon such as UAG, UAA or UGA to appear in the reading frame which terminates translation. Using misaminoacylated tRNAs which code for suppressor tRNAs, such transcripts can be rapidly and directly detected in inexpensive kits. These kits would contain a translation system, charged suppressor tRNAs containing detectable markers, for example photocleavable coumarin-biotin, and appropriate buffers and reagents. Such a kit might also contain primers or "pre-primers," the former comprising a promoter, RBS, start codon, a region coding an affinity tag and a region complementary to the template, the latter comprising a promoter, RBS, start codon, and region coding an affinity tag—but lacking a region complementary to the template. The pre-primer permits ligation of the region complementary to the template (allowing for customization for the specific template used). A biological sample, such as diseased cells, tissue or isolated DNA or mRNA or PCR products of the DNA, is added to the system, the system is incubated and the products analyzed. Analysis and, if desired, isolation is facilitated by a marker such as coumarin or biotin which can be specifically detected by its fluorescence using streptavidin coupled to HRP. Such kits provide a rapid, sensitive and selective non-radioactive diagnostic assay for the presence or absence of the disease.

J. Colorectal Cancer PTT Detection

The present invention contemplates the isolation, detection and identification of expressed proteins having an altered primary amino acid sequence. One example of an altered primary sequence is a protein chain truncation. A protein chain truncation is most easily explained by a frameshift mutation that generates a stop codon (i.e., AUG) within the open reading frame. The resulting translation of the mRNA from this mutated gene synthesizes a nonfunctional or malfunctional protein. One example of such a truncated protein is derived from the APC gene, and is known to be a diagnostic marker for colorectal cancer.

Many attempts have been reported to detect and analyze biological samples using a noninvasive diagnostic marker of colorectal cancer. Currently, the most reliable method to identify and treat colorectal cancer requires a colonoscopy. While colonoscopy is not a high risk procedure, except for the associated general anesthesia, it is expensive and there is a serious problem regarding obtaining compliance for one time or repeated testing due to the invasive nature of the examination and the extensive bowel preparation required. One possible non-invasive source of diagnostic markers is fecal matter.

The Protein Truncation Test (PTT) was first reported by Roest et al., *Protein Truncation Test (PTT) For Rapid Detection Of Translation-Terminating Mutations*. Hum Mol Genet 2:1719-1721 (1993), and applied to the detection of truncating mutations in the APC gene by Powell et al., *Molecular Diagnosis Of Familial Adenomatous Polyposis*. N Engl J Med 329:1982-1987 (1993). In traditional PTT, the region of the gene to be analyzed is amplified by PCR (or RT-PCR for an mRNA template) using a primer pair that incorporates additional sequences into the PCR amplicons required for efficient cell-free translation. The amplified DNA is then added to a cell-free transcription-translation extract along with radioactive amino acids ($^{35}$S-methionine or $^{14}$C-leucine). The expressed protein is analyzed by SDS-PAGE and autoradiography. Chain truncation mutations are detected by the presence of a lower molecular weight (increased mobility) species relative to the wild-type (WT) protein band. Non-radioactive Western blot-based PTT-methods utilizing a combination of N-terminal and C-terminal epitopes have also been reported. Rowan et al., *Introduction Of A myc Reporter Tag To Improve The Quality Of Mutation Detection Using The Protein Truncation Test*. Hum Mutat 9:172-176 (1997); de Koning Gans et al., *A Protein Truncation Test For Emery-Dreifuss Muscular Dystrophy (EMU): Detection Of N-Terminal Truncating Mutations*. Neuromuscul Disord 9:247-250 (1999); and Kahamnn et al., *A Non-Radioactive Protein Truncation Test For The Sensitive Detection Of All Stop And Frameshift Mutations*. Hum Mutat 19:165-172 (2002). However, these approaches still involve lengthy steps of SDS-PAGE, electroblotting and membrane-based immunoassay.

Capillary electrophoreses provides an alternative to traditional SDS-PAGE gels. For example, a translation carried out in presence of BODIPY-FL tRNA results in a nascent protein (WT or mutant) having incorporated the BODIPY-FL. As with SDS-PAGE, a mutant protein expressing a premature termination codon, will have faster mobility when using CE (i.e., a truncated protein). Capillary electrophoresis analysis of these translation samples run under denaturing conditions will result in normal (i.e., WT) and mutant signal patterns as shown in FIG. 56. The relative mobility difference determines the exact location if the mutant relative to the normal protein, and depends on the position of the truncation mutation(s).

As an alternative to SDS-PAGE based PTT, the present invention contemplates a high throughput solid-phase protein truncation test (HTS-PTT) that is compatible with multi-well or microarray formats. The schematics for one embodiment of the HTS-PTT are shown in FIG. 41. Amplified DNA corresponding to the region of interest in the target gene is first generated using PCR with primers that incorporate N- and C-terminal epitope tags as well as a T7 promoter, Kozak sequence and start codon (ATG) in the amplicons. (see Example 29) The resulting amplified DNA is subsequently added to a cell-free protein expression system. (see Example 30) The cell-free transcription-translation reaction mixture is also supplemented with various misaminoacylated tRNAs carrying affinity and/or detection tags. As illustrated in FIG. 41, the incorporated affinity tags (e.g., biotins) are used to capture the translated protein from the cell-free expression mixture onto a solid surface. The N- and C-terminal epitope tags are used to compare the total amount of target protein bound (N-terminal signal) versus the fraction that is truncated (i.e., lacks a C-terminal). In addition, optional incorporation of a fluorescent label allows non-isotopic, direct detection of WT and truncated bands following SDS-PAGE. This feature is useful during initial assay development allowing the results of the HTS-PTT to be compared with the results from fluorescent-based SDS-PAGE. In the case of a positive diagnostic test for a chain truncating mutation, the approximate position of the mutation can be determined using the fluorescent label feature followed by local DNA sequencing to determine the exact position and nature of the mutation.

As an initial evaluation of HTS-PTT, an ELISA-based multi-well assay was developed to detect truncating mutations in a region of the APC gene (segment 3; amino acids 1098-1696) using genomic DNA as a PCR template. Extensive screening of various epitope tag sequences including His-6, c-myc, P53 (derived from the P53 sequence), FLAG, VSV-G, Fil-16 (filamin derived) and StrepTag was performed in order to determine which were optimal with respect to signal-to-noise ratio. Based on this, VSV-G and a P53-derived tag were chosen as the N- and C-terminal epitopes, respectively. The target protein was expressed using a cell-free transcription-translation system in the presence of a misaminoacylated tRNAs (biotin-lysyl-tRNA and/or BODIPY-FL-lysyl-tRNA) designed to incorporate lysine residues modified with biotin or a fluorophore (BODIPY-FL) at random lysine positions. In order to enhance throughput, the nascent APC segment 3 was selectively captured from the reaction mixture via the incorporated biotin onto a 96-well ELISA plate and simultaneously treated with the appropriate antibodies in a single step. Furthermore, to increase accuracy, the N- and C-terminal epitope tags were measured in the same well plate using differentially labeled antibodies (HRP and alkaline phosphatase (AP), respectively).

DNA derived from patients with familial adenomatous polyposis (FAP) as well as cell-line DNA with known mutations in segment 3 was analyzed by HTS-PTT (FIG. 42). WT APC yielded N- and C-terminal signals which were 400 and 100-fold larger, respectively, than the background. The C/N terminal ratio of WT APC was standardized to 100 and all other samples are expressed relative to the WT. For the case of cell-line DNA, which contains homozygous mutations at codons 1367, 1416 and 1338 (FIG. 42; C1-C3, respectively), the C/N terminal ratio is close to 0 as expected. Since the N-terminal signals in all cases were approximately 200-fold greater than background, this indicates that significant chain truncated fragment is expressed and captured but essentially none are full-length. The C/N terminal ratio of samples derived from individuals with FAP (FIG. 42; P1-P4) ranged from 37% to 47% relative to the WT. The variation in the C/N terminal ratios is likely to reflect differences in translation efficiency of the WT and mutant transcripts, as well as differences in capture and epitope accessibility which may depend on the position of the mutation.

Validation of the HTS-PTT results was performed using the incorporated fluorescent BODIPY labels FIG. 43 shows results obtained from fluorescent imaging after SDS-PAGE on a small aliquots (4 µl) of the same translation mixtures used in FIG. 42. The WT sample produces a band of expected molecular mass (~70 kDa), while the mutant APC cell-lines exhibited bands at approximately 35, 40 and 32 kDa (C1-C3 respectively), in agreement with the position of the chain truncating mutations as determined by DNA sequencing. In contrast, samples derived from individuals diagnosed with FAP all exhibited two bands corresponding to one WT and one mutant allele as expected for a heterozygote (lanes P1-P4). Furthermore, the band corresponding to the truncated fragment exhibited an apparent molecular mass which is predicted by direct DNA sequencing (FIG. 43 caption).

While heterozygous mutations in germ-line cells are expected to comprise 50% of the total DNA in a sample, sporadic mutations are often present in significantly lower abundance, such as the case of stool samples from individuals with colorectal cancer. Traverso et al., *Detection Of APC Mutations In Fecal DNA From Patients With Colorectal Tumors.* N Engl J. Med 346:311-320 (2002); Deuter et al., *Detection Of APC Mutations In Stool DNA Of Patients With Colorectal Cancer By HD-PCR.* Hum Mutat, 11:84-89 (1998); and Doolittle et al., *Detection Of The Mutated K-Ras Biomarker In Colorectal Carcinoma.* Exp Mol Pathol 70:289-301 (2001). One recent approach which can detect as low as 0.40% mutant DNA relative to WT, termed digital PTT, was utilized as part of a non-invasive assay for colorectal tumors. A key feature of this approach is the serial dilution of DNA prior to PCR amplification, so that each reaction contains no more than 4 copies of the APC gene. Detection of a mutation thus requires that the PTT assay have sensitivity sufficient to detect 1 out of 4 (25%) mutated copies of the gene. 144 individual cell-free translation reactions were performed for each patient sample and each reaction then analyzed by SDS-PAGE and autoradiography. Traverso et al. (2002). However, it would be desirable to replace the radioactive gel-based analyses with HTS-PTT in order to more efficiently screen such large numbers of samples per patient.

In an experiment designed to measure the sensitivity of HTS-PTT, various amounts of amplified WT and mutant APC DNA (cell-line C3) were mixed and translated as described earlier. As expected, the C/N terminal ratio decreased with increasing levels of mutant DNA (FIGS. 44 & 45). C/N terminal ratios were 100±6 (WT) versus 70±4 (25% mutant mixture; 3 WT:1 mutant) and 42±4 (50% mutant mixture; 1 WT:1 mutant). An unpaired two-tailed t-test shows that the difference in raw C/N terminal ratios between the WT and WT:mutant mixtures is statistically significant with p values of $1 \times 10^{-11}$ for WT versus 50% mixture and $1 \times 10^{-8}$ for WT versus 25% mixture (n=7). These results indicated that HTS-PTT may be suitable to replace the radioactive gel-based analysis in the digital PTT. Specifically, the above results indicated that the C/N ratio for the 50% and 25% mutant mixture deviate slightly from expected values of 0.5 and 0.75, respectively. This deviation may possibly be due to unequal binding and N-terminal accessibility of the full-length and truncated fragments.

Experiments were also carried out using mRNA isolated from cell line C3 which was then amplified using RT-PCR. The results (FIG. 44, broken line) are very similar to those obtained using DNA as starting material (C/N terminal ratios for mRNA based HTS-PTT were 100±5, 64±3, 44±3 for WT, 25% mutant mixture and 50% mutant mixture, respectively). This demonstrates the suitability of the HTS-PTT for analyzing chain truncating mutation using mRNA. However, it is noted that most clinical laboratories normally avoid the use of mRNA for PTT analysis because of problems such as the process of nonsense mediated mRNA decay, can make detection of the mutated allele difficult in some cases. Frieschmeyer et al., *Nonsense-Mediated mRNA Decay In Health And Disease,* Hum Mol Genet 8:1893-1900 (1999).

Several improvements are envisioned, for the basic HTS-PTT approach presented herein. The use of biotin-lysyl-tRNA to incorporate biotin affinity tags at lysine residues would result in no capture if the chain truncation occurs upstream of the first lysine. This problem and the overall efficiency of capture can be improved if a tRNA mixture containing most, or all, of the normal cellular tRNAs is misaminoacylated with a biotin-labeled amino acid (i.e., tRNA$^{TOTAL}$). This "total tRNA mixture" is then used instead of lysyl-tRNA, thereby making the biotin incorporation less dependent on the amino acid sequence of the nascent protein. It may also be possible to incorporate an affinity tag uniquely at the first residue in the sequence, thereby ensuring capture of any size truncated protein. This has been achieved for the case of an *E. coli* expression system using a suppressor initiator tRNA in conjunction with a nonsense codon for initiation. Because the HTS-PTT is not limited by the resolution of SDS-PAGE, it is possible to reduce the number of cell-free reactions per patient sample by translating larger segments of the target gene (or the whole gene itself). In fact, initial studies indicate that HTS-PTT analysis of fragments of at least 140 kDa in size is possible. Finally, the HTS-PTT is not limited to a multi-well ELISA/chemiluminescence format. For example, a microarray format is possible where the target proteins are captured on NeutrAvidin™ coated glass slides and detected using fluorescently labeled antibodies.

In contrast to traditional methods of PTT, the HTS-PTT described herein is non-isotopic, rapid and amenable to automation. The high throughput capabilities of the HTS-PTT should be useful in order to facilitate population-wide colorectal cancer (CRC) screening and other diseases that have prevalent truncation mutations.

The present invention contemplates the isolation, detection and identification of mutated genes by methods that do not require extensive and expensive purification, isolation and sequencing procedures. Furthermore, the present invention contemplates the use of nucleic acid material from any tissue or fluid sample, and is not restricted to fecal samples. Specifically, sample DNA from a patient suspected of having cancer is amplified by PCR using primers comprising sequences encoding a N-terminal and C-terminal epitope. The epitope-containing sample DNA is placed in a translation system (i.e., resulting in the production of mRNA followed by protein synthesis) containing at least one misaminoacylated marker tRNA. The marker is inserted into the nascent peptide for affinity capture following protein synthesis. It is not intended that the tRNA be limited to a single misaminoacylated tRNA (i.e., for example, lysine). The present invention contemplates the misaminoacylation of all amino acid tRNA's with a marker (i.e., the "total tRNA" embodiment or tRNA$^{TOTAL}$). This approach uniformly labels any length of any nascent protein with the affinity marker. Importantly, even if an amino acid in the C-terminal or N-terminal epitope receives a marker, the expected 1% incorporation rate (i.e., due to a low misaminoacylated tRNA concentration) will not reduce the ability to detect the affected epitope.

The present invention identifies a gene mutation by the ratio of detected N-terminal and C-terminal epitopes present in the nascent proteins. The epitopes may be identified by detection with enzyme-conjugated antibodies.

One embodiment of the present invention contemplates an HTS-PTT test combined with a DNA-based method of detecting specific mutations in one or more genes that have been associated with the series of genetic changes which result in neoplastic transformation of normal colonic epithelium to benign adenomas and subsequently to malignant adenocarcinomas (Seung Myung Dong et al., *J. Natl. Cancer Inst.*, 93:858-865 (2001)). It is also advantageous to utilize DNA-based assays which are compatible with the HTS-PTT platform and can be easily implemented in a clinical laboratory. For example, the TaqMan® assay and Invader® assay can be implemented on a 96, 384 or 1536 well luminescent/fluorescent reader to detect missense, deletion and insertion mutations which commonly occur in many genes, including APC. Even in cases where a large panel of known mutations is screened using DNA-based probes (specifically designed for those mutations) a significant percentage (i.e., approximately 20%) of de novo mutations are likely to appear in the APC gene and not be detected (Gavert et. al., *Molecular Analysis Of The APC Gene In 71 Israeli Families: 17 Novel Mutations.*, Hum Mutat 19(6): 664 (2002). These mutations can be detected using HTS-PTT. In contrast, such a panel combined with PTT is likely to detect such new mutations in the APC gene.

K. p53 Variants

The present invention contemplates PCR-mediated incorporation of a p53 epitope variant into a diagnostic protein.

In one embodiment, the present invention contemplates variants of the general formula:

T F S D L [x] K L L, wherein [x] can be any amino acid other than W (SEQ ID NO:51).

Examples of such variants include (but are not limited to):

```
T F S D L H K L L        (SEQ ID NO:24)
T F S D L Y K L L        (SEQ ID NO:25)
T F S D L G K L L        (SEQ ID NO:26)
T F S D L N K L L        (SEQ ID NO:27)
T F S D L F K L L        (SEQ ID NO:28)
T F S D L D K L L        (SEQ ID NO:29)
T F S D L T K L L        (SEQ ID NO:30)
```

In another embodiment, the present invention contemplates variants of the general formula:

$[z]_y$ T F S D L [x] K L L, wherein [x] can be any amino acid other than W, [z] can be any amino acid including but not limited to the amino acids corresponding to the wild-type sequence, and y is an integer between 1 and 10 (SEQ ID NO:52).

Examples of such variants include (but are not limited to):

```
E T F S D L H K L L          (SEQ ID NO:31)
Q E T F S D L H K L L        (SEQ ID NO:32)
S Q E T F S D L H K L L      (SEQ ID NO:33)
L S Q E T F S D L H K L L    (SEQ ID NO:34)
```

In another embodiment, the present invention contemplates variants of the general formula:

$[z]_y$ T F S D L [x] K L L $[z]_y$, wherein [x] can be any amino acid other than W, [z] can be any amino acid including but not limited to the amino acids corresponding to the wild-type sequence, and y is an integer between 1 and 10 (SEQ ID NO:53).

Examples of such variants include (but are not limited to):

```
E T F S D L H K L L P        (SEQ ID NO:35)

Q E T F S D L H K L L P      (SEQ ID NO:36)

S Q E T F S D L H K L L P    (SEQ ID NO:37)

L S Q E T F S D L H K L L P E  (SEQ ID NO:38)
```

L. VSV-G Variants

The present invention contemplates PCR-mediated incorporation of an eleven amino acid VSV-G epitope (residues 497-506) and variants thereof, into a diagnostic protein. This particular epitope is known to bind both monovalent and polyclonal antibodies and affects intracellular transport to the cell membrane. Kries, T. E., *Microinjected Antibodies Against The Cytoplasmic Domain Of Vesicular Stomatitis Virus Glycoprotein Block It's Transport To The Cell Surface.* EMBO J, 5(5):931-941 (1986). The incorporation of this VSV-G epitope into amphotropic leukemia virus envelope glycoprotein retained compatibility with envelope processing, transport and incorporation, although some temperature-sensitive mutants were generated. Battini et al., *Definition Of A 14-Amino Acid Peptide Essential For The Interaction Between The Murine Leukemia Virus Amphotropic Envelope Glycoprotein And Its Receptor.* J. Virol., 72(1): 428-435 (1998).

By "variants" it is meant that the sequence need not comprise the exact sequence; up to three (3) amino acid substitutions are contemplated. For example, Leu or Ser may be substituted for the Gly; Ser may be substituted for the Leu; and Ser or Ala may be substituted for the T.

In one embodiment, the present invention contemplates the wild type sequence:

```
Y T D I E M N R L G K        (SEQ ID NO:39)
```

In another embodiment, the present invention contemplates variants of the general formula:

Y [x] D I E M N R L G K, wherein [x] can be S or A (SEQ ID NO:54).

An example of such a variant includes, but is not limited to:

```
Y A D I E M N R L G K        (SEQ ID NO:40)
```

In another embodiment, the present invention contemplates variants of the general formula:

Y T D I E M N R [y] G K, wherein [y] can be S (SEQ ID NO:55).

An examples of such a variant includes, but is not limited to:

```
Y T D I E M N R S G K        (SEQ ID NO:41)
```

In another embodiment, the present invention contemplates variants of the general formula:

Y T D I E M N R L [z] K, wherein [z] can be S or L (SEQ ID NO:56).

An examples of such a variant includes, but is not limited to:

```
Y T D I E M N R L S K        (SEQ ID NO:42)
```

In another embodiment, the present invention contemplates variants of the general formula:

Y [x] D I E M N R [y] G K, wherein [x] can be S or A and [y] can be S (SEQ ID NO:57).

An examples of such a variant includes, but is not limited to:

```
Y S D I E M N R S G K        (SEQ ID NO:43)
```

In another embodiment, the present invention contemplates variants of the general formula:

Y [x] D I E M N R L [z] K, wherein [x] can be S or A and [z] can be G or S (SEQ ID NO:58).

An examples of such a variant includes, but is not limited to:

```
Y A D I E M N R L L K        (SEQ ID NO:44)
```

In another embodiment, the present invention contemplates variants of the general formula;

Y T D I E M N R [y] [z] K, wherein [y] can be S and [z] can be L or S (SEQ ID NO:59).

An examples of such a variant includes, but is not limited to:

```
Y T D I E M N R S S K        (SEQ ID NO:45)
```

In another embodiment, the present invention contemplates variants of the general formula;

Y [x] D I E M N R [y] [z] K, wherein [x] can be S or A; [y] can be S and [z] can be G, L or S (SEQ ID NO:60).

An examples of such a variant includes, but is not limited to:

```
Y A D I E M N R S G K        (SEQ ID NO:46)
```

One embodiment of the present invention contemplates that by using a microfluidic platform the amount of the translation mixture used for HTS-PTT assay can be lowered further than that contemplated in Example 43. Technically, the entire HTS-PTT assay can be performed using disposable micro-fluidic chip.

First, translation is carried out in a first nano-channel where the DNA sample and misaminoacylated tRNA is injected into translation extract and mixed in a microchamber. After a short incubation, the whole translation mixture is then transported through a capillary coated with streptavidin where binding of the translation products will occur. After binding, the capillary is washed and fluorescently labeled antibody solution, for example, dual color N-terminal and C-terminal antibodies, are passed through this capillary to allow the antibody to bind to the streptavidin-bound protein. Finally, the capillary is read for N-terminal and C-terminal signal using fluorescence based detection (LIF-based detector).

A similar approach can be performed using a system consisting of a plurality of small through holes which can be loaded with fluids with a volume less than 1 microliter and even more preferable less than 100 nl. One example is described in U.S. Pat. No. 6,387,331 Method and apparatus for performing microassays. Issued May 14, 2002, hereby incorporated by reference. In a preferred embodiment, a perforated platen is used having substantially parallel planar surfaces for manipulating distinct liquid samples, each sample having a volume less than 1 microliter, the platen comprising:
a. an inner layer of hydrophilic material;
b. two outer layers of hydrophobic material coupled to opposite sides of the inner layer in such a manner as to isolate the distinct liquid samples from each other; and
c. a two-dimensional array of through-holes for retaining the distinct liquid samples, the through-holes each having a characteristic cross-sectional dimension of between 100 and 400 micrometers, the through-holes spaced on a two-dimensional grid with a center-to-center spacing between nearest neighbors of twice the characteristic cross-sectional dimension or less, each through-hole traversing the inner layer and the two outer layers in a direction substantially perpendicular to the planar surfaces of the platen.

Using this system, a protein translation mixture such as a rabbit reticulocyte lysate can be loaded into the through-holes by capillary action. Loading may include drawing the said protein translation system from a planar surface by capillary action. DNA is added to the protein translation mixture along with any desired addition components such as misaminoacylated tRNA by loading a second set of samples in liquid form into the through-holes of the second perforated platen; registering the through-holes of the first perforated platen with the through-holes of the second perforated platen; and combining the first set of samples with the second set of samples. Protein translation is carried out in the through-holes by incubating the mixture using methods well-known in the field. The translation mixture is then transported into the through-holes of a third perforated platen. In order to facilitate nascent protein capture, these through-holes (e.g. the surface) are coated with streptavidin, avidin or its derivatives where binding of the translation products (e.g. nascent protein) occurs. After binding, the through-holes are washed and fluorescently labeled antibody solution, for example dual color N-terminal and C-terminal antibodies are introduced into the through holes to allow the antibody to bind to the streptavidin-bound protein. Finally, the through-holes are read for N-terminal and C-terminal signal using detection methods described in U.S. Pat. No. 6,387,331 employing an optical arrangement including a detector array for separately analyzing light emanating from each of the plurality of illuminated through-holes. In another embodiment, tRNA misaminoacylated with photocleavable biotin is utilized to produce nascent proteins which can be capture in streptavidin-coated through-holes and then released for subsequent microanalysis of the proteins.

Another embodiment of the present invention contemplates a method for rapidly measuring cDNA library expression products. In this approach, the products were identified by Expression ELISA Assay.

Briefly, this method quickly assesses the product of the translation reaction in a high throughput manner. After the deconvolution of the cDNA pool, single colonies were grown and the DNA was isolated using standard mini-prep methods. The high-throughput ELISA-PTT assay was then used to rapidly screen the DNA from several clones in order to determine if the DNA was expressed.

Specifically, FIG. 62 exemplifies the rapid assessment of the translation of individual clones from the cDNA library. The translation of individual DNA was carried out in rabbit reticulocyte lysate in the presence of an equimolar mixture of BODIPY-FL-Lys-tRNA (or total BODIPY-FL-Lys-tRNA) and Biotin-Lys-tRNA. After translation, the nascent protein was transferred to neutravidin-coated plate and incubated for 30 min. The plate was then washed extensively and the bound protein (i.e., containing BODIPY) was detected using anti-BODIPY-FL antibody (Molecular Probes, Eugene, Oreg.) and HRP-conjugated anti-rabbit secondary antibody (Amersham Pharmacia Biotech, Piscataway, N.J.). Finally, the signal was read using chemiluminescent ELISA reader Lumi-96 (Packard Biosciences, Meridian, Conn.).

Experimental

The following examples illustrate embodiments of the invention, but should not be viewed as limiting the scope of the invention. In some of the examples below, particular reagents and methods were employed as follows:

Reagents: tRNA$^{fmet}$, aminoacyl-tRNA synthetase, amino acids, buffer salts, and RNase free water were purchased from Sigma (St. Louis, Mo.). Many of the fluorescent dyes were obtained from Molecular Probes (Eugene, Oreg.). The translation supplies including routine kits were purchased from Promega (Madison, Wis.). Sephadex G-25 was from Amersham-Pharmacia Biotech (Piscataway, N.J.). The in vitro translation kits and plasmid DNAs coding for CAT (PinPoint™) and Luciferase (PBESTluc™) were from Promega (Wisconsin-Madison, Wis.) while DHFR plasmid DNA (pQE16-DHFR) was obtained from Qiagen (Valencia, Calif.). The plasmid DNA for a-hemolysin, pT7-WT-H6-αHL was kindly supplied by Prof. Hagan Bayley (Texas A &M University) and large scale preparation of α-HL DNA was carried out using Qiagen plasmid isolation kit. The bacterioopsin plasmid DNA (pKKbop) was from the laboratory stock.

Preparation of FluoroTag tRNAs: The purified tRNA$^{fmet}$ was first aminoacylated with the methionine. In typical reaction, 1500 picomoles (~1.0 OD$_{260}$) of tRNA was incubated for 45 min at 37° C. in aminoacylation mix using excess of aminoacyl tRNA-synthetases. After incubation, the mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μl). The coupling of NHS-derivatives of fluorescent molecules to the α-amino group of methionine was carried out in 50 mM sodium carbonate, pH 8.5 by incubating the aminoacylated tRNAf$^{met}$ (25 μl) with fluorescent reagent (final concentration=2 mM) for 10 min at 0° C. and the reaction was quenched by the addition of lysine (final concentration=100 mM). The modified tRNA was precipitated with ethanol and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. This tRNA was found to stable at least for 6 month if stored properly.

Cell free synthesis of proteins and their detection: The in vitro translation reactions were typically carried out using *E. coli* T7 transcription-translation system (Promega) with optimized premix. The typical translation reaction mixture (10 μl) contained 3 μl of extract, 4 μl of premix, 1 μl of complete amino acid mix, 30 picomoles of fluorescent-methionyl-tRNA and 0.5 μg of appropriate plasmid DNA. The optimized premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. The translation reaction was allowed to proceed for 45 min at 37° C. For SDS-PAGE, 4-10 μl aliquot of the reaction mix was precipitated with 5-volume acetone and the precipitated proteins were collected by centrifugation. The pellet was dissolved in 1× loading buffer and subjected to SDS-PAGE after boiling for 5 min. SDS-PAGE was carried out according to Laemmli and the gel was scan using Molecular Dynamics FluorImager 595 using Argon laser as excitation source. Alternatively, the nascent proteins in polyacrylamide gels were also detected using an UV-transilluminator and the photographs were carried out using Polaroid camera fitted with green filter (Tiffen green #58, Polaroid DS34 camera filter kit).

For visualization of BODIPY-FL labeled protein, 488 nm as excitation source was used along with a 530+/−30 narrow band excitation filter. The gel was scanned using PMT voltage 1000 volts and either 100 or 200 micron pixel size.

Enzyme/Protein activities: Biological activity of α-hemolysin was carried out as follows. Briefly, various aliquots (0.5-2 µl) of in vitro translation reaction mixture were added to 500 µl of TBSA (Tris-buffered saline containing 1 mg/ml BSA, pH 7.5). To this, 25 µl of 10% solution of rabbit red blood cells (rRBCs) was added and incubated at room temperature for 20 min. After incubation, the assay mix was centrifuged for 1 min and the absorbance of supernatant was measured at 415 nm (release of hemoglobin). The equal amount of rRBCs incubated in 500 µl of TBSA is taken as control while rRBCs incubated with 500 µl of water as taken 100% lysis. The DHFR activity was measured spectrophotometrically. Luciferase activity was determined using luciferase assay system (Promega) and luminescence was measures using Packard Lumi-96 luminometer.

Purification of α-HL and measurement BODIPY-FL incorporation into α-HL: The translation of plasmid coding for α-HL ($His_6$) was carried out at 100 µl scale and the α-HL produced was purified using Talon-Sepharose (ClonTech) according manufacturer instructions. The fluorescence incorporated into α-HL was then measured on Molecular Dynamics FluorImager along with the several known concentration of free BODIPY-FL (used as standard). The amount of protein in the same sample was measured using a standard Bradford assay using Pierce Protein Assay kit (Pierce, Rockford, Ill.).

FLAG Capture Assay

Biotinylation of FLAG Antibody

A 4.4 mg/mL stock of FLAG M2 monoclonal antibody (SIGMA Chemical, St. Louis, Mo.) is diluted with equal volume of 100 mM sodium bicarbonate (~15 mM final antibody concentration). Subsequently, NHS-LC-Biotin (Pierce Chemical, Rockford, Ill.) is added from a 2 mM stock (in DMF) to a final 150 mM. The reaction is incubated for 2 hours on ice. The mixture is then clarified by centrifugation in a microcentrifuge (14,000 R.P.M.) for 2.5 minutes. Unreacted labeling reagent is removed by gel filtration chromatography.

Preparation of FLAG Antibody Coated ELISA Plates

NeutrAvidin™ biotin binding protein (Pierce Chemical, Rockford, Ill.) is diluted to a final concentration of 50 mg/mL in 100 mM sodium bicarbonate and used to coat Microlite (2+ white opaque 96-well ELISA plates (Dynex Technologies, Chantilly, Va.). Plates are washed with TBS-T and coated using a solution of 5 mg/mL biotinylated FLAG M2 antibody in TBS-T. Plates are washed with TBS-T and blocked in Translation Dilution Buffer (TDB) [4.5% Teleostean Gelatin, 2% non-fat milk powder, 10 mM EDTA, 0.1% Tween-20, 1.25 mg/mL pre-immune mouse IgG, 2.5 mM d-biotin, in TBS, pH 7.5.].

Binding and Detection of Target Protein

Triple-epitope-tagged target proteins produced by in vitro translation using rabbit reticulocyte extract are diluted ½5-⅟75 in TDB and added to the antibody coated ELISA plates. Following capture of the target protein, plates are washed with TBS-T. Detection of c-myc is performed using a polyclonal antibody (Santa Cruz Biotechnology, Santa Cruz, Calif.) followed by a peroxidase labeled secondary antibody, whereas detection of the $His_6$ tag is achieved with a peroxidase labeled nickel chelate-based probe (India(His Probe-HRP, Pierce, Rockford, Ill.). Antibodies are diluted in TDB and the India (His Probe-HRP is diluted in TBS-T supplemented with 5 mg/mL pre-immune mouse IgG. In all cases, signal is generated using a chemiluminescent substrate system.

His-Tag Metal Affinity Capture ELISA Assay

Binding and Detection of Target Protein

Triple-epitope-tagged target proteins produced by in vitro translation using rabbit reticulocyte extract are diluted ½5-⅟75in 1% BSA/TBS-T and added to nickel chelate coated ELISA plates (Pierce Chemical, Rockford, Ill.). Following capture of the target protein, plates are washed with TBS-T and blocked with 1% BSA/TBS-T. Detection of epitope tags on the bound target protein is achieved using a monoclonal FLAG M2 antibody (SIGMA Chemical, St. Louis, Mo.) or a polyclonal c-myc antibody (Santa Cruz Biotechnology, Santa Cruz, Calif.) in conjunction with the appropriate peroxidase labeled secondary antibody. Detection of biotin incorporated into the target protein via Biotin-lysyl-$tRNA^{lys}$ is achieved using NeutrAvidin™ biotin binding protein conjugated to peroxidase (Pierce Chemical, Rockford, Ill.). The NeutrAvidin™ conjugate and all antibodies are diluted in 1% BSA/TBS-T. In all cases, signal is generated using a chemiluminescent substrate system.

EXAMPLE 1

Preparation of Markers

Synthesis of Coumarin Amino Acid: 4-(Bromomethyl)-7-methoxy coumarin (FIG. 15, compound 1; 6.18 mmole) and diethylacetamidomalonate (FIG. 15, compound 2; 6.18 mmole) were added to a solution of sodium ethoxide in absolute ethanol and the mixture refluxed for 4 hours. The intermediate obtained (FIG. 15, compound 3) after neutralization of the reaction mixture and chloroform extraction was further purified by crystallization from methanolic solution. This intermediate was dissolved in a mixture of acetone and HCl (1:1) and refluxed for one hour. The reaction mixture was evaporated to dryness, and the amino acid hydrochloride precipitated using acetone. This hydrochloride was converted to free amino acid (FIG. 15, compound 4) by dissolving in 50% ethanol and adding pyridine to pH 4-5. The proton ($^1H$) NMR spectrum of the free amino acid was as follows: (m.p. 274-276° C., decomp.) —$OCH_3$ (δ 3.85 s, 3H), —$CH_2$-(δ 3.5 d, 2H), α-CH— (δ 2.9 t, 1H), CH—CO (δ 6.25 s, 1H), ring H (δ 7.05 s, 1H), (δ 7.8 d, 2H).

Synthesis of Fmoc derivative of coumarin: Coumarin amino acid (1.14 mmol) was reacted with Fluorenylmethyloxycarbonyl N-hydroxysuccininmidyl ester (Fmoc-NHS ester) 1.08 mmol) in the presence of 1.14 mmol of triethylamine for 30 minutes at room temperature. The reaction mixture was acidified and the precipitate washed with 1 N HCl and dried. The NMR spectrum of the free amino acid was as follows: (MP 223-225° C.) —$OCH_3$ (δ 3.85 s, 3H), —$CH_2Br$ (δ 3.5 broad singlet, 2H), α-CH— (δ 3.0 t, 1H), CH—CO (δ 6.22 m, 1H), ring H (δ 7.05 s, 1H), (δ 7.8 d, 2H), fluorene H CH$_2$—CH (δ 4.2 m, 2H), CH$_2$—CH (δ 4.25 m, 1H), aromatic regions showed characteristic multiplets.

Synthesis of PCB: Photocleavable biotin was synthesized as described below. 2-bromo, 2'-nitroacetophenone (FIG. 15, compound 5) was converted first into its hexamethyltetraamommonium salt which was decomposed to obtain 2-amino, 2'-nitroacetophenone (FIG. 15, compound 6). Biotin N-hydroxysuccinimidyl ester (FIG. 15, compound 7; Sigma Chemical; St. Louis, Mo.) was reacted with a 6-aminocaproic acid (FIG. 15, compound 8) to obtain the corresponding acid (FIG. 15, compound 9). This acid was coupled with the 2-amino, 2'-nitroacetophenone using DCC to obtain the ketone (FIG. 15, compound 10). The ketone was reduced using sodium borohydride to obtain the alcohol (FIG. 15, compound 11) which was further converted into its chloroformate derivative (FIG. 15, compound 12). The proton NMR spectrum of the derivative (compound 12) was as follows: (δ 1.3 m, 3H), (δ 1.4 m, 2H), (δ 1.5 m, 5H) (δ 1.62 m, 1H), (δ 2.1 t, 2H) (δ 2.4 t, 2H), (δ 2.6 d, 1H), (δ 2.8 m, 1H), (δ 3.0 t, 1H), (δ 3.1 m 1H), (δ 4.15 qt, 1H) (δ 4.42 qt, 1H), (δ 5.8 t, 1H), (δ 6.25 s, 1H), (δ 6.45 s, 1H), (δ 7.5 t, 1H), (δ 7.75 m, 4H), (δ 7.9 d, 1H).

EXAMPLE 2

Misaminoacylation of tRNA

The general strategy used for generating misaminoacylated tRNA is shown in FIG. 16 and involved truncation of tRNA molecules, dinucleotide synthesis (FIG. 17), aminoacylation of the dinucleotide (FIG. 18) and ligase mediated coupling.

a) Truncated tRNA molecules were generated by periodate degradation in the presence of lysine and alkaline phosphatase basically as described by Neu and Heppel (J. Biol. Chem. 239:2927-34, 1964). Briefly, 4 mmoles of uncharged *E. coli* tRNA$^{Lys}$ molecules (Sigma Chemical; St. Louis, Mo.) were truncated with two successive treatments of 50 mM sodium metaperiodate and 0.5 M lysine, pH 9.0, at 60° C. for 30 minutes in a total volume of 50 μl. Reaction conditions were always above 50° C. and utilized a 10-fold excess of metaperiodate. Excess periodate was destroyed treatment with 5 μl of 1M glycerol. The pH of the solution was adjusted to 8.5 by adding 15 μl of Tris-HCl to a final concentration of 0.1 M. The reaction volume was increased to 150 μl by adding 100 μl of water. Alkaline phosphatase (15 μl, 30 units) was added and the reaction mixture incubated again at 60° C. for two hours. Incubation was followed by ethanol precipitation of total tRNA, ethanol washing, drying the pellet and dissolving the pellet in 20 μl water. This process was repeated twice to obtain the truncated tRNA.

b) Dinucleotide synthesis was carried out basically as performed by Hudson (J. Org. Chem. 53:617-24, 1988), and can be described as a three step process, deoxycytidine protection, adenosine protection and dinucleotide synthesis.

Deoxycytidine protection: All reaction were conducted at room temperature unless otherwise indicated. First, the 5' and 3' hydroxyl groups of deoxycytidine were protected by reacting with 4.1 equivalents of trimethylsilyl chloride for 2 hours with constant stirring. Exocyclic amine function was protected by reacting it with 1.1 equivalents of Fmoc-Cl for 3 hours. Deprotection of the 5' and 3' hydroxyl was accomplished by the addition of 0.05 equivalents of KF and incubation for 30 minutes. The resulting product (FIG. 17, compound 19) was produced at an 87% yield. Phosphate groups were added by incubating this compound with 1 equivalent of bis-(2-chlorophenyl)phosphorochloridate and incubating the mixture for 2 hours at 0° C. The yield in this case was 25-30%.

Adenosine protection: Trimethylsilyl chloride (4.1 equivalents) was added to adenosine residue and incubated for 2 hours, after which, 1.1 equivalents of Fmoc-Cl introduced and incubation continued for 3 hours. The TMS groups were deprotected with 0.5 equivalents of fluoride ions as described above. The Fmoc protected adenosine (compound 22) was obtained in a 56% yield. To further protect the 2'-hydroxyl, compound 22 was reacted with 1.1 equivalents of tetraisopropyl disiloxyl chloride (TIPDSCl$_2$) for 3 hours which produces compound 23 at a 68-70% yield. The compound was converted to compound 24 by incubation with 20 equivalents of dihydropyran and 0.33 equivalents of p-toluenesulfonic acid in dioxane for about 4-5 hours. This compound was directly converted without isolation into compound 25 (FIG. 17) by the addition of 8 equivalents of tetrabutyl ammonium fluoride in a mixture of tetrahydro-furan, pyridine and water.

Dinucleotide synthesis: The protected deoxycytidine, compound 20, and the protected adenosine, compound 25 (FIG. 17), were coupled by the addition of 1.1 equivalents of 2-chlorophenyl bis-(1-hydroxy benzotriazolyl)phosphate in tetrahydrofuran with constant stirring for 30 minutes. This was followed by the addition of 1.3 equivalents of protected adenosine, compound 25, in the presence of N-methylimidazole for 30 minutes. The coupling yield was about 70% and the proton NMR spectrum of the coupled product, compound 26 (FIG. 17), was as follows: (δ 8.76 m, 2H), (δ 8.0 m, 3H), (δ 7.8 m, 3H) (δ 7.6 m, 4H), (δ 7.5 m, 3H), (δ 7.4 m, 18H), (δ 7.0 m, 2H), (δ 4.85 m, 14H), (δ 4.25 m, 1H); (δ 3.6 m, 2H), (δ 3.2 m, 2H) (δ 2.9 m, 3H), (δ 2.6 m, 1H), (δ 2.0-1.2 m, 7H).

c) Aminoacylation of the dinucleotide was accomplished by linking the protected marker amino acid, Fmoc-coumarin, to the dinucleotide with an ester linkage. First, the protected amino acid was activated with 6 equivalents of benzotriazol-1-yl-oxy tris-(dimethylamino)phosphonium hexafluoro phosphate and 60 equivalents of 1-hydroxybenzotriazole in tetrahydrofuran. The mixture was incubated for 20 minutes with continuous stirring. This was followed with the addition of 1 equivalent of dinucleotide in 3 equivalents N-methylimidazole, and the reaction continued at room temperature for 2 hours. Deprotection was carried out by the addition of tetramethyl guanidine and 4-nitrobenzaldoxime, and continuous stirring for another 3 hours. The reaction was completed by the addition of acetic acid and incubation, again with continuous stirring for 30 minutes at 0° C. which produced the aminoacylated dinucleotide (FIG. 18).

d) Ligation of the tRNA to the aminoacylated dinucleotide was performed basically as described by T. G. Heckler et al. (Tetrahedron 40: 87-94, 1984). Briefly, truncated tRNA molecules (8.6 O.D.$_{260}$ units/ml) and aminoacylated dinucleotides (4.6 O.D.$_{260}$ units/ml), were incubated with 340 units/ml T4 RNA ligase for 16 hours at 4° C. The reaction buffer included 55 mM Na-Hepes, pH 7.5, 15 mM MgCl$_2$, 250 μM ATP, 20 μg/ml BSA and 10% DMSO. After incubation, the reaction mixture was diluted to a final concentration of 50 mM NaOAc, pH 4.5, containing 10 mM MgCl$_2$. The resulting mixture was applied to a DEAE-cellulose column (1 ml), equilibrated with 50 mM NaOAc, pH 4.5, 10 mM MgCl$_2$, at 4° C. The column was washed with 0.25 mM NaCl to remove RNA ligase and other non-tRNA components. The tRNA-containing factions were pooled and loaded onto a BD-cellulose column at 4° C., that had been equilibrated with 50 mM NaOAc, pH 4.5, 10 mM MgCl$_2$, and 1.0 M NaCl. Unreacted tRNA was removed by washes with 10 ml of the same buffer. Pure misaminoacylated tRNA was obtained by eluting the column with buffer containing 25% ethanol.

EXAMPLE 3

Preparation of Extract and Template

Preparation of extract: Wheat germ embryo extract was prepared by floatation of wheat germs to enrich for embryos using a mixture of cyclohexane and carbon tetrachloride (1:6), followed by drying overnight (about 14 hours). Floated wheat germ embryos (5 g) were ground in a mortar with 5 grams of powdered glass to obtain a fine powder. Extraction medium (Buffer I: 10 mM trisacetate buffer, pH 7.6, 1 nM magnesium acetate, 90 mM potassium acetate, and 1 mM DTT) was added to small portions until a smooth paste was obtained. The homogenate containing disrupted embryos and 25 ml of extraction medium was centrifuged twice at 23,000×g. The extract was applied to a Sephadex G-25 fine column and eluted in Buffer II (10 mM trisacetate buffer, pH 7.6, 3 mM magnesium acetate, 50 mM potassium acetate, and 1 mM DTT). A bright yellow band migrating in void volume and was collected (S-23) as one ml fractions which were frozen in liquid nitrogen.

Preparation of template: Template DNA was prepared by linearizing plasmid pSP72-bop with EcoRI. Restricted linear template DNA was purified by phenol extraction and DNA precipitation. Large scale mRNA synthesis was carried out by in vitro transcription using the SP6-ribomax system (Promega; Madison, Wis.). Purified mRNA was denatured at 67° C. for 10 minutes immediately prior to use.

EXAMPLE 4

Cell-Free Translation Reactions

The incorporation mixture (100 µl) contained 50 µl of S-23 extract, 5 mM magnesium acetate, 5 mM Tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 µg/ml creatine kinase, and 100 µg/ml mRNA containing the genetic sequence which codes for bacterioopsin. Misaminoacylated PCB-lysine or coumarin amino acid-tRNA$^{lys}$ molecules were added at 170 µg/ml and concentrations of magnesium ions and ATP were optimized. The mixture was incubated at 25° C. for one hour.

EXAMPLE 5

Isolation of Nascent Proteins Containing PCB-Lysine

Streptavidin coated magnetic Dynabeads M-280 (Dynal; Oslo, Norway), having a binding capacity of 10 µg of biotinylated protein per mg of bead. Beads at concentrations of 2 mg/ml, were washed at least 3 times to remove stabilizing BSA. The translation mixture containing PCB-lysine incorporated into nascent protein was mixed with streptavidin coated beads and incubated at room temperature for 30 minutes. A magnetic field was applied using a magnetic particle concentrator (MPC) (Dynal; Oslo, Norway) for 0.5-1.0 minute and the supernatant removed with pipettes. The reaction mixture was washed 3 times and the magnetic beads suspended in 50 µl of water.

Photolysis was carried out in a quartz cuvette using a Black-Ray longwave UV lamp, Model B-100 (UV Products, Inc.; San Gabriel, Calif.). The emission peak intensity was approximately 1100 µW/cm$^2$ at 365 nm. Magnetic capture was repeated to remove the beads. Nascent proteins obtained were quantitated and yields estimated at 70-95%.

EXAMPLE 6

The Lower Limit of Detection Using Fluorescence

Bovine serum albumin (BSA), suspended at 0.25 mg/ml in borate buffer, pH 8.0, was combined with a 25 fold molar excess fluorescamine (Sigma Chemical; St. Louis, Mo.) at 50 mg/ml to produce a modified, fluorescent BSA. Various amounts of modified protein (1 ng, 5 ng, 10 ng, 25 ng, 50 ng, 75 ng, 100 ng, 150 ng, 200 ng) were suspended in loading buffer (bromophenol blue, glycerol, 2-mercaptoethanol, Tris-HCl, pH 6.8, SDS), and added to individual wells of a 1.5 mm thick, 12% polyacrylamide gel with a 3% stacker. The water cooled gel was electrophoresed for 4 hours at 50 volts. After electrophoresis, the gel was removed from the electrophoresis apparatus, placed on a UV transilluminator and photographed with polaroid Type 667 film using an exposure time of 10 seconds. The lowest limit of detection observed under theses conditions was 10 ng. These results indicate that using equipment found in a typical molecular biology lab, fluorescently labeled proteins can be detected at ng quantities. Using even more sophisticated detection procedures and devices the level of detection can be increased even further.

EXAMPLE 7

Nascent Proteins Containing Coumarin-Amino Acid

Cell-free translation is performed as described using charged tRNA$^{lys}$ molecules misaminoacylated with lysine coupled to a benzopyrene fluorophore moiety and human γ-interferon mRNA which contains 21 codons for lysine. Samples of the mixture are supplemented with buffer containing bromophenol blue, glycerol, 2-mercaptoethanol, Tris-HCl, pH 6.8, and SDS, and directly applied to a 12% poly-acrylamide gel (3% stacker) along with a set of molecular weight markers. Electrophoresis is performed for 3 hours at 50 volts. The gel is removed from the electrophoresis apparatus and photographed under UV light. Bands of fluorescently labeled interferon protein are specifically detected at a molecular weight of about 25 KDa. No other significant fluorescent activity is observed on the gel. Free misaminoacylated tRNA molecules may be electrophoresed off of the gel and not specifically detected.

EXAMPLE 8

In Vivo Half-life of a Pharmaceutical Composition

Cell-free translation reactions are performed by mixing 10 µl of PCB-coumarin amino acid-tRNA$^{leu}$, prepared by chemical misaminoacylation as described above and suspended in TE at 1.7 mg/ml), 50 µl of S-23 extract, 10 µl water and 10 µl of a solution of 50 mM magnesium acetate, 50 mM Tris-acetate, pH 7.6, 200 mM Hepes-KOH buffer, pH 7.5; 1 M potassium acetate, 5 mM DTT, 3.75 mM GTP, 25 mM ATP, 100 mM creatine phosphate and 600 µg/ml creatine kinase. This mixture is kept on ice until the addition of 20 µl of 500 µg/ml human IL-2 mRNA (containing 26 leucine codons) transcribed and isolated from recombinant IL-2 cDNA. The mixture is incubated at 25° C. for one hour and placed on ice. 100 µl of streptavidin coated magnetic Dynabeads (2 mg/ml) are added to the mixture which is placed at room temperature for 30 minutes. After incubation, the mixture is centrifuged for 5 minutes in a microfuge at 3,000×g or, a magnetic field is applied to the solution using a MPC. Supernatant is removed and the procedure repeated three times with TE. The final washed pellet is resuspended in 50 µl of 50 mM Tris-HCl, pH 7.5 and transferred to a quartz cuvette. UV light from a Black-Ray longwave UV lamp is applied to the suspension for approximately 1 second. A magnetic field is applied to the solution with a MPC for 1.0 minute and the supernatant removed with a pipette. The supernatant is sterile filtered and mixed with equal volumes of sterile buffer containing 50% glycerol, 1.8% NaCl and 25 mM sodium bicarbonate. Protein concentration is determined by measuring the O.D.$_{260}$.

0.25 ml of the resulting composition is injected i.v. into the tail vein of 2 Balb/c mice at concentrations of 1 mg/ml. Two control mice are also injected with a comparable volume of buffer. At various time points (0, 5 minutes, 15 minutes, 30 minutes, 60 minutes, 2 hours and 6 hours), 100 µl serum samples are obtained from foot pads and added to 400 µl of 0.9% saline. Serum sample are added to a solution of dynabeads (2 mg/ml) coated with anti-coumarin antibody and incubated at room temperature for 30 minutes. A magnetic field is applied to the solution with a MPC for 1 minute and the supernatant removed with a pipette. Fluorescence at 470 nm is measured and the samples treated with monoclonal antibody specific for rat IL-2 protein. IL-2 protein content is quantitated for each sample and equated with the amount of fluorescence detected. From the results obtained, in vivo IL-2 half-life is accurately determined.

EXAMPLE 9

Incorporation of Various Fluorophores into α-Hemolysin

E. coli tRNA$^{fmet}$ was first quantitatively aminoacylated with methionine and the α-amino group was specifically modified using NHS-derivatives of several fluorophores. The list of fluorescent reporter molecules (fluorophores) tested and their properties are given in Table 2. Under the modification conditions, the modified Met-tRNA$^{fmet}$ is found to be stable as assessed by acid-urea gel. Since all the fluorescent molecules tested have different optical properties (excitation and emission), we have determined their relative fluorescence intensity under the condition which were used for the quantitation of gels containing nascent protein.

Fluorescent detection of nascent protein was first evaluated using α-hemolysin (α-HL) as a model protein (with C-terminal His$_6$-tag). α-HL is a relatively small protein (32 kDa) and could be produced efficiently in in vitro translation. In addition, its activity can be measured directly in the protein translation mixture using a rabbit red blood cell hemolysis assay. In vitro translation of α-HL was carried out using an E. coli T7 S30 transcription/translation extract (Promega Corp., Madison, Wis.) in the presence of several different modified methionyl-tRNA$^{fmet}$ as described above. After the reaction, an aliquot (3-5 µl) was subjected to SDS-PAGE analysis and the fluorescent bands were detected and quantitated using a FluorImager F595 (Molecular Dynamics, Sunnyvale, Calif.).

The data is presented in FIG. 20. Lane 1 is a no DNA control. Lane 2 shows the results with BODIPY-FL-SSE. Lane 3 shows the results with BODIPY-FL-SE. Lane 4 shows the results with NBD (see Table 2 for the structure). Lane 5 shows the results with Bodipy-TMR. Lane 6 shows the results with BODIPY R6G. Lanes 7, 8, 9 and 10 show the results achieved with FAM, SFX, PYMPO and TAMRA, respectively (see Table 2 for structures).

The results clearly indicate the α-HL produced in presence of BODIPY-FL-methionyl-tRNA$^{fmet}$ (lanes 2 and 3) exhibited the highest fluorescence (all the data is normalized to the BODIPY-FL-SSE. The two different BODIPY-FL reagents (BODIPY-FL sulfosuccinimidyl ester (SSE) and BODIPY-FL succinimidyl ester (SE)), differ only with respect to solubility. The next best fluorophore evaluated, 6-(tetramethylrhodamine-5-(and-6)-carboxamido)hexanoic acid, succinimidyl ester (TAMRA-X, SE), exhibited 35% of the fluorescence (corrected for relative fluorescence) of BODIPY-FL-SSE. Two other forms of BODIPY, BODIPY-TMR, SE (6-((4,4-difluoro-1,3-dimethyl-5-(4-methoxyphenyl)-4-bora-3a,4a-diaza-s-indacene-2-propionyl)amino) hexanoic acid, succinimidyl ester) and BODIPY-R6G, SE (4,4-difluoro-5-phenyl-4-bora-3a,4a-diaza-s-indacene-3-propionic acid, succinimidyl ester) exhibited less than 3% of the fluorescence of BODIPY-FL, SSE. Succinimidyl 6-(7-nitrobenz-2-oxa-1,3-diazol-4-yl)aminohexanoate (NBD-X-SE), a fluorescent molecule which has previously been incorporated into the neuorkinin-2 receptor exhibited only 6% of the BODIPY-FL-SSE. The two fluorescein analogs 5-(and-6)-carboxyfluorescein, succinimidyl-ester (FAM, SE) and 6-(fluorescein-5-(and-6)carboxamido)hexanoic acid, succinimidyl ester (SFX, SE) also showed very low fluorescence (8.4% and 4.6%, respectively relative to BODIPY-FL).

EXAMPLE 10

Optimizing Incorporation

In order to optimize the amount of BODIPY-FL incorporated into nascent proteins, the translation reaction for α-HL was carried out in presence of increasing amounts of BODIPY-FL-methionyl-tRNA$^{fmet}$ ranging from 3-60 picomoles per reaction. All reactions yielded similar amount of α-HL as determined by hemolysis activity of rabbit red blood cells indicating that the exogenously added BODIPY-FL-methionyl-tRNAe$^{fmet}$ in this range did not inhibit protein synthesis. In contrast, the intensity of the fluorescent band corresponding to α-HL continued to increase up to 30 picomoles BODIPY-FL-methionyl-tRNA per 10 µl reaction (data not shown). Increases above this level produced no further increase in fluorescence, thus subsequent reactions were performed using this level of BODIPY-FL-methionyl-tRNA.

A second step used to optimize BODIPY-FL incorporation was based on eliminating N-formyl-tetrahydrofolate (fTHF) from the reaction mixture. In prokaryotes, N-formyl-tetrahydrofolate (fTHF) acts as a cofactor for the enzyme methionyl-tRNA transformylase, which formylates the initiator tRNA after its aminoacylation with methionine. Protein synthesis is then initiated using this modified tRNA (formyl-methionine-tRNA). Without limiting the invention to any particular mechanism, it is believed that eliminating fTHF from the reaction mixture reduces the competition for initiation of protein synthesis between this endogenous initiator tRNA and exogenously added modified-initiator RNA by preventing the formylation of endogenous initiator tRNA. This was confirmed by measuring fluorescence directly from SDS-PAGE for reactions for which fTHF was present and absent from the reaction mixture. In the later case, a 2-3 fold increase in fluorescence was found (data not shown).

EXAMPLE 11

Incorporation into other Proteins

In order to explore the general applicability of this approach, transcription/translation reactions with BODIPY-FL-methionyl-tRNA$^{fmet}$ were carried out using various plasmid DNAs coding for dihydrofolate reductase (DHFR), luciferase, chloramphenicol acetyl-transferase (CAT) and bacteriorhodopsin (BR). BR was included because it represents membrane proteins, which are typically very hydrophobic. An optimized coupled transcription/translation system was used along with free BODIPY-FL and BODIPY-FL-methionyl-tRNA$^{fmet}$ using the Talon metal chelate resin (ClonTech, Palo Alto, Calif.) in order to examine incorporation into other proteins. The results are shown in FIGS. 21A (visualization using laser based Molecular Dynamics FluorImager 595) and 21B (visualization using a UV-transilluminator). Lane 1 is a no DNA control. Lanes 2, 3, 4, 5 and 6 are hemolysin, DHFR, Luciferase, CAT and bacteriohodopsin, respectively.

Fluoresceht bands are observed using a fluorescence scanner for each of the proteins at positions corresponding to their relative molecular. In the case of luciferase, bands are observed which correspond to the expected products of false initiation at internal methionines (Promega Technical Bulletin TB219). Bands corresponding to all of the proteins could also be observed visually and recorded photographically using a UV transilluminator (UVP TMW-20) combined with an emission filter that allows light with λ>450 nm (FIG. 21B). Excitation in this case is likely occur in the UV absorbing band of BODIPY-FL which extends from 300-400 nm.

The amount of BODIPY incorporation was then determined by measuring the amount of incorporated BODIPY-FL and protein present in the purified sample by comparison with solutions of different concentrations of BODIPY-FL and using a Bradford protein assay, respectively. The average of three such measurements yielded a molar ratio of 0.29+/−0.03%. However, the incorporation yield is likely to be higher since fluorescence quenching of BODIPY-FL with protein residues such as tryptophan and tyrosine may lower the fluorescence quantum yield compared to BODIPY-FL in aqueous solution.

The effects of the fluorescence labeling procedure on the activity of the nascent proteins synthesized was also evaluated. This is important in cases where it is desirable to perform downstream functional analysis such as in the case of in vitro expression cloning and other proteomic applications of in vitro technology. Although it is possible for the N-terminal fluorescent label to alter the function of a protein, the low molar incorporation level (~0.3%) should not significantly alter the overall activity of the extract. This is confirmed by various enzyme assays and no significant difference is found for the activity measured for DHFR, α-HL and luciferase synthesized in the presence and absence of the BODIPY-FL-methionyl-tRNA$^{fmet}$ (see Table 3).

EXAMPLE 12

Measuring the Sensitivity

In order to estimate the sensitivity of the method, various dilutions of the translation extract corresponding to 0.003- 0.5 µl of the original reaction mixture were analyzed by SDS-PAGE. As a control, extract from a reaction performed without DNA was analyzed. As seen in FIG. 22B, fluorescence from α-HL bands corresponding to as small as 0.007 µl of the original reaction mixture were detectable. Based on the our estimation of total nascent protein produced in the in vitro system, which ranged from 50-80 µg/ml, this corresponds to 0.35-0.5 nanograms of α-hemolysin. This compares favorably with the sensitivity obtainable using radioisotope labeling of nascent proteins where such a low expression of nascent protein may required longer exposure to X-ray film which might result in serious background problem. It also exceeds the sensitivity of measuring proteins on gels currently with commercially available dyes such as Coomassie Blue (8-100 nanograms). Further improvements in sensitivity are expected by increasing the level of BODIPY-FL incorporation and by reducing background fluorescence, which appears to be due to fluorescent impurities in the gel material, extract and modified tRNA added.

EXAMPLE 13

Synthesis as a Function of Time

The ability of the fluorescent labeling approach to monitor the nascent protein synthesis as a function of time was also evaluated. For this purpose, small aliquots of the α-HL transcription/translation mixture (4 µl) were withdrawn at various times during the reaction and analyzed by SDS-PAGE. As seen in FIG. 22A, bands due to α-HL can clearly be detected as early as 5 minutes after initiation of the incubation. Synthesis of fluorescently labeled α-HL appears to saturate after 15 minutes of translation.

EXAMPLE 14

The Modifying Reagent

In the case of post-aminoacylation modifications used to form a misaminoacylated tRNA, an important factor is the modifying reagent used to add the modification to the natural amino acid. For example, in the case of the fluorophore BODIPY FL, there are two different commercially available BODIPY FL NHS reagents known as BODIPY-FL-SE and BODIPY-FL-SSE (Molecular Probes). Both reagents are based on N-hydroxysucinimide (NHS) as the leaving group. However, the two forms differ in aqueous solubility due to the presence in one form (SSE) of a sulfonate (sulfo) group (see Table 2 for structures). In this example, optimized reactions based on standard biochemical procedures were performed aimed at adding the BODIPY FL fluorophore to a purified tRNA$^{fmet}$ which is aminoacylated with methionine using these two different reagents. For this purpose, first the tRNA$^{fmet}$ was aminoacylated with the methionine. In typical reaction, 1500 picomoles (~1.0 OD$_{260}$) of tRNA was incubated for 45 min at 37° C. in aminoacylation mix using excess of aminoacyl tRNA-synthetases. The aminoacylation mix consisted of 20 mM imidazole-HCl buffer, pH 7.5, 150 mM NaCl, 10 mM MgCl$_2$, 2 mM ATP and 1600 units of aminoacyl tRNA-synthetase. The extent of aminoacylation was determined by acid-urea gel as well as using $^{35}$S-methionine. After incubation, the mixture was neutralized by adding 0.1 volume of 3 M sodium acetate, pH 5.0 and subjected to chloroform: acid phenol (pH 5.0) extraction (1:1). Ethanol (2.5 volumes) was added to the aqueous phase and the tRNA pellet obtained was dissolved in water (37.5 (1) and used for modification.

A. Modification of Aminoacylated tRNA with BODIPY-FL-SSE

To the above aminoacylated-tRNA solution, 2.5 (1 of 1N NaHCO$_3$ was added (final conc. 50 mM, pH=8.5) followed by 10 (1 of 10 mM solution of BODIPY-FL-SSE (Molecular Probes) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ml microliters of water and purified on Sephadex G-25 gel filtration column (0.5×5 cm) to remove any free fluorescent reagent, if present. The modified tRNA was stored frozen (−70° C.) in small aliquots in order to avoid free-thaws.

B. Modification of Aminoacylated tRNA with BODIPY-FL-SE

To the above aminoacylated-tRNA solution, 2.5 (1 of 1N NaHCO$_3$ (final conc. 50 mM, pH=8.5) and 20 (1 of DMSO was added followed by 10 (1 of 10 mM solution of BODIPY-FL-SE (Molecular Probes) in DMSO. The mixture was incubated for 10 min at 0° C. and the reaction was quenched by the addition of lysine (final concentration=100 mM). To the resulting solution 0.1 volume of 3 M NaOAc, pH =5.0 was added and the modified tRNA was precipitated with 3 volumes of ethanol. Precipitate was dissolved in 50 ml of water and purified on Sephadex G-25 gel filtration column (0.5×5 cm) to remove any free fluorescent reagent, if present. The modified tRNA was stored frozen (−70° C.) in small aliquots in order to avoid free-thaws.

C. Analysis

It was found empirically using HPLC that the extent of modification of the alpha-amino group of methionine is substantially greater using the sulfonated form of NHS BODIPY FL compared to the non-sulfonated form of NHS-BODIPY FL reagent. In addition the misaminoacylated tRNA$^{fmet}$ formed using the sulfonated form was found to exhibit superior properties. When used in an optimized S30 E. coli translation systems to incorporate BIDOPY FL into the protein (hemolysin using a plasmid containing the HL gene under control of a T7 promoter), the band on an SDS-PAGE gel corresponding to the expressed HL exhibited an approximately 2 times higher level of fluorescence when detected using a argon laser based fluoroimager compared to a similar system using the misaminoacylated formed using the non-sulfonated form.

D. Coumarin

A similar result to that described above was obtained by comparing the non-sulfonated and sulfonated NHS derivatives of coumarin, which are also commercially available and referred to respectively as succinimidyl 7-amino-methyl-amino-coumarin acetate (AMCA-NHS; Molecular Probes) and sulfosuccinimidyl 7-amino-4-methylcoumarin-3-acetate (AMCA-sulfo-NHS; Pierce Chemicals). In this case, optimized reactions were performed using these two different reagents based on standard biochemical procedures in order to add the coumarin fluorophore to a purified tRNA$^{fmet}$ which is aminoacylated with methionine.

To the aminoacylated-tRNA solution described above, 2.5 (1 of 1N NaHCO$_3$ was added (final conc. 50 mM, pH=8.5) followed by 10 (1 of 10 mM solution of sulfosuccinimidyl 7-amino-4-methylcoumarin-3-acetate (AMCA-sulfo-NHS; Pierce Chemicals) in water. The mixture was incubated for 10 min at 0(C and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 microliters of water and purified on Sephadex G-25 gel filtration column (0.5×5 cm) to remove any free fluorescent reagent, if present. The modified tRNA was stored frozen (−70° C.) in small aliquots in order to avoid free-thaws.

To the above aminoacylated-tRNA solution, 2.5 (1 of 1N NaHCO$_3$ (final conc. 50 mM, pH=8.5) and 20 (1 of DMSO was added followed by 10 (1 of 10 mM solution of succinimidyl 7-amino-methyl-amino-coumarin acetate (AMCA-NHS; Molecular Probes) in DMSO. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 microliter of water and purified on Sephadex G-25 gel filtration column (0.5×5 cm) to remove any free fluorescent reagent, if present. The modified tRNA was stored frozen (−70° C.) in small aliquots in order to avoid free-thaws.

In this case, the coumarin-methionine-tRNA$^{fmet}$ formed using the non-sulfonated form of coumarin-NHS (AMCA-NHS) when used in standard E. coli S30 translation mixtures generated very low levels of detectable fluorescent bands when detected using UV light from a standard UV transilluminator. In contrast, the sulfonated form (AMCA-sulfo-NHS) when added using the same procedures led to easily detectable bands using the UV-transilluminator.

Attempts to incorporate coumarin using an initiator tRNA by modifying the α-amino group of methionine have been reported in the literature but failed. Coumarin attachment to a initiator tRNA subsequently required more extensive and complicated chemical attachment using a chemical cross linker. This was achieved by first aminoacylating the tRNA with methionine followed by reaction of aminoacylated tRNA with DTDG monosuccinimidyl ester (DTDG is Dithiodiglycolic acid). The reaction product was then reduced using DTT and subsequently reacted with CPM (3-(4'-Maleimidophenyl)-4-methyl-diethylamino coumarin. (Odom, 0. W, Kudlicki, W and Hardestry, B. 1998. In vitro engineering using acyl-derivatized tRNA, In Protein synthesis: Methods and Protocols, PP. 93-103, Humana press, Totowa, N.J.). Due to the need for special procedures designed for each marker, such an approach is not practical for general attachment of a wide variety of markers to tRNAs through post-chemical aminoacylation procedures.

One likely factor that makes sulfonated NHS reagents used for postchemical aminoacylation of tRNAs is its solubility in aqueous buffer. In contrast, non-sulfonated reagents such as the BIDOPY FL NHS reagent require organic buffer such as DMSO for postchemical modification. While it is still not clear why use of organic buffers lowers the overall marker incorporation, one possibility is that hydrolysis of the aminoacyl bond formed between the amino acid and tRNA reduces the overall level of modification.

EXAMPLE 15

Imparting Water Solubility

In general, the property of water solubility can be imparted to chemical reagents in several ways. Some of these are summarized below:

Introduction of polar functional group into leaving group (such as sulfonated-NHS).

Introduction of the polar functional group into a spacer arm.
Introduction of the polar functional group into the reagent moiety itself.

While the introduction of the —SO$_3^-$Na$^+$ (sulfo-) group is preferred, other polar ionizable groups (such as DSP) can also be used where DSP is shown below:

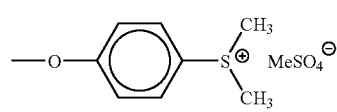

Final water solubility can be engineered into a spacer arm for example by using a polyether spacer (e.g. one based on tetraethylene glycol). In general, any moiety that has a free carboxyl group can be converted into its sulfo-NHS active ester. This reaction involves N-hydroxy-sulfosuccinimide (monosodium salt), the marker (M) and a coupling agent such as DCC (dicyclohexylcarbodiimide):

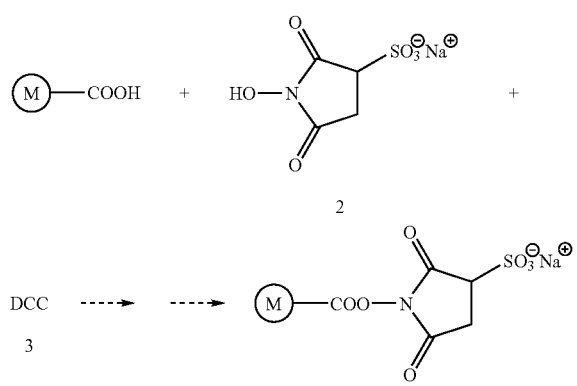

In a typical reaction, marker 1, 55 mmol, is dissolved in 10 ml DMF (dimethylformamide) and (2) (5 mmol) is added, followed by (3) (1.1 equivalents). The mixture is stirred overnight at room temperature, precipitate filtered off, and the filtrate evaporated under reduced pressure at room temperature. The product is purified if necessary using column chromatography or is recrystallized.

One preferred embodiment of this invention involves the post-chemical modification of tRNAs to form a misaminoacylated tRNA by using markers that contain a sulfonated NHS reagent. While such reagents are not generally available commercially, such reagents can be routinely produced out of a variety of useful markers. For example, fluorescein, which has a high fluorescent quantum yield for both UV and visible excitation could be prepared in a form which contains a sulfonated NHS ester.

EXAMPLE 16

Triple Marker System

In this example, a three marker system is employed to detect nascent proteins, i.e. an N-terminus marker, a C-terminus marker, and an affinity marker (the latter being an endogenous affinity marker). The experiment involves 1) preparation of a tRNA with a marker, so that a marker can be introduced (during translation) at the N-terminus of the protein; 2) translation of hemolysin with nucleic acid coding for wild type and mutant hemolysin; and 4) quantitation of the markers.

1. Preparation of Biotin-Methionyl-tRNA$^{fmet}$

The purified tRNA$^{fmet}$ (Sigma Chemicals, St. Louis, Mo.) was first aminoacylated with methionine. The typical aminoacylation reaction contained 1500 picomoles (~1.0 OD$_{260}$) of tRNA, 20 mM imidazole-HCl buffer, pH 7.5, 10 mM MgCl$_2$, 1 mM methionine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μl). The coupling of NHS-biotin to the α-amino group of methionine was carried out in 50 mM sodium bicarbonate buffer, pH 8.0 by incubating the aminoacylated tRNA$^{fmet}$ (25 μl) with NHS-biotin (final concentration=2 mM) for 10 min at 0° C. and the reaction was quenched by the addition of free lysine (final concentration=100 mM). The modified tRNA was precipitated with ethanol and passed through Sephadex G-25 gel filtration column (0.5×5 cm) to remove any free reagent, if present.

2. In Vitro Translation of α-HL DNA

A WT and Amber (at position 135) mutant plasmid DNA was using coding for α-hemolysin (α-HL), a 32 kDa protein bearing amino acid sequence His-His-His-His-His-His (His-6) (SEQ ID NO: 5) at its C-terminal. In vitro translation of WT and amber mutant α-HL gene (Amb 135) was carried out using E. coli T7 circular transcription/translation system (Promega Corp., Wisconsin, Wis.) in presence of Biotin-methionyl-tRNA$^{fmet}$ (AmberGen, Inc.). The translation reaction of 100 μl contained 30 μl E. coli extract (Promega Corp., Wisconsin, Wis.), 40 μl premix without amino acids, 10 μl amino acid mixture (1 mM), 5 μg of plasmid DNA coding for WT and mutant α-HL, 150 picomoles of biotin-methionyl-tRNA$^{fmet}$ and RNase-free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control. After the translation reaction mixture was diluted with equal volume of TBS (Tris-buffered saline, pH 7.5). Each sample was divided into two aliquots and processed individually as described below.

3. Preparation of Anti-α-HL Antibody Microtiter Plate

Anti-rabbit-IgG coated microtiter plate (Pierce Chemicals, Rockford, Il) was washed with Superblock buffer solution (Pierce) and incubated with 100 μg/ml of anti-α-HL polyclonal antibody solution (Sigma Chemicals, St. Louis, Mo.) prepared in Superblock buffer on microtiter plate shaker for 1 hour at room temperature. The plate was then washed (3 times×200 μl) with Superblock buffer and stored at 4° C. till further use.

4. Quantitation of N-Terminal (Biotin) Marker

The translation reaction mixture (50 μl) for the control, WT and amber α-HL DNA were incubated in different wells of anti-α-HL microtiter plate for 30 minutes on the shaker at room temperature. After incubation, the wells were washed 5 times (5-10 min each) with 200 μl Superblock buffer and the supernatant were discarded. To these wells, 100 μl of 1:1000 diluted streptavidin-horse radish peroxidase (Streptavidin-HRP; 0.25 mg/ml; Promega) was added and the plate was incubated at room temperature for 20 min under shaking conditions. After the incubation, excess streptavidin-HRP was removed by extensive washing with Superblock buffer (5 times×5 min each). Finally, 200 μl of substrate for HRP (OPD in HRP buffer; Pierce) was added and the HRP activity was determined using spectrophotometer by measuring absorbance at 441 nm.

5. Quantitation of C-Terminal (His-6-taq) Marker

Translation reaction mixture (50 μl) from example 2 for control, WT and Amber α-HL DNA were incubated in different wells of anti-α-HL microtiter plate for 30 min on the shaker at room temperature. After incubation, the wells were washed 5 times (5-10 min each) with 200 μl Superblock buffer and the supernatant were discarded. To these wells, 100 μl of 1:1000 diluted anti-His-6 antibody (ClonTech, Palo Alto, Calif.) was added to the well and incubated at room temperature for 20 min under shaking conditions. After the incubation, excess antibodies were removed with extensive washing with Superblock buffer (5 times×5 min each). Subsequently, the wells were incubated with secondary antibody (anti-mouse IgG-HRP, Roche-BM, Indianapolis, Ind.) for 20 min at room temperature. After washing excess $2^{nd}$ antibodies, HRP activity was determined as described above.

6. Gel-Free Quantitation of N- and C-Terminal Markers

The results of the above-described quantitation are shown in FIG. 23A (quantitation of N-terminal, Biotin marker) and FIG. 23B (quantitation of C-terminal, His-6 marker). In case of in vitro transcription/translation of WT α-HL DNA in presence of biotin-methionyl-tRNA, the protein synthesized will have translated His-6 tag at the C-terminal of the protein and some of the α-HL molecules will also carry biotin at their N-terminus which has been incorporated using biotinylated-methionine-tRNA. When the total translation reaction mixture containing α-HL was incubated on anti-α-HL antibody plate, selectively all the α-HL will bind to the plate via interaction of the antibody with the endogenous affinity marker. The unbound proteins can be washed away and the N- and C-terminal of the bound protein can be quantitated using Streptavidin-HRP and anti-His-6 antibodies, respectively. In case of WT α-HL, the protein will carry both the N-terminal (biotin) and C-terminal (His-6) tags and hence it will produce HRP signal in both the cases where streptavidin-HRP and secondary antibody-HRP conjugates against His-6 antibody used (HL, FIG. 23A). On the other hand, in case of amber mutant α-HL, only N-terminal fragment of α-HL (first 134 amino acids) will be produced and will have only N-terminal marker, biotin, but will not have His-6 marker due to amber mutation at codon number 135. As a result of this mutation, the protein produced using amber α-HL DNA will bind to the antibody plate but will only produce a signal in the case of strepavidin-HRP (HL-AMB, FIG. 23A) and not for anti-H is ×6 antibodies (HL-AMB, FIG. 23B).

EXAMPLE 17

Electrophoretic Mobility Shift Assay

To demonstrate the changes in the electrophoretic mobility of fluorescently labeled nascent protein on the SDS-gels either due to proteolysis or oligomerization in presence of membranes, we have use plasmid DNA of α-hemolysin (α-HL) which codes 32 kDa protein bearing a sequence His-His-His-His-His-His (His-6) (SEQ ID NO:5) at its C-terminal. In vitro translation of α-HL gene was carried out using E. coli T7 circular transcription/translation system (Promega Corp., Wisconsin-Madison, Wis.) in presence of BODIPY-FL-methionyl-tRNA$^{fmet}$ (AmberGen, Inc.) This experiment involved 1) preparation of the tRNA-marker for introduction of the N-terminus marker during translation, 2) translation, 3) purification, 4) protease treatment or 5) oligomerization.

1. Preparation of BODIPY-FL-Methionyl-tRNA:

BODIPY-FL-methionyl-tRNA was prepared by first aminoacylating pure tRNA$^{fmet}$ (Sigma Chemicals, St. Louis, Mo.) using methionine and subsequently modifying α-amino group of methionine using BODIPY-FL-SSE (4-difluoro-5,7-dimethyl-4-bora-3a,4a-diaza-s-indacene propionic acid, sulfosuccinimidyl ester; Molecular Probes, Eugene, Oreg.). The typical aminoacylation reaction (100 μl) contained 1500 picomoles (~1.0 $OD_{260}$) of tRNA, 20 mM imidazole-HCl buffer, pH 7.5, 10 mM $MgCl_2$, 1 mM methionine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μl). The coupling of BODIPY-FL-SSE to the α-amino group of methionine was carried out in 50 μl reaction volume using 50 mM sodium bicarbonate buffer, pH 8.0 by incubating 25 μl aminoacylated tRNA$^{fmet}$ (1.5 nanomoles) with 10 μl of BODIPY-FL-SSE (10 mM) for 10 min at 0° C. and the reaction was quenched by the addition of free lysine (final concentration=100 mM). The modified tRNA was precipitated with ethanol, and the pellet was dissolved in RNase-free water and passed through Sephadex G-25 gel filtration column (0.5×5 cm) to remove any free fluorescent reagent, if present.

2. In Vitro Translation of α-Hemolysin DNA

The translation reaction of 100 μL contained 30 μl E. coli extract (Promega Corp., Wisconsin, Wis.), 40 μl premix without amino acids, 10 μl amino acid mixture (1 mM), 5 μg of plasmid DNA coding for α-HL, 150 picomoles of BODIPY-FL-methionyl-tRNA$^{fmet}$ and RNase free water. The premix (1×) contains 57 mM HEPES, pH 8.2, 36 mM ammonium acetate, 210 mM potassium glutamate, 1.7 mM DTT, 4% PEG 8000. 1.25 mM ATP, 0.8 mM GTP, 0.8 mM UTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control.

3. Purification of Hls-6-α-α-HL

Fifty microliters of the translation reaction mixture (from above) was subjected to Talon-Sepharose (ClonTech, Palo Alto, Calif.) chromatography for the purification of Hls-6-α-HL. This was carried out by loading the crude extract onto the Talon-Sepharose column which was pre-equilibrated with 50 mM Tris-HCl, pH 8.0 containing 150 mM NaCl and washing the column to remove unbound proteins. The bound protein was then eluted by adding 100 mM imidazole in the above buffer. The eluted α-HL was dialyzed against 50 mM Tris-HCl buffer, pH 7.5.

4. EMSA for Protease Detection

The purified fluorescently labeled α-HL (~5 µg) (example 3) was incubated with 0.0.5 µg of pure trypsin (Sigma Chemicals, St. Louis, Mo.) in 50 nM acetate buffer, pH 5.0 (100:1; protein:protease ratio) for 5 min at 37° C. The proteolysis reaction was arrested by the addition of 1×SDS-gel loading buffer and boiling the samples for 5 min. The SDS-PAGE was carried out as described by Laemmli (Laemmli, U. K. 1970, Nature 227, 680-685) using 4-20% gradient gel (ready-gel, Bio-Rad, Richmond, Calif.). After the gel electrophoresis, the gel was visualized using FluorImager F595 (Molecular Dynamics, Sunnyvale, Calif.).

Trypsin was used under very limited conditions (single-hit kinetics) to obtain very defined cleavage of α-HL (50 mM acetate buffer, pH 5.0, 100:1: protein:protease ratio, 5 min at 37° C.). Under these conditions, the glycine rich loop in α-HL is most susceptible to cleavage and as a result proteolytic fragment of 17 kDa was observed (Vecesey-Semjen, B., Knapp, S., Mollby, R., Goot, F. G. 1999, Biochemistry, 38 4296-4302). When the fluorescently labeled α-HL was subjected to very mild trypsin treatment, it resulted a cleavage of α-HL yielding the N-terminal fragment of approximately 17-18 kDa mass as evidence by change in the mobility of fluorescent band on SDS-PAGE (FIG. 24: Lane 1 shows untreated protein and Lane 2 shows protease treated protein). This result indicates that such assay could be used to screen for proteases or any other enzymatic activities like kinase, transferase etc. that could potentially result in the electrophoretic mobility shift of the nascent protein. Though we have used pure nascent protein for this particular assay, there is no reason why one can not use a nascent protein without any purification (total translation reaction mixture).

5. EMSA for Oligomerization of Nascent Protein on Membranes

The total translation reaction mixture (10 µl) (see above) was incubated in absence and in presence of rabbit red blood cells (rRBCs, Charles River Farm, Conn.) for 30 min. at 0° C. After the incubation, rRBCs were washed free of excess unbound α-HL and the rRBCs were incubated in Tris buffer saline (TBS) containing 1 mg/ml BSA (TBSA) at 37° C. for 20 min during which lysis of rRBCs occurred. The rRBC membranes were isolated after centrifugation, dissolved in 1×SDS-gel loading buffer and subjected to SDS-PAGE (4-20% gradient gel) without heating the sample. After the gel electrophoresis, the gel was visualized using FluorImager F595.

α-HL is expressed a soluble monomeric protein and in presence of various membranes it can oligomerize to form heptameric pore (Walker, B., Krishnasastry, M., Zorn, L., Kasianowicz, J. and Bayley, H., 1992, J. Biol. Chem. 267, 10902-10909). In addition, some intermediate forms of the oligomers were also observed. In this experiment, in order to see the applicability of EMSA to detect the shift in mobility of α-HL due to oligomerization in presence lipid membranes, the total translation reaction mixture (with out any purification) was used. When the total translation extract containing nascent α-HL was incubated with rRBCs, it resulted in the oligomerization of α-HL on the rRBC membranes yielding a distinct fluorescent bands corresponding to various molecular masses that were SDS-resistant (FIG. 25: Lane 1 shows untreated protein only and Lane 2 shows protein treated with rRBCs).

This result demonstrates that such assay could be used to study proteins, interact with variety of natural and artificial membranes and as a result the mobility of the protein in shifted.

EXAMPLE 18

Incorporation Using Lysyl-tRNA$^{lys}$

This example describes the incorporation of fluorescent labels into nascent protein using lysyl-tRNA$^{lys}$. More specifically, a variety of fluorescent molecules were incorporated into 1) hemolysin during translation in an E coli translation system, and 2) luciferase during translation in a wheat germ system, using lysyl tRNA$^{lys}$. The experiment involved 1) preparation of the tRNA-marker compounds, 2) translation, and 3) detection on gels.

1. Preparation of Fluorescent Labeled Misaminoacylated tRNA$^{lys}$

The purified tRNA$^{lys}$ (Sigma Chemicals, St. Louis, Mo.) was first amino-acylated with lysine. The typical aminoacylation reaction (100 µl) contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-derivatives of various fluorescent molecules (see Table 2) to the α-amino group of lysine was carried out in 50 mM CAPS buffer, pH 10.5 by incubating the aminoacylated tRNA$^{lys}$ (25 µl) with fluorescent reagent (final concentration=2 mM) for 10 min at 0° C. and the reaction was quenched by the addition of free lysine (final concentration=100 mM). The modified tRNA was precipitated with ethanol, dissolved in 50 µl of RNase-free water and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991 J. Biol. Chem. 266, 24712-24718).

2. Cell Free Synthesis of Proteins in Prokaryotic (E. coli) Translation Extracts The typical translation reaction mixture (10 µl) contained 3 µl of E. coli extract (Promega Corp., Wisconsin-Madison, Wis.), 4 µl of premix, 1 µl of amino acid mix (1 mM), 30 picomoles of fluorescent-lysyl-tRNA and 0.5 µg of a hemolysin (αHL) plasmid DNA. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM CTP, 60 mM phosphoenolpyruvate, 0.6 mM cAMP and 6 mM magnesium acetate. The translation reaction was allowed to proceed for 45 min at 37° C. For SDS-PAGE, 4-10 µl aliquot of the reaction mix was precipitated with 5-volume acetone and the precipitated proteins were collected by centrifugation. The pellet was dissolved in 1×loading buffer and subjected to SDS-PAGE after boiling for 5 min. SDS-PAGE was carried out according to Laemmmli (Lammli, U.K. 1970, Nature, 227, 680-685).

3. Cell-Free Synthesis in Eukaryotic (TnT Wheat Germ) Translation Extracts.

The typical translation reaction mixture (10 µl) contained 5 µl of TnT wheat germ extract (Promega Corp., Wisconsin-Madison, Wis.), 0.4 µl of TnT reaction buffer, 1 µl of amino acid mix (1 mM), 0.2 µl of T7 RNA polymerase, 30 picomoles of fluorescent-lysyl-tRNA and 0.5 µg of luciferase RNA (Promega) and RNase-free water. The translation reaction was allowed to proceed for 45 min at 30° C. and reaction mixture was centrifuged for 5 min to remove insoluble material. The clarified extract was then precipitated with 5-volume acetone and the precipitated proteins were collected by centrifugation. The pellet was dissolved in 1× loading buffer and subjected to SDS-PAGE after boiling for 5 min. SDS-PAGE was carried out according to Laemmli (Lammli, U.K. 1970), Nature, 227, 680-685).

4. Detection of Nascent Protein

The gel containing nascent proteins was scanned using FluorImager F595 (Molecular Dynamics, Sunnyvale, Calif. using Argon laser (488 nm) as excitation source, in addition, the nascent proteins in polyacrylamide gels were also detected using an UV-transilluminator and the photographs were carried out using Polaroid camera fitted with Tiffen green filter (Polaroid, Cambridge, Mass.). FIGS. 26A and 26B show the results of in vitro translation of α-HL produced in presence of various fluorescent tRNA$^{lys}$. It is clear from the results one can incorporate a variety of fluorescent molecules into nascent protein using misaminoacylated tRNA (fluorophore-modified lysyl-tRNA$^{lys}$) including dyes like NBD, fluorescein derivatives etc. (Lane 1: No DNA control; lane 2: BODIPY-FL-SSE (4,4-difluoro-5,7-dimethyl-4-bora-3a,4a-diaza-s-indacene propionic acid, sulfosuccinimidyl ester); lane 3: BODIPY-FL-SE (4,4-difluoro-5, 7-dimethyl-4-bora-3a,4a-diaza-s-indacene propionic acid, succinimidyl ester); lane 4: NBD-X-SE (Succinimidyl 6-(7-nitrobenz-2-oxa-1,3-diazol-4-yl)aminohexanoate); lane 5; BODIPY-TMR-SE ((6-994,4-difluoro-1,3-dimethyl-5-(4-methoxyphenyl)-4-bora-3a,4a-diaza-s-indacene-2-propionyl) amino)hexanoic acid, succinimidyl ester); lane 6: BODIPY-R6G-SE ((4,4-difluoro-5-phenyl-4-bora-3a,4a-diaza-s-indacene-3-propionic acid, succinimidyl ester); lane 7; FAM-SE (5-(6-)-carboxyfluorescein, succinimidyl ester); lane 8:SFX-SE (6-fluorescein-5-(and 6-)carboxyamido)hexonoic acid, succinimidyl ester); lane 9: PyMPO-SE (1-(3-(succinimidyloxycarbonyl)benzyl)-4-(5-(4-methoxyphenyl) oxazol-2-yl)pyridininium bromide (PyMPO)) and lane 10: TAMRA-SE (6-(tetramethylrhodamine-5-(and-6)-carboxamido)hexanoic acid, succinimidyl ester).

EXAMPLE 19

NHS-Derivatives of Coumarin

Given the above noted results for the two BODIPY molecules (i.e. BODIPY-FL-SSE and BODIPY-FL-SE), attempts were made to derivatize other markers to make them suitable for incorporation. The present example involves 1) the preparation of the labeled tRNA, 2) translation, and 3) detection of the nascent protein containing the label (or marker).

1. Preparation of Fluorescent Labeled Misaminoacylated tRNA$^{fmet}$

The purified tRNA$^{fmet}$ (Sigma Chemicals, St. Louis, Mo.) was first aminoacylated with methionine. The typical aminoacylation reaction (100 µl) contained 1500 picomoles (approximately 1.0 OD$_{260}$) of tRNA, 20 mM imidazole-HCl buffer, pH 7.5, 10 MM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-derivatives of coumarin [namely sulfosuccinimidyl 7-amino-4-methylcoumarin-3-acetate [1] (AMCA-sulfo-NHS; Pierce Chemicals), Alexa 350-N-hydroxy-succinimide ester (Molecular Probes) and succinimidyl 7-amethyl-amino-coumarin acetate (AMCA-NHS: Molecular Probes)] to the α-amino group of methionine was carried out in 50 mM sodium bicarbonate buffer, pH 8.5 by incubating the aminoacylated tRNA$^{fmet}$ (25 µl) with fluorescent reagent (final concentration=2 mM) for 10 min at 0° C. and the reaction was quenched by the addition of free lysine (final concentration=100 mM). In case of AMCA-NHS, reagent was dissolved in DMSO and the coupling reaction was carried out in presence of 40% DMSO. The modified tRNA was precipitated with ethanol, dissolved in 50 µl of RNase-free water and passed through Sephadex G-25 gel filtration column (0.5×5 cm) to remove any free fluorescent reagent, if present. The modified tRNA was stored frozen (–70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991, J. Biol. Chem. 266, 24712-24718).

2. Cell Free Synthesis of Proteins in Prokaryotic (E. coli) Translation Extracts:

The typical translation reaction mixture (10 µl) contained 3 µl of E. coli S-30 extract (Promega Corp., Wisconsin-Madison, Wis.), 4 µl of premix, 1 µl of amino acid mix (1 mM), 30 picomoles of fluorescent-methionyl-tRNA and 0.5 µg of α-hemolysin (α-HL) plasmid DNA. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. The translation reaction was allowed to proceed for 45 min at 37° C. For SDS-PAGE, 4-10 µl aliquot of the reaction mix was precipitated with 5-volume acetone and the precipitated proteins were collected by centrifugation. The pellet was dissolved in IX loading buffer and subjected to SDS-PAGE after boiling for 5 min. SDS-PAGE was carried out according to Laemmli (Laemmli, U. K. 1970, Nature, 277, 680-685).

3. Detection of Nascent Protein

The gel containing nascent proteins was visualized using an UV-transilluminator equipped with long wavelength UV bulb (>300 nm) and the photographs were carried out using Polaroid camera fitted with Tiffen green filter (Polaroid, Cambridge, Mass.). FIG. 27 indicates that the result in vitro translation of α-HL produced in presence of various fluorescent tRNAs (Lane 1 shows the results for the no DNA control; Lane 2 shows the results with Met-tRNA$^{fmet}$ modified with AMCA-NHS; Lane 3 shows the results with Met-tRNA$^{fmet}$ modified with AMCA-sulfo-NHS; and Lane 4 shows the results with Met-tRNA$^{fmet}$ modified with Alexa-NHS). Clearly, one can incorporate the coumarin derivative molecules into nascent protein using misaminoacylated tRNA which are modified with the water soluble NHS-esters of fluorescent molecules (lane 3). Moreover, a dye with negative charge (Alexa, lane 4) seems to not incorporate as well as its neutral counterpart (AMCA; lane 3).

From the above results and general teachings of the present specification, one skilled in the art can select other markers and render them (e.g. chemically render them) suitable for incorporation in accordance with the methods of the present invention.

EXAMPLE 20

Capillary Electrophoresis

The example describes the use of capillary electrophoresis (CE) for detection of in vitro synthesized fluorescent proteins by mobility shift. The example describes 1) the preparation of the tRNA comprising a BODIPY marker, 2) in vitro translation, 3) purification, 4) protease digestion and 5) detection by mobility shift assay.

1. Preparation of BODIPY-FL-Methionyl-tRNA$^{fmet}$

The tRNA$^{fmet}$ was amino acylated with the methionine. In typical reaction, 1500 picomoles (~1.0 OD$_{260}$) of tRNA was incubated for 45 min at 37° C. in aminoacylation mix using an excess of aminoacyl tRNA-synthetases. The aminoacylation mix comprised 20 mM imidazole-HCl buffer, pH 7.5, 150 mM NaCl, 10 mM MgCl$_2$, 2 mM ATP and 1600 units of aminoacyl tRNA-synthetase. The extent of aminoacylation was determined by acid-urea gel as well as by using $^{35}$S-methionine. After incubation, the mixture was neutralized by adding 0.1 volume of 3 M sodium acetate, pH 5.0 and subjected to chloroform:acid phenol (pH 5.0) extraction (1:1). Ethanol (2.5 volumes) was added to the aqueous phase and the tRNA pellet obtained was dissolved in water (37.5 ul) and used for modification. To the above aminoacylated-tRNA solution, 2.5 ul of 1N NaHCO$_3$ was added (final conc. 50 mM, pH=8.5) followed by 10 ul of 10 mM solution of BODIPY-FL-SSE (Molecular Probes) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 µl of water and purified on Sephadex-G-25 gel filtration column (0.5×5 cm) to remove any free fluorescent reagent, if present. The modified tRNA was stored frozen (−70° C.) in small aliquots in order to avoid free-thaws.

2. In Vitro Translation of α-Hemolysin DNA

The translation reaction of 500 ul contained 150 ul *E. coli* extract (Promega Corp., Wisconsin, Wis.), 200 ul premix without amino acids, 50 ul amino acid mixture (1 mM), 25 ug of plasmid DNA coding for α-HL, 1000 picomoles of BODIPY-FL-methionyl-tRNA$^{fmet}$ and RNase free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. From the translation reaction premix, n-formyl-tetrahydrofolate (fTHF) was omitted. The translation was carried out at 37° C. for 1 hour. The translation reaction mixture incubated without DNA is taken as control.

3. Purification of His-6-α-HL

Five hundred microliters of the translation reaction mixture (see step 2 above) was subjected to Talon-Sepharose (ClonTech, Polo Alto, Calif.) chromatography for the purification of His-6-α-HL. This was carried out by loading the crude extract onto the Talon-Sepharose column which was pre-equilibrated with 50 mM Tris-HCl, pH 8.0 containing 150 mM NaCl and washing the column to remove unbound proteins. The bound protein was then eluted by adding 100 mM imidazole in the above buffer. The eluted α-HL was dialyzed against 50 mM Tris-HCl buffer, pH 7.5. The fluorescence of purified and dialyzed α-HL was checked on Molecular Dynamics FluorImager F595.

4. Protease Digestion

The purified fluorescently labeled α-HL (~5 ug) (see step 3 above) was incubated with 0.1 ug of pure trypsin (Sigma Chemicals, St. Louis, Mo.) in 50 mM Tris-HCl buffer, pH 7.5 (50:1; protein:protease ratio) for 10 min at room temperature. The proteolysis reaction was arrested by the addition of 1×CE-SDS-gel loading buffer and boiling the samples for 10 min.

5. Mobility Shift Assay

The SDS-capillary gel electrophoresis (SDS-CGE) was performed on a Bio-Rad BioFocus 3000CE system. The capillary was fused-silica with a 75 um ID, 24 cm total length and 19.5 cm to the detector. Fifty microliters of fluorescently labeled protein sample (α-HL) was mixed with 50 ul of SDS-CGE-sample loading buffer and incubated at 95° C. for 10 min. The capillary was rinsed with 0.1 M NaOH, 0.1 M HCl and SDS-run buffer for 60, 60 and 120 sec respectively, prior to each injection. Sample were injected using electrophoretic injection (20 sec at 10 kV). Separation was performed at 15 kV (constant voltage) for 25 min. Capillary and sample was maintained at 20° C. The detection of sample was carried out using 488 nm Argon laser and 520 nm emission filter.

The results of SDS-CGE are shown in the FIG. 28. As seen in the Figure, fluorescently label α-HL migrates as a major species eluting around 24 min under the electrophoresis conditions (Top panel). In addition, the electrophoregram also show the presence of minor impurities present in the sample, which are eluting around 17 and 20.5 min. When the fluorescently labeled-α-HL sample was treated with trypsin and analyzed using SDS-CGE, it showed peaks eluting earlier (13, 14 and 15 min) and major peak at 21 min (Bottom panel). This result indicated that the α-HL was proteolysed by the trypsin and various proteolytic fragments have N-terminal fluorescently labeled are seen in the electrophoregram.

EXAMPLE 21

Incorporation of Three Markers into Hemolysin

This is an example wherein a protein is generated in vitro under conditions where N- and C-terminal markers are incorporated along with a marker incorporated using a misaminoacylated tRNA. The Example involves 1) PCR with primers harboring N-terminal and C-terminal detectable markers, 2) preparation of the tRNA, 3) in vitro translation, 4) detection of nascent protein.

1. PCR of α-Hemolysin DNA

Plasmid DNA for α-hemolysin, pT7-WT-H6-αHL, was amplified by PCR using following primers. The forward primer (HL-5) was: 5'-GAATTC-<u>TAATACGAC TCACTATAGG</u>GTTAACTTTAAGAAGGAGATATACAT ATGGAACAAAAATTAATCTCGGAAGAGGATTTGGC AGATTCTGATATTAATATTAAAACC-3' (SEQ ID NO:11) and the reverse primer (HL-3) was: 5'-AGCTTCATTA-<u>ATGATGGTGATGG</u>-TGGTGAC 3' (SEQ ID NO:12). The underlined sequence in forward primer is T7 promoter, the region in bold corresponds to ribosome binding site (Shine-Dalgarno's sequence), the bold and underlined sequences involve the C-myc epitope and nucleotides shown in italics are the complimentary region of α-hemolysin sequence. In the reverse primer, the underlined sequence corresponds to that of His×6 epitope. The PCR reaction mixture of 100 ul contained 100 ng template DNA, 0.5 uM each primer, 1 mM MgCl$_2$, 50 ul of PCR master mix (Qiagen, CA.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 2 min, followed by 35 cycles consisted of 95° C. for 1 min, 61° C. for 1 min and 72° C. for 2 min and the final extension at 72° C. for 7 min. The PCR product was then purified using Qiagen PCR clean-up kit (Qiagen, CA.). The purified PCR DNA was used in the translation reaction.

2. Preparation of BODIPY-FL-lysyl-tRNA$^{lys}$

The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 ul). To this solution 5 ul of 0.5 M CAPS buffer, pH 10.5 was added (50 mM final conc.) followed by 10 ul of 10 mM solution of BODIPY-FL-SSE. The mixture was incubated for 10 min at 0° C. and the reaction was quenched by the addition of lysine (final concentration 100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. Varshney et al., *J. Biol. Chem.* 266:24712-24718 (1991).

3. Cell-Free Synthesis of Proteins in Eukaryotic (Wheat Germ) Translation Extracts.

The typical translation reaction mixture (20 ul) contained 10 ul of TnT wheat germ extract (Promega Corp., Wisconsin-Madison, Wis.), 0.8 ul of TnT reaction buffer, 2 ul of amino acid mix (1 mM), 0.4 ul of T7 RNA polymerase, 30 picomoles of BODIPY-FL-lysyl-tRNA$^{lys}$, 1-2 ug plasmid or PCR DNA (Example 1) and RNase-free water. The translation reaction was allowed to proceed for 60 min at 30° C. and reaction mixture was centrifuged for 5 min to remove insoluble material. The clarified extract was then precipitated with 5-volumes of acetone and the precipitated proteins were collected by centrifugation. The pellet was dissolved in 1× loading buffer and subjected to SDS-PAGE after boiling for 5 min. SDS-PAGE was carried out according to Laemmli, *Nature*, 227:680-685.

4. Detection of Nascent Protein

After the electrophoresis, gel was scanned using FluorImager 595 (Molecular Dymanics, Sunnyvale, Calif.) equipped with argon laser as excitation source. For visualization of BODIPY-FL labeled nascent protein, we have used 488 nm as the excitation source as it is the closest to its excitation maximum and for emission, we have used 530+/−30 filter. The gel was scanned using PMT voltage 1000 volts and either 100 or 200 micron pixel size.

The results are shown in FIG. 29. It can be seen from the Figure that one can in vitro produce the protein from the PCR DNA containing desired marker(s) present. In the present case, the protein (α-hemolysin) has a C-myc epitope at N-terminal and His×6 epitope at C-terminal. In addition, BODIPY-FL, a fluorescent reporter molecule is incorporated into the protein. Lane 1: α-Hemolysin plasmid DNA control; lane 2: no DNA control; lane 3: PCR α-hemolysin DNA and lane 4: hemolysin amber 135 DNA. The top (T) and bottom (B) bands in all the lane are from the non-specific binding of fluorescent tRNA to some proteins in wheat germ extract and free fluorescent-tRNA present in the translation reaction, respectively.

EXAMPLE 22

Primer Design

It is not intended that the present invention be limited to particular primers. A variety of primers are contemplated for use in the present invention to ultimately incorporate markers in the nascent protein (as explained above). The Example involves 1) PCR with primers harboring markers, 2) in vitro translation, and 3) detection of nascent protein.

For PCR the following primers were used:

```
forward primer:                        (SEQ ID NO:13)
5' GGATCCTAATACGACTCACTATAGGGAGACCACCATG GAACAAAAA
TTAATATCGGAAGAGGATTTGAATGTTTCTCCATACAGGTCACGGGGA-
3'.

Reverse primer:                        (SEQ ID NO:14)
5'-TTATTAATGATGGTGATGGTGGTG-TTCTGTAGGAATGGTATCTCG
TTTTTC-3'
``` sequence in the forward primer is T7 promoter, the bold and underlined sequences involve the C-myc epitope and nucleotides shown in italics are the complimentary region of α-hemolysin sequence. In the reverse primer, the bold sequence corresponds to that of His-6 epitope and the underlined sequence corresponds to the complimentary region of the α-hemolysin sequence. A PCR reaction mixture of 100 ul can be used containing 100 ng template DNA, 0.5 uM each primer, 1 mM MgCl$_2$, 50 ul of PCR master mix (Qiagen, CA.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 2 min, followed by 35 cycles consisted of 95° C. for 1 min, 61° C. for 1 min and 72° C. for 2 min and the final extension at 72° C. for 7 min. The PCR product can then be purified using Qiagen PCR clean-up kit (Qiagen, CA.). The purified PCR DNA can then be used in a variety of translation reactions. Detection can be done as described above.

Overall, the present invention contemplates a variety of primer designs based on the particular epitopes desired (see Table 4 for a list of illustrative epitopes). In general, the epitopes can be inserted as the N-terminus or C-terminus. In addition, they can be used to introduce an affinity region (i.e. a region which will bind to antibody or other ligand) into the protein.

EXAMPLE 23

Antibody Detection of Primer-Encoded Epitopes

This is an example wherein a protein is generated in vitro under conditions where affinity regions are incorporated in a protein and thereafter detected. The Example involves 1) PCR with primers containing sequences that encode epitopes, 2) preparation of the tRNA, 3) in vitro translation, 4) detection of nascent protein.

1. PCR with Primer-Encoded Epitopes

The total RNA from the human colon (Clontech, Palo Alto, Calif.) was subjected to one-step RT-PCR reaction using ClonTech RT-PCR Kit. The forward Primer, PTT-T7-P53, was 5'-GGATCC<u>TAATACGACTCACTATAGGG</u>AGACCACCA-TGGGACACCACCATCACCATCACG-GAGATTACAAAGATGACGATGACAAA-GAGGAGC-CGCAGTCAGATCCTAGCGTCGA-3' (SEQ ID NO:15) and the reverse primer, Myc-P53-3', was 5'-ATTATTA<u>CAAATCCTCTTCCGAGATTAATTTTTGTTCGTCTGA</u> GTCAGGCCCTTCTGTCTTGAACATG-3' (SEQ ID NO:16). The underlined sequence in forward primer is T7 promoter, the nucleotides shown in italics corresponds to that of His-6 tag while the sequence in bold codes for FLAG-epitope and the rest of primer is the complementary region for P53 DNA. In the reverse primer, the underlined sequence corresponds to that of c-Myc epitope.

The RT-PCR/PCR reaction mixture of 50 µl contained 1 µg total human colon RNA, 0.5 µM each primer, 43.5 µl of RT-PCR master mix (ClonTech) and nuclease free water (Sigma Chemicals, St. Louis, Mo.) water. The RT-PCR/PCR was carried out in PTC-150 thermocyler (MJ Research, Waltham, Mass.) using following conditions: 50° C. for 1 hour, 95° C. for 5 min followed by 40 cycles consisted of 95° C. for 45 sec, 60° C. for 1 min and 70° C. for 2 min and the final extension at 70° C. for 7 min. The PCR product was analyzed on 1% agarose gel and the PCR amplified DNA was used in the translation reaction without any further purification. The artificial C-terminal truncated mutant of P53 was prepared using the identical procedure described above except the reverse primer, 3'-P53-Mut, was 5'-CT-CATTCAGCTCTCGGAACATC-TCGAAGCG-3' (SEQ ID NO: 17).

2. tRNA Labelling

Purified tRNA$^{lys}$ (Sigma Chemicals, St. Louis, Mo.) was first amino-acylated with lysine. The typical aminoacylation reaction (100 µl) contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (35 µl). To this solution 5 ul of 0.5M CAPS buffer, pH 10.5 was added (final concentration of 50 mM) followed by 10 ul of 10 mM solution of BODIPY-FL-SSE. The mixture was incubated for 10 minutes at 0° C. and the reaction was quenched by the addition of free lysine (final concentration=100 mM). To the resulting solution 0.1 volumes of 3 M NAOAc (pH=5.0) was added and the modified tRNA was precipitated with 3 volumes of ethanol. Precipitate was dissolved in 50 µl of RNase-free water and passed through Sephadex G-25 gel filtration column (0.5×5 cm) to remove any free fluorescent reagent, if present. The modified tRNA was stored frozen (−70° C.) in small aliquots in order to avoid freeze-thaws. The modification extent of the aminoacylated-tRNA was assessed by acid-urea gel electrophoresis [Varshney, U., Lee, C. P. & RajBhandary, U. L., J. Biol. Chem. 266, 24712-24718 (1991)] or by HPLC [Anal. Biochem. 279:218-225 (2000)].

3. Translation

Translation of P53 DNA (see step 1, above) was carried out in rabbit reticulocyte translation extract in presence of fluorescent-tRNA (step 2, above).

4. Detection

Once the translation was over, an aliquot (5 µl) was subjected to SDS-PAGE and the nascent proteins were visualized using FluorImager SI (Molecular Dynamics, Sunnyvale, Calif.). After visualization, the gel was soaked in the transfer buffer (12 mM Tris, 100 mM glycine and 0.01% SDS, pH 8.5) for 10 min. Proteins from the gels were then transferred to PVDF membrane by standard western blotting protocol using Bio-Rad submersion transfer unit for 1 hr. After the transfer, then membrane was reversibly stained using Ferrozine/ferrous total protein stain for 1 min to check the quality of transfer and then the membrane was blocked using amber blocking solution (4.5% v/v teleostean gelatin, 2% w/v non-fat milk powder, 0.1% w/v Tween-20 in Tris-buffered saline, pH 7.5) for 2 hours followed by overnight incubation (12-15 hours at 4° C. on constant speed shaker) with appropriately diluted antibodies. For Flag detection, we have used 2000-fold diluted anti-Flag M2 Antibody (Sigma), for His-6 detection, we have used 500-fold anti-His6 antibody (Santa-Cruz Biotech, CA.) and for c-Myc detection, we have used 500-fold diluted anti-C-Myc antibody (Santa-Cruz Biotech, CA.).

After primary antibody incubation, the membrane was washed with TBST (Tris-buffered saline, pH 7.5 with 0.1% Tween-20) four times (10 min each wash) and incubated with appropriately diluted secondary antibodies (10,000-fold diluted) for 1 hour at room temperature on constant speed shaker. The unbound secondary antibodies were washed with TBST (4 washes/10 min each) and the blot was visualized using an ECL-Plus chemiluminescence detection system (Amersham-Pharmacia Biotech, NJ).

The results are shown in FIGS. 30A and 30B. FIG. 30A shows the total protein stain of PVDF membranes following protein transfer from the gel for three replicate blots containing a minus DNA negative control and a plus p53 DNA sample respectively. FIG. 30B shows the same blots (total protein staining is reversible) are probed with antibodies against the three epitope tags using standard chemiluminescent Western blotting techniques. Arrows indicate the position of p53.

EXAMPLE 24

Gel-Based PTT for Cancer Genes

The detection of truncating mutations in proteins was first reported by Roest and co-workers and applied to the detection of truncating mutations in the APC gene by Vogelstein, Kinzler and co-workers. Truncations in a translated protein can occur due to frameshift, splicing and point mutations which result in the occurrence of a stop codon in the reading frame of a gene. Truncated polypeptides can be detected by translating a specific region of the DNA corresponding to the target gene in an in vitro system in the presence of radioactive labels (e.g. $^{35}$S-methionine) and then analyzing the resulting polypeptide using standard PAGE. Such an approach has been reported for the analysis of truncating mutations in a variety of cancer-linked genes including BRCA1/BRCA2, ATM, MHS2, MLH1. However, the use of radioactive isotopes presents problems in terms of the time needed for detection (>5 hours), which is critical for high-throughput analysis. For this reason, it would be highly advantageous to replace radioactivity with a more rapid means of detection.

In this example, we demonstrate the feasibility of rapid truncation analysis based on the use of N-terminal tags. The present invention provides a convenient, accurate and rapid method to screen for truncation mutations in a wide range of genes of clinical significance. The Example involves 1) PCR with primers having sequences complementary to the APC gene, 2) preparation of the tRNA, 3) in vitro translation, 4) detection of nascent protein.

1. PCR of Clinical Samples

Clinical samples were submitted to the Washington University Molecular Diagnostics laboratory for screening of chain truncations in the APC gene, which are characteristic of the autosomal dominant cancer syndrome familial adenomatous polyposis (FAP). Genomic DNA was isolated and a specific region of the APC gene (Exon 15-segment 2) was first amplified by PCR using primers which incorporate a T7 promoter, and Kozak sequence into the DNA. The forward Primer, T7-APC2 was 5'-GGATCC TAATACGACTCACTATAGGGAGA CCACCATGGATG-CATGTGGA-ACTTTGTGG-3' (SEQ ID NO:18) and the reverse primer 3'-APC2 was 5'-GAGGATCCATTAGAT-GAAGGTGTGGACG-3' (SEQ ID NO:19). The underlined sequence in forward primer is T7 promoter and the sequence shown in italics corresponds to that of Kozak sequence which is necessary for efficient eukaryotic translation initiation. The PCR reaction mixture of 50 µl contained 200-500 ng template DNA (either WT or mutant), 0.5 µM each primer and 25 µl of PCR master mix (Qiagen, CA.) and nuclease free water (Sigma Chemicals, St. Louis. Mo.) water. The PCR was carried out using Hybaid Omni-E thermocyler (Hybaid, Franklin, Mass.) fitted with hot-lid following conditions: 95° C. for 3 min, followed by 40 cycles consisted of 95° C. for 45 sec. 55° C. for 1 min and 72° C. for 2 min and the final extension at 72° C. for 7 min. The PCR product was analyzed on 1% agarose gel and the PCR amplified DNA was used in the translation reaction without any further purification.

2. Preparation of the tRNA

The purified tRNA$^{lys}$ (Sigma Chemicals, St. Louis, Mo.) was first amino-acylated with lysine. The typical aminoacylation reaction (100 µl) contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (35 µl). To this solution 5 ul of 0.5M CAPS buffer, pH 10.5 was added (final concentration of 50 mM) followed by 10 ul of 10 mM solution of BODIPY-FL-SSE. The mixture was incubating for 10 minutes at 0° C. and the reaction was quenched by the addition of free lysine (final concentration=100 mM). To the resulting solution 0.1 volumes of 3 M NAOAc (pH=5.0) was added and the modified tRNA was precipitated with 3 volumes of ethanol. Precipitate was dissolved in 50 µl of RNase-free water and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991 J. Biol. Chem. 266, 24712-24718).

3. Translation

The PCR products (see step 1 above) were directly added without purification to a small aliquot of a Promega rabbit reticulocyte TnT Quick system which also contained the BODIPY-Lys-tRNA (see step 2 above). More specifically, after PCR, 0.5-1 µl of PCR product was directly added to translation reaction mixture containing 8 µl of rabbit reticulocyte extract for PCR product (Promega), 0.5 µl of 1 mM complete amino acid mix, 1 µl of BODIPY-FL-Lysyl-tRNA. The translation reaction was allowed to proceed for 1 hour and the reaction product were analyzed by 14% SDS-PAGE. Imaging was performed in under 1-2 minute using a Molecular Dynamics FluorImager.

4. Detection

FIG. 31 shows the results for analysis of several different human genomic samples using BODIPY-FL-lysyl-tRNA$^{lys}$ to incorporate a fluorescent label into fragments of the APC protein. Lane 1 is a minus DNA control. Lane 2 shows the results for wild-type DNA, while lanes 3-8 show the results for various mutant DNA isolated from patients having FAP (colon cancer). The last lane is fluorescent molecular weight markers. As seen in FIG. 31, the WT DNA (lane 2) produces a band, which corresponds to the normal Exon 15, segment 2 fragment of the APC gene. In contrast, all other lanes (except lane 6) exhibit the WT band and an additional band which corresponds to truncated fragments of Exon 15, segment 2. Thus, these individuals are heterozygous and carry one WT and one chain truncating mutation in the APC gene. In contrast, the lane 6 results indicates normal WT sequence in this region for both genes. Similar conclusion was reached independently using conventional radioactive PAGE analysis of patient samples by the University Molecular Diagnostics laboratory.

A similar analysis was performed to detect chain-truncating mutations in Exon 15-segment 3 (FIG. 32). Proteins were synthesized using the rabbit reticulocyte in vitro translation system in conjunction with BODIPY-FL-lysyl-tRNA$^{lys}$. Following separation by SDS-PAGE, translated proteins were visualized by fluorescence imaging to (FIG. 32A) or by chemiluminescent Western blotting procedures using a polyclonal antibody directed against the BODIPY fluorophore (FIG. 32B). Lane 1 is a minus DNA control. Lane 2 shows the results for APC3 wild-type DNA, while lane 3 shows the results for APC3 truncated mutant. Lane 4 shows the results for APC2 wild-type DNA, while lane 5 shows the results for APC2 heterozygous mutant.

Overall, these results demonstrate the ability to replace radioactive PTT screening with fluorescent-based screening of chain truncations involved in human inherited diseases.

EXAMPLE 25

Gel-Free PTT for Cancer Genes

Although the replacement of radioactivity in Example 24 (above) with fluorescent labels represents an improvement in current PTT technology, it still relies on the use of gels, which are not easily adaptable for high-throughput screening applications. For this reason, this example demonstrates a non-gel approach based on the use of chemiluminescent detection. In this approach, a cancer-linked protein or polypeptide fragment from the protein is expressed in vitro from the corresponding gene with different detection and binding tags incorporated at the N-terminal, C-terminal and between the two ends of the protein using a combination of specially designed primers and tRNAs. The detection and binding tags provide a means to quantitate the fraction of protein or protein fragment which is truncated while the tags located between the two ends of the protein can be used to determine the region of truncation. For example, a full-length protein would contain both an N and C-terminal tag, whereas a truncated protein would contain only the N-terminal tag. The signal from a tag incorporated at random lysines between the two ends of the protein (intrachain signal) would be reduced proportional to the size of the truncated fragment. It is important to also capture the protein with a marker located close to the N-terminus in order to avoid interference of chain truncations with binding.

In order to evaluate this method, we performed experiments on the APC and p53 genes containing either a WT sequence or truncating mutations. In both cases, a combination of primers and specially designed tRNAs were used to incorporate a series of markers into the target proteins during their in vitro synthesis in a rabbit reticulocyte system. After in vitro expression, the expressed protein was captured in 96-well ELISA plates using an affinity element bound to the plate. The relative amount of N-terminal, C-terminal and intrachain signal was then determined using separate chemiluminescent-based assays.

1. PCR of Cancer Genes
   A. APC Segment 3

First, the genomic DNA (WT and isolated from cell lines harboring mutant APC gene) was amplified by PCR using following primers. The forward primer, PTT-T7-APC3, was 5'-GGATCC<u>TAATACGACTCACACTATAG</u>GGAGACCA CCATGC*ACCACCATCACCATCACG*GAGGAGATTAC AAAGATGACGATGACAAA-GTTTCTCCATACAGGT-CACGGGGAGCCAAT-3' (SEQ ID NO:20) and the reverse primer, PTT-Myc-APC3, was 5'-ATTATTA <u>CAAATCCTCTTCCGAGATTAATTTTTGTTC</u>ACTTCTG CCTTCTGTAGGAATGGTATCTCG-3' (SEQ ID NO:21). The underlined sequence in forward primer is T7 promoter, nucleotides shown in italics corresponds to that of His-6 tag while the nucleotides sequence shown in the bold codes for FLAG-epitope and the rest of the primer is the complementary region for APC segment 3 DNA. In the reverse primer, the underlined sequence corresponds to that of c-Myc epitope. The PCR\reaction mixture of 50 μl contained 200-500 ng template DNA (either WT or mutant), 0.5 μM each primer and 25 μl of PCR master mix (Qiagen, CA.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 3 min, followed by 40 cycles consisting of 95° C. for 45 sec, 55° C. for 1 min and 72° C. for 2 min and the final extension at 72° C. for 7 min. The PCR product was analyzed on 1% agarose gel and the PCR amplified DNA was used in the translation reaction without any further purification.

B. P53

The p53 DNA was prepared as described in Example 23 (above).

2. Preparation of the tRNA

The BODIPY-FL-lysyl-tRNA$^{lys}$ was prepared as described in Example 23 (above). Preparation of Biotin-lysyl-tRNA$^{lys}$ and PC-Biotin-lysyl-tRNA$^{lys}$ was achieved as follows. The purified tRNA$^{lys}$ (Sigma Chemicals, St. Louis, Mo.) was first aminoacylated with lysine. The typical aminoacylation reaction contained 1500 picomoles (~1.0 $OD_{260}$) of tRNA, 20 mM imidazole-HCl buffer, pH 7.5, 10 mM $MgCl_2$, 1 mM lysine, 2 mM ATP, 150 mM NaCl and excess of aminoacyl-tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 μl). To this solution 5 μl of 0.5 M CAPS buffer, pH 10.5 was added (50 mM final conc.) followed by 10 μl of 10 mM solution of either Biotin or photocleavable-Biotin. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991, J. Biol. Chem. 266, 2471224718).

3. Translation

The typical translation reaction mixture (20 μl) contained 16 μl of TNT rabbit reticulocyte extract for PCR DNA (Promega, Madison, Wis.), 1 μl of amino acid mix (1 mM), 1-2 μl of PCR DNA (see APC and p53 preparation described above) and RNase-free water. For fluorescence detection, the BODIPY-FL-lysyl-tRNA$^{lys}$ was included into the translation reaction mixture. The translation reaction was allowed to proceed for 60 min at 30° C.

4. Detection

FIG. 33A shows the results of an initial experiment designed to detect a chain truncation introduced into the p53 protein during RT-PCR In this case an N-terminal FLAG epitope was used for capture (see the description of the capture assay using 96-well ELISA plates at the beginning of the EXPERIMENTAL section), and His$_6$ and c-myc used for the N- and C-terminal markers, respectively. Detection of the N-terminus His-tag was achieved using a peroxidase labeled nickel chelate-based detection probe (India™ His Probe-HRP, Pierce, Rockford, Ill.). Detection of the C-terminus was performed using a rabbit polyclonal antibody directed against the human c-myc epitope followed by a peroxidase labeled mouse anti-[rabbit IgG] secondary antibody. As seen, the ratio of C/N terminal signals is reduced approximately 25-fold for the truncated protein compared to WT. Further optimization of this assay should result in sensitivity sufficient to detect truncating mutations in 1/100 mutant/WT p53 proteins, thus enabling applications to non-invasive colon cancer screening.

In a second experiment (FIG. 33B), capture was facilitated with an N-terminal His$_6$-tag, while FLAG and c-myc were used as N and C-terminal markers, respectively. In addition, an intrachain photocleavable biotin marker was incorporated by adding PC-Biotin-Lys-tRNA to the in vitro mixture. Biotin detection was achieved using peroxidase labeled NeutrAvidin™ (Pierce). The results show a 13-fold reduction in the C/N ratio for truncated p53 compared to WT. Furthermore, the intrachain biotin signal drops by 75% relative to the N-terminal signal.

A third chemiluminescent protein truncation assay was designed to detect chain truncation in the APC gene of a mutant cell line (FIG. 33C). Capture was facilitated with an N-terminal His$_6$-tag, while FLAG and c-myc were used as N and C-terminal markers, respectively. As seen in FIG. 33C, the truncated APC exhibits a marked drop in the C/N ratio (⅙) again indicating the presence of a chain truncation.

Overall, these experiments demonstrate the ability to detect chain-truncating mutations in cancer-linked proteins using a gel-free chemiluminescent approach.

EXAMPLE 26

Fluorescent Immunoprecipitation Method

In this Example, the use of Fluor-tag tRNA in immunoprecipitation is demonstrated. In this experiment, once the nascent protein was synthesized in the presence of the labeled tRNA, it was captured on protein-G beads using specific antibodies. All other (unbound) material is removed. The bound protein of interest is then released from the bead by SDS-treatment and analyzed by PAGE.

The in vitro translation was carried out using either the PCR DNA coding for P53 protein or a plasmid DNA coding for α-hemolysin (prepared as described in previous examples). After the translation reaction, equal amounts of 10% SDS (w/v) was added to the reaction mixture and the samples were boiled for 5 min. The samples were diluted with I buffer (Tris-buffer saline with 1% Triton X-100) and 2 μg of either anti-P53 antibody (Santa Cruz Biotech, CA) or anti-HL antibody (Sigma, St. Louis, Mo.) was added and incubated for several hours at 4° C. with mixing. As a negative control, immunoprecipitation was carried out using non-specific mouse IgG antibodies. After antibody incubation, Protein-G beads (Pierce, Ill.) were added to the reaction mixture and further incubated for 1 hour with constant mixing. The beads were then pelleted and washed three time with TBS with 0.1% SDS. Finally, the beads were suspended into 50 μl of 2×SDS-gel loading buffer and boiled for 5 min. The SDS-PAGE was carried out according to Laemmli (Laemmli, U. K. 1970, Nature, 227, 680-685).

The gel was then scanned using FluorImager S1 (Molecular Dymanics. Sunnyvale, Calif.) equipped with argon laser as excitation source. For visualization of BODIPY-FL labeled nascent protein, 488 nm was used as excitation source as it is the closest to its excitation maximum and for emission (we have used 530±30 filter). The gel was scanned using PMT voltage 1000 volts and either 100 or 200 micron pixel size.

FIG. 34 shows the results. Lane M contains fluorescent markers. Lane 1 is a minus DNA control (+anti-HL antibody). Lane 2 shows the results for HL DNA+mouse IgG. Lane 3 shows the results for HL DNA+anti-HL antibody. Lane 4 is a minus DNA control (+anti-P53 antibody). Lane 5 shows the results for p53 DNA+mouse IgG. Lane 6 shows the results for p53 DNA+anti-p53 antibody. It should be clear that the immunoprecipitation method provides specific results and a very clean signal without any substantial background.

EXAMPLE 26

Suppressor tRNAs

When using BODIPY-labeled initiator tRNAs, a competition occurs between endogenous initiator tRNA (unlabeled) which causes reduced incorporation of the label. To overcome this competition, the present invention contemplates using an amber stop codon and a corresponding suppressor tRNA.

1. Preparation of BODIPY-Val-pdCpA

The first step involves the preparation of a BODIPY-amino acid conjugate for attachment to the suppressor tRNA. The synthesis is set forth in FIG. 35. The synthesis begins with the preparation of 5-Methyl-1(2-Nitrophenyl)ethanol (compound 2). To begin, 5-Methyl-2-nitroacetophenone (Olejnik, J., S. Sonar, E. Krzymanska-Olejnik, and K. J. Rothschild. 1995 *Proc Natl Acad Sci USA*. 92:7590-4; Olejnik, J., E. Krzymanska-Olejnik, and K. J. Rothschild. 1998. *Methods Enzymol*. 291:135-54.) was dissolved in 5 ml of ethanol. To this solution 5 mg of sodium borohydride was added in small portions until analytical TLC showed complete conversion to 5-Methyl-1(2-Nitrophenyl)ethanol. The reaction was quenched by addition of 5 ml acetone and acidified to pH=3.0 with 1 N HCl, followed by extraction with chloroform. The organic layer was dried and evaporated to give the target compound as yellowish oil. This compound was used without any further purification.

Continuing with the synthesis scheme, 5-Methyl-1(2-Nitrophenyl)ethanol (350 mg; 1.95 mmol) (compound 2) was dissolved in 10 ml of acetonitrile. To this solution 407 ul of triethylamine (1.5 eq) was added followed by N,N'-disuccinimidyl carbonate (750 mg, 1.5 eq.). The reaction mixture was stirred at room temperature until analytical TLC (silica gel, chloroform) showed quantitative conversion to compound 3. The resulting solution was added directly to the solution of triethylammonium salt of valine.

Valine (218 mg; 1.86 mmol) was suspended in 2 ml of water to which was added 260 ul of triethylamine. To this solution a solution of compound 3 was added xx over 15 min. period, during which pH value of the mixture was adjusted if necessary by the addition of triethylamine. The mixture was stirred for 30 min and acidified by addition of 10 ml of 0.1 N HCl, followed by extraction with 3×20 ml AcOEt. Organic layers were combined, dried and evaporated to dryness. The crude product was dissolved in 20 ml chloroform and extracted with 4×30 ml of 0.1 N NaHCO3, the aqueous layer acidified and re-extracted by chloroform to give 320 mg of pure target Npe-Val (compound 4).

Npe-Val (compound 4) (320 mg, 1 mmol) was dissolved in 320 ul of acetonitrile. To this solution was added triethylamine (280 ul, 2 eq.) and chloroacetonitrile (190 ul, 3 eq.). The mixture was stirred overnight at room temperature. 20 ml of methylene chloride was added followed by 20 ml of 1N NaHSO4, the mixture was extracted with 4×20 ml methylene chloride. Organics were evaporated to dryness and purified on silica gel column using step gradient of ethyl acetate in hexane (10-50%) to give 300 mg of pure product (compound 5).

20 OD of pdCpA (Annovis) containing 2.2 equiv of tetrabutylammonium counterion was dissolved in 40 ul of dry DMF. To this solution was added a solution of 2 equivalents of Npe-Val-COOCH2CN (0.66 mg) in 10 ul DMF. The reaction was kept at RT for 2 hrs, then the product was isolated using preparative HPLC to give 15 OD of compound 6.

15 OD$_{260}$ of Npe-Val-pdCpA was dissolved in 500 ul of 25 mM NaOAc, pH=4.5 and irradiated for 20 minutes using 365 nm light (BlakRay XX-15, UVP). 166 ul of BODIPY-FL-SE (@10 mg/ml; 7 equivs. was added) followed by 140 ul of 1N NaHCO$_3$. Additional portions of BODIPY-FL-SE solution (2×166 ul, total 21 equivs) were added after 5 and 10 minutes, respectively, and the reaction mixture was vortexed at room temperature for 45 minutes. The product (compound 7) was isolated using preparative HPLC Novapak C18, 10×100 mm, linear gradient of acetonitrile in 50 mM TEAA, pH 5.4 over 90 min., flow 2 ml/min) and characterized by absorption at both 260 and 505 nm. Yield 7.25 $OD_{260}$.

2. Expression and Purification of Amber-Suppressor fMet-tRNA.

PstI fragment of nusA operon containing a gene for mutamt $tRNA^{fmet}$ (S. Ishi et al. PNAS v.81, pp409-413, 1984) was cloned into pGEM4 vector (Promega, Madison, Wis.). Total tRNA was isolated from overnight culture (100 ml) of E. coli XL-blue 2 cells by phenol extraction and ethanol precipitation. Suppressor $tRNA^{fmet}$ was purified using native PAGE (Seong and RajBhandary, PNAS v. 84 pp. 334-338, 1987).

3. tRNA Truncation by Venom Phosphodiesterase I (VPD I) (FIG. 36)

1 $OD_{260}$ of purified initiator suppressor tRNA was dissolved in in 50 uL of 50 mM Tris-HCl pH 7.5;10 mM $MgCl_2$ and 100 mM NaCl. To this solution 0.5 unit of VPD I was added and the mixture was incubated for 30 min at 0° C. After phenol extraction tRNA was precipitated by EtOH, dried and dissolved in 100 uL of water. Selective (—CA) dinucleotide removal from the 3'-terminus was confirmed by 8%, 7M Urea PAGE analysis.

4. Ligation with BODIPY-Val-pdCpA with Truncated Initiator Suppressor tRNA

As shown in the scheme of FIG. 36, the tRNA is charged with the BODIPY-amino acid conjugate in a ligation reaction. 0.5 $OD_{260}$ of tRNA was incubated with 0.5 $OD_{260}$ unit of pdCpA in 100 ul of ligation buffer (50 mM Tris-HCl pH 7.8; 10 mM $MgCl_2$; 10 mM DTT; 1 mM ATP 30% of DMSO) and 200 units of T4 RNA ligase (New England Biolabs, Beverly, Mass.) for 1 hour at 37° C. After the incubation tRNA was precipitated by 3-4 volumes of EtOH, dissolved in 50 ul of water and spine-filtered using G25 MicroSpin column (Amersham Pharmacia Biotech Inc.). Ligated tRNA was aliquoted and stored at −70° C. The product will be referred to as an initiator/amber suppressor tRNA.

5. Translation and Analysis

Translation was performed in a cell-free E. coli S30 extract (Promega, Madison, Wis.) in 20 ul total volume. The mixture contained DNA coding for the particular protein (1 ug) and initiator amber suppressor tRNA prepared by chemical aminoacylation (1 ug). The mixture was incubated for 1 hour at 37° C. and then 1 ul was mixed with the loading buffer, heat denatured and run on a 14% SDS-PAGE (150 V, 1 hr). The gel was then rinsed briefly and analyzed using Fluoroimager in case of BODIPY label. In case of PC-Biotin the gel was blotted onto PVDF membrane and the biotin detected using streptavidin-HRP.

FIG. 37 shows the results. Lane 1 is a minus DNA control+BODIPY-Val initiator/amber suppressor tRNA. Lane 2 shows the results for luciferase DNA+BODIPY-Lys-tRNA. Lane 3 shows the results for amber-1 luciferase DNA+BODIPY-Lys-tRNA, while lane 4 shows the improved results for amber-1 luciferase DNA+BODIPY-Val initiator/amber suppressor tRNA.

Lane 5 shows the results for hemolysin DNA+BODIPY-Lys-tRNA. Lane 6 shows the results for amber-1 hemolysin DNA+BODIPY-Lys-tRNA, while lane 7 shows the improved results with amber-1 hemolysin DNA+BODIPY-Val initiator/amber suppressor tRNA.

Lane 8 shows the results for DHFR DNA+BODIPY-Lys tRNA. Lane 9 shows the results for amber-1 DHFR DNA+BODIPY-Lys tRNA, while lane 10 shows the improved results for amber-1 DHFR DNA+BODIPY-Val initiator/amber suppressor tRNA.

EXAMPLE 28

Drug-Proteome Screening

The completion of the human genome project has opened a new chapter in drug discovery. In contrast to conventional methods, where a drug library is screened against a single protein, the entire proteome is now available for screening. However, such drug-proteomic screens are difficult to accomplish using conventional technology because of the need to rapidly convert genome to proteome, engineer specially labeled proteins and screen thousands of samples per hour.

The present invention provides methods and compositions that aim at removing these limitations by screening drug-protein interactions using cell-free expressed labeled proteins and 2-D microarrays. The present invention contemplates incorporating the above-described labels and markers (e.g. fluorescent and affinity tags) into proteins during their cell-free expression. Fluorescent tags (e.g. at the N-terminal, C-terminal, within and/or throughout the protein) provide a means to monitor protein expression and detect their interactions with potential drug compounds. Affinity tags provide a means to rapidly isolate cell-free expressed proteins from the cell-free lysate. Drug screens performed on 2-D microarrays of cell-free expressed proteins, reflecting all or part of the human proteome, provide a system for high sensitivity detection, high throughput and low sample volume requirements.

The proteomic screening assays of the present invention greatly accelerate the drug discovery process by allowing potential interactions between a lead drug compound and an entire proteome (or part of a proteome) to be screened. Such information is valuable to explore the molecular basis of a drug's action and to identify possible side effects of a drug by constructing a drug interaction map.

A drug-interaction map provides information about the interaction of a specific compound (e.g. a lead drug) with the human proteome. In order to establish a drug-interaction map, methods are contemplated that allow systematic expression and labeling of entire proteomes using a formatted cDNA library that consists of a series of plasmid cDNA pools. Each pool, consisting of approximately 50 plasmids or less (more preferably approximately 40 plasmids or less, still more preferably approximately 30 plasmids or less, and most preferably approximately 25 plasmids or less), is simultaneously expressed in a cell-free reaction mixture (e.g. Promega TnT rabbit reticulocyte expression system). The proteins are affinity purified from the mixture using linkers such as PC-biotin incorporated during translation with tRNAs. The expressed proteins are then exposed to a surface (e.g. a bead or slide), which has the immobilized test drug compound on the surface. Interaction of one or more proteins from each pool is then detected using the incorporated fluorescent labels. The identity of a particular protein(s) from the pool which interacts with a drug compound is then determined using either a procedure which subdivides the plasmid pool or through microanalysis of the immobilized protein. Alternatively, the expressed proteins in each pool are transferred to a solid medium using incorporated affinity tags. Each pool of proteins are arranged on a 2-D array and interrogated with compounds, which are immobilized on labeled beads. High throughput screening can be accomplished using 2-D microarrays and fluorescent imagers similar to DNA-based microchips.

An important advantage of the use of cell-free expressed proteins with non-radioactive markers, such as incorporated fluorescent and/or affinity markers, compared to conventional methods of radioactive labeling is the ability to perform rapid isolation of nascent proteins and rapid detection with the sensitivity necessary for high throughput analysis. This approach is especially advantageous in the case of 2-d microarrays where radioactive detection is precluded. In addition, it is important to limit the number of the plasmids in each pool (e.g. less than 50) so that each protein coded by the cDNA is expressed at a sufficient level to detect. While large volumes of reaction mixture (e.g. 1 ml) can always be utilized to express pools of plasmids, large volume reactions would be prohibitively expensive for practical proteomic-screening. For example, utilization of 2000 1 ml reaction volumes would be necessary to express 2000 plasmids pools. Using current commercial costs of TnT rabbit reticulocyte this would cost approximately $800,000. In contrast, smaller volume 50 microliter reactions compatible with 2-d microarray formats would cost only $20,000. Earlier methods of in vitro expression cloning such as described in U.S. Pat. No. 5,654,150 (hereby incorporated by reference) are based on collecting pools of about 100 individual bacterial colonies and expressing proteins encoded by the cDNAs in the pools in vitro. While this approach represents an improvement of earlier (non-in vitro) expression cloning methods such as described in U.S. Pat. No. 4,675,285 (also incorporated by reference), it still does not generally provide a sufficiently sensitive method to perform high throughput drug-proteomic screening provided by the present invention. In addition to drug-proteomic screening, the present invention would also allow for the rapid throughput screening of interactions of the proteome with DNA and other biomolecules.

Two different related approaches for drug-proteomic screening are contemplated, both based on the utilization of 2-D arrays or microarrays and detection using fluorescence, luminescence, chemiluminescence, absorption or other means of electromagnetic detection (either directly or indirectly). As shown in FIG. 38, the first approach utilizes cell-free expressed proteins produced from pools of plasmids, which comprise a formatted genomic library. In order to eliminate interference from preexisting protein in the reaction mixture, which exist at much higher levels than the expressed proteins, a pre-purification step may be necessary using incorporated affinity tags and complementary capture molecules coated on a surface. Each sample from an individual pool containing the expressed proteins is then applied to a spot on the surface containing the immobilized target drug. The incorporated fluorescence marker is then used to identify those samples, which contain proteins, which interact with the target drug. Alternatively, a fluorescently labeled molecule (e.g. an antibody), which interacts with an incorporated affinity marker can be used. In one preferred embodiment, a biotin is used as the affinity marker, which interacts with a streptavidin-horse radish peroxidase (HRP) complex which catalyzes a reaction that produces a detectable signal (e.g. chemiluminescent or fluorescent).

Once a protein pool is identified which exhibits an interaction with the target drug through detection of fluorescence from the particular spot, the actual interacting protein can be identified using a variety of procedures. One method relies on the retransformation of the individual plasmids in the pool followed by in vitro expression of proteins from each individual plasmids in the presence of FluoroTags or Affinity Tags. An alternative approach is to recover the actual bound protein(s) from a spot showing positive fluorescence and perform sequence analysis either using mass spectrometry or through chemical means.

A second related approach for drug-proteome screening is also contemplated (FIG. 39). In this case, the samples containing the cell-free expressed proteins produced from pools of plasmids are first bound to surfaces and then interrogated with a specific target drug, which is conjugated to a fluorescent moiety. The incorporated affinity tags are used for the binding of the in vitro expressed protein to a specially prepared surface containing a capture molecule which interacts with the affinity tag. Incorporated fluorophores are used to monitor surface binding. Target drug binding is detected using dual wavelength fluorescence detection or alternatively fluorescence resonance energy transfer, which assures that the protein and bound drug are in close proximity. The drug-protein complex can also be released using a photocleavable biotin linker, for downstream analysis to confirm the drug-protein interaction and for further mass spectrometric analysis of the drug or protein identity.

In both scenarios described above, parallel expression of the genomic library, which is estimated to consist of 2000 individual plasmid pools of approximately 50 plasmids per pool, provides the basis to perform rapid drug-proteomic analysis. For example, using a preformatted set of reaction wells (50 microliters each) and plasmid sets, the entire parallel expression reaction could be accomplished in less than 1 hour. The purification of the expressed proteins from each sample could also be extremely rapid, provided that suitable equipment (e.g. 96 well-pipetters operated by robotic arms) were utilized. For example, pipette filter tips can be prepared that contain an affinity media for capture via the in vitro incorporated photocleavable tag (e.g. streptavidin bound to beads) and light can be used for subsequent release.

In both scenarios, the samples can be rapidly transferred to a surface for subsequent drug-protein fluorescent assays. For example, in the case of slides coated with the target drug, individual samples can be spotted using a commercial arrayer such as the Affymetrix 417 arrayer, which offers 125 um resolution spot size. In principle, a single microscope slide would be sufficient to array the entire proteome with 5-fold redundancy in less than 10 minutes. Larger spots sizes or greater redundancy would require more slides, however the entire preparation of the arrayed proteome would still rapid and amenable to high throughput processing. The entire "proteome on a slide" concept is particularly attractive, since the rapid production of such slides would enable screening of the entire proteome versus libraries of drugs.

For the above mentioned format, rapid read-out can be achieved using a fluorescent 2-D microarray reader. For example, the Affymetrix 418 scanner can scan an entire slide in approximately 10 minutes and is able to perform 3 color imaging. Furthermore, the array reader offers high precision (10 microns), speed (18 mm/min) and sensitivity (less than 1 Cy3 dye molecules per 1 square micron with >3.5 S/N).

In order to evaluate the screening assays of the present invention, experiments were performed which involved the incorporation of PC-Biotin or BODIPY into the test protein dihydrofolate reductase (DHFR). Experiments were aimed at evaluating whether PC-Biotin or BODIPY markers incorporated into DHFR during its in vitro synthesis could be used to assay for its interaction with the small ligand methotrexate, a competitive inhibitor for DHFR whose normal ligand is dihydrofolate. Since methotrexate can reduce the rate of cell growth, it is widely used as an anticancer drug in chemotherapy.

In one assay, PC-Biotin was incorporated into DHFR during its in vitro expression in S30 in the presence of PC-Biotin-Lys-tRNA. After expression, the crude mixture was exposed to methotrexate-coated agarose beads. After extensive washing, specific binding of the DHFR to the beads was assayed using streptavidin-HRP. As seen in FIG. 40, a signal is obtained only when PC-Biotin-Lys-tRNA is included in the expression system. UV-light exposure prior to binding, abolishes the signal relative to control levels (data not shown), providing a convenient method to measure background levels during automated assays.

In a second experiment, capillary electrophoresis (CE-LIF) was used as a homogenous solution assay to detect the interaction of DHFR and methotrexate. In this case, BODIPY was incorporated at the N-terminus of DHFR during its in vitro synthesis using BODIPY-fmet-tRNA. The electropherogram for free DHFR exhibited a peak at 2.9 minutes (data not shown). In comparison, the electropherogram of DHFR preincubated with methotrexate for 30 minutes at room temperature exhibited a broadened peak at 2.8 min (data not shown). The change in migration time is attributed to the complex formation between DHFR and methotrexate.

In a third series of experiments, the ability to selectively bind and detect an in vitro expressed target protein using an antibody was explored. For this purpose, PC-Biotin was incorporated into p53 expressed in rabbit reticulocyte lysate after RT-PCR of a pooled human mRNA sample using the PC-Biotin-Lys-tRNA. The protein was then specifically captured on ELISA plates using monoclonal antibody clone BP53-12 (Santa Cruz Biotechnology, Santa Cruz, Calif.) which recognizes both WT and mutant conformations. As a negative control, an identical quantity of pre-immune mouse IgG was used for capture, in place of the p53 specific antibody. Detection of the biotin was achieved using peroxidase labeled NeutrAvidin biotin binding protein (Pierce, Rockford, Ill.) in a standard ELISA assay. The results (not shown) indicated that only specific binding with the p53 antibody results in a significant signal. These data demonstrate the feasibility of studying p53 binding using a panel of conformation specific antibodies which selectively react with different p53 mutants.

EXAMPLE 29

Incorporation of VSV-G and p53-Derived Epitopes

Genomic DNA and RNA (WT and APC mutant) was isolated from established cell lines CaCo-2 (C1), HCT-8 (C2) and SW480 (C3) as well as from patient blood samples using commercially available kits (Qiagen, Valencia, Calif.). PCR amplification of a selected region of the APC gene (APC segment 3) was carried out using 250-500 ng of genomic DNA, 0.2 µM primer mix (forward and reverse) and 1×PCR master mix (Qiagen, Valencia, Calif.). Amplification was performed as follows: an initial cycle of denaturation at 95° C., forty cycles of denaturation at 95° C. for 45 sec. annealing at 57° C. for 45 sec, extension at 72° C. for 2 min and a final extension step at 72° C. for 10 min. RT-PCR amplification of APC gene (APC segment 3) was carried out using one-step RT-PCR/PCR kit from ClonTech (Palo Alto, Calif.). RT-PCR reaction contained 500 ng of total RNA, 0.2 µM primer mix (forward and reverse) and 1×RT-PCR master mix. Amplification conditions were the same as above with an additional initial cycle of reverse transcription at 50° C. for 1 hour. The primer pair was:

Forward:
(SEQ ID NO:22)
5'-GGA*TCCTAATACGACTCACTATAGG*GAGACCACC<u>ATG</u>GGCTACACCG ACAT-CGAGATGAACCGCCTGGCAAGGTTTCTCCATACAGGTCACGGGA GCC-3'

Reverse:
(SEQ ID NO:23)
5'-*TTATTA*CAGCAGCTTGTGCAGGTCGCTGAAGGTACTTCTGCCTTCTG T-AGGAATGTATC-3'

The italicized nucleotides in the forward primer correspond to the T7 promoter, the underlined ATG is the initiation codon, the boldface nucleotide region codes for the N-terminal tag (VSV-G; YTDIEMNRLGK: SEQ ID NO:39) and the remaining nucleotide sequences correspond to the complementary region of the APC gene. In the reverse primer, the boldface nucleotides code for the C-terminal tag (P53 sequence derived tag; TFSDLHKLL: SEQ ID NO:24) while the rest of the nucleotide sequence is complementary to the APC gene and nucleotides in italics codes for 2 successive stop codons. After amplification, the quality and quantity of the PCR products was analyzed by agarose gel electrophoresis.

EXAMPLE 30

Cell-Free Protein Synthesis

The cell-free reaction mixture contained 8 µl of TNT T7 Quick Rabbit Reticulocyte lysate for PCR DNA (Promega, Madison, Wis.), 0.5 µl of a complete amino acid mix and 0.5 µl of DNA (approximately 200 ng) and either 1 µl of biotin-lysyl-tRNA or a tRNA mix consisting of equal amount of Biotin-lysyl tRNA and BODIPY-FL-lysyl-tRNA. The translation reaction was allowed to proceed for 45 min at 30° C. For electrophoresis, a 4-6 µl aliquot was used for SDS-PAGE. SDS-PAGE was carried out according to Laemmli. Kahmann et al., *A Non-Radioactive Protein Truncation Test For The Sensitive Detection Of All Stop And Frameshift Mutations,* Hum Mutat 19; 165-172 (2002). After electrophoresis, polyacrylamide gels were scanned using a FluorImager SI (Molecular Dynamics, Sunnyvale, Calif.) equipped with an Argon laser as an excitation source (488 nm line) and a 530±30 nm emission filter.

EXAMPLE 31

High-Throughput Solid-Phase PTT (HTS-PTT)

After the translation exemplified in Example 30, the reaction mixture was diluted 30-fold with TBS containing 0.05% Tween-20, 0.1% Triton X-100, 5% BSA, and both antibodies (anti-VSV-G-HRP (Roche Applied Sciences, Indianapolis, Ind.) at 80 ng/mL and anti-p53-alkaline phosphatase at 100 ng/mL (Santa Cruz Biotechnology, Santa Cruz, Calif.)). Subsequently, 100 µl of the diluted reaction mixture was added to each well of a NeutrAvidin™ coated 96-well plate (pre-blocked with 5% BSA) and incubated for 45 min on an orbital shaker. NeutrAvidin™ was obtained from Pierce Chemicals (Rockford, Ill.) and Microlite2+ multiwell plates were obtained from Dynex Technologies (Chantilly, Va.). The plate was washed 5×with TBS-T (TBS with 0.05% Tween-20) followed by 2× with TBS and developed using a chemiluminescent HRP substrate (Super Signal Femto, Pierce Chemicals, Rockford, Ill.). Finally, the plate was washed twice in 100 mM Tris-HCl, pH 9.5, 100 mM NaCl and 50 mM magnesium acetate, a chemiluminescent alkaline-phosphatase reaction mixture.

EXAMPLE 32

Comparison of tRNA$^{TOTAL}$ Versus tRNA$^{lys}$

The use of biotin-lysyl-tRNA (i.e., biotin-tRNA$^{lys}$) to incorporate biotin affinity tags at lysine residues would result in no capture if the chain truncation occurs upstream of the first lysine. This problem and the overall efficiency of capture can be improved if a tRNA mixture containing most, or all, of the normal cellular tRNAs is misaminoacylated with a biotin-labeled amino acid. This "total tRNA mixture" (i.e., tRNA$^{TOTAL}$) is then used instead of lysyl-tRNA (i.e., tRNA$^{lys}$), thereby making the biotin incorporation less dependent on the amino acid sequence of the nascent protein.

The translation was essentially carried out as described in Example 30 in the presence of biotinylated-tRNA$^{lys}$ and biotinylated HTS-PTT. ELISA was carried out as described in Example 31. FIG. 46 depicts ELISA data showing samples translated in presence of biotin-tRNA$^{TOTAL}$ have 2-4 times higher signals than that of samples translated in presence of biotin-tRNA$^{lys}$.

EXAMPLE 33

A Penta-Lysine 5'-Tag

The use of biotin-lysyl-tRNA to incorporate biotin affinity tags at lysine residues would result in no capture if the chain truncation occurs upstream of the first lysine. This problem and the overall efficiency of capture can be improved if an extra lysine sequence are artificially added in the beginning the transcript. This can be achieved by adding 5 extra lysine coding nucleotides in the 5' primer after an ATG codon or after the epitope coding nucleotides. This design of the transcript then can increase the overall number of lysine residues resulting in the increased incorporation of biotin using biotin-tRNA$^{lys}$. It is contemplated that the lysine tag includes, but is not limited to, from between 3-10 lysine residues.

The translation was essentially carried out as described in Example 30. ELISA HTS-PTT was carried out as described in Example 31. FIG. 47 depicts ELISA data showing increased signal in samples having extra lysine residues using shorter nascent proteins (WT is 70 kD nascent protein while is N3 is a mixture of 70 and 30 kD nascent proteins).

EXAMPLE 34

Gel Electrophoresis: APC-23 and APC-3

This example demonstrates SDS-PAGE separation of the nascent 140 kD APC-23 protein fragment from the 70 kD APC-3 protein fragment.

The HTS-PTT is not limited by the resolution of SDS-PAGE, therefore, it is possible to reduce the number of cell-free reactions per patient sample by translating larger segments of the target gene (or the whole gene itself). The translation was essentially carried out as described in Example 30. This study demonstrates that HTS-PTT analysis of fragments of at least 140 kDa in size is possible. (See FIG. 48)

EXAMPLE 35

Comparison of APC-3 and APC-23 Template DNA

HTS-PTT was carried out using either APC-3 (1.7 kb DNA fragment) or APC-23 (3.56 kb DNA fragment). The translation was essentially carried out as described in Example 30. FIG. 49 shows bar graph data demonstrating that there are no significant differences in the C/N ratio irrespective of the template used. This result indicates that even larger templates can be used for HTS-PTT, thus reducing the overall number of reactions per analysis.

EXAMPLE 36

Minimal Copy PCR Amplification

This example demonstrates that a single copy DNA may be amplified and isolated using HTS-PTT.

A defined amount of genomic DNA (WT APC) and cell line DNA (mutant APC) was used as the template for PCR. Low copy PCR was carried out in two sequential PCR amplifications. To test the limit of PCR, template DNA was diluted to various ratios to obtain 1-300,000 copies of DNA/µl. In the first PCR amplification, a selected region of the APC gene (APC long, 3.8 kb region) was carried out using various amounts of genomic DNA, 0.2 µM primer mix (Long 5' and Long 3') and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 4 min and a final extension step at 72° C. for 10 min. The product after this PCR was used as the template for the second PCR reaction. PCR amplification of a selected region of the APC gene (APC-3) was carried out using 5 µl of above PCR product (after APC Long PCR), 0.2 µM primer mix (forward and reverse) and 1×PCR master mix (Qiagen, Valencia, Calif.). Amplification was performed as follows: an initial cycle of denaturation at 95° C., forty cycles of denaturation at 95° C. for 45 sec, annealing at 57° C. for 45 sec, extension at 72° C. for 4 min and a final extension step at 72° C. for 10 min.

The primer pairs were:
Long 5': 5'-TTTTTGGTTGGCACTCTTACTTACCG-GAGC-3' SEQ ID NO: 47
Long 3': 5'-AGATGCTTGCTGGACCTGGTCCAT-TATCTT-3' SEQ ID NO: 48
Forward: SEQ ID NO: 22
5'-GGATCCTAATACGACTCACTATAGGGAGACCACC ATGGGCTACACCGACAT CGAGATGAACCGCCTG-GCAAGGTTTCTCCATACAGGTCACGGGAGCC-3'
Reverse: SEQ ID NO: 23
5'-TTATTACAGCAGCTTGTGCAGGTCGCT-GAAGGTACTTCTGCCTTCTGTA GGAATGGTATC-3'

The italicized nucleotides in the forward primer correspond to the T7 promoter, the underlined ATG is the initiation codon, the boldface nucleotide region codes for the N-terminal tag (VSV-G; YTDIEMNRLGK, SEQ ID NO:39) and the remaining nucleotide sequences correspond to the complementary region of the APC gene. In the reverse primer, the boldface nucleotides code for the C-terminal tag (P53 sequence derived tag: TFSDLHKLL, SEQ ID NO:24). The nucleotides in italics (TTATTA) codes for 2 successive stop codons. After amplification, the quality and quantity of the PCR products were analyzed by agarose gel electrophoresis. FIG. 50 demonstrates that the PCR product corresponds to a single copy of DNA.

EXAMPLE 37

MicroArray-Based HTS-PTT

This example checks the feasibility of MicroArrays for PTT. Specifically, various amount of amplified WT and mutant APC DNA (cell-line) were mixed and translated. The translation was essentially carried out as described in Example 30.

Each reaction mixture received an equal amount of spotting buffer (Tris-buffered saline, 0.05% Tween-20 with 40% glycerol) and 0.1 µl of reaction mixture without any pre-purification was spotted on streptavidin-coated glass slides (pre-blocked with 5% bovine serum albumin, BSA). After 30 min incubation at 37° C. in a humidified chamber, all the excess biotin-binding sites on the slides were blocked by immersing the slide into 5 mM biotin solution. Then the slide was incubated for 45 min at room temperature with anti-P53 antibody (BP-P53-12; Santa Cruz Biotechnology, Santa Cruz, Calif.) with shaking. After removal of excess antibody from the slide, the slide was developed using Alexa-488-conjugated anti-mouse secondary antibody (Molecular Probes, Eugene Oreg.). Visualization of the slide (see FIG. 51) shows a concentration-dependent color intensity pattern. (Molecular Dynamics FluorImager SI.).

EXAMPLE 38

High Sensitivity Gel-Free ELISA-PTT

This example demonstrates the incorporation of reporter molecules at the position of the mutation in order to obtain a mutation-specific positive signal. This procedure utilizes a high sensitivity, chemiluminescent "Gel-Free" PTT for non-invasive CRC screening.

Although the HTS-PTT for inherited mutations (e.g., 50% mutant DNA and 50% wild-type DNA) works well, it is insufficient for non-invasive colon cancer screening, which requires a truncating mutation detection sensitivity of 1:100 mutant:WT-APC. To achieve this, a different approach is contemplated by this invention involving production of a positive signal only when a truncation mutation is encountered, instead of attempting to measure a decrease in C-terminal signal as described above. FIG. 52 exemplifies the assay.

For example, α-hemolysin (HL) may be translated as a model test protein in an *E. coli* cell-free translation system. Two types of DNA, wild type DNA (WT) and mutant DNA (e.g., Amb-1) are introduced into the cell-free translation system. Amb-1 introduces an inappropriate/misplaced amber (UAG) stop codon into the mRNA. The DNA was mixed at various ratios of mutant to wild-type while maintaining a constant amount of total DNA. The translation was performed with an amber suppressor tRNA misaminoacylated with photocleavable (PC)-Biotin.

Following translation, the mutant protein is selectively captured via the incorporated biotin moiety using NeutrA-vidin™ coated 96-well ELISA plates (removal of unused biotinylated tRNA was found not to be necessary). Plates were then probed with an antibody directed against the HL protein and signal is generated using a typical enzyme-linked chemiluminescence detection system. A translation reaction performed with 100% wild-type DNA is used as the negative control (i.e., Blank) to account for the level of non-specific binding of HL to the ELISA plate. FIG. 53 panel A indicates that as little as 0.4% mutant (i.e., 1 mutant per 250 wild-type) can be detected with statistical significance versus the Blank. The p value of the statistical analysis is 0.002 (n=3) based on a two-tailed, unpaired, homoscedastic t-test and is 25-fold better than the 0.05 required for statistical significance. As seen in FIG. 53 panel B, larger ratios of mutant to wild type are easily detectable using this system. FIG. 54 demonstrates signal linearity with various ratios of mutant to wild-type DNA. Linear regression analysis yields a linear correlation coefficient of 0.9963 (99.63% linear correlation) for the data points tested shows the linearity of the assay.

EXAMPLE 39

High Sensitivity Gel-Based PTT

This example demonstrates the application of a highly sensitive PTT detection system to identify mutated DNA within a mixture of normal DNA from stool samples.

The gel-based PTT test is designed to detect mutant protein derived from a DNA sample containing 1 mutant gene in a pool of 100 wild-type genes. The data from this experiment using a gel-based PTT (See FIG. 55) shows that when wild-type and mutant DNA from stool samples of an FAP patient was mixed at various ratios, as little as 4% mutant DNA is detectable (i.e., 4 copies of mutant DNA in a pool of 96 wild-type genes). Specific embodiments of this invention contemplate improving detection sensitivity further by affinity purification and immunoprecipitation, incorporating linkers, markers and epitopes, improving FluoroTag sensitivity and improving overall translation yields.

This protocol provides a high sensitivity gel-based fluorescent PTT analysis of APC segment 2 (APC2) for non-invasive CRC screening. Specifically, PCR amplified DNA was derived from a clinical sample known to be positive for an inherited (FAP) heterozygous truncation mutation in APC2. Mutant DNA was mixed at various ratios with the WT DNA and used to perform an in vitro translation of APC2. A constant level of total DNA was used for all translation reactions. Translations are performed using BODIPY-FL-Lys-tRNA$^{lys}$ to label the nascent protein. FIG. 55 panel A shows the fluorescently imaged gel following SDS-PAGE. Lane "–DNA" (i.e., minus DNA) corresponds to a translation reaction performed where only the DNA was omitted. The six middle lanes each contain a different percentage of mutant DNA (i.e., 0% is pure WT DNA), while lane M corresponds to 100% mutant (heterozygote) DNA. The asterisk located at the bottom of the 4% lane indicates the lowest level of mutant DNA that can be detected reliably with the current technique. The arrow located at the bottom left corner indicates the position of the truncated APC-2 fragment. FIG. 55 Panel B depicts quantification of the banding intensity for the truncated APC-2 fragment (see arrow) by computer-assisted densitometry. The integrated intensity values is plotted versus the percent of mutant DNA (lowest point plotted is 4% mutant DNA). Linear regression analysis solved the line equation and linear correlation coefficient are shown on the graph.

EXAMPLE 40

MALDI-Mass Spectrometry (MALDI-MS) Mutation Detection

This example utilizes α-HL with a C-terminal His6-tag, which was expressed in a S30 reaction mixture using a high-expression plasmid containing the α-HL gene under control of the T7 promoter.

For comparison, a mutant of α-HL (S302W) was also expressed in *E. coli* translation extract. In both cases, the proteins were isolated from the translation reaction mixture using $Co^{2+}$-NTA chromatography. The isolated protein was dialyzed, concentrated and deposited on a MALDI substrate. As seen in FIG. 57, a peak is observed at 34,884 Da for WT α-HL and 34,982 Da for the mutant α-HL, in good agreement with calculated masses (34,890 and 34,989 Da, respectively). This demonstrates the ability of MALDI to detect a mutation in an in vitro expressed protein.

EXAMPLE 41

Improved Signal-to-Noise Ratios

This example demonstrates an improved method of ELISA antibody-based detection following HTS-PTT. The translation and HTS-PTT was essentially carried out as described in Examples 30 and 31, respectively.

The data shown in FIG. 58 indicates that using enzymes directly conjugated to the primary antibody (i.e., HRP or AP) improves the signal to noise ratio relative to the traditional combination of primary antibodies and enzyme-conjugated secondary antibodies. A direct comparison of the signals and backgrounds obtained using anti-VSV primary followed by secondary HRP-conjugated antibody as well as using HRP-conjugated anti-VSV primary antibody demonstrates a greater signal for the directly conjugated VSV-HRP. Similar analysis was also carried out using anti-P53 antibodies (data not shown).

EXAMPLE 42

Single-Step ELISA

This example demonstrates a shortened ELISA protocol to reduce overall analysis time. The translation and HTS-PTT was essentially carried out as described in Examples 30 and 31, respectively.

The traditional ELISA process includes putting the nascent protein (translation extract) onto plate, washing of the plate, antibody incubation, washing of the plate and then development of signals. In the shortened protocol, however, the antibody is mixed with nascent protein (i.e., translation extract) prior to putting onto the plate. After the extract-antibody incubation, this mixture was put on the plate and incubated. This protocol consolidates the steps of binding of the antibodies to nascent protein and binding of the nascent protein-antibody complexes to the plate. This consolidation does not result in any significant difference in signal or C/N ratio obtained for N-terminal and C-terminal by using either method. (See FIG. 59)

EXAMPLE 43

Simultaneous Single-Well C-& N-Terminal Signal Detection

This example provides one embodiment of HTS-PTT that contemplates the detection of N-terminal and C-terminal signals in a single well (i.e., from the same sample). The translation and HTS-PTT was essentially carried out as described in Examples 30 and 31, respectively.

Traditionally, HTS-PTT samples are first divided and subjected to N-terminal and C-terminal detection using two different antibodies in separate wells. This step assumes that the biotin-binding capability of the nascent protein does not vary from well to well. Although this assumption may be correct, detection of N- and C-terminals in the same well on the same sample reduces the overall risk of error.

This simultaneous assay uses two differentially conjugated antibodies in the same well and sequentially measures their respective signals. In this particular assay, the N-terminal is marked using HRP-conjugated anti-VSV antibody and the C-terminal is marked using AP-conjugated anti-P53 antibody. (See FIG. 60) After the antibody incubation, the HRP signal was read. Then wells were washed with 100 mM Tris-HCl, pH 9.5 containing 100 mM NaCl and 50 mM magnesium acetate to completely inhibit HRP activity thus forming an optimum environment to detect AP activity using appropriate substrates. The data clearly shows that simultaneous incubation and sequential signal detection provided equivalent data as the more traditional separate-well assay.

EXAMPLE 44

HTS-PTT High Sensitivity

This example demonstrates the high sensitivity of the ELISA-PTT assay contemplated by one embodiment of this invention. The translation and HTS-PTT was essentially carried out as described in Examples 30 and 31, respectively.

FIG. 61 shows signal intensity using various amounts of translation extracts of N-terminal, C-terminal signals and signal-to-noise ratios (i.e., 0.0 translation/well). Very low amounts are detectable (i.e., 0.1 ul of translation mix per well) when compared against a signal-to-noise ratio of approximately 10 and 30 for N- and C-terminal, respectively.

EXAMPLE 45

Enzyme Substrate Discovery

This example demonstrates that the technology contemplated by this invention comprising the incorporation of N-terminal and C-terminal tags into nascent protein can be used very effectively for discovery of the substrates for enzymes. The translation was carried out as described in Example 30. Two examples of these enzymes include, but are not limited to, proteases and kinases. In one embodiment, Caspase-3 degraded N- and C-terminally tagged MDM and APC protein in a time-dependent manner, while similarly tagged PKA was unaffected. (see FIG. 63). Concurrently, the time-dependent appearance of the digestion product is shown in FIG. 64. Similar results were also obtained for several other proteins expressed in vitro in presence of either FluoroTag (gel-based) or biotin-tRNA (ELISA-based)(data not shown). It is contemplated that any enzyme resulting in a physical alteration of the substrate is capable of being monitored using this assay system.

EXAMPLE 46

Enzyme Discovery

This method demonstrates an ability for one embodiment of the present invention to label a plasmid with a marker protein. The translation was described as carried out in Example 30.

For example, multiple plasmid pools in vitro rabbit reticulocyte translation extracts are able to express a variety of protein/protein fragments. After doping one of the plasmid pools with the small amount of the plasmid coding for enzyme luciferase this specific expression vector was subsequently identified. Following transformation, the nascent proteins was translated in presence of biotin-tRNA and subsequently captured on streptavidin-coated plate. After washing unbound protein, the doped plasmid pool was identified by detecting luciferase activity using a chemiluminescent substrate and plate reader. (See FIG. 65). Similar methods can be used for kinase enzyme discovery.

Other embodiments and uses of the invention will be apparent to those skilled in the art from consideration of the specification and practice of the invention disclosed herein. It is intended that the specification and examples be considered exemplary only, with the scope of particular embodiments of the invention indicated by the following claims.

| Name and Molecular weight | Formula | Fluorescence Properties |
|---|---|---|
| BODIPY-FL, SSE M. WT. 491 | 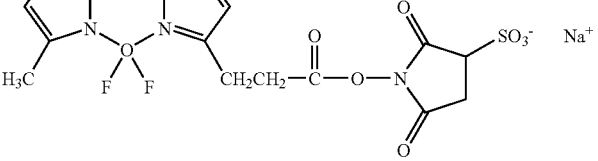 | Excitation = 502 nm Emmision = 510 nm Extinction = 75,000 |
| NBD M. WT. 391 | 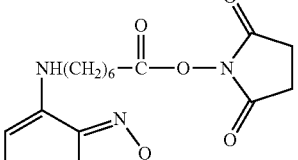 | Excitation = 466 nm Emmision = 535 nm Extinction = 22,000 |
| Bodipy-TMR-X, SE M. WT. 608 | 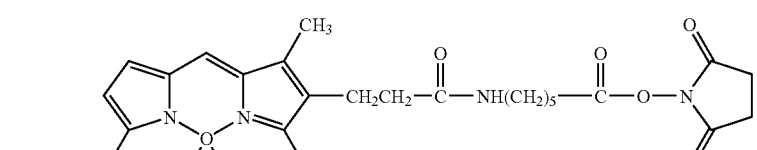 | Excitation = 544 nm Emmision = 570 nm Extinction = 56,000 |
| Bodipy-R8G M. WT. 437 | 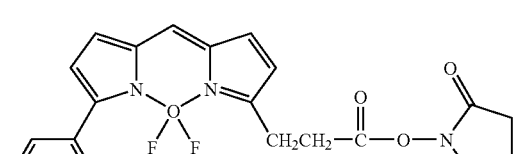 | Excitation = 528 nm Emmision = 547 nm Extinction = 70,000 |
| Fluorescein (FAM) M. WT. 473 | 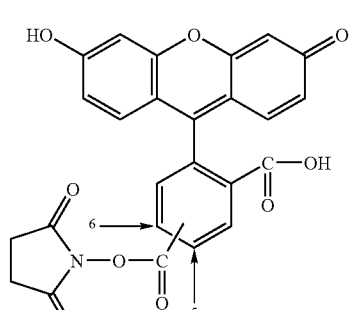 | Excitation = 495 nm Emmision = 520 nm Extinction = 74,000 |

-continued

| Name and Molecular weight | Formula | Fluorescence Properties |
|---|---|---|
| Fluorescein (SFX) M. WT. 587 | 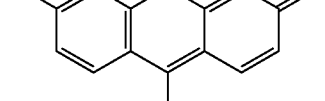 | Excitation = 494 nm Emmision = 520 nm Extinction = 73,000 |
| PyMPO M. WT. 582 | 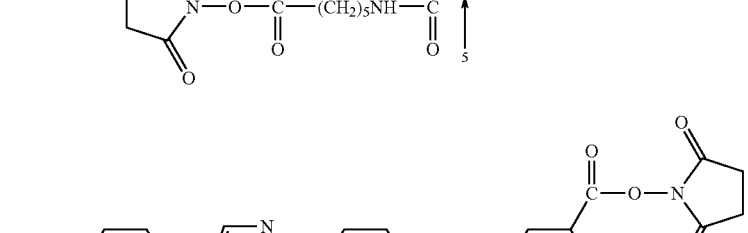 | Excitation = 415 nm Emmision = 570 nm Extinction = 26,000 |
| 5/6-TAMRA M. WT. 528 | 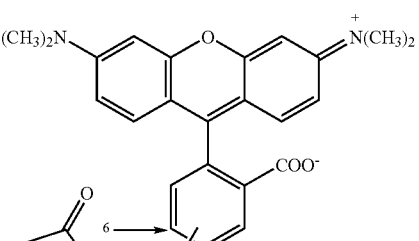 | Excitation = 546 nm Emmision = 576 nm Extinction = 95,000 |

TABLE 3

| Enzyme/Protein | −FluoroTag ™ tRNA Translation reaction | +FluoroTag ™ tRNA Translation reaction |
|---|---|---|
| α-Hemolysin $OD_{415nm}/\mu l$ | 0.085 | 0.083 |
| Luciferase $RLU/\mu l$ | 79052 | 78842 |
| DHFR $\Delta OD_{339nm}/\mu l$ | 0.050 | 0.064 |

TABLE 4

Various Epitopes and Their Sequences

| Name | Amino acid sequence | Nucleotide sequence (5'→ 3') |
|---|---|---|
| His-6 | HHHHHH (SEQ ID NO:61) | CATCACCATCACCATCAC (SEQ ID NO:62) |
| FLAG | DYKDDDDK (SEQ ID NO:63) | GACTACAAGGACGACGACGACAAG (SEQ ID NO:64) |
| c-Myc | EQKLISEEDL | GAGCAGAAGCTGATCAGCGAGGAGGACCTG (SEQ ID NO:66) |

TABLE 4-continued

Various Epitopes and Their Sequences

| Name | Amino acid sequence | Nucleotide sequence (5'→ 3') |
|---|---|---|
| Strep-Tag | (SEQ ID NO:65) WSHPQFEK (SEQ ID NO:67) | TGGAGCCACCCCCAGTTCGAGAAG (SEQ ID NO:68) |
| Amber-16 | CSPFEVQVSPEAGAQK (SEQ ID NO:69) | TGCAGCCCCTTCGAGGTGCAGGTGAGCCCCGAGGCCGGCGCCCAGAAG (SEQ ID NO:70) |
| T7-Tag | MASMTGGQQMG (SEQ ID NO:71) | ATGGCCAGCATGACCGGCGGCCAGCAGATGGGC (SEQ ID NO:72) |
| VSV-G[#]-Tag | YTDIEMNRLGK (SEQ ID NO:73) | TACACCGACATCGAGATGAACCGCCTGGGCAAG (SEQ ID NO:74) |
| HA*-Tag | YPYDVPDYA (SEQ ID NO:75) | TACCCCTACGACGTGCCCGACTACGCC (SEQ ID NO:76) |
| Protein-C Tag | EDQVDPRLIDGK (SEQ ID NO:77) | GAGGACCAGGTGGACCCCCGCCTGATCGACGGCAAG (SEQ ID NO:78) |
| HSV[$]-Tag | QPELAPEDPED (SEQ ID NO:79) | CAGCCCGAGCTGGCCCCCGAGGACCCCGAGGAC (SEQ ID NO:80) |

[#]Vesicular Stomatitis Virus Glycoprotein
*HemAgglutinin
[$]Herpes Simplex Virus glycoprotein

---

The invention claimed is:

1. An oligonucleotide having the sequence set forth in SEQ ID NO: 22.

2. A kit comprising the oligonucleotide of claim 1.

3. The kit of claim 2, further comprising a polymerase.

* * * * *